US009707282B2

(12) United States Patent
Hancock et al.

(10) Patent No.: US 9,707,282 B2
(45) Date of Patent: Jul. 18, 2017

(54) SMALL CATIONIC ANTIMICROBIAL PEPTIDES

(71) Applicant: The University of British Columbia, Vancouver (CA)

(72) Inventors: Robert E. W. Hancock, Vancouver (CA); Kai Hilpert, Vancouver (CA); Artem Cherkasov, Vancouver (CA); Christopher Fjell, Vancouver (CA)

(73) Assignee: THE UNIVERSITY OF BRITISH COLUMBIA, Vancouver, British Columbia (CA)

( * ) Notice: Subject to any disclaimer, the term of this patent is extended or adjusted under 35 U.S.C. 154(b) by 0 days.

(21) Appl. No.: 14/684,136

(22) Filed: Apr. 10, 2015

(65) Prior Publication Data
US 2015/0315240 A1    Nov. 5, 2015

Related U.S. Application Data

(62) Division of application No. 13/725,327, filed on Dec. 21, 2012, now Pat. No. 9,017,656, which is a division of application No. 12/438,055, filed as application No. PCT/CA2007/001453 on Aug. 21, 2007, now Pat. No. 8,343,475.

(60) Provisional application No. 60/839,253, filed on Aug. 21, 2006.

(51) Int. Cl.
| | |
|---|---|
| *A61K 38/10* | (2006.01) |
| *C07K 7/08* | (2006.01) |
| *A61K 39/00* | (2006.01) |
| *A01N 37/46* | (2006.01) |
| *C07K 7/06* | (2006.01) |
| *C07K 14/47* | (2006.01) |
| *A61K 45/06* | (2006.01) |
| *A61K 38/00* | (2006.01) |

(52) U.S. Cl.
CPC .............. *A61K 39/00* (2013.01); *A01N 37/46* (2013.01); *A61K 39/0005* (2013.01); *A61K 45/06* (2013.01); *C07K 7/06* (2013.01); *C07K 7/08* (2013.01); *C07K 14/4723* (2013.01); *A61K 38/00* (2013.01)

(58) Field of Classification Search
CPC .................................. A61K 38/10; C07K 7/08
See application file for complete search history.

(56) References Cited

U.S. PATENT DOCUMENTS

| | | | |
|---|---|---|---|
| 8,343,475 B2 | 1/2013 | Hancock et al. | |
| 9,017,656 B2 | 4/2015 | Hancock et al. | |

FOREIGN PATENT DOCUMENTS

| | | |
|---|---|---|
| WO | 9522338 | 8/1995 |
| WO | 9958141 | 11/1999 |
| WO | 0071175 | 11/2000 |
| WO | 0348383 | 6/2003 |
| WO | 2005025607 | 3/2005 |
| WO | 2005068492 | 7/2005 |
| WO | 2006050611 | 5/2006 |
| WO | 2008022444 | 2/2008 |

OTHER PUBLICATIONS

U.S. Appl. No. 12/438,055 , "Non-Final Office Action", Apr. 11, 2012, 9 pages.
U.S. Appl. No. 12/438,055 , "Notice of Allowance", Aug. 27, 2012, 16 pages.
U.S. Appl. No. 13/725,327 , "Non-Final Office Action", Jul. 9, 2014, 6 pages.
U.S. Appl. No. 13/725,327 , "Notice of Allowance", Jan. 6, 2015, 7 pages.
Alkhatib et al., "cc CKR5: A RANTES, MIP-1 a, MIP-1β receptor as a fusion cofactor for macrophage-tropic HIV-1", Science, vol. 272, Jun. 28, 1996, pp. 1955-1958.
Al-Obeidi et al., "Peptide and peptidomimetic libraries. Molecular diversity and drug design.", Molecular Biotechnology, vol. 9, No. 3, Jun. 1998, pp. 205-223.
AU2007288080 , "Australian Examination Report", Jul. 7, 2012, 4 pages.
Beall et al., "Conversion of Monocyte Chemoattractant Protein-1 into a Neutrophil Attractant by Substitution of Two Amino Acids", The Journal of Biological Chemistry, vol. 267, No. 5, Feb. 15, 1992, pp. 3455-3459.
Belousov et al., "Sequence-Specific Targeting and Covalent Modification of Human Genomic DNA", Nucleic Acids Research, vol. 25, No. 17, 1997, pp. 3440-3444.
Bendelac et al., "Adjuvants of Immunity: Harnessing Innate Immunity to Promote Adaptive Immunity", Journal of Experimental Medicine, vol. 195, No. 5, Mar. 4, 2002, pp. F19-F23.
Blommers et al., "Effects of the Introduction of L-Nucleotides into DNA Solution Structure of the Heterochiral Duplex d(G-C-G-(L)T-G-C-G)d(C-G-C-A-C-G-C) Studied by NMR Spectroscopy", Biochemistry, vol. 33, No. 25, Jun. 28, 1994, pp. 7886-7896.
Bork et al., "Go hunting in sequence databases but watch out for the traps.", Trends in Genetics, vol. 12, No. 10, Oct. 1996, pp. 425-427.
Bowdish et al., "Anti-Endotoxin Properties of Cationic Host Defence Peptides and Proteins", Journal of Endotoxin Research, vol. 11, 2005, pp. 230-236.
Bowdish et al., "Impact of LL-37 on anti-infective immunity", Journal of Leukocyte Biology, vol. 77, Apr. 2005, pp. 451-459.
Bowdish et al., "Immunomodulatory Activities of Small Host Defense Peptides", Antimicrobial Agents and Chemotherapy, vol. 49, No. 5, May 2005, pp. 1727-1732.
Bowdish et al., "Immunomodulatory Properties of Defensins and Cathelicidins", Current Topics in Microbiology and Immunology, vol. 306, 2006, pp. 27-66.
Brenner , "Errors in genome annotation", Trends in Genetics, vol. 15, No. 4, Apr. 1999, pp. 132-133.
Brogden , "Antimicrobial Peptides: Pore Formers or Metabolic Inhibitors in Bacteria?", Nature Reviews Microbiology, vol. 3, Mar. 2005, pp. 238-250.
CA2,660,668 , "Office Action", Jun. 4, 2013, 2 pages.

(Continued)

*Primary Examiner* — Gyan Chandra

(57) ABSTRACT

The present invention relates generally to peptides and more specifically to antimicrobial and immunomodulatory host defense peptides.

4 Claims, 24 Drawing Sheets

(56) References Cited

OTHER PUBLICATIONS

CDC, AJIC NNIS Report, "National Nosocomial Infections Surveillance (NNIS) System Report, data summary from Jan. 1992 through Jun. 2004, issued Oct. 2004", (Dec. 2004), pp. 470-485.
Cherkasov, "Can 'Bacterial-Metabolite- Likeness' Model Improve Odds of 'in Silica' Antibiotic Discovery", Journal of Chemical Information and Modelling, vol. 46, 2006, pp. 1214-1222.
Cherkasov, "Inductive' Descriptors. 10 Successful Years in QSAR", Current Computer-Aided Drug Design, vol. 1, 2005, pp. 21-42.
Clark, "Novel Antibiotic Hypersensitive Mutants of Escherichia coli Genetic Mapping and Chemical Characterization", FEMS Microbiology Letters, vol. 21, 1984, pp. 189-195.
Dragic et al., "HIV-1 Entry Into CD4+ Cells is Mediated by the Chemokine Receptor CC-CKR-5", Nature, vol. 381, Jun. 20,1996, pp. 667-674.
Eisenberg et al., "Analysis of Membrane and Surface Protein Sequences with the Hydrophobic Moment Plot", J. Mol. Biol., 1984, 179:125-142.
Engel et al., "Basic Overview of Chemoinformatics", Journal of Chemical Information and Modelling, vol. 46, No. 6, 2006, pp. 2267-2277.
EP07800481.9, "European Communication Pursuant to Rules 70(2) and 70a(2) EPC", Nov. 23, 2010, 1 page.
EP07800481.9, "Examination Report", Jun. 7, 2013, 3 pages.
EP07800481.9, "Extended European Search Report", Nov. 5, 2010, 6 pages.
Finlay, "Can Innate Immunity be Enhanced to Treat Infections?", Nature Reviews Microbiology, vol. 2, Jun. 2004, pp. 497-504.
Frank, "Spot Synthesis: an Easy Technique for the Positionally Addressable Parallel Chemical Synthesis on a Membrane Support", Tetrahedron, vol. 48, No. 42, 1992, pp. 9217-9232.
Frenkel et al., "7,12-Dimethyl benz[a]anthracene Induces Oxidative DNA Modification in Vivo", Free Radical Biology & Medicine, vol. 19, No. 3, Sep. 19, 1995, pp. 373-380.
Friedrich et al., "Antibacterial Action of Structurally Diverse Cationic Peptides on Gram-Positive Bacteria", Antimicrobial Agents and Chemotherapy, vol. 44, No. 8, Aug. 2000, pp. 2086-2092.
Gao et al., "Binary Quantitative Structure-Activity Relationship (QSAR) Analysis of Estrogen Receptor Ligands", J. Chem. Inf., vol. 39, No. 1, 1999, pp. 164-168.
Gong et al., "Rantes and Mcp-3 Antagonists Bind Multiple Chemokine Receptors", The Journal of Biological Chemistry, vol. 271, No. 18, May 3, 1996, pp. 10521-10527.
Gough et al., "Antiendotoxin Activity of Cationic Peptide Antimicrobial Agents", Infection and Immunity, vol. 64, No. 12, Dec. 1996, pp. 4922-4927.
Hancock et al., "Cationic Peptides: a New Source of Antibiotics", Trends in Biotechnology, vol. 16, No. 2, Feb. 1998, pp. 82-88.
Hancock et al., "Cationic Peptides: Effectors in Innate Immunity and Novel Antimicrobials", The Lancet Infectious Diseases, vol. 1, No. 3, Oct. 2001, pp. 156-164.
Hancock et al., "The Role of Cationic Antimicrobial Peptides in Innate Host Defences", Trends in Microbiology, vol. 8, No. 9, Sep. 2000, pp. 402-410.
Hilpert et al., "High-Throughput Generation of Small Antibacterial Peptides with Improved Activity", Nature Biotechnology, vol. 23, No. 8, Aug. 2005, pp. 1008-1012.
Hilpert et al., "Sequence Requirements and an Optimization Strategy for Short Antimicrobial Peptides", Chemistry & Biology, vol. 13, No. 10, Oct. 2006, pp. 1101-1107.
Hilpert et al., "Use of luminescent bacteria for rapid screening and characterization of short cationic antimicrobial peptides synthesized on cellulose using peptide array technology", Nature Protocols, vol. 2, No. 7, 2007, pp. 1652-1660.

Horuk et al., "Identification and characterization of a promiscuous chemokine-binding protein in a human erythroleukemic cell line.", The Journal of Biological Chemistry, vol. 269, No. 26, Jul. 1, 1994, pp. 17730-17733.
Horuk, "Molecular properties of the chemokine receptor family", Trends Pharmaceutical sciences, vol. 15, No. 5, May 1994, pp. 159-165.
Hruby et al., "Synthesis of Oligopeptide and Peptidomimetic Libraries", Current Opinion in Chemical Biology, vol. 1, No. 1, 1997, pp. 114-119.
IN1495/CHENP/2009, "Office Action", Aug. 30, 2013, 2 pages.
Kamradt et al., "Cross-reactivity of T lymphocytes in infection and autoimmunity.", Molecular Diversity, vol. 8, No. 3, 2004, pp. 271-280.
Karakoc et al., "Comparative QSAR-and Fragments Distribution Analysis of Drugs, Druglikes, Metabolic Substances, and Antimicrobial Compounds", Journal of Chemical Information and Modelling, vol. 46, No. 5, 2006, pp. 2167-2182.
Kelner et al., "Lymphotactin: A Cytokine That Represents a New Class of Chemokine", Science, vol. 266, No. 5189, Nov. 25, 1994, pp. 1395-1399.
Kramer et al., "Combinatorial Cellulose-Bound Peptide Libraries: Screening Tools for the Identification of Peptides That Bind Ligands with Predefined Specificity", A Companion to Methods in Enzymology, vol. 6, No. 4, Dec. 1994, pp. 388-395.
Kramer et al., "Molecular Basis for the Binding Promiscuity of an Anti-p24 (HIV-1) Monoclonal Antibody", Cell, vol. 91, Dec. 12, 1997, pp. 799-809.
Lewenza et al., "Construction of a mini-Tn5-IuxCDABE mutant library in Pseudomonas aeruginosa PAO1: a tool for identifying differentially regulated genes", Genome Research, vol. 15, No. 4, 2005, pp. 583-583.
McPhee et al., "Design of Host Defence Peptides for Antimicrobial and Immunity Enhancing Activities", Combinatorial Chemistry & High Throughput Screening, vol. 8, 2005, pp. 257-272.
Mookherjee et al., "Intracellular Receptor for Human Host Defence Peptide LL-37 in Monocytes", The Journal of Immunology, vol. 183, No. 4, Aug. 15, 2009, pp. 2688-2696.
Murphy, "The molecular biology of leukocyte chemoattractant receptors.", Annual Review of Immunology, vol. 12, 1994, pp. 593-633.
Neote et al., "Functional and biochemical analysis of the cloned Duffy antigen: identity with the red blood cell chemokine receptor", Blood, vol. 84, No. 1, Jul. 1, 1994, pp. 44-52.
Neote et al., "Identification of a promiscuous inflammatory peptide receptor on the surface of red blood cells", The Journal of Biological Chemistry, vol. 268, No. 17, Jun. 15, 1993, pp. 12247-12249.
Neote et al., "Molecular cloning, functional expression, and signaling characteristics of a C-C chemokine receptor", Cell, vol. 72, No. 3, Feb. 12, 1993, pp. 415-425.
Nijnik et al., "Synthetic cationic peptide IDR-1002 provides protection against bacterial infections through chemokine induction and enhanced leukocyte recruitment", The Journal of Immunology, vol. 184, No. 5, Mar. 1, 2010, pp. 2539-2550.
Ostergaard et al., "Peptomers: a versatile approach for the preparation of diverse combinatorial peptidomimetic bead libraries", Molecular Diversity, vol. 3, No. 1, 1997, pp. 17-21.
Ostresh et al., "Generation and use of nonsupport-bound peptide and peptidomimetic combinatorial libraries", Methods in Enzymology, vol. 267, 1996, pp. 220-234.
Papo et al., "Can we predict biological activity of antimicrobial peptides from their interactions with model phospholipid membranes?", Peptides, vol. 24, No. 11, Nov. 2003, pp. 1693-1703.
Papo et al., "Effect of Drastic Sequence Alteration and d-Amino Acid Incorporation on the Membrane Binding Behavior of Lytic Peptides", Biochemistry, vol. 43, No. 21, Jun. 1, 2004, pp. 6393-6403.
Papo et al., "The consequence of sequence alteration of an amphipathic alpha-helical antimicrobial peptide and its diastereomers", The Journal of Biological Chemistry, vol. 277, No. 37, Sep. 13, 2002, pp. 33913-33921.
PCT/CA2007/001453, "International Search Report and written opinion", Dec. 20, 2007, 15 pages.

(56) References Cited

OTHER PUBLICATIONS

Periti et al., "New criteria for selecting the proper antimicrobial chemotherapy for severe sepsis and septic shock", International Journal of Antimicrobial Agents, vol. 12, No. 2, Jul. 1999, pp. 97-105.

Power et al., "Molecular cloning and functional expression of a novel CC chemokine receptor cDNA from a human basophilic cell line", The Journal of Biological Chemistry, vol. 270, No. 33, Aug. 18, 1995, pp. 19495-19500.

Proudfoot et al., "Extension of recombinant human RANTES by the retention of the initiating methionine produces a potent antagonist", The Journal of Biological Chemistry, vol. 271, No. 5, Feb. 2, 1996, pp. 2599-2603.

Radermacher et al., "Bactenecin, a leukocytic antimicrobial peptide, is cytotoxic to neuronal and glial cells", Journal of Neuroscience Research, vol. 36, No. 6, Dec. 15, 1993, pp. 657-662.

Romeo et al., "Structure and Bactericidal Activity of an Antibiotic Dodecapeptide Purified from Bovine Neutrophils", The Journal of Biological Chemistry, vol. 263, No. 20, Jul. 15, 1988, pp. 9573-9575.

Ryge et al., "New Indolicidin Analogues with Potent Antibacterial activity", Journal of Peptide Research, vol. 64, No. 5, Nov. 2004, pp. 171-185.

Schall, "Biology of the rantes/sis cytokine family", vol. 3, No. 3, May 1991, pp. 165-183.

Scott et al., "An anti-infective peptide that selectively modulates the innate immune response", Nature Biotechnology, vol. 25, No. 4, Apr. 2007, pp. 465-472.

Scott et al., "The Human Antimicrobial Peptide LL-37 Is a Multifunctional Modulator of Innate Immune Responses", Journal of Immunology, vol. 169, No. 7, Oct. 1, 2002, pp. 3883-3891.

Selsted et al., "Indolicidin, a novel bactericidal tridecapeptide amide from neutrophils", The Journal of Biological Chemistry, vol. 267, No. 7, Mar. 5, 1992, pp. 4292-4295.

Sims et al., "Studies on the mechanism by which cyanine dyes measure membrane potential in red blood cells and phosphatidylcholine vesicles", Biochemistry, vol. 13, No. 16, 1974, pp. 3315-3330.

Skolnick, "From Genes to Protein Structure and Function: Novel Applications of Computational Approaches in the Genomic Era", Trends in Biotech., vol. 18, No. 1, 2000, pp. 34-39.

Smith et al., "The challenges of genome sequence annotation or "the devil is in the details"", Nature Biotechnology, vol. 15, No. 12, Nov. 1997, pp. 1222-1223.

Wieczorek et al., "Structural studies of a peptide with immune modulating and direct antimicrobial activity", Chemistry & Biology, vol. 17, No. 9, Sep. 24, 2010, pp. 970-980.

Wu et al., "Improved Derivatives of Bactenecin, a Cyclic Dodecameric Antimicrobial Cationic Peptide", Antimicrobial Agents and Chemotherapy, vol. 43, No. 5, May 1999, pp. 1274-1276.

Wu et al., "Interaction of the cyclic antimicrobial cationic peptide bactenecin with the outer and cytoplasmic membrane", The Journal of Biological Chemistry, vol. 274, No. 1, Jan. 1, 1999, pp. 29-35.

Wu et al., "Mechanism of Interaction of Different Classes of Cationic Antimicrobial Peptides with Planar Bilayers and with the Cytoplasmic Membrane of *Escherichia colii*", Biochemistry, vol. 38, No. 22, 1999, pp. 7235-7242.

Yoshida et al., "Molecular Cloning of a Novel CorY Type Chemokine", SCM-1 FEBS Lett., vol. 360, 1995, pp. 155-159.

Yu et al., "Sequestosome-1/p62 is the Key Intracellular Target of Innate Defense Regulator Peptide", The Journal of Biological Chemistry, vol. 284, No. 52, Dec. 25, 2009, pp. 36007-36011.

ZA574758, "Examination Report", Jun. 29, 2010, 2 pages.

ZA597391, "Examination Report", Jan. 6, 2012, 2 pages.

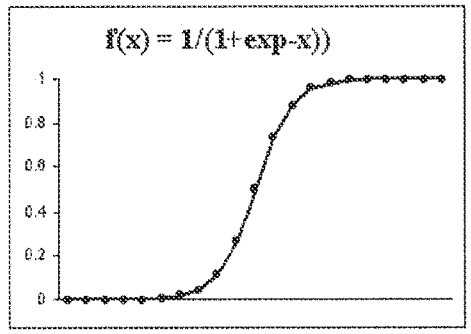
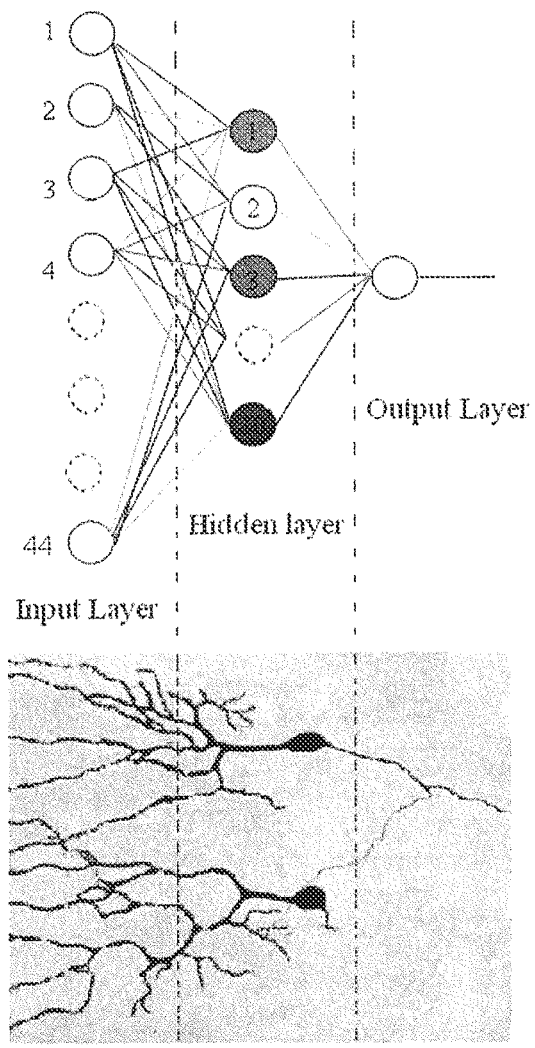
FIGURE 1B

PREDICTION PHASE
VIRTUAL PEPTIDE CANDIDATES
|   | Sequence |
|---|---|
| 1 | FRRWWKWKF |
| 2 | LRVWWVKRI |
| 3 | RKRLKVWVIY |
| ... | ... |
| ... | ... |
| 100,000 | RKVWIVRVVFL |
3D Structures of peptides
|  | 1 | ... | ... | ... | 41 | 42 | 43 | 44 |
|---|---|---|---|---|---|---|---|---|
| FRRVWVKVVFK | 1443.8 | ... | ... | ... | 0.12 | 6 | 4.1558 | 0.56 |
| LRVWWVIKRI | 1359.7 | ... | ... | ... | 0.33 | 16.5 | 12.135 | 0.67 |
| RKRLKVWVIY | 1352.7 | ... | ... | ... | 0.18 | 9 | 6.6534 | 0.56 |
| ... | ... | ... | ... | ... | ... | ... | ... | ... |
| ... | ... | ... | ... | ... | ... | ... | ... | ... |
| RKVWIVVRWFL | 1393.7 | ... | ... | ... | 0.15 | 7.5 | 5.3812 | 0.67 |
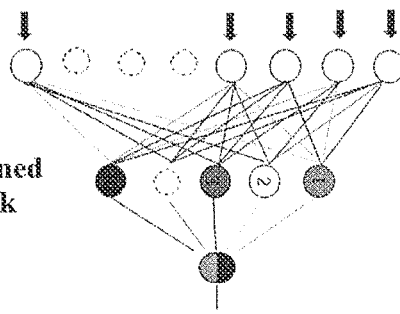
Pretrained Network
|   | Sequence | Active (Yes/No) |
|---|---|---|
| 1 | FRRWWKWKF | 1 |
| 2 | LRVWWVKRI | 0 |
| 3 | RKRLKVWVIY | 1 |
| ... | ... | ... |
| ... | ... | ... |
| N | RKVWIVRVVFL | 1 |
Predicted activity of peptide candidates
FIGURE 1C

FIGURE 2A

| 2B. Original Amino Acids | | 1 A | 2 D | 3 E | 4 F | 5 G | 6 H | 7 I | 8 K | 9 L | 10 M | 11 N | 12 P | 13 Q | 14 R | 15 S | 16 T | 17 V | 18 W | 19 Y |
|---|---|---|---|---|---|---|---|---|---|---|---|---|---|---|---|---|---|---|---|---|
| 1 | V | 253 | 254 | 255 | 256 | 257 | 258 | 259 | 260 | 261 | 262 | 263 | 264 | 265 | 266 | 267 | 268 | 972 | 269 | 270 |
| 2 | R | 271 | 272 | 273 | 274 | 275 | 276 | 277 | 278 | 279 | 280 | 281 | 282 | 283 | 972 | 284 | 285 | 286 | 287 | 288 |
| 3 | L | 289 | 290 | 291 | 292 | 293 | 294 | 295 | 296 | 972 | 297 | 298 | 299 | 300 | 301 | 302 | 303 | 304 | 305 | 306 |
| 4 | R | 307 | 308 | 309 | 310 | 311 | 312 | 313 | 314 | 315 | 316 | 317 | 318 | 319 | 972 | 320 | 321 | 322 | 323 | 324 |
| 5 | I | 325 | 326 | 327 | 328 | 329 | 330 | 972 | 331 | 332 | 333 | 334 | 335 | 336 | 337 | 338 | 339 | 340 | 341 | 342 |
| 6 | R | 343 | 344 | 345 | 346 | 347 | 348 | 349 | 350 | 351 | 352 | 353 | 354 | 355 | 972 | 356 | 357 | 358 | 359 | 360 |
| 7 | V | 361 | 362 | 363 | 364 | 365 | 366 | 367 | 368 | 369 | 370 | 371 | 372 | 373 | 374 | 375 | 376 | 972 | 377 | 378 |
| 8 | A | 972 | 379 | 380 | 381 | 382 | 383 | 384 | 385 | 386 | 387 | 388 | 389 | 390 | 391 | 392 | 393 | 394 | 395 | 396 |
| 9 | V | 397 | 398 | 399 | 400 | 401 | 402 | 403 | 404 | 405 | 406 | 407 | 408 | 409 | 410 | 411 | 412 | 972 | 413 | 414 |
| 10 | I | 415 | 416 | 417 | 418 | 419 | 420 | 972 | 421 | 422 | 423 | 424 | 425 | 426 | 427 | 428 | 429 | 430 | 431 | 432 |
| 11 | R | 433 | 434 | 435 | 436 | 437 | 438 | 439 | 440 | 441 | 442 | 443 | 444 | 445 | 972 | 446 | 447 | 448 | 449 | 450 |
| 12 | A | 972 | 451 | 452 | 453 | 454 | 455 | 456 | 457 | 458 | 459 | 460 | 461 | 462 | 463 | 464 | 465 | 466 | 467 | 468 |

| 3B. Original Amino Acids | | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| | | A | D | E | F | G | H | I | K | L | M | N | P | Q | R | S | T | V | W | Y |
| 1 | I | 19 | 32 | 45 | 58 | 71 | 84 | 971 | 109 | 121 | 133 | 146 | 159 | 169 | 182 | 193 | 206 | 219 | 232 | 240 |
| 2 | L | 20 | 33 | 46 | 59 | 72 | 85 | 97 | 110 | 971 | 134 | 147 | 160 | 170 | 183 | 194 | 207 | 220 | 233 | 241 |
| 3 | P | 21 | 34 | 47 | 60 | 73 | 86 | 98 | 111 | 122 | 135 | 148 | 971 | 171 | 184 | 195 | 208 | 221 | 234 | 242 |
| 4 | W | 22 | 35 | 48 | 61 | 74 | 87 | 99 | 112 | 123 | 136 | 149 | 161 | 172 | 185 | 196 | 209 | 222 | 971 | 243 |
| 5 | K | 23 | 36 | 49 | 62 | 75 | 88 | 100 | 971 | 124 | 137 | 150 | 162 | 173 | 186 | 197 | 210 | 223 | 235 | 244 |
| 6 | W | 24 | 37 | 50 | 63 | 76 | 89 | 101 | 113 | 125 | 138 | 151 | 163 | 174 | 187 | 198 | 211 | 224 | 971 | 245 |
| 7 | P | 25 | 38 | 51 | 64 | 77 | 90 | 102 | 114 | 126 | 139 | 152 | 971 | 175 | 188 | 199 | 212 | 225 | 236 | 246 |
| 8 | W | 26 | 39 | 52 | 65 | 78 | 91 | 103 | 115 | 127 | 140 | 153 | 164 | 176 | 189 | 200 | 213 | 226 | 971 | 247 |
| 9 | W | 27 | 40 | 53 | 66 | 79 | 92 | 104 | 116 | 128 | 141 | 154 | 165 | 177 | 190 | 201 | 214 | 227 | 971 | 248 |
| 10 | P | 28 | 41 | 54 | 67 | 80 | 93 | 105 | 117 | 129 | 142 | 155 | 971 | 178 | 191 | 202 | 215 | 228 | 237 | 249 |
| 11 | W | 29 | 42 | 55 | 68 | 81 | 94 | 106 | 118 | 130 | 143 | 156 | 166 | 179 | 192 | 203 | 216 | 229 | 971 | 250 |
| 12 | R | 30 | 43 | 56 | 69 | 82 | 95 | 107 | 119 | 131 | 144 | 157 | 167 | 180 | 971 | 204 | 217 | 230 | 238 | 251 |
| 13 | R | 31 | 44 | 57 | 70 | 83 | 96 | 108 | 120 | 132 | 145 | 158 | 168 | 181 | 971 | 205 | 218 | 231 | 239 | 252 |

SEQ ID NOS of peptides with given Substituted Amino Acids

FIGURE 3B $$Rs_{j \to G} = R_j^2 \sum_{i \neq j, i \in G}^{N-1} \frac{1}{r_{j-i}^2} \quad (1)$$

$$Rs_{G \to j} = \sum_{i \in G, i \neq j}^{n} \frac{R_i^2}{r_{i-j}^2} \quad (2)$$

$$\sigma_{j \to G}^* = \sum_{i \neq j, i \in G}^{n} \frac{(\chi_j^0 - \chi_i^0) R_i^2}{r_{j-i}^2} \quad (3)$$

$$\sigma_{G \to j}^* = \sum_{i \in G, i \neq j}^{n} \frac{(\chi_i^0 - \chi_j^0) R_i^2}{r_{i-j}^2} \quad (4)$$

$$\chi_{G \to j}^0 = \frac{\sum_{i \neq j, i \in G}^{n} \frac{\chi_i^0 (R_i^2 + R_j^2)}{r_{j-i}^2}}{\sum_{i \neq j, i \in G}^{n} \frac{R_i^2 + R_j^2}{r_{j-i}^2}} \quad$$

$$\Delta N_j = Q_j + \sum_{i \neq j}^{N-1} \frac{(\chi_j - \chi_i)(R_j^2 + R_i^2)}{r_{j-i}^2} \quad (5)$$

($Q_j$ - formal charge of atom $j$)

$$\eta_j = \frac{1}{2 \sum_{j \neq i}^{N-1} \frac{R_j^2 + R_i^2}{r_{j-i}^2}} \quad (7)$$

$$\eta_{MOL} = \frac{1}{s_{MOL}} = \frac{1}{2 \sum_{j \neq i}^{N-1} \frac{R_j^2 + R_i^2}{r_{j-i}^2}} \quad (8)$$

$$s_j = 2 \sum_{j \neq i}^{N-1} \frac{R_j^2 + R_i^2}{r_{j-i}^2} \quad (9)$$

$$s_{MOL} = \sum_{j \neq i}^{N-1} \sum_{j \neq i}^{N-1} \frac{R_j^2 + R_i^2}{r_{j-i}^2} \quad (10)$$

FIGURE 8

SMALL CATIONIC ANTIMICROBIAL PEPTIDES

CROSS REFERENCE TO RELATED APPLICATIONS

This application is a divisional of U.S. patent application Ser. No. 13/725,327, filed Dec. 21, 2012, which is a divisional of U.S. patent application Ser. No. 12/438,055, filed Jun. 7, 2011, now U.S. Pat. No. 8,343,475, which is the National Stage of International Application No. PCT/CA2007/001453, filed Aug. 21, 2007, and claims priority to U.S. Provisional Application No. 60/839,253, filed Aug. 21, 2006, the entire contents of each of which are incorporated by reference herein for all purposes.

REFERENCE TO A SEQUENCE LISTING

This application includes a Sequence Listing submitted electronically as a text file named 222_Sequence_Listing.txt, created on Apr. 10, 2013, with a size of 256 kb and comprising 1268 sequences. The sequence listing is hereby incorporated by reference in its entirety for all purposes.

FIELD

The present invention relates generally to peptides and more specifically to antimicrobial and immunomodulatory host defense peptides.

BACKGROUND

The treatment of bacterial infections with antibiotics is one of the mainstays of human medicine. Unfortunately the effectiveness of antibiotics has become limited due to an increase in bacterial antibiotic resistance in the face of a decreasing efforts and success in discovery of new classes of antibiotics. Today, infectious diseases are the second leading cause of death worldwide and the largest cause of premature deaths and loss of work productivity in industrialized countries. Nosocomial bacterial infections that are resistant to therapy result in annual costs of more than $2 billion and account for more than 80,000 direct and indirect deaths in North America alone, whereas a major complication of microbial diseases, namely sepsis, accounts for 700,000 cases and 140,000 deaths in North America.

A major limitation in antibiotic development has been difficulties in finding new structures with equivalent properties to the conventional antibiotics, namely low toxicity for the host and a broad spectrum of action against bacterial pathogens. Recent novel antibiotic classes, including the oxazolidinones (linezolid), the streptogramins (synercid) and the glycolipids (daptomycin) are all active only against Gram positive pathogens. Cationic antimicrobial peptides, found in most species of life, represent a good template for a new generation of antimicrobials. They kill both Gram negative and Gram positive microorganisms rapidly and directly, do not easily select mutants, work against common clinically-resistant bacteria such as methicillin-resistant *Staphylococcus aureus* (MRSA) and vancomycin resistant *Enterococcus* (VRE), show a synergistic effect with conventional antibiotics, and can often activate host innate immunity without displaying immunogenicity (Hancock R E W. 2001. Cationic peptides: effectors in innate immunity and novel antimicrobials. Lancet Infectious Diseases 1, 156-164). Moreover, they seem to counteract some of the more harmful aspects of inflammation (e.g. sepsis, endotoxaemia), which is extremely important since rapid killing of bacteria and subsequent liberation of bacterial components such as LPS or peptidoglycan can induce fatal immune dysregulation (Jarisch-Herxheimer reaction) (Gough M, Hancock R E W, Kelly N M. 1996. Anti-endotoxic potential of cationic peptide antimicrobials. Infect. Immun. 64, 4922-4927). A need exists in the art for developing new treatments for infections to be used as broad spectrum antibiotics and/or as agents that selectively enhance aspects of innate immunity while suppressing potentially harmful inflammation.

The innate immune system is a highly effective and evolved general defense system that involves a variety of effector functions including phagocytic cells, complement, and the like, but is generally incompletely understood. Elements of innate immunity are always present at low levels and are activated very rapidly when stimulated by pathogens, acting to prevent these pathogens from causing disease. Generally speaking many known innate immune responses are "triggered" by the binding of microbial signaling molecules, like lipopolysaccharide (LPS), with pattern recognition receptors such as Toll-like receptors (TLR) on the surface of host cells. Many of the effector functions of innate immunity are grouped together in the inflammatory response. However, too severe an inflammatory response can result in responses that are harmful to the body, and, in an extreme case, sepsis and potentially death can occur; indeed sepsis occurs in approximately 780,000 patients in North America annually with 140,000 deaths. Thus, a therapeutic intervention to boost innate immunity, which is based on stimulation of TLR signaling (for example using a TLR agonist), has the potential disadvantage that it could stimulate a potentially harmful inflammatory response and/or exacerbate the natural inflammatory response to infection. A further need exists in the art for therapeutic inverterventions to boost innate immunity that are effective and have fewer undesirable side effects or adverse reactions.

SUMMARY

The invention features antimicrobial and immunomodulatory polypeptides. In some preferred aspects, the polypeptides comprise 7 to 13 amino acids. Exemplary polypeptides comprise the amino acid sequences of SEQ ID NOS: 1-969 and 973-1264, and all analogs, homologs, derivatives, and conservative variations thereof. The invention also features addition variants of these polypeptides, which can comprise up to fifty additional amino acids on the amino or carboxy terminal ends of SEQ ID NOS:1-969 and 973-1264, and all analogs, homologs, derivatives, and conservative variations thereof. Where additional amino acids are present at the amino and carboxy terminal ends, the amino acids at the amino terminus can be the same as or different from the amino acids at the carboxy terminus. Polynucleotides encoding the inventive polypeptides are also provided Also featured are polypeptides having the sequence X1-RIRVAV (SEQ ID NO:1265)-X2, X1-WKWPWWPW (SEQ ID NO:1266)-X2, or X1-KIWVIRWWR (SEQ ID NO:1267)-X2, or functional variants or mimetics thereof, wherein X1 and X2 independently of one another are 0-5 additional amino acids. X1 and X2 can, but need not be, identical.

The invention further provides methods for inhibiting the growth of bacteria cells. The methods generally comprise contacting bacteria with an effective amount of at least one polypeptide having SEQ ID NOS: 1-969 and 973-1012, or analogs, derivatives, amidated variations or conservative variations thereof. Polypeptides having the sequence X1-RIRVAV (SEQ ID NO:1265)-X2, X1-WKWPWWPW (SEQ ID NO:1266)-X2, or X1-KIWVIRWWR (SEQ ID NO:1267)-X2, or functional variants or mimetics thereof can also be used in the inventive methods. The polypeptide can be preset as part of a composition. The bacteria can be a Gram negative bacterium, such as *Pseudomonas aeruginosa, Escherichia coli*, or *Salmonella enteritidis* ssp *Typhimurium*. The bacteria can be a Gram positive bacterium, such as *Staphylococcus aureus, Staphylococcus epidermidis*, or *Enterococcus faecaelis*. The methods can, in some aspects, further comprise contacting the bacteria with at least one antibiotic or lysozyme. The at least one antibiotic or lysozyme can be contacted to the bacteria before, after, or contemporaneously with the polypeptide or polypeptide composition.

Also featured in accordance with the present invention are methods for enhancing innate immunity. The methods generally comprise contacting a cell that expresses at least one polypeptide involved in innate immunity with an effective amount of a composition comprising at least one polypeptide having SEQ ID NOS: 1-969 and 973-1012, or analogs, derivatives, amidated variations or conservative variations thereof. Polypeptides having the sequence X1-RIRVAV (SEQ ID NO:1265)-X2, X1-WKWPWWPW (SEQ ID NO:1266)-X2, or X1-KIWVIRWWR (SEQ ID NO:1267)-X2, or functional variants or mimetics thereof can also be used in these inventive methods. Contacting the cell with the composition modulates, for example inhibits or enhances, the expression of the at least one polypeptide involved in innate immunity. The polypeptide involved in innate immunity can a chemokine or cytokine. The polypeptide involved in innate immunity can be encoded by the gene MCP-1, MCP-3, IL-8, or Gro-α.

The invention also features methods for suppressing a pro-inflammatory response. The methods generally comprise contacting a cell that expresses at least one pro-inflammatory cytokine, mediator or protein in response to a pro-inflammatory stimulus with an effective amount of a composition comprising at least one polypeptide having SEQ ID NOS: 1-969 and 973-1012, or analogs, derivatives, amidated variations or conservative variations thereof. Polypeptides having the sequence X1-RIRVAV (SEQ ID NO:1265)-X2, X1-WKWPWWPW (SEQ ID NO:1266)-X2, or X1-KIWVIRWWR (SEQ ID NO:1267)-X2, or functional variants or mimetics thereof can also be used in these inventive methods. Contacting the cell with the composition inhibits the expression of the at least one pro-inflammatory cytokine, mediator, or protein. In some aspects, the composition inhibits the inflammatory or septic response. In some aspects, the composition inhibits the expression of a pro-inflammatory gene or molecule in the cell. In highly preferred aspects, the composition inhibits the expression of TNF-α in the cell. The methods are applicable to suppress the pro-inflammatory response induced by any stimulus. In preferred aspects, the methods are utilized to suppress the inflammatory response induced by a microbe or a microbial ligand acting on a Toll-like receptor. For example, the microbial ligand can be a bacterial endotoxin or lipopolysaccharide.

BRIEF DESCRIPTION OF THE DRAWINGS

FIGS. 1A-1C show the general workflow of the QSAR modeling of antimicrobial peptides. FIG. 1A. Illustration of learning phase. The upper panel shows experimentally tested peptides IWWKWRRWV (SEQ ID NO: 1089), RRFZFKFIRWW (SEQ ID NO: 1112), AVWKFVKRV (SEQ ID NO: 1135), ... AIRRWRIRK (SEQ ID NO:1154). FIG. 1B. Illustration of learning function. FIG. 1C. Illustration of prediction phase. Virtual peptide candidates FRRWWKWFK (SEQ ID NO: 1065), LRWWWIKRI (SEQ ID NO: 1069), RKRLKWWIY (SEQ ID NO: 1078), ... RKWIWRWFL (SEQ ID NO: 1087) are shown.

FIG. 2A and 2B show the complete substitution analysis of the peptide VRLRIRVAVIRA (SEQ ID NO: 972). FIG. 2A. Activity. The first two columns give the position (indicated as the row number) and the one-letter code sequence of the original peptide indolicidin. The second and third rows give respectively the column number and the amino acids substituted at each amino acid position. Thus for example the peptide in the upper left hand corner (column 1, row 1) is ARLRIRVAVIRA (HH253) (SEQ ID NO: 253) and in the lower right corner (column 110, row 12) VRLRIRVAVIRY (H11468) (SEQ ID NO:468). The results presented within each box represent the relative $EC_{50}$ value, i.e. the concentration resulting in a 50% decrease in luminescence relative to the parent peptide which appears once in each row (e.g. row 1 column 17, row 2 column 14, etc), as determined by treatment of the lux reporter strain H1001 with peptide for four hours. Results are colour coded as black =superior activity to the parent peptide indolicidin; dark grey with white lettering =modestly stronger activity than the parent peptide; light grey with black lettering =similar activity to the parent peptide; white =very little activity. I* symbols for no activity, the $EC_{50}$ could not be determined since the curve showed no bottom. FIG. 2B. An index to FIG. 2A showing the sequence identification numbers of each substitution peptide.

FIGS. 3A and 3B show the complete substitution analysis of the bovine host defense peptide indolicidin ILLPWKWPWWPWRR (SEQ ID NO: 971). FIG. 3A. Activity The first two columns give the position (indicated as the row number) and the one-letter code sequence of the original peptide indolicidin. The second and third rows give respectively the column number and the amino acids substituted at each amino acid position. Thus for example the peptide in the upper left hand corner (column 1, row 1) is ALPWKWPWWPWRR (HH19) (SEQ ID NO: 19) and in the lower right corner (column 10, row 13) ILPWKWPWWPWRY (HH252) (SEQ ID NO: 252). The results presented within each box represent the relative $EC_{53}$ value, i.e. the concentration resulting in a 50% decrease in luminescence relative to the parent peptide which appears once in each row (e.g. row 1column 7, row 2 column 9, etc), as determined by treatment of the lux reporter strain H1001 with peptide for four hours. Results are colour coded as black =superior activity to the parent peptide indolicidin; dark grey with white lettering =modestly stronger activity than the parent peptide; light grey with black lettering =similar activity to the parent peptide; white =very little activity. I* symbols for no activity, the $EC_{50}$ could not be determined since the curve showed no bottom. FIG. 3B. An index to FIG. 1A showing the sequence identification numbers of each substitution peptide.

FIG. 8. Basis for customized SVL scripts for inductive parameters. Customized SVL scripts (a specialized language of the MOE) were calculated by using the following fundamental equations) for steric effect parameters $R_S$, parameters of inductive influence $\sigma^*$, inductive partial charge $\Delta N$, group 'inductive' electronegativity $\chi_G$ and inductive analogues of local ($\eta_i$ and $s_i$) and global chemical hardness and softness ($\eta_i$ and $s_i$). Here R is the covalent atomic radii, r—interatomic distance, $\chi$—atomic electronegativity. The variables indexed with j subscript describe the influence of a singe atom onto a group G of n atoms (typically the rest of N-atomic molecule) while G indices designate group (molecular) quantities. The linear character of equations (1)-(6) makes inductive descriptors readily computable and suitable for sizable databases and positions them as appropriate parameters for large-scale QSAR models.

DETAILED DESCRIPTION

A. Introduction

Figure 1A:
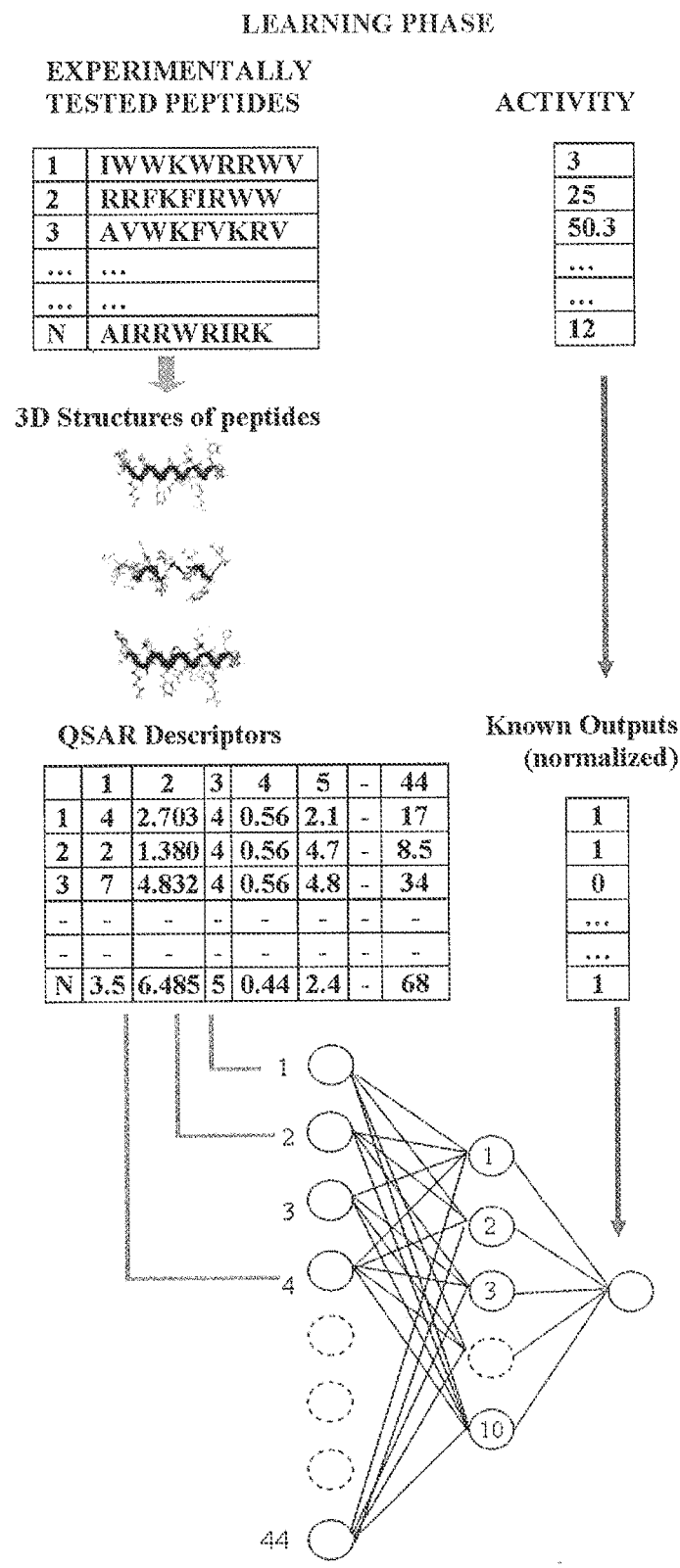

The present invention is based on the discovery that certain peptides originally identified from the small cationic antimicrobial and immunomodulatory peptides bactenecin and indolicidin have antimicrobial activity. Exemplary peptides of the invention include peptides having the amino acid sequences of SEQ ID NOS: 1-969, 973-1264, and analogs, derivatives, amidated variations and conservative variations thereof.

The invention further provides a bioinformatic method of predicting new peptides with good antimicrobial activity through the creation of a random library of peptides with biased amino acid composition based on the activity spectrum of the most active peptides investigated, and then applying a series of Quantitative Structure-Activity Relationship (QSAR) descriptors and utilizing Artificial Intelligence/Machine-learning approaches to predict further active peptides.

The invention also provides a method of inhibiting the growth of bacteria including contacting the bacteria with an inhibiting effective amount of at least one peptide of the invention alone, or in combination with at least one antibiotic. Classes of antibiotics that can be used in synergistic therapy with the peptides of the invention include, but are not limited to, aminoglycoside, penicillin, cephalosporin, fluoroquinolone, carbapenem, tetracycline and macrolide.

The invention further provides polynucleotides that encode the peptides of the invention. Exemplary polynucleotides encode peptides having the amino acid sequences of SEQ ID NOS: 1-969, 973-1264, and analogs, derivatives and conservative variations thereof.

The invention further provides a method of identifying an antimicrobial peptide having 8 to 12 amino acids that is derived from Bac2A and indolicidin. The method includes contacting a test peptide with a microbe under conditions sufficient for antimicrobial activity, and detecting a change in growth or proliferation of the microbe as compared to the growth or proliferation of the microbe prior to contacting with the test peptide. In one aspect, the peptide is synthesized in a multi-spot format on a solid support. The peptides of the invention will retain antimicrobial activity when cleaved from the solid support or retain activity when still associated with the solid support. The microbe can be a Gram negative bacterium, such as *Pseudomonas aeruginosa, Escherichia coli,* or *Salmonella enteritidis* ssp *Typhimurium*. In another aspect, the microbe can be a Gram positive bacterium, such as *Staphylococcus aureus, Staphylococcus epidermidis,* or *Enterococcus faecaelis*. In yet another aspect, the microbe can be a yeast, such as *Candida albicans*. The detection can include detecting luminescence in a microtiter plate luminescence reader over time. In this aspect, the microbe contains a reporter system, such as a bacterial luciferase construct inserted into the chromosome. For example, the bacterial luciferase construct is inserted into the fliC gene in *Pseudomonas aeruginosa*.

The invention further provides a method of protecting medical devices from colonization with pathogenic bacteria by coating at least one peptide of the invention on the surface of the medical device.

Cationic host defense peptides (also known as antimicrobial peptides) are crucial molecules in host defense against pathogenic microbe challenge. Their major effects include direct antimicrobial activity (Hancock, R. E. W., and R. Lehrer. 1998. Cationic peptides: a new source of antibiotics. Trends in Biotechnology 16: 82-88), and an ability to modulate innate immunity (Hancock, R. E. W. and G. Diamond. 2000. The role of cationic peptides in innate host defenses. Trends in Microbiology 8:402-410; Hancock, R. E. W. 2001. Cationic peptides: effectors in innate immunity and novel antimicrobials. Lancet Infectious Diseases 1:156-164).

The bovine neutrophil cationic peptides bactenecin (also called bovine dodecapeptide) and indolicidin are arguably the smallest naturally occurring antimicrobial peptides. Bactenecin (RLCRIVVIRVCR-NH2) (SEQ ID NO:1268) was discovered in bovine neutrophils by Romeo and coworkers in 1988 (Romeo D, Skerlavaj B, Bolognesi M, Gennaro R. 1988. Structure and bactericidal activity of an antibiotic dodecapeptide purified from bovine neutrophils. J Biol Chem 263, 9573-5). Bactenecin is stabilized by an internal disulfide bridge. A linear variant Bac2A (RLARIVVIRVAR-NH2) (SEQ ID NO:970) shows a similar activity against Gram negative bacteria and an improved activity against Gram positive bacteria (Wu M, Hancock R E W. 1999. Improved derivatives of bactenecin, a cyclic dodecameric antimicrobial cationic peptide. Antimicrob Agents Chemother 43, 1274-6). The C-terminally amidated cationic tridecapeptide indolicidin (ILPWKWPWWPWRR-NH2, (SEQ ID NO:971) MW=1906), was originally isolated from the large cytoplasmic granules of bovine neutrophils (Selsted, M. E., M. J. Novotny, W. L. Morris, Y. Q. Tang, W. Smith and J. S. Cullor. 1992. Indolicidin, a novel bactericidal tridecapeptide amide from neutrophils. J Biol Chem 267:4292-4295). Indolicidin is active against Gram positive and Gram negative bacteria, viruses, fungal pathogens, and protozoa (Ryge T S, Doisy X, Ifrah D, Olsen J E, and Hansen P R. New indolicidin analogues with potent antibacterial activity. J Peptide Research 64:171-85, 2004). Both Indolicidin and Bac2A, are known to have immunomodulatory activities (Bowdish D M, Davidson D J, Scott M G, Hancock R E W. Immunomodulatory activities of small host defense peptides. Antimicrobial Agents Chemotherapy 49:1727-32, 2005). Their common features, small size, linearity and multiple activities make these peptides ideal candidates for semi-random design methods such as spot peptide synthesis on cellulose membranes.

The field of chemoinformatics involves computer-aided identification of new lead structures and their optimization into drug candidates (Engel T. Basic Overview of Chemoinformatics. Journal of Chemical Information and Modelling, 46:2267-2277, 2006). One of the most broadly used chemoinformatics approaches is called Quantitative Structure-Activity Relationship (QSAR) modeling, which seeks to relate structural characteristics of a molecule (known as descriptors) to its measurable properties, such as biological activity.

The QSAR analysis found a broad application in antimicrobial discovery. In the series of pilot studies we have also utilized a variety of QSAR descriptors in combination with the approaches of the Artificial Intelligence to successfully predict antimicrobial activity of limited sets of organic molecules and cationic peptides (Cherkasov A. 'Inductive' descriptors. 10 successful years in QSAR. Current Computer-Aided Drug Design 1:21-42, 2005; Karakoc E, Sahinalp S C, and Cherkasov A. Comparative QSAR- and fragments distribution analysis of drugs, druglikes, metabolic substances, and antimicrobial compounds. Journal of Chemical Information and Modelling. 46, 2167-2182, 2006; Cherkasov A. Can 'bacterial-metabolite-likeness' model improve odds of 'in silico' antibiotic discovery? Journal of Chemical Information and Modelling, 46, 1214-1222, 2006). An overview of the process used is presented in FIG. 1.

The method of synthesizing an array of peptides in parallel on cellulose sheets was developed by Ronald Frank in 1992 (Frank, R. Spot synthesis: an easy technique for the positionally addressable, parallel chemical synthesis on a membrane support Tetrahedron. 1992 48, 9217-9232). This technique was first carried out manually and used for the identification of antibody epitopes. Now, with the help of pipetting robots, up to 8000 peptides can be synthesized on one cellulose sheet (20×30 cm) (Kramer A, Keitel T, Winkler K, Stocklein W, Hohne W, Schneider-Mergener J. 1997. Molecular basis for the binding promiscuity of an anti-p24 (HIV-1) monoclonal antibody. Cell 91, 799-809). Today, the applications of this technology include characterizing homodimer interfaces, screening for kinase recognition sites, optimizing protease inhibitors, and screening for DNA binding sites of proteins. We previously adapted this methodology to create a large number of variants through sequence scrambling, truncations and systematic modifications of peptide sequence, and used a luciferase-based screen to investigate their ability to kill *Pseudomonas aeruginosa* (Hilpert K, Volkmer-Engert R, Walter T, Hancock R E W. High-throughput generation of small antibacterial peptides with improved activity. Nature Biotech 23:1008-1012, 2005). This permitted us to screen hundreds of 12-mer peptides based on the sequence of the bovine analog Bac2A and determine optimal amino acid substitutions, and using combinations of amino acid substitutions to define peptides of both 8 and 12 amino acids in length that had excellent broad spectrum antimicrobial activity.

This method for broad screening represents a rapid and efficient method to investigate antimicrobial peptide activity. It permits a systematic and highly detailed investigation of the determinants of peptide activity in very small peptides. Previously, attempts to make smaller peptides tended to create molecules with modest activities or with good activities only when measured in dilute medium. In the studies described here we have used a combination of sequence scrambling and single amino acid substitutions to create a wide range of novel peptides. We have also examined a range of peptides for anti-endotoxic activity and ability to induce chemokines in human peripheral blood mononuclear cells (equivalent to protective immunomodulatory activity) and demonstrate that this procedure can be used to optimize 12-mer cationic peptides for these properties. This then indicates that the peptides have potential for modulating immunity.

The present invention adapts this methodology to create a large number of variants through sequence scrambling, truncations and systematic modifications of peptide sequence, and uses a luciferase-based screen to investigate their ability to kill Pseudomonas aeruginosa. This broad screening program represents a rapid and efficient method to investigate antimicrobial peptide activity. It has permitted for the first time a systematic and highly detailed investigation of the determinants of peptide activity in very small peptides. Previous attempts to make smaller peptides have tended to create molecules with modest activities or with good activities only when measured in dilute medium.

The peptides of the invention retain activities in the typical media used to test in vitro antibiotic activity, making them candidates for clinical therapeutic usage. In addition some of the peptides remain effective when bound to cellulose sheets, indicating that they have huge potential for use in coating medical devices, including catheters, to prevent them from becoming colonized with pathogenic bacteria.

The invention provides a number of methods, reagents, and compounds that can be used for inhibiting microbial infection or growth. It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a peptide" includes a combination of two or more peptides, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Antimicrobial" as used herein means that the peptides of the present invention inhibit, prevent, or destroy the growth or proliferation of microbes such as bacteria, fungi, viruses, parasites or the like. "Antiviral" as used herein means that the peptides of the present invention inhibit, prevent or destroy the growth or proliferation of viruses or of virally-infected cells. "Anti-tumor" as used herein means that the peptides of the present invention may be used to inhibit the growth of or destroy tumors. "Antifungal" as used herein means that the peptides of the present invention may be used to inhibit the growth of or destroy fungi. "Antiparasite" as used herein means that the peptides of the present invention inhibit, prevent, or destroy the growth or proliferation of any organism that lives at the expense of a host organism.

"Selective enhancement of innate immunity" as used herein means that the peptides of the invention are able to upregulate, in mammalian cells, genes and molecules that are natural components of the innate immune response and assist in the resolution of infections without excessive increases of pro-inflammatory cytokines like TNFα which can cause potentially harmful inflammation and thus stimulate a sepsis reaction in a subject. The peptides do not stimulate a septic reaction, but do stimulate expression of the one or more genes encoding chemokines or interleukins that attract immune cells including MCP-1, MCP-3, IL8, and CXCL-1. The peptide may also possess anti-sepsis activity including an ability to reduce the expression of TNFα in response to bacterial ligands like LPS.

The "amino acid" residues identified herein are in the natural L-configuration. In keeping with standard polypeptide nomenclature, J. Biol. Chem., 243:3557-59, (1969), abbreviations for amino acid residues are as shown in the following table.

| 1-Letter | 3-Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

B. Peptides

The invention provides an isolated peptide with antimicrobial and/or immunomodulatory activity. Exemplary peptides of the invention have an amino acid sequence including those listed in Table 1, and analogs, derivatives, amidated variations and conservative variations thereof, wherein the peptides have antimicrobial activity. The peptides of the invention include SEQ ID NOS:1-969 and 973-1264, as well as the broader groups of peptides having hydrophilic and hydrophobic substitutions, and conservative variations thereof.

"Isolated" when used in reference to a peptide, refers to a peptide substantially free of proteins, lipids, nucleic acids, for example, with which it might be naturally associated. Those of skill in the art can make similar substitutions to achieve peptides with greater antimicrobial activity and a broader host range. For example, the invention includes the peptides depicted in SEQ ID NOS:1-969 and 973-1264, as well as analogs or derivatives thereof, as long as the bioactivity (e.g., antimicrobial) of the peptide remains. Minor modifications of the primary amino acid sequence of the peptides of the invention may result in peptides that have substantially equivalent activity as compared to the specific peptides described herein. Such modifications may be deliberate, as by site-directed mutagenesis, or may be spontaneous. All of the peptides produced by these modifications are included herein as long as the biological activity of the original peptide still exists.

Further, deletion of one or more amino acids can also result in a modification of the structure of the resultant molecule without significantly altering its biological activity. This can lead to the development of a smaller active molecule that would also have utility. For example, amino or carboxy terminal amino acids that may not be required for biological activity of the particular peptide can be removed. Peptides of the invention include any analog, homolog, mutant, isomer or derivative of the peptides disclosed in the present invention, so long as the bioactivity as described herein remains. All peptides were synthesized using L amino acids, however, all D forms of the peptides can be synthetically produced. In addition, C-terminal derivatives can be produced, such as C-terminal methyl esters and C-terminal amidates, in order to increase the antimicrobial activity of a peptide of the invention. The peptide can be synthesized such that the sequence is reversed whereby the last amino acid in the sequence becomes the first amino acid, and the penultimate amino acid becomes the second amino acid, and so on. It is well known that such reversed peptides usually have similar antimicrobial activities to the original sequence.

In certain aspects, the peptides of the invention include peptide analogs and peptide mimetics. Indeed, the peptides of the invention include peptides having any of a variety of different modifications, including those described herein.

Peptide analogs of the invention are generally designed and produced by chemical modifications of a lead peptide, including, e.g., any of the particular peptides described herein, such as any of the following sequences disclosed in the tables. The present invention clearly establishes that these peptides in their entirety and derivatives created by modifying any side chains of the constituent amino acids have the ability to inhibit, prevent, or destroy the growth or proliferation of microbes such as bacteria, fungi, viruses, parasites or the like. The present invention further encompasses polypeptides up to about 50 amino acids in length that include the amino acid sequences and functional variants or peptide mimetics of the sequences described herein.

In another aspect, a peptide of the present invention is a pseudopeptide. Pseudopeptides or amide bond surrogates refers to peptides containing chemical modifications of some (or all) of the peptide bonds. The introduction of amide bond surrogates not only decreases peptide degradation but also may significantly modify some of the biochemical properties of the peptides, particularly the conformational flexibility and hydrophobicity.

To improve or alter the characteristics of polypeptides of the present invention, protein engineering can be employed. Recombinant DNA technology known to those skilled in the art can be used to create novel mutant proteins or muteins including single or multiple amino acid substitutions, deletions, additions, or fusion proteins. Such modified polypeptides can show, e.g., increased/decreased biological activity or increased/decreased stability. In addition, they can be purified in higher yields and show better solubility than the corresponding natural polypeptide, at least under certain purification and storage conditions. Further, the polypeptides of the present invention can be produced as multimers including dimers, trimers and tetramers. Multimerization can be facilitated by linkers, introduction of cysteines to permit creation of interchain disulphide bonds, or recombinantly though heterologous polypeptides such as Fc regions.

It is known in the art that one or more amino acids can be deleted from the N-terminus or C-terminus without substantial loss of biological function. See, e.g., Ron, et al., Biol Chem., 268: 2984-2988, 1993. Accordingly, the present invention provides polypeptides having one or more residues deleted from the amino terminus. Similarly, many examples of biologically functional C-terminal deletion mutants are known (see, e.g., Dobeli, et al., 1988). Accordingly, the present invention provides polypeptides having one or more residues deleted from the carboxy terminus. The invention also provides polypeptides having one or more amino acids deleted from both the amino and the carboxyl termini as described below.

Other mutants in addition to N- and C-terminal deletion forms of the protein discussed above are included in the present invention. Thus, the invention further includes variations of the polypeptides which show substantial chaperone polypeptide activity. Such mutants include deletions, insertions, inversions, repeats, and substitutions selected according to general rules known in the art so as to have little effect on activity.

There are two main approaches for studying the tolerance of an amino acid sequence to change, see, Bowie, et al., Science, 247: 1306-1310, 1994. The first method relies on the process of evolution, in which mutations are either accepted or rejected by natural selection. The second approach uses genetic engineering to introduce amino acid changes at specific positions of a cloned gene and selections or screens to identify sequences that maintain functionality. These studies have revealed that proteins are surprisingly tolerant of amino acid substitutions.

Typically seen as conservative substitutions are the replacements, one for another, among the aliphatic amino acids Ala, Val, Leu and Phe; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Thus, the polypeptide of the present invention can be, for example: (i) one in which one or more of the amino acid residues are substituted with a conserved or non-conserved amino acid residue (preferably a conserved amino acid residue) and such substituted amino acid residue can or cannot be one encoded by the genetic code; or (ii) one in which one or more of the amino acid residues includes a substituent group; or (iii) one in which the polypeptide is fused with another compound, such as a compound to increase the half-life of the polypeptide (for example, polyethylene glycol); or (iv) one in which the additional amino acids are fused to the above form of the polypeptide, such as an IgG Fc fusion region peptide or leader or secretory sequence or a sequence which is employed for purification of the above form of the polypeptide or a pro-protein sequence.

Thus, the polypeptides of the present invention can include one or more amino acid substitutions, deletions, or additions, either from natural mutations or human manipulation. As indicated, changes are preferably of a minor nature, such as conservative amino acid substitutions that do not significantly affect the folding or activity of the protein. The following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

Furthermore, polypeptides of the present invention can include one or more amino acid substitutions that mimic modified amino acids. An example of this type of substitution includes replacing amino acids that are capable of being phosphorylated (e.g., serine, threonine, or tyrosine) with a negatively charged amino acid that resembles the negative charge of the phosphorylated amino acid (e.g., aspartic acid or glutamic acid). Also included is substitution of amino acids that are capable of being modified by hydrophobic groups (e.g., arginine) with amino acids carrying bulky hydrophobic side chains, such as tryptophan or phenylalanine Therefore, a specific aspect of the invention includes polypeptides that include one or more amino acid substitutions that mimic modified amino acids at positions where amino acids that are capable of being modified are normally positioned. Further included are polypeptides where any subset of modifiable amino acids is substituted. For example, a polypeptide that includes three serine residues can be substituted at any one, any two, or all three of said serines. Furthermore, any polypeptide amino acid capable of being modified can be excluded from substitution with a modification-mimicking amino acid.

The present invention is further directed to fragments of the polypeptides of the present invention. More specifically, the present invention embodies purified, isolated, and recombinant polypeptides comprising at least any one integer between 6 and 504 (or the length of the polypeptides amino acid residues minus 1 if the length is less than 1000) of consecutive amino acid residues. Preferably, the fragments are at least 6, preferably at least 8 to 10, more preferably 12, 15, 20, 25, 30, 35, 40, 50 or more consecutive amino acids of a polypeptide of the present invention.

The present invention also provides for the exclusion of any species of polypeptide fragments of the present invention specified by 5' and 3' positions or sub-genuses of polypeptides specified by size in amino acids as described above. Any number of fragments specified by 5' and 3' positions or by size in amino acids, as described above, can be excluded.

In addition, it should be understood that in certain aspects, the peptides of the present invention include two or more modifications, including, but not limited to those described herein. By taking into the account the features of the peptide drugs on the market or under current development, it is clear that most of the peptides successfully stabilized against proteolysis consist of a mixture of several types of the above described modifications. This conclusion is understood in the light of the knowledge that many different enzymes are implicated in peptide degradation.

C. Peptides, Peptide Variants, and Peptide Mimetics

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but which functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings (See also, table entitled "Non-Natural Amino Acids" in Appendix below).

"Peptide" as used herein includes peptides that are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids that can be substituted for one another include asparagine, glutamine, serine and threonine. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as is used to refer to any peptide that possesses sufficient positively charged amino acids to have a pI (isoelectric point) greater than about 9.0.

The biological activity of the peptides can be determined by standard methods known to those of skill in the art, such as "minimal inhibitory concentration (MIC)" assay described in the present examples, whereby the lowest concentration at which no change in OD is observed for a given period of time is recorded as MIC.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, a mimetic composition is within the scope of the invention if, when administered to or expressed in a cell, e.g., a polypeptide fragment of an antimicrobial protein having antimicrobial activity.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC) Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

Mimetics of acidic amino acids can be generated by substitution by, e.g., non-carboxylate amino acids while maintaining a negative charge; (phosphono) alanine; sulfated threonine. Carboxyl side groups (e.g., aspartyl or glutamyl) can also be selectively modified by reaction with carbodiimides (R'—N—C—NR') such as, e.g., 1-cyclohexyl-3(2-morpholin-yl-(4-ethyl) carbodiimide or 1-ethyl-3 (4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, or citrulline. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Histidine residue mimetics can be generated by reacting histidyl with, e.g., diethylprocarbonate or para-bromophenacyl bromide. Other mimetics include, e.g., those generated by hydroxylation of lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but which can additionally be referred to as the R- or S-form The invention also provides polypeptides that are "substantially identical" to an exemplary polypeptide of the invention. A "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an antimicrobial polypeptide having antimicrobial activity of the invention, resulting in modification of the structure of the polypeptide, without significantly altering its biological activity. For example, amino- or carboxyl-terminal, or internal, amino acids that are not required for antimicrobial activity can be removed.

The skilled artisan will recognize that individual synthetic residues and polypeptides incorporating these mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi, Mol. Biotechnol. 9: 205-223, 1998; Hruby, Curr. Opin. Chem. Biol. 1: 114-119, 1997; Ostergaard, Mol. Divers. 3: 17-27, 1997; Ostresh, Methods Enzymol. 267: 220-234, 1996. Modified peptides of the invention can be further produced by chemical modification methods, see, e.g., Belousov, Nucleic Acids Res. 25: 3440-3444, 1997; Frenkel, Free Radic. Biol. Med. 19: 373-380, 1995; Blommers, Biochemistry 33: 7886-7896, 1994.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers, Nucleic Acids Res. Symp. Ser. 215-223, 1980; Horn, Nucleic Acids Res. Symp. Ser. 225-232, 1980; Banga, Therapeutic Peptides and Proteins, Formulation, Processing and Delivery Systems Technomic Publishing Co., Lancaster, Pa., 1995. For example, peptide synthesis can be performed using various solid-phase techniques (see e.g., Roberge, Science 269: 202, 1995; Merrifield, Methods Enzymol. 289: 3-13, 1997) and automated synthesis can be achieved, e.g., using the ABI 431A Peptide Synthesizer (Perkin Elmer) in accordance with the instructions provided by the manufacturer.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., Current Protocols in Immunology, Wiley Interscience, 1991, Unit 9). Peptides of the invention can also be synthesized by the well known solid phase peptide synthesis methods described in Merrifield, J. Am. Chem. Soc., 85:2149, (1962), and Stewart and Young, Solid Phase Peptides Synthesis, (Freeman, San Francisco, 1969, pp. 27-62), using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Analogs, polypeptide fragment of antimicrobial protein having antimicrobial activity, are generally designed and produced by chemical modifications of a lead peptide, including, e.g., any of the particular peptides described herein, such as any of the sequences including SEQ ID NOS:1-969 and 973-1264.

The terms "identical" or percent "identity", in the context of two or more nucleic acids or polypeptide sequences, refers to two or more sequences or subsequences that are the same or have a specified percentage of amino acid residues or nucleotides that are the same (i.e., about 60% identity, preferably 65%, 66%, 67%, 68%, 69%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2: 482, 1981, by the homology alignment algorithm of Needleman & Wunsch, J. Mol. Biol. 48: 443, 1970, by the search for similarity method of Pearson & Lipman, Proc. Nat'l. Acad. Sci. USA 85: 2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, Ausubel et al., eds. 1995 supplement).

Programs for searching for alignments are well known in the art, e.g., BLAST and the like. For example, if the target species is human, a source of such amino acid sequences or gene sequences (germline or rearranged antibody sequences) can be found in any suitable reference database such as Genbank, the NCBI protein databank (found on the web at the site: ncbi.nlm.nih.gov/BLAST/), VBASE, a database of human antibody genes (found on the web at the site: mrc-cpe.cam.ac.uk/imt-doc), and the Kabat database of immunoglobulins (found on the web at the site: immuno.b-me.nwu.edu) or translated products thereof. If the alignments are done based on the nucleotide sequences, then the selected genes should be analyzed to determine which genes of that subset have the closest amino acid homology to the originating species antibody. It is contemplated that amino acid sequences or gene sequences which approach a higher degree homology as compared to other sequences in the database can be utilized and manipulated in accordance with the procedures described herein. Moreover, amino acid sequences or genes which have lesser homology can be utilized when they encode products which, when manipulated and selected in accordance with the procedures described herein, exhibit specificity for the predetermined target antigen. In certain aspects, an acceptable range of homology is greater than about 50%. It should be understood that target species can be other than human.

A preferred example of algorithm that is suitable for determining percent sequence identity and sequence similarity are the BLAST and BLAST 2.0 algorithms, which are described in Altschul et al., Nuc. Acids Res. 25: 3389-3402, 1977 and Altschul et al., J. Mol. Biol. 215: 403-410, 1990, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (found on the web at the site: ncbi.nlm.nih.gov/). This algorithm involves first identifying high scoring sequence pairs (HSPs) by identifying short words of length (W) in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89: 10915, 1989) alignments (B) of 50, expectation (E) of 10, M=5, N=−4, and a comparison of both strands.

D. Polypeptides and Functional Variants Thereof

"Polypeptide" includes proteins, fusion proteins, oligopeptides and polypeptide derivatives, with the exception that peptidomimetics are considered to be small molecules herein.

A "protein" is a molecule having a sequence of amino acids that are linked to each other in a linear molecule by peptide bonds. The term protein refers to a polypeptide that is isolated from a natural source, or produced from an isolated cDNA using recombinant DNA technology; and has a sequence of amino acids having a length of at least about 200 amino acids.

A "fusion protein" is a type of recombinant protein that has an amino acid sequence that results from the linkage of the amino acid sequences of two or more normally separate polypeptides.

A "protein fragment" is a proteolytic fragment of a larger polypeptide, which may be a protein or a fusion protein. A proteolytic fragment may be prepared by in vivo or in vitro proteolytic cleavage of a larger polypeptide, and is generally too large to be prepared by chemical synthesis. Proteolytic fragments have amino acid sequences having a length from about 200 to about 1,000 amino acids.

An "oligopeptide" or "peptide" is a polypeptide having a short amino acid sequence (i.e., 2 to about 200 amino acids). An oligopeptide is generally prepared by chemical synthesis.

Although oligopeptides and protein fragments may be otherwise prepared, it is possible to use recombinant DNA technology and/or in vitro biochemical manipulations. For example, a nucleic acid encoding an amino acid sequence may be prepared and used as a template for in vitro transcription/translation reactions. In such reactions, an exogenous nucleic acid encoding a preselected polypeptide is introduced into a mixture that is essentially depleted of exogenous nucleic acids that contains all of the cellular components required for transcription and translation. One or more radiolabeled amino acids are added before or with the exogenous DNA, and transcription and translation are allowed to proceed. Because the only nucleic acid present in the reaction mix is the exogenous nucleic acid added to the reaction, only polypeptides encoded thereby are produced, and incorporate the radiolabeled amino acid(s). In this manner, polypeptides encoded by a preselected exogenous nucleic acid are radiolabeled. Although other proteins are present in the reaction mix, the preselected polypeptide is the only one that is produced in the presence of the radiolabeled amino acids and is thus uniquely labeled.

As is explained in detail below, "polypeptide derivatives" include without limitation mutant polypeptides, chemically modified polypeptides, and peptidomimetics.

The polypeptides of this invention, including the analogs and other modified variants, may generally be prepared following known techniques. Preferably, synthetic production of the polypeptide of the invention may be according to the solid phase synthetic method. For example, the solid phase synthesis is well understood and is a common method for preparation of polypeptides, as are a variety of modifications of that technique. Merrifield, J. Am. Chem. Soc., 85: 2149, 1964; Stewart and Young, Solid Phase polypeptide Synthesis, Pierce Chemical Company, Rockford, Ill., 1984; Bodanszky and Bodanszky, The Practice of polypeptide Synthesis, Springer-Verlag, New York, 1984; Atherton and Sheppard, Solid Phase polypeptide Synthesis: A Practical Approach, IRL Press, New York, 1989. See, also, the specific method described in Example 1 below.

Alternatively, polypeptides of this invention may be prepared in recombinant systems using polynucleotide sequences encoding the polypeptides.

A "variant" or "functional variant" of a polypeptide is a compound that is not, by definition, a polypeptide, i.e., it contains at least one chemical linkage that is not a peptide bond. Thus, polypeptide derivatives include without limitation proteins that naturally undergo post-translational modifications such as, e.g., glycosylation. It is understood that a polypeptide of the invention may contain more than one of the following modifications within the same polypeptide. Preferred polypeptide derivatives retain a desirable attribute, which may be biological activity; more preferably, a polypeptide derivative is enhanced with regard to one or more desirable attributes, or has one or more desirable attributes not found in the parent polypeptide. Although they are described in this section, peptidomimetics are taken as small molecules in the present disclosure.

A polypeptide having an amino acid sequence identical to that found in a protein prepared from a natural source is a "wildtype" polypeptide. Functional variants of polypeptides can be prepared by chemical synthesis, including without limitation combinatorial synthesis.

Functional variants of polypeptides larger than oligopeptides can be prepared using recombinant DNA technology by altering the nucleotide sequence of a nucleic acid encoding a polypeptide. Although some alterations in the nucleotide sequence will not alter the amino acid sequence of the polypeptide encoded thereby ("silent" mutations), many will result in a polypeptide having an altered amino acid sequence that is altered relative to the parent sequence. Such altered amino acid sequences may comprise substitutions, deletions and additions of amino acids, with the proviso that such amino acids are naturally occurring amino acids.

Thus, subjecting a nucleic acid that encodes a polypeptide to mutagenesis is one technique that can be used to prepare Functional variants of polypeptides, particularly ones having substitutions of amino acids but no deletions or insertions thereof. A variety of mutagenic techniques are known that can be used in vitro or in vivo including without limitation chemical mutagenesis and PCR-mediated mutagenesis. Such mutagenesis may be randomly targeted (i.e., mutations may occur anywhere within the nucleic acid) or directed to a section of the nucleic acid that encodes a stretch of amino acids of particular interest. Using such techniques, it is possible to prepare randomized, combinatorial or focused compound libraries, pools and mixtures.

Polypeptides having deletions or insertions of naturally occurring amino acids may be synthetic oligopeptides that result from the chemical synthesis of amino acid sequences that are based on the amino acid sequence of a parent polypeptide but which have one or more amino acids inserted or deleted relative to the sequence of the parent polypeptide. Insertions and deletions of amino acid residues in polypeptides having longer amino acid sequences may be prepared by directed mutagenesis.

As contemplated by this invention, "polypeptide" includes those having one or more chemical modification relative to another polypeptide, i.e., chemically modified polypeptides. The polypeptide from which a chemically modified polypeptide is derived may be a wildtype protein, a functional variant protein or a functional variant polypeptide, or polypeptide fragments thereof; an antibody or other polypeptide ligand according to the invention including without limitation single-chain antibodies, crystalline proteins and polypeptide derivatives thereof; or polypeptide ligands prepared according to the disclosure. Preferably, the chemical modification(s) confer(s) or improve(s) desirable attributes of the polypeptide but does not substantially alter or compromise the biological activity thereof. Desirable attributes include but are limited to increased shelf-life; enhanced serum or other in vivo stability; resistance to proteases; and the like. Such modifications include by way of non-limiting example N-terminal acetylation, glycosylation, and biotinylation.

An effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., Pharma. Res. 10: 1268-1273, 1993). Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group.

The presence of an N-terminal D-amino acid increases the serum stability of a polypeptide that otherwise contains L-amino acids, because exopeptidases acting on the N-terminal residue cannot utilize a D-amino acid as a substrate. Similarly, the presence of a C-terminal D-amino acid also stabilizes a polypeptide, because serum exopeptidases acting on the C-terminal residue cannot utilize a D-amino acid as a substrate. With the exception of these terminal modifications, the amino acid sequences of polypeptides with N-terminal and/or C-terminal D-amino acids are usually identical to the sequences of the parent L-amino acid polypeptide.

Substitution of unnatural amino acids for natural amino acids in a subsequence of a polypeptide can confer or enhance desirable attributes including biological activity. Such a substitution can, for example, confer resistance to proteolysis by exopeptidases acting on the N-terminus. The synthesis of polypeptides with unnatural amino acids is routine and known in the art (see, for example, Coller, et al. 1993, cited above).

Different host cells will contain different post-translational modification mechanisms that may provide particular types of post-translational modification of a fusion protein if the amino acid sequences required for such modifications is present in the fusion protein. A large number (about 100) of post-translational modifications have been described, a few of which are discussed herein. One skilled in the art will be able to choose appropriate host cells, and design chimeric genes that encode protein members comprising the amino acid sequence needed for a particular type of modification.

Glycosylation is one type of post-translational chemical modification that occurs in many eukaryotic systems, and may influence the activity, stability, pharmacogenetics, immunogenicity and/or antigenicity of proteins. However, specific amino acids must be present at such sites to recruit the appropriate glycosylation machinery, and not all host cells have the appropriate molecular machinery. *Saccharomyces cerevisieae* and *Pichia pastoris* provide for the production of glycosylated proteins, as do expression systems that utilize insect cells, although the pattern of glycosylation may vary depending on which host cells are used to produce the fusion protein.

Another type of post-translation modification is the phosphorylation of a free hydroxyl group of the side chain of one or more Ser, Thr or Tyr residues, Protein kinases catalyze such reactions. Phosphorylation is often reversible due to the action of a protein phosphatase, an enzyme that catalyzes the dephosphorylation of amino acid residues.

Differences in the chemical structure of amino terminal residues result from different host cells, each of which may have a different chemical version of the methionine residue encoded by a start codon, and these will result in amino termini with different chemical modifications.

For example, many or most bacterial proteins are synthesized with an amino terminal amino acid that is a modified form of methionine, i.e., N-formyl-methionine (fMet). Although the statement is often made that all bacterial proteins are synthesized with an fMet initiator amino acid; although this may be true for *E. coli*, recent studies have shown that it is not true in the case of other bacteria such as *Pseudomonas aeruginosa* (Newton et al., J. Biol. Chem. 274: 22143-22146, 1999). In any event, in *E. coli*, the formyl group of fMet is usually enzymatically removed after translation to yield an amino terminal methionine residue, although the entire fMet residue is sometimes removed (see Hershey, Chapter 40, "Protein Synthesis" in: *Escherichia coli* and *Salmonella typhimurium*: Cellular and Molecular Biology, Neidhardt, Frederick C., Editor in Chief, American Society for Microbiology, Washington, D.C., 1987, Volume 1, pages 613-647, and references cited therein). *E. coli* mutants that lack the enzymes (such as, e.g., formylase) that catalyze such post-translational modifications will produce proteins having an amino terminal fMet residue (Guillon et al., J. Bacteriol. 174: 4294-4301, 1992).

In eukaryotes, acetylation of the initiator methionine residue, or the penultimate residue if the initiator methionine has been removed, typically occurs co- or post-translationally. The acetylation reactions are catalyzed by N-terminal acetyltransferases (NATs, a.k.a. N-alpha-acetyltransferases), whereas removal of the initiator methionine residue is catalyzed by methionine aminopeptidases (for reviews, see Bradshaw et al., Trends Biochem. Sci. 23: 263-267, 1998; and Driessen et al., CRC Crit. Rev. Biochem. 18: 281-325, 1985). Amino terminally acetylated proteins are said to be "N-acetylated," "N alpha acetylated" or simply "acetylated."

Another post-translational process that occurs in eukaryotes is the alpha-amidation of the carboxy terminus. For reviews, see Eipper et al. Annu Rev. Physiol. 50: 333-344, 1988, and Bradbury et al. Lung Cancer 14: 239-251, 1996. About 50% of known endocrine and neuroendocrine peptide hormones are alpha-amidated (Treston et al., Cell Growth Differ. 4: 911-920, 1993). In most cases, carboxy alpha-amidation is required to activate these peptide hormones.

E. Polypeptide Mimetic

In general, a polypeptide mimetic ("peptidomimetic") is a molecule that mimics the biological activity of a polypeptide but is no longer peptidic in chemical nature. By strict definition, a peptidomimetic is a molecule that contains no peptide bonds (that is, amide bonds between amino acids). However, the term peptidomimetic is sometimes used to describe molecules that are no longer completely peptidic in nature, such as pseudo-peptides, semi-peptides and peptoids. Examples of some peptidomimetics by the broader definition (where part of a polypeptide is replaced by a structure lacking peptide bonds) are described below. Whether completely or partially non-peptide, peptidomimetics according to this invention provide a spatial arrangement of reactive chemical moieties that closely resembles the three-dimensional arrangement of active groups in the polypeptide on which the peptidomimetic is based. As a result of this similar active-site geometry, the peptidomimetic has effects on biological systems that are similar to the biological activity of the polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that are not experienced with peptidomimetics.

Candidate, lead and other polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean, BioEssays, 16: 683-687, 1994; Cohen and Shatzmiller, J. Mol. Graph., 11: 166-173, 1993; Wiley and Rich, Med. Res. Rev., 13: 327-384, 1993; Moore, Trends Pharmacol. Sci., 15: 124-129, 1994; Hruby, Biopolymers, 33: 1073-1082, 1993; Bugg et al., Sci. Am., 269: 92-98, 1993, all incorporated herein by reference).

Thus, through use of the methods described above, the present invention provides compounds exhibiting enhanced therapeutic activity in comparison to the polypeptides described above. The peptidomimetic compounds obtained by the above methods, having the biological activity of the above named polypeptides and similar three-dimensional structure, are encompassed by this invention. It will be readily apparent to one skilled in the art that a peptidomimetic can be generated from any of the modified polypeptides described in the previous section or from a polypeptide bearing more than one of the modifications described from the previous section. It will furthermore be apparent that the peptidomimetics of this invention can be further used for the development of even more potent non-peptidic compounds, in addition to their utility as therapeutic compounds.

Specific examples of peptidomimetics derived from the polypeptides described in the previous section are presented below. These examples are illustrative and not limiting in terms of the other or additional modifications.

Proteases act on peptide bonds. It therefore follows that substitution of peptide bonds by pseudopeptide bonds confers resistance to proteolysis. A number of pseudopeptide bonds have been described that in general do not affect polypeptide structure and biological activity. The reduced isostere pseudopeptide bond is a suitable pseudopeptide bond that is known to enhance stability to enzymatic cleavage with no or little loss of biological activity (Couder, et al., Int. J. Polypeptide Protein Res. 41: 181-184, 1993, incorporated herein by reference). Thus, the amino acid sequences of these compounds may be identical to the sequences of their parent L-amino acid polypeptides, except that one or more of the peptide bonds are replaced by an isosteric pseudopeptide bond. Preferably the most N-terminal peptide bond is substituted, since such a substitution would confer resistance to proteolysis by exopeptidases acting on the N-terminus.

To confer resistance to proteolysis, peptide bonds may also be substituted by retro-inverso pseudopeptide bonds (Dalpozzo, et al., Int. J. Polypeptide Protein Res. 41: 561-566, incorporated herein by reference). According to this modification, the amino acid sequences of the compounds may be identical to the sequences of their L-amino acid parent polypeptides, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

Peptoid derivatives of polypeptides represent another form of modified polypeptides that retain the important structural determinants for biological activity, yet eliminate the peptide bonds, thereby conferring resistance to proteolysis (Simon, et al., Proc. Natl. Acad. Sci. USA, 89: 9367-9371, 1992, and incorporated herein by reference). Peptoids are oligomers of N-substituted glycines. A number of N-alkyl groups have been described, each corresponding to the side chain of a natural amino acid.

F. Polynucleotides

The invention includes polynucleotides encoding peptides of the invention. Exemplary polynucleotides encode peptides including those listed in Table 1, and analogs, derivatives, amidated variations and conservative variations thereof, wherein the peptides have antimicrobial activity. The peptides of the invention include SEQ ID NOS:1-969 and 973-1264, as well as the broader groups of peptides having hydrophilic and hydrophobic substitutions, and conservative variations thereof.

"Isolated" when used in reference to a polynucleotide, refers to a polynucleotide substantially free of proteins, lipids, nucleic acids, for example, with which it is naturally associated. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code. Such polynucleotides are useful for the recombinant production of large quantities of a peptide of interest, such as the peptide of SEQ ID NOS:1-969 and 973-1264.

In the present invention, the polynucleotides encoding the peptides of the invention may be inserted into a recombinant "expression vector". The term "expression vector" refers to a plasmid, virus or other vehicle known in the art that has been manipulated by insertion or incorporation of genetic sequences. Such expression vectors of the invention are preferably plasmids that contain a promoter sequence that facilitates the efficient transcription of the inserted genetic sequence in the host. The expression vector typically contains an origin of replication, a promoter, as well as specific genes that allow phenotypic selection of the transformed cells. For example, the expression of the peptides of the invention can be placed under control of $E.$ $coli$ chromosomal DNA comprising a lactose or lac operon which mediates lactose utilization by elaborating the enzyme beta-galactosidase. The lac control system can be induced by IPTG. A plasmid can be constructed to contain the lac Iq repressor gene, permitting repression of the lac promoter until IPTG is added. Other promoter systems known in the art include beta-lactamase, lambda promoters, the protein A promoter, and the tryptophan promoter systems. While these are the most commonly used, other microbial promoters, both inducible and constitutive, can be utilized as well. The vector contains a replicon site and control sequences which are derived from species compatible with the host cell. In addition, the vector may carry specific gene(s) which are capable of providing phenotypic selection in transformed cells. For example, the beta-lactamase gene confers ampicillin resistance to those transformed cells containing the vector with the beta-lactamase gene. An exemplary expression system for production of the peptides of the invention is described in U.S. Pat. No. 5,707,855.

Transformation of a host cell with the polynucleotide may be carried out by conventional techniques known to those skilled in the art. For example, where the host is prokaryotic, such as $E.$ $coli$, competent cells that are capable of DNA uptake can be prepared from cells harvested after exponential growth and subsequently treated by the $CaCl_2$ method using procedures known in the art. Alternatively, $MgCl_2$ or RbCl could be used.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods known in the art. Additionally, cloned DNA can be introduced into host cells by protoplast fusion, using methods known in the art.

DNA sequences encoding the peptides can be expressed in vivo by DNA transfer into a suitable host cell. "Host cells" of the invention are those in which a vector can be propagated and its DNA expressed. The term also includes any progeny of the subject host cell. It is understood that not all progeny are identical to the parental cell, since there may be mutations that occur during replication. However, such progeny are included when the terms above are used. Preferred host cells of the invention include $E.$ $coli,$ $S.$ $aureus$ and $P.$ $aeruginosa$, although other Gram negative and Gram positive organisms known in the art can be utilized as long as the expression vectors contain an origin of replication to permit expression in the host.

The polynucleotide sequence encoding the peptide used according to the method of the invention can be isolated from an organism or synthesized in the laboratory. Specific DNA sequences encoding the peptide of interest can be obtained by: 1) isolation of a double-stranded DNA sequence from the genomic DNA; 2) chemical manufacture of a DNA sequence to provide the necessary codons for the peptide of interest; and 3) in vitro synthesis of a double-stranded DNA sequence by reverse transcription of mRNA isolated from a donor cell. In the latter case, a double-stranded DNA complement of mRNA is eventually formed that is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons that are more likely to be recognized by a bacterial host, thereby permitting high level expression without difficulties in translation. In addition, virtually any peptide can be synthesized, including those encoding natural peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries that are derived from reverse transcription of mRNA that is abundant in donor cells that have a high level of genetic expression. When used in combination with polymerase chain reaction technology, even rare expression products can be cloned. In those cases where significant portions of the amino acid sequence of the peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single stranded form (Jay et al., Nuc. Acid Res., 11:2325, 1983).

G. QSAR Descriptors and Machine Learning Methods

The invention further provides a bioinformatic method of predicting new peptides with good antimicrobial activity through the creation of a random library of peptides with biased amino acid composition based on the activity spectrum of the most active peptides investigated, and then applying a series of Quantitative Structure-Activity Relationship (QSAR) descriptors and utilizing Artificial Intelligence/Machine-learning approaches to predict further active peptides.

H. Methods of Use—Direct Antimicrobial

The invention also provides a method of inhibiting the growth of bacteria including contacting the bacteria with an inhibiting effective amount of a peptide of the invention, including SEQ ID NOS:1-969 and 973-1264, and analogs, derivatives, amidated variations and conservative variations thereof, wherein the peptides have antimicrobial activity.

The term "contacting" refers to exposing the bacteria to the peptide so that the peptide can effectively inhibit, kill, or lyse bacteria, bind endotoxin (LPS), or permeabilize Gram negative bacterial outer membranes. Contacting may be in vitro, for example by adding the peptide to a bacterial culture to test for susceptibility of the bacteria to the peptide. Contacting may be in vivo, for example administering the peptide to a subject with a bacterial disorder, such as septic shock or infection. Contacting may further involve coating an object (e.g., medical device) such as a catheter to inhibit bacteria with which it comes into contact, thus preventing it from becoming colonized with the bacteria. "Inhibiting" or "inhibiting effective amount" refers to the amount of peptide that is required to cause a bacteriostatic or bactericidal effect. Examples of bacteria that may be inhibited include *Escherichia coli, Pseudomonas aeruginosa, Enterobacter cloacae, Salmonella enteritidis* subspecies *Typhimurium, Staphylococcus aureus, Enterococcus facaelis, Listeria monocytogenes, Corynebacterium xerosis, Streptococcus pyogenes, Streptococcus pneumoniae, Streptococcus mitis* and *Staphylococcus epidermidis.*

The method of inhibiting the growth of bacteria may further include the addition of antibiotics for combination or synergistic therapy. The appropriate antibiotic administered will typically depend on the susceptibility of the bacteria such as whether the bacteria is Gram negative or Gram positive, and will be easily discernable by one of skill in the art. Examples of particular classes of antibiotics useful for synergistic therapy with the peptides of the invention include aminoglycosides (e.g., tobramycin), penicillins (e.g., piperacillin), cephalosporins (e.g., ceftazidime), fluoroquinolones (e.g., ciprofloxacin), carbapenems (e.g., imipenem), tetracyclines and macrolides (e.g., erythromycin and clarithromycin). The method of inhibiting the growth of bacteria may further include the addition of antibiotics for combination or synergistic therapy. The appropriate antibiotic administered will typically depend on the susceptibility of the bacteria such as whether the bacteria is Gram negative or Gram positive, and will be easily discernable by one of skill in the art. Further to the antibiotics listed above, typical antibiotics include aminoglycosides (amikacin, gentamicin, kanamycin, netilmicin, t-obramycin, streptomycin), macrolides (azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin) or carbapenems (e.g., imipenem, meropenem, panipenem), or monobactams (e.g., aztreonam). Other classes of antibiotics include quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin, linezolid, synercid, polymyxin B, colisitin, colimycin, methotrexate, daptomycin, phosphonomycin and mupirocin.

The peptides and/or analogs or derivatives thereof may be administered to any host, including a human or non-human animal, in an amount effective to inhibit not only growth of a bacterium, but also a virus, parasite or fungus. These peptides are useful as antimicrobial agents, antiviral agents, and antifungal agents. The peptides and/or analogs or derivatives thereof may be administered to any host, including a human or non-human animal, in an amount effective to inhibit not only growth of a bacterium, but also a virus or fungus. These peptides are useful as antimicrobial agents, antiviral agents, and antifungal agents.

In addition to being active against a broad range of pathogens, bactenecin has been shown to be cytotoxic to rat embryonic neurons, fetal rat astrocytes and human glioblastoma cells (Radermacher et al., J. Neuro. Res. 36:657, 1993). Thus, it is envisioned that the peptides of the present invention can be used to inhibit the growth of a eukaryotic cell by contacting the eukaryotic cell with an inhibiting effective amount of a peptide of the invention. Such a method would be useful, for example, for inhibiting a cell proliferation-associated disorder in a subject having or at risk of having such a disorder. The method can involve, for example, administering to the subject a therapeutically effective amount of a peptide of the present invention to inhibit the over-growth of cells in a subject in need of such treatment. Such disorders would include, for example, neurological related disorders.

The invention further provides a method of protecting objects from bacterial colonization. The peptides of the invention remain active when conjugated to solid surfaces. Thus, the peptides may be used for protecting objects such as medical devices from colonization with pathogenic bacteria by chemically conjugating, or coating by any other means, at least one peptide of the invention to the surface of the medical device. Such medical devices include indwelling catheters, and the like.

I. Methods of Use—Immunomodulatory

The present invention provides novel cationic peptides, characterized by a group of generic formulas which have ability to modulate (e.g., up- and/or down regulate) polypeptide expression, thereby regulating sepsis and inflammatory responses and/or innate immunity.

"Innate immunity" as used herein refers to the natural ability of an organism to defend itself against invasions by pathogens. Pathogens or microbes as used herein, may include, but are not limited to bacteria, fungi, parasite, and viruses. Innate immunity is contrasted with acquired/adaptive immunity in which the organism develops a defensive mechanism based substantially on antibodies and/or immune lymphocytes that is characterized by specificity, amplifiability and self vs. non-self discrimination. With innate immunity, broad, nonspecific immunity is provided and there is no immunologic memory of prior exposure. The hallmarks of innate immunity are effectiveness against a broad variety of potential pathogens, independence of prior exposure to a pathogen, and immediate effectiveness (in contrast to the specific immune response which takes days to weeks to be elicited). In addition, innate immunity includes immune responses that affect other diseases, such as cancer, inflammatory diseases, multiple sclerosis, various viral infections, and the like.

In innate immunity, the immune response is not dependent upon antigens. The innate immunity process may include the production of secretory molecules and cellular components as set forth above. In innate immunity, the pathogens are recognized by receptors (for example, Toll-like receptors) that have broad specificity, are capable of recognizing many pathogens, and are encoded in the germline. These Toll-like receptors have broad specificity and are capable of recognizing many pathogens. When cationic peptides are present in the immune response, they aid in the host response to pathogens. This change in the immune response induces the release of chemokines, which promote the recruitment of immune cells to the site of infection.

Chemokines, or chemoattractant cytokines, are a subgroup of immune factors that mediate chemotactic and other pro-inflammatory phenomena (See, Schall, 1991, Cytokine 3:165-183). Chemokines are small molecules of approximately 70-80 residues in length and can generally be divided into two subgroups, α which have two N-terminal cysteines separated by a single amino acid (CxC) and β which have two adjacent cysteines at the N terminus (CC). RANTES, MIP-1α and MIP-1β are members of the β subgroup (reviewed by Horuk, R., 1994, Trends Pharmacol. Sci, 15:159-165; Murphy, P. M., 1994, Annu Rev. Immunol., 12:593-633). The amino terminus of the β chemokines RANTES, MCP-1, and MCP-3 have been implicated in the mediation of cell migration and inflammation induced by these chemokines. This involvement is suggested by the observation that the deletion of the amino terminal 8 residues of MCP-1, amino terminal 9 residues of MCP-3, and amino terminal 8 residues of RANTES and the addition of a methionine to the amino terminus of RANTES, antagonize the chemotaxis, calcium mobilization and/or enzyme release stimulated by their native counterparts (Gong et al., 1996 J. Biol. Chem. 271:10521-10527; Proudfoot et al., 1996 J. Biol. Chem. 271:2599-2603). Additionally, α chemokine-like chemotactic activity has been introduced into MCP-1 via a double mutation of Tyr 28 and Arg 30 to leucine and valine, respectively, indicating that internal regions of this protein also play a role in regulating chemotactic activity (Beall et al., 1992, J. Biol. Chem. 267:3455-3459).

The monomeric forms of all chemokines characterized thus far share significant structural homology, although the quaternary structures of α and β groups are distinct. While the monomeric structures of the β and α chemokines are very similar, the dimeric structures of the two groups are completely different. An additional chemokine, lymphotactin, which has only one N-terminal cysteine has also been identified and may represent an additional subgroup (γ) of chemokines (Yoshida et al., 1995, FEBS Lett. 360:155-159; and Kelner et al., 1994, Science 266:1395-1399).

Receptors for chemokines belong to the large family of G-protein coupled, 7 transmembrane domain receptors (GCR's) (See, reviews by Horuk, R., 1994, Trends Pharmacol. Sci. 15:159-165; and Murphy, P. M., 1994, Annu Rev. Immunol. 12:593-633). Competition binding and cross-desensitization studies have shown that chemokine receptors exhibit considerable promiscuity in ligand binding. Examples demonstrating the promiscuity among β chemokine receptors include: CC CKR-1, which binds RANTES and MIP-1α (Neote et al., 1993, Cell 72: 415-425), CC CKR-4, which binds RANTES, MIP-1α, and MCP-1 (Power et al., 1995, J. Biol. Chem. 270:19495-19500), and CC CKR-5, which binds RANTES, MIP-1α, and MIP-1β (Alkhatib et al., 1996, Science 272:1955-1958 and Dragic et al., 1996, Nature 381:667-674). Erythrocytes possess a receptor (known as the Duffy antigen) which binds both α and β chemokines (Horuk et al., 1994, J. Biol. Chem. 269:17730-17733; Neote et al., 1994, Blood 84:44-52; and Neote et al., 1993, J. Biol. Chem. 268:12247-12249). Thus the sequence and structural homologies evident among chemokines and their receptors allows some overlap in receptor-ligand interactions.

In one aspect, the present invention provides the use of compounds including peptides of the invention to reduce sepsis and inflammatory responses by acting directly on host cells. In this aspect, a method of identification of a polynucleotide or polynucleotides that are regulated by one or more sepsis or inflammatory inducing agents is provided, where the regulation is altered by a cationic peptide. Such sepsis or inflammatory inducing agents include, but are not limited to endotoxic lipopolysaccharide (LPS), lipoteichoic acid (LTA) and/or CpG DNA or intact bacteria or other bacterial components. The identification is performed by contacting the host cell with the sepsis or inflammatory inducing agents and further contacting with a cationic peptide either simultaneously or immediately after. The expression of the polynucleotide or polypeptide in the presence and absence of the cationic peptide is observed and a change in expression is indicative of a polynucleotide or polypeptide or pattern of polynucleotides or polypeptides that is regulated by a sepsis or inflammatory inducing agent and inhibited by a cationic peptide. In another aspect, the invention provides a polynucleotide identified by the method.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, and the like to produce structural analogs. Candidate agents are also found among biomolecules including, but not limited to: peptides, peptidiomimetics, saccharides, fatty acids, steroids, purines, pyrimidines, polypeptides, polynucleotides, chemical compounds, derivatives, 2structural analogs or combinations thereof.

Generally, in the methods of the invention, a cationic peptide is utilized to detect and locate a polynucleotide or polypeptide that is essential in the process of sepsis or inflammation. Once identified, a pattern of polynucleotide or polypeptide expression may be obtained by observing the expression in the presence and absence of the cationic peptide. The pattern obtained in the presence of the cationic peptide is then useful in identifying additional compounds that can inhibit expression of the polynucleotide and therefore block sepsis or inflammation. It is well known to one of skill in the art that non-peptidic chemicals and peptidomimetics can mimic the ability of peptides to bind to receptors and enzyme binding sites and thus can be used to block or stimulate biological reactions. Where an additional compound of interest provides a pattern of polynucleotide or polypeptide expression similar to that of the expression in the presence of a cationic peptide, that compound is also useful in the modulation of sepsis or an innate immune response. In this manner, the cationic peptides of the invention, which are known inhibitors of sepsis and inflammation and enhancers of innate immunity are useful as tools in the identification of additional compounds that inhibit sepsis and inflammation and enhance innate immunity.

As can be seen in the Examples below, peptides of the invention have an ability to reduce the expression of polynucleotides or polypeptides regulated by LPS, particularly the quintessential pro-inflammatory cytokine TNFα. High levels of endotoxin in the blood are responsible for many of the symptoms seen during a serious infection or inflammation such as fever and an elevated white blood cell count, and many of these effects reflect or are caused by high levels of induced TNFα. Endotoxin (also called lipopolysaccharide) is a component of the cell wall of Gram negative bacteria and is a potent trigger of the pathophysiology of sepsis. The basic mechanisms of inflammation and sepsis are related.

In another aspect, the invention identifies agents that enhances innate immunity. Human cells that contain a polynucleotide or polynucleotides that encode a polypeptide or polypeptides involved in innate immunity are contacted with an agent of interest. Expression of the polynucleotide is determined, both in the presence and absence of the agent. The expression is compared and of the specific modulation of expression was indicative of an enhancement of innate immunity. In another aspect, the agent does not stimulate a septic reaction as revealed by the lack of upregulation of the pro-inflammatory cytokine TNF-α. In still another aspect the agent reduces or blocks the inflammatory or septic response.

In another aspect, the invention provides methods of direct polynucleotide or polypeptide regulation by cationic peptides and the use of compounds including cationic peptides to stimulate elements of innate immunity. In this aspect, the invention provides a method of identification of a pattern of polynucleotide or polypeptide expression for identification of a compound that enhances innate immunity. In the method of the invention, an initial detection of a pattern of polypeptide expression for cells contacted in the presence and absence of a cationic peptide is made. The pattern resulting from polypeptide expression in the presence of the peptide represents stimulation of innate immunity. A pattern of polypeptide expression is then detected in the presence of a test compound, where a resulting pattern with the test compound that is similar to the pattern observed in the presence of the cationic peptide is indicative of a compound that enhances innate immunity. In another aspect, the invention provides compounds that are identified in the above methods. In another aspect, the compound of the invention stimulates chemokine expression. Chemokine or chemokine receptors may include, but are not limited to IL8, Gro-α, MCP-1, and MCP-3. In still another aspect, the compound is a peptide, peptidomimetic, chemical compound, or a nucleic acid molecule.

Figure 2A:
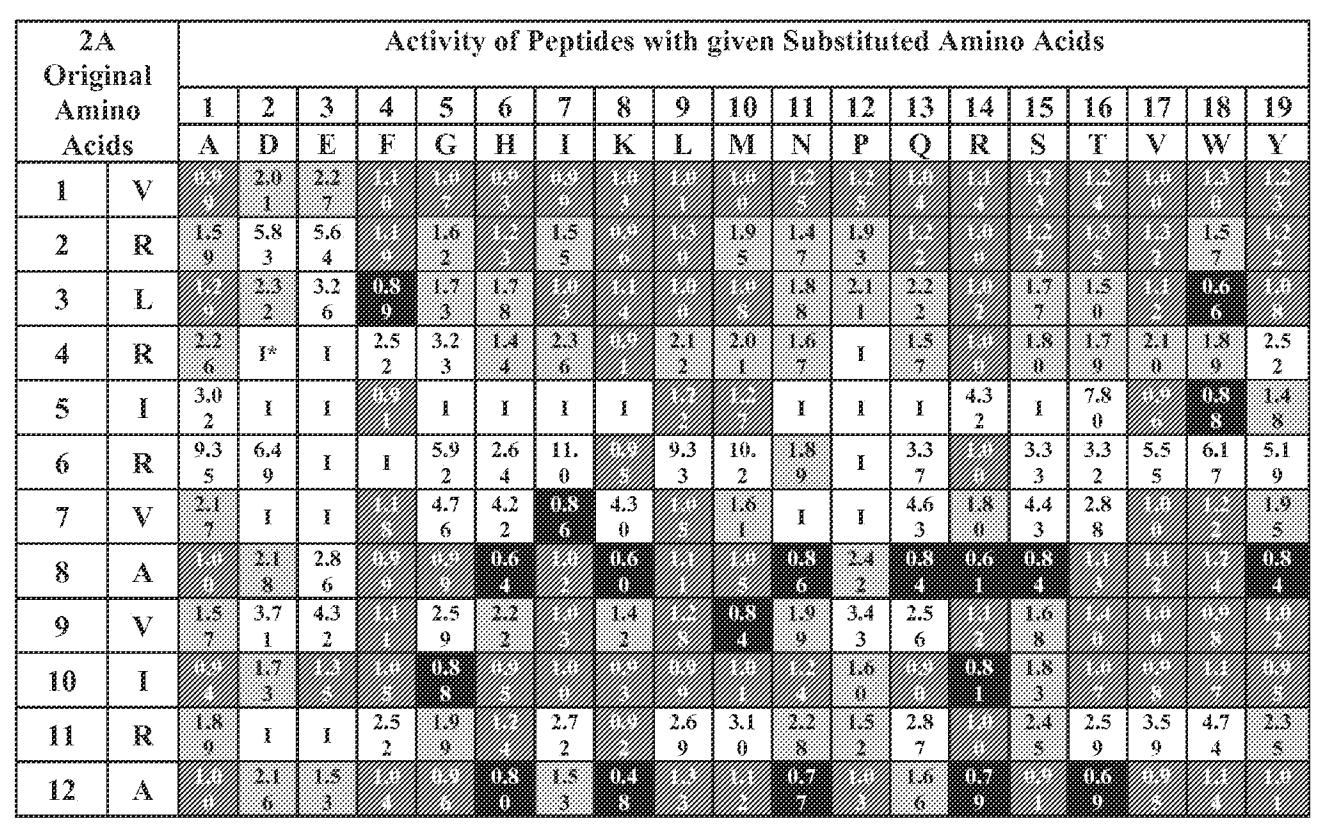

It is shown below, for example, in FIG. 2, that cationic peptides can neutralize the host response to the signaling molecules of infectious agents as well as modify the transcriptional responses of host cells, mainly by down-regulating the pro-inflammatory response and/or up-regulating the anti-inflammatory response. Example 5 shows that the cationic peptides can selectively suppress the induction of the sepsis inducing cytokine TNFα in host cells. Example 6 shows that the cationic peptides can aid in the host response to pathogens by inducing the release of chemokines, which promote the recruitment of immune cells to the site of infection.

It is seen from the examples below that cationic peptides have a substantial influence on the host response to pathogens in that they assist in regulation of the host immune response by inducing selective pro-inflammatory responses that for example promote the recruitment of immune cells to the site of infection but not inducing potentially harmful pro-inflammatory cytokines Sepsis appears to be caused in part by an overwhelming pro-inflammatory response to infectious agents. Peptides can aid the host in a "balanced" response to pathogens by inducing an anti-inflammatory response and suppressing certain potentially harmful pro-inflammatory responses.

The present invention features methods for enhancing a vaccine-induced adaptive immune response in a subject comprising administering to the subject an adjuvant composition comprising a pharmaceutically acceptable carrier and an immunomodulatory peptides of the invention in an amount effective to enhance the vaccine-induced adaptive immune response in the subject. In some aspects, the methods comprise administering to a subject an effective amount of an adjuvant composition comprising a pharmaceutically effective carrier and a polypeptide having the amino acid sequence SEQ ID NO: 2, 7, 12, 15, 1213, 1214, 1215, 1216, 1221, 1222, 1223, 1224, 1229, 1230, 1231, 1232, 1237, 1238, 1239, 1240, 1245, 1246, 1248, or analogs, derivatives, amidated variations and conservative variations thereof. In other aspects, the methods comprise administering to a subject an effective amount of an adjuvant composition comprising a pharmaceutically effective carrier and a polypeptide having the amino acid sequence SEQ ID NO: 1020, 1021, 1022, 1032, 1065, 1069, 1078, 1081, 1087, 1089, 1135, 1145, 1160, 1217, 1218, 1219, 1220, 1225, 1227, 1228, 1233, 1234, 1241, 1242, 1243, 1244, 1250, 1251, 1252, or analogs, derivatives, amidated variations and conservative variations thereof. In other aspects, the methods comprise administering to a subject an effective amount of an adjuvant composition comprising a pharmaceutically effective carrier and a polypeptide having the amino acid sequence SEQ ID NO: 18, 1253, 1255, 1256, 1257, 1258, or analogs, derivatives, amidated variations and conservative variations thereof.

The vaccine compositions can comprise agents that enhance the protective efficacy of the vaccine, such as adjuvants. Adjuvants include any compound or compounds that acts to enhance a vaccine-induced adaptive immune response, thereby reducing the quantity of antigen necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, synthetic oligonucleotides and combinations thereof (Schijns et al. (2000) Curr. Opin. Immunol. 12:456), *Mycobacterial phlei* (*M. phlei*) cell wall extract (MCWE) (U.S. Pat. No. 4,744,984), *M. phlei* DNA (M-DNA), M-DNA-*M. phlei* cell wall complex (MCC). Compounds which can serve as emulsifiers include natural and synthetic emulsifying agents, as well as anionic, cationic and nonionic compounds.

Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-$\alpha$), interleukin-2 (IL-2), and granulocyte macrophage-colony stimulating factor (GM-CSF), or combinations thereof. GM-CSF is highly preferred.

Vaccine compositions comprising the immunomodulatory peptides of the invention and further comprising adjuvants can be prepared using techniques well known to those skilled in the art including, but not limited to, mixing, sonication and microfluidation. The adjuvant can comprise from about 10% to about 50% (v/v) of the vaccine composition, more preferably about 20% to about 40% (v/v), and more preferably about 20% to about 30% (v/v), or any integer within these ranges. About 25% (v/v) is highly preferred.

J. Treatment Regimes

The invention provides pharmaceutical compositions comprising one or a combination of antimicrobial peptides, for example, formulated together with a pharmaceutically acceptable carrier. Some compositions include a combination of multiple (e.g., two or more) peptides of the invention.

As used herein "pharmaceutically acceptable carrier" includes any and all solvents, dispersion media, coatings, antibacterial and antifungal agents, isotonic and absorption delaying agents, and the like that are physiologically compatible. In one aspect, the carrier is suitable for parenteral administration. Alternatively, the carrier can be suitable for intravenous, intraperitoneal or intramuscular administration. In another aspect, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is compatible with the active compound, use thereof in the pharmaceutical compositions is contemplated. Supplementary active compounds can also be incorporated into the compositions.

A "pharmaceutically acceptable salt" refers to a salt that retains the desired biological activity of the parent compound and does not impart any undesired toxicological effects (See, e.g., Berge, et al., J. Pharm. Sci., 66: 1-19, 1977). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

In prophylactic applications, pharmaceutical compositions or medicaments are administered to a patient susceptible to, or otherwise at risk of a disease or condition (i.e., as a result of bacteria, fungi, viruses, parasites or the like) in an amount sufficient to eliminate or reduce the risk, lessen the severity, or delay the onset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease or condition in an amount sufficient to cure, or at least partially arrest, the symptoms of the disease or condition (e.g., biochemical and/or histologic), including its complications and intermediate pathological phenotypes in development of the disease or condition. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, the response is monitored and repeated dosages are given if the response starts to wane.

The pharmaceutical composition of the present invention should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound can be orally administered, for example, with an inert diluent or an assimilable edible carrier.

Pharmaceutical compositions of the invention also can be administered in combination therapy, i.e., combined with other agents. For example, in treatment of bacteria, the combination therapy can include a composition of the present invention with at least one agent or other conventional therapy.

K. Routes of Administration

A composition of the present invention can be administered by a variety of methods known in the art. The route and/or mode of administration vary depending upon the desired results. The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. The peptide of the invention can be administered parenterally by injection or by gradual infusion over time. The peptide can also be prepared with carriers that protect the compound against rapid release, such as a controlled release formulation, including implants, transdermal patches, and microencapsulated delivery systems. Further methods for delivery of the peptide include orally, by encapsulation in microspheres or proteinoids, by aerosol delivery to the lungs, or transdermally by iontophoresis or transdermal electroporation. To administer a peptide of the invention by certain routes of administration, it can be necessary to coat the compound with, or co-administer the compound with, a material to prevent its inactivation. The method of the invention also includes delivery systems such as microencapsulation of peptides into liposomes or a diluent. Microencapsulation also allows co-entrapment of antimicrobial molecules along with the antigens, so that these molecules, such as antibiotics, may be delivered to a site in need of such treatment in conjunction with the peptides of the invention. Liposomes in the blood stream are generally taken up by the liver and spleen. Pharmaceutically acceptable diluents include saline and aqueous buffer solutions. Liposomes include water-in-oil-in-water CGF emulsions as well as conventional liposomes (Strejan et al., J. Neuroimmunol., 7: 27, 1984). Thus, the method of the invention is particularly useful for delivering antimicrobial peptides to such organs. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, Ed., 1978, Marcel Dekker, Inc., New York. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Therapeutic compositions typically must be sterile, substantially isotonic, and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions can also be administered with medical devices known in the art. For example, in a preferred aspect, a therapeutic composition of the invention can be administered with a needleless hypodermic injection device, such as the devices disclosed in, e.g., U.S. Pat. No. 5,399,163, 5,383,851, 5,312,335, 5,064,413, 4,941,880, 4,790,824, or 4,596,556. Examples of implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

When the peptides of the present invention are administered as pharmaceuticals, to humans and animals, they can be given alone or as a pharmaceutical composition containing, for example, 0.01 to 99.5% (or 0.1 to 90%) of active ingredient in combination with a pharmaceutically acceptable carrier.

L. Effective Dosages

"Therapeutically effective amount" as used herein for treatment of antimicrobial related diseases and conditions refers to the amount of peptide used that is of sufficient quantity to decrease the numbers of bacteria, viruses, fungi, and parasites in the body of a subject. The dosage ranges for the administration of peptides are those large enough to produce the desired effect. The amount of peptide adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's (Remington's Pharmaceutical Science, Mack Publishing Company, Easton, Pa.); Egleton, Peptides 18: 1431-1439, 1997; Langer Science 249: 1527-1533, 1990. The dosage regimen can be adjusted by the individual physician in the event of any contraindications.

Dosage regimens of the pharmaceutical compositions of the present invention are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Administration of the vaccine compositions can be by infusion or injection (e.g., intravenously, intramuscularly, intracutaneously, subcutaneously, intrathecal, intraduodenally, intraperitoneally, and the like). The vaccine compositions can also be administered intranasally, vaginally, rectally, orally, or transdermally as discussed herein. Preferably, the compositions are administered by intradermal injection. Administration can be at the direction of a physician.

The injections can be split into multiple injections, with such split inoculations administered preferably substantially concurrently. When administered as a split inoculation, the dose of the immunogen is preferably, but not necessarily, proportioned equally in each separate injection. If an adjuvant is present in the vaccine composition, the dose of the adjuvant is preferably, but not necessarily, proportioned equally in each separate injection. The separate injections for the split inoculation are preferably administered substantially proximal to each other on the patient's body. In some preferred aspects, the injections are administered at least about 1 cm apart from each other on the body. In some preferred aspects, the injections are administered at least about 2.5 cm apart from each other on the body. In highly preferred aspects, the injections are administered at least about 5 cm apart from each other on the body. In some aspects, the injections are administered at least about 10 cm apart from each other on the body. In some aspects, the injections are administered more than 10 cm apart from each other on the body, for example, at least about 12.5. 15, 17.5, 20, or more cm apart from each other on the body. Primary immunization injections and booster injections can be administered as a split inoculation as described and exemplified herein.

In some aspects, patients can be administered the vaccine compositions 1, 2, 3, 4, 5, 6, 7, 8, or more times per month. Four to six times per month are preferred to establish the protective immune response, particularly with respect to the primary immunization schedule. In some aspects, boosters can be administered at regular intervals such as every 2, 3, 4, 5, or 6 days, every 2, 3, 4, 5, 6, 7, 8, 9, 10, or more weeks, or every 2, 3, 4, 5, 6, 7, 8, 9, 10, 11, 12, or more months. Administration of the booster is preferably every 6 months. Boosters can also be administered on an as-needed basis.

The vaccine administration schedule, including primary immunization and booster administration, can continue as long as needed for the patient, for example, over the course of several weeks, to several months, to several years, to over the lifetime of the patient. In some aspects, the vaccine schedule includes more frequent administration at the beginning of the vaccine regimen, and includes less frequent administration (e.g., boosters) over time to maintain the protective immunity. "Booster" refers to a dose of an immunogen administered to a patient to enhance, prolong, or maintain protective immunity.

The vaccines can be administered at lower doses at the beginning of the vaccine regimen, with higher doses administered over time. The vaccines can also be administered at higher doses at the beginning of the vaccine regimen, with lower doses administered over time. The frequency of primary vaccine and booster administration and dose of the immunomodulatory peptides of the invention administered can be tailored and/or adjusted to meet the particular needs of individual patients, as determined by the administering physician according to any means suitable in the art.

In some aspects, the vaccine compositions, including compositions for administration as a booster, comprise from about 0.001 mg to about 10 mg of the immunomodulatory peptide or peptides. In some preferred aspects, the compositions comprise about 0.1 mg of the immunomodulatory peptide or peptides. In some preferred aspects, the compositions comprise about 0.5 mg of the immunomodulatory peptide or peptides. In some preferred aspects, the compositions comprise about 1 mg of the immunomodulatory peptide or peptides.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the compounds of the invention employed in the pharmaceutical composition at levels lower than that required to achieve the desired therapeutic effect and gradually increase the dosage until the desired effect is achieved. In general, a suitable daily dose of a compound of the invention is that amount of the compound which is the lowest dose effective to produce a therapeutic effect. Such an effective dose generally depends upon the factors described above. It is preferred that administration be intravenous, intramuscular, intraperitoneal, or subcutaneous, or administered proximal to the site of the target. If desired, the effective daily dose of a therapeutic composition can be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

An effective dose of each of the peptides disclosed herein as potential therapeutics for use in treating microbial diseases and conditions is from about 1 μg to 500 mg/kg body weight, per single administration, which can readily be determined by one skilled in the art. As discussed above, the dosage depends upon the age, sex, health, and weight of the recipient, kind of concurrent therapy, if any, and frequency of treatment. Other effective dosage range upper limits are 100 mg/kg body weight, 50 mg/kg body weight, 25 mg/kg body weight, and 10 mg/kg body weight.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Some compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, See, e.g., U.S. Pat. Nos. 4,522,811; 5,374,548; and 5,399,331. The liposomes can comprise one or more moieties which are selectively transported into specific cells or organs, thus enhance targeted drug delivery (See, e.g., Ranade, J. Clin. Pharmacol., 29: 685, 1989). Exemplary targeting moieties include folate or biotin (See, e.g., U.S. Pat. No. 5,416,016 to Low, et al.); mannosides (Umezawa, et al., Biochem. Biophys. Res. Commun., 153: 1038, 1988); antibodies (Bloeman, et al., FEBS Lett., 357: 140, 1995; Owais, et al., Antimicrob. Agents Chemother., 39: 180, 1995); surfactant protein A receptor (Briscoe, et al., Am. J. Physiol., 1233: 134, 1995), different species of which can comprise the formulations of the inventions, as well as components of the invented molecules; p120 (Schreier, et al., J. Biol. Chem., 269: 9090, 1994). See also Keinanen, et al., FEBS Lett., 346: 123, 1994; Killion, et al., Immunomethods, 4: 273, 1994. In some methods, the therapeutic compounds of the invention are formulated in liposomes; in a more preferred aspect, the liposomes include a targeting moiety. In some methods, the therapeutic compounds in the liposomes are delivered by bolus injection to a site proximal to the tumor or infection. The composition should be fluid to the extent that easy syringability exists. It should be stable under the conditions of manufacture and storage and should be preserved against the contaminating action of microorganisms such as bacteria and fungi.

"Bactericidal amount" as used herein refers to an amount sufficient to achieve a bacteria-killing blood concentration in the subject receiving the treatment. The bactericidal amount of antibiotic generally recognized as safe for administration to a human is well known in the art, and as is known in the art, varies with the specific antibiotic and the type of bacterial infection being treated.

Because of the antibiotic, antimicrobial, and antiviral properties of the peptides, they may also be used as preservatives or sterillants of materials susceptible to microbial or viral contamination. The peptides of the invention can be utilized as broad spectrum antimicrobial agents directed toward various specific applications. Such applications include use of the peptides as preservatives in processed foods (organisms including *Salmonella, Yersinia*, and *Shigella*), either alone or in combination with antibacterial food additives such as lysozymes; as a topical agent (*Pseudomonas, Streptococcus*) and to kill odor producing microbes (*Micrococci*). The relative effectiveness of the peptides of the invention for the applications described can be readily determined by one of skill in the art by determining the sensitivity of any organism to one of the peptides.

M. Formulation

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., Eur. J. Immunol. 25: 3521-24, 1995; Cevc et al., Biochem. Biophys. Acta 1368: 201-15, 1998.

The pharmaceutical compositions are generally formulated as sterile, substantially isotonic and in full compliance with all Good Manufacturing Practice (GMP) regulations of the U.S. Food and Drug Administration.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

All publications and patent documents cited above are hereby incorporated by reference in their entirety for all purposes to the same extent as if each were so individually denoted.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

EXEMPLARY EMBODIMENTS

Example 1

Materials, Methods and Peptides

Peptide Synthesis—Peptide syntheses on cellulose were performed using a pipetting robot (Abimed, Langenfeld, Germany) and Whatman 50 cellulose membranes (Whatman, Maidstone, United Kingdom) as described previously (Kramer A, Schuster A, Reinecke U, Malin R, Volkmer-Engert R, Landgraf C, Schneider-Mergener J. 1994. Combinatorial cellulose-bound peptide libraries: screening tool for the identification of peptides that bind ligands with predefined specificity. Comp. Meth. Enzymol. 6, 388-395; Kramer A, Keitel T, Winkler K, Stocklein W, Hohne W, Schneider-Mergener J. 1997. Molecular basis for the binding promiscuity of an anti-p24 (HIV-1) monoclonal antibody. Cell 91, 799-809). The HPLC purified peptides used for further characterization (CD, membrane permeability, MIC) were purchased from Thermo electron cooperation (Ulm, Germany). Table 2A

TABLE 2A

Peptides utilized in these studies. All peptides were amidated at the C-terminus unless otherwise noted.

| Name | Sequence | ID |
|---|---|---|
| HH1 | QRLRIRVAVIRA | SEQ ID NO 1 |
| HH2 | VQLRIRVAVIRA | SEQ ID NO 2 |
| HH3 | VRFRIRVAVIRA | SEQ ID NO 3 |
| HH4 | VRWRIRVAVIRA | SEQ ID NO 4 |
| HH5 | VRLWIRVAVIRA | SEQ ID NO 5 |
| HH6 | VRLRIRVWVIRA | SEQ ID NO 6 |
| HH7 | VRLRIRVAVRRA | SEQ ID NO 7 |
| HH8 | VRLRIRVAVIRK | SEQ ID NO 8 |
| HH9 | VQLRIRVRVIRK | SEQ ID NO 9 |
| HH10 | KRFRIRVAVRRA | SEQ ID NO 10 |
| HH11 | VRLRIRVRVIRK | SEQ ID NO 11 |
| HH12 | KQFRIRVRVIRK | SEQ ID NO 12 |
| HH13 | HQFRFRFRVRRK | SEQ ID NO 13 |
| HH14 | HQWRIRVAVRRH | SEQ ID NO 14 |
| HH15 | KRFRIRVRVIRK | SEQ ID NO 15 |
| HH16 | KRWRIRVRVIRK | SEQ ID NO 16 |
| HH17 | KIWVRWK | SEQ ID NO 17 |
| HH18 | IWVIWRR | SEQ ID NO 18 |
| HH19 | ALPWKWPWWPWRR | SEQ ID NO 19 |
| HH20 | IAPWKWPWWPWRR | SEQ ID NO 20 |
| HH21 | ILAWKWPWWPWRR | SEQ ID NO 21 |
| HH22 | ILPAKWPWWPWRR | SEQ ID NO 22 |
| HH23 | ILPWAWPWWPWRR | SEQ ID NO 23 |
| HH24 | ILPWKAPWWPWRR | SEQ ID NO 24 |
| HH25 | ILPWKWAWWPWRR | SEQ ID NO 25 |
| HH26 | ILPWKWPAWPWRR | SEQ ID NO 26 |
| HH27 | ILPWKWPWAPWRR | SEQ ID NO 27 |
| HH28 | ILPWKWPWWAWRR | SEQ ID NO 28 |
| HH29 | ILPWKWPWWPARR | SEQ ID NO 29 |
| HH30 | ILPWKWPWWPWAR | SEQ ID NO 30 |
| HH31 | ILPWKWPWWPWRA | SEQ ID NO 31 |
| HH32 | DLPWKWPWWPWRR | SEQ ID NO 32 |
| HH33 | IDPWKWPWWPWRR | SEQ ID NO 33 |
| HH34 | ILDWKWPWWPWRR | SEQ ID NO 34 |
| HH35 | ILPDKWPWWPWRR | SEQ ID NO 35 |
| HH36 | ILPWDWPWWPWRR | SEQ ID NO 36 |
| HH37 | ILPWKDPWWPWRR | SEQ ID NO 37 |
| HH38 | ILPWKWDWWPWRR | SEQ ID NO 38 |
| HH39 | ILPWKWPDWPWRR | SEQ ID NO 39 |
| HH40 | ILPWKWPWDPWRR | SEQ ID NO 40 |
| HH41 | ILPWKWPWWDWRR | SEQ ID NO 41 |
| HH42 | ILPWKWPWWPDRR | SEQ ID NO 42 |
| HH43 | ILPWKWPWWPWDR | SEQ ID NO 43 |
| HH44 | ILPWKWPWWPWRD | SEQ ID NO 44 |
| HH45 | ELPWKWPWWPWRR | SEQ ID NO 45 |
| HH46 | IEPWKWPWWPWRR | SEQ ID NO 46 |
| HH47 | ILEWKWPWWPWRR | SEQ ID NO 47 |
| HH48 | ILPEKWPWWPWRR | SEQ ID NO 48 |

TABLE 2A-continued

Peptides utilized in these studies. All peptides were amidated at the C-terminus unless otherwise noted.

| Name | Sequence | ID |
|---|---|---|
| HH49 | ILPWEWPWWPWRR | SEQ ID NO 49 |
| HH50 | ILPWKEPWWPWRR | SEQ ID NO 50 |
| HH51 | ILPWKWEWWPWRR | SEQ ID NO 51 |
| HH52 | ILPWKWPEWPWRR | SEQ ID NO 52 |
| HH53 | ILPWKWPWEPWRR | SEQ ID NO 53 |
| HH54 | ILPWKWPWWEWRR | SEQ ID NO 54 |
| HH55 | ILPWKWPWWPERR | SEQ ID NO 55 |
| HH56 | ILPWKWPWWPWER | SEQ ID NO 56 |
| HH57 | ILPWKWPWWPWRE | SEQ ID NO 57 |
| HH58 | FLPWKWPWWPWRR | SEQ ID NO 58 |
| HH59 | IFPWKWPWWPWRR | SEQ ID NO 59 |
| HH60 | ILFWKWPWWPWRR | SEQ ID NO 60 |
| HH61 | ILPFKWPWWPWRR | SEQ ID NO 61 |
| HH62 | ILPWFWPWWPWRR | SEQ ID NO 62 |
| HH63 | ILPWKFPWWPWRR | SEQ ID NO 63 |
| HH64 | ILPWKWFWWPWRR | SEQ ID NO 64 |
| HH65 | ILPWKWPFWPWRR | SEQ ID NO 65 |
| HH66 | ILPWKWPWFPWRR | SEQ ID NO 66 |
| HH67 | ILPWKWPWWFWRR | SEQ ID NO 67 |
| HH68 | ILPWKWPWWPFRR | SEQ ID NO 68 |
| HH69 | ILPWKWPWWPWFR | SEQ ID NO 69 |
| HH70 | ILPWKWPWWPWRF | SEQ ID NO 70 |
| HH71 | GLPWKWPWWPWRR | SEQ ID NO 71 |
| HH72 | IGPWKWPWWPWRR | SEQ ID NO 72 |
| HH73 | ILGWKWPWWPWRR | SEQ ID NO 73 |
| HH74 | ILPGKWPWWPWRR | SEQ ID NO 74 |
| HH75 | ILPWGWPWWPWRR | SEQ ID NO 75 |
| HH76 | ILPWKGPWWPWRR | SEQ ID NO 76 |
| HH77 | ILPWKWGWWPWRR | SEQ ID NO 77 |
| HH78 | ILPWKWPGWPWRR | SEQ ID NO 78 |
| HH79 | ILPWKWPWGPWRR | SEQ ID NO 79 |
| HH80 | ILPWKWPWWGWRR | SEQ ID NO 80 |
| HH81 | ILPWKWPWWPGRR | SEQ ID NO 81 |
| HH82 | ILPWKWPWWPWGR | SEQ ID NO 82 |
| HH83 | ILPWKWPWWPWRG | SEQ ID NO 83 |
| HH84 | HLPWKWPWWPWRR | SEQ ID NO 84 |
| HH85 | IHPWKWPWWPWRR | SEQ ID NO 85 |
| HH86 | ILHWKWPWWPWRR | SEQ ID NO 86 |
| HH87 | ILPHKWPWWPWRR | SEQ ID NO 87 |
| HH88 | ILPWHWPWWPWRR | SEQ ID NO 88 |
| HH89 | ILPWKHPWWPWRR | SEQ ID NO 89 |
| HH90 | ILPWKWHWWPWRR | SEQ ID NO 90 |
| HH91 | ILPWKWPHWPWRR | SEQ ID NO 91 |
| HH92 | ILPWKWPWHPWRR | SEQ ID NO 92 |
| HH93 | ILPWKWPWWHWRR | SEQ ID NO 93 |
| HH94 | ILPWKWPWWPHRR | SEQ ID NO 94 |
| HH95 | ILPWKWPWWPWHR | SEQ ID NO 95 |
| HH96 | ILPWKWPWWPWRH | SEQ ID NO 96 |
| HH97 | IIPWKWPWWPWRR | SEQ ID NO 97 |
| HH98 | ILIWKWPWWPWRR | SEQ ID NO 98 |
| HH99 | ILPIKWPWWPWRR | SEQ ID NO 99 |
| HH100 | ILPWIWPWWPWRR | SEQ ID NO 100 |
| HH101 | ILPWKIPWWPWRR | SEQ ID NO 101 |
| HH102 | ILPWKWIWWPWRR | SEQ ID NO 102 |
| HH103 | ILPWKWPIWPWRR | SEQ ID NO 103 |
| HH104 | ILPWKWPWIPWRR | SEQ ID NO 104 |
| HH105 | ILPWKWPWWIWRR | SEQ ID NO 105 |
| HH106 | ILPWKWPWWPIRR | SEQ ID NO 106 |
| HH107 | ILPWKWPWWPWIR | SEQ ID NO 107 |
| HH108 | ILPWKWPWWPWRI | SEQ ID NO 108 |
| HH109 | KLPWKWPWWPWRR | SEQ ID NO 109 |
| HH110 | IKPWKWPWWPWRR | SEQ ID NO 110 |
| HH111 | ILKWKWPWWPWRR | SEQ ID NO 111 |
| HH112 | ILPKKWPWWPWRR | SEQ ID NO 112 |
| HH113 | ILPWKKPWWPWRR | SEQ ID NO 113 |
| HH114 | ILPWKWKWWPWRR | SEQ ID NO 114 |
| HH115 | ILPWKWPKWPWRR | SEQ ID NO 115 |
| HH116 | ILPWKWPWKPWRR | SEQ ID NO 116 |
| HH117 | ILPWKWPWWKWRR | SEQ ID NO 117 |
| HH118 | ILPWKWPWWPKRR | SEQ ID NO 118 |
| HH119 | ILPWKWPWWPWKR | SEQ ID NO 119 |
| HH120 | ILPWKWPWWPWRK | SEQ ID NO 120 |
| HH121 | LLPWKWPWWPWRR | SEQ ID NO 121 |
| HH122 | ILLWKWPWWPWRR | SEQ ID NO 122 |

TABLE 2A-continued

Peptides utilized in these studies. All peptides were amidated at the C-terminus unless otherwise noted.

| Name | Sequence | ID |
|------|----------|-----|
| HH123 | ILPLKWPWWPWRR | SEQ ID NO 123 |
| HH124 | ILPWLWPWWPWRR | SEQ ID NO 124 |
| HH125 | ILPWKLPWWPWRR | SEQ ID NO 125 |
| HH126 | ILPWKWLWWPWRR | SEQ ID NO 126 |
| HH127 | ILPWKWPLWPWRR | SEQ ID NO 127 |
| HH128 | ILPWKWPWLPWRR | SEQ ID NO 128 |
| HH129 | ILPWKWPWWLWRR | SEQ ID NO 129 |
| HH130 | ILPWKWPWWPLRR | SEQ ID NO 130 |
| HH131 | ILPWKWPWWPWLR | SEQ ID NO 131 |
| HH132 | ILPWKWPWWPWRL | SEQ ID NO 132 |
| HH133 | MLPWKWPWWPWRR | SEQ ID NO 133 |
| HH134 | IMPWKWPWWPWRR | SEQ ID NO 134 |
| HH135 | ILMWKWPWWPWRR | SEQ ID NO 135 |
| HH136 | ILPWMPWWPWRR | SEQ ID NO 136 |
| HH137 | ILPWMWPWWPWRR | SEQ ID NO 137 |
| HH138 | ILPWKMPWWPWRR | SEQ ID NO 138 |
| HH139 | ILPWKMPWWPWRR | SEQ ID NO 139 |
| HH140 | ILPWKWPMWPWRR | SEQ ID NO 140 |
| HH141 | ILPWKWPWMPWRR | SEQ ID NO 141 |
| HH142 | ILPWKWPWWMWRR | SEQ ID NO 142 |
| HH143 | ILPWKWPWWPMRR | SEQ ID NO 143 |
| HH144 | ILPWKWPWWPWMR | SEQ ID NO 144 |
| HH145 | ILPWKWPWWPWRM | SEQ ID NO 145 |
| HH146 | NLPWKWPWWPWRR | SEQ ID NO 146 |
| HH147 | INPWKWPWWPWRR | SEQ ID NO 147 |
| HH148 | ILMWKWPWWPWRR | SEQ ID NO 148 |
| HH149 | ILPNKWPWWPWRR | SEQ ID NO 149 |
| HH150 | ILPWMPWWPWRR | SEQ ID NO 150 |
| HH151 | ILPWKNPWWPWRR | SEQ ID NO 151 |
| HH152 | ILPWKNWWPWRR | SEQ ID NO 152 |
| HH153 | ILPWKPNWPWRR | SEQ ID NO 153 |
| HH154 | ILPWKWPWNPWRR | SEQ ID NO 154 |
| HH155 | ILPWKWPWWMWRR | SEQ ID NO 155 |
| HH156 | ILPWKWPWWPNRR | SEQ ID NO 156 |
| HH157 | ILPWKWPWWPWNR | SEQ ID NO 157 |
| HH158 | ILPWKWPWWPWRN | SEQ ID NO 158 |
| HH159 | PLPWKWPWWPWRR | SEQ ID NO 159 |
| HH160 | IPPWKWPWWPWRR | SEQ ID NO 160 |
| HH161 | ILPPKWPWWPWRR | SEQ ID NO 161 |
| HH162 | ILPWPWPWWPWRR | SEQ ID NO 162 |
| HH163 | ILPWKMPWWPWRR | SEQ ID NO 163 |
| HH164 | ILPWKWPPWPWRR | SEQ ID NO 164 |
| HH165 | ILPWKWPWPPWRR | SEQ ID NO 165 |
| HH166 | ILPWKWPWWPPRR | SEQ ID NO 166 |
| HH167 | ILPWKWPWWPWPR | SEQ ID NO 167 |
| HH168 | ILPWKWPWWPWRP | SEQ ID NO 168 |
| HH169 | QLPWKWPWWPWRR | SEQ ID NO 169 |
| HH170 | IQPWKWPWWPWRR | SEQ ID NO 170 |
| HH171 | ILQWKWPWWPWRR | SEQ ID NO 171 |
| HH172 | ILPQKWPWWPWRR | SEQ ID NO 172 |
| HH173 | ILPWQPWWPWRR | SEQ ID NO 173 |
| HH174 | ILPWKQPWWPWRR | SEQ ID NO 174 |
| HH175 | ILPWKWQWPWRR | SEQ ID NO 175 |
| HH176 | ILPWKWPQWPWRR | SEQ ID NO 176 |
| HH177 | ILPWKWPWQPWRR | SEQ ID NO 177 |
| HH178 | ILPWKWPWWQWRR | SEQ ID NO 178 |
| HH179 | ILPWKWPWWPQRR | SEQ ID NO 179 |
| HH180 | ILPWKWPWWPWQR | SEQ ID NO 180 |
| HH181 | ILPWKWPWWPWRQ | SEQ ID NO 181 |
| HH182 | RLPWKWPWWPWRR | SEQ ID NO 182 |
| HH183 | IRPWKWPWWPWRR | SEQ ID NO 183 |
| HH184 | ILRWKWPWWPWRR | SEQ ID NO 184 |
| HH185 | ILPRKWPWWPWRR | SEQ ID NO 185 |
| HH186 | ILPWRPWWPWRR | SEQ ID NO 186 |
| HH187 | ILPWKRPWWPWRR | SEQ ID NO 187 |
| HH188 | ILPWKRWWPWRR | SEQ ID NO 188 |
| HH189 | ILPWKWPRWPWRR | SEQ ID NO 189 |
| HH190 | ILPWKWPWRPWRR | SEQ ID NO 190 |
| HH191 | ILPWKWPWWRWRR | SEQ ID NO 191 |
| HH192 | ILPWKWPWWPRRR | SEQ ID NO 192 |
| HH193 | SLPWKWPWWPWRR | SEQ ID NO 193 |
| HH194 | ISPWKWPWWPWRR | SEQ ID NO 194 |
| HH195 | ILSWKWPWWPWRR | SEQ ID NO 195 |
| HH196 | ILPSKWPWWPWRR | SEQ ID NO 196 |

TABLE 2A-continued

Peptides utilized in these studies. All peptides were amidated at the C-terminus unless otherwise noted.

| Name | Sequence | ID |
|---|---|---|
| HH197 | ILPWSWPWWPWRR | SEQ ID NO 197 |
| HH198 | ILPWKSPWWPWRR | SEQ ID NO 198 |
| HH199 | ILPWKWSWWPWRR | SEQ ID NO 199 |
| HH200 | ILPWKWPSWPWRR | SEQ ID NO 200 |
| HH201 | ILPWKWPWSPWRR | SEQ ID NO 201 |
| HH202 | ILPWKWPWWSWRR | SEQ ID NO 202 |
| HH203 | ILPWKWPWWPSRR | SEQ ID NO 203 |
| HH204 | ILPWKWPWWPWSR | SEQ ID NO 204 |
| HH205 | ILPWKWPWWPWRS | SEQ ID NO 205 |
| HH206 | TLPWKWPWWPWRR | SEQ ID NO 206 |
| HH207 | ITPWKWPWWPWRR | SEQ ID NO 207 |
| HH208 | ILTWKWPWWPWRR | SEQ ID NO 208 |
| HH209 | ILPTKWPWWPWRR | SEQ ID NO 209 |
| HH210 | ILPWTWPWWPWRR | SEQ ID NO 210 |
| HH211 | ILPWKTPWWPWRR | SEQ ID NO 211 |
| HH212 | ILPWKWTWWPWRR | SEQ ID NO 212 |
| HH213 | ILPWKWPTWPWRR | SEQ ID NO 213 |
| HH214 | ILPWKWPWTPWRR | SEQ ID NO 214 |
| HH215 | ILPWKWPWWTWRR | SEQ ID NO 215 |
| HH216 | ILPWKWPWWPTRR | SEQ ID NO 216 |
| HH217 | ILPWKWPWWPWTR | SEQ ID NO 217 |
| HH218 | ILPWKWPWWPWRT | SEQ ID NO 218 |
| HH219 | VLPWKWPWWPWRR | SEQ ID NO 219 |
| HH220 | IVPWKWPWWPWRR | SEQ ID NO 220 |
| HH221 | ILVWKWPWWPWRR | SEQ ID NO 221 |
| HH222 | ILPVKWPWWPWRR | SEQ ID NO 222 |
| HH223 | ILPWRWPWWPWRR | SEQ ID NO 223 |
| HH224 | ILPWKVPWWPWRR | SEQ ID NO 224 |
| HH225 | ILPWKVWWWPWRR | SEQ ID NO 225 |
| HH226 | ILPWKWPVWPWRR | SEQ ID NO 226 |
| HH227 | ILPWKWPWVPWRR | SEQ ID NO 227 |
| HH228 | ILPWKWPWWVWRR | SEQ ID NO 228 |
| HH229 | ILPWKWPWWPVRR | SEQ ID NO 229 |
| HH230 | ILPWKWPWWPWVR | SEQ ID NO 230 |
| HH231 | ILPWKWPWWPWRV | SEQ ID NO 231 |
| HH232 | WLPWKWPWWPWRR | SEQ ID NO 232 |
| HH233 | IWPWKWPWWPWRR | SEQ ID NO 233 |
| HH234 | ILWWKWPWWPWRR | SEQ ID NO 234 |
| HH235 | ILPWWWPWWPWRR | SEQ ID NO 235 |
| HH236 | ILPWKVWWWPWRR | SEQ ID NO 236 |
| HH237 | ILPWKWPWVWRR | SEQ ID NO 237 |
| HH238 | ILPWKWPWWPWWR | SEQ ID NO 238 |
| HH239 | ILPWKWPWWPWRW | SEQ ID NO 239 |
| HH240 | YLPWKWPWWPWRR | SEQ ID NO 240 |
| HH241 | IYPWKWPWWPWRR | SEQ ID NO 241 |
| HH242 | ILYWKWPWWPWRR | SEQ ID NO 242 |
| HH243 | ILPYKWPWWPWRR | SEQ ID NO 243 |
| HH244 | ILPWYWPWWPWRR | SEQ ID NO 244 |
| HH245 | ILPWKYPWWPWRR | SEQ ID NO 245 |
| HH246 | ILPWKWYWWPWRR | SEQ ID NO 246 |
| HH247 | ILPWKWPYWPWRR | SEQ ID NO 247 |
| HH248 | ILPWKWPWYPWRR | SEQ ID NO 248 |
| HH249 | ILPWKWPWWYWRR | SEQ ID NO 249 |
| HH250 | ILPWKWPWWPYRR | SEQ ID NO 250 |
| HH251 | ILPWKWPWWPWYR | SEQ ID NO 251 |
| HH252 | ILPWKWPWWPWRY | SEQ ID NO 252 |
| HH253 | ARLRIRVAVIRA | SEQ ID NO 253 |
| HH254 | DRLRIRVAVIRA | SEQ ID NO 254 |
| HH255 | ERLRIRVAVIRA | SEQ ID NO 255 |
| HH256 | FRLRIRVAVIRA | SEQ ID NO 256 |
| HH257 | GRLRIRVAVIRA | SEQ ID NO 257 |
| HH258 | HRLRIRVAVIRA | SEQ ID NO 258 |
| HH259 | IRLRIRVAVIRA | SEQ ID NO 259 |
| HH260 | KRLRIRVAVIRA | SEQ ID NO 260 |
| HH261 | LRLRIRVAVIRA | SEQ ID NO 261 |
| HH262 | MRLRIRVAVIRA | SEQ ID NO 262 |
| HH263 | NRLRIRVAVIRA | SEQ ID NO 263 |
| HH264 | PRLRIRVAVIRA | SEQ ID NO 264 |
| HH265 | QRLRIRVAVIRA | SEQ ID NO 265 |
| HH266 | RRLRIRVAVIRA | SEQ ID NO 266 |
| HH267 | SRLRIRVAVIRA | SEQ ID NO 267 |
| HH268 | TRLRIRVAVIRA | SEQ ID NO 268 |
| HH269 | WRLRIRVAVIRA | SEQ ID NO 269 |
| HH270 | YRLRIRVAVIRA | SEQ ID NO 270 |

TABLE 2A-continued

Peptides utilized in these studies. All peptides were amidated at the C-terminus unless otherwise noted.

| Name | Sequence | ID |
|---|---|---|
| HH271 | VALRIRVAVIRA | SEQ ID NO 271 |
| HH272 | VDLRIRVAVIRA | SEQ ID NO 272 |
| HH273 | VELRIRVAVIRA | SEQ ID NO 273 |
| HH274 | VFLRIRVAVIRA | SEQ ID NO 274 |
| HH275 | VGLRIRVAVIRA | SEQ ID NO 275 |
| HH276 | VHLRIRVAVIRA | SEQ ID NO 276 |
| HH277 | VILRIRVAVIRA | SEQ ID NO 277 |
| HH278 | VKLRIRVAVIRA | SEQ ID NO 278 |
| HH279 | VLLRIRVAVIRA | SEQ ID NO 279 |
| HH280 | VALRIRVAVIRA | SEQ ID NO 280 |
| HH281 | VNLRIRVAVIRA | SEQ ID NO 281 |
| HH282 | VPLRIRVAVIRA | SEQ ID NO 282 |
| HH283 | VQLRIRVAVIRA | SEQ ID NO 283 |
| HH284 | VSLRIRVAVIRA | SEQ ID NO 284 |
| HH285 | VTLRIRVAVIRA | SEQ ID NO 285 |
| HH286 | VVLRIRVAVIRA | SEQ ID NO 286 |
| HH287 | VALRIRVAVIRA | SEQ ID NO 287 |
| HH288 | VYLRIRVAVIRA | SEQ ID NO 288 |
| HH289 | VRARIRVAVIRA | SEQ ID NO 289 |
| HH290 | VRDRIRVAVIRA | SEQ ID NO 290 |
| HH291 | VRERIRVAVIRA | SEQ ID NO 291 |
| HH292 | VRFRIRVAVIRA | SEQ ID NO 292 |
| HH293 | VRGRIRVAVIRA | SEQ ID NO 293 |
| HH294 | VRHRIRVAVIRA | SEQ ID NO 294 |
| HH295 | VRIRIRVAVIRA | SEQ ID NO 295 |
| HH296 | VRKRIRVAVIRA | SEQ ID NO 296 |
| HH297 | VRMRIRVAVIRA | SEQ ID NO 297 |
| HH298 | VRNRIRVAVIRA | SEQ ID NO 298 |
| HH299 | VRPRIRVAVIRA | SEQ ID NO 299 |
| HH300 | VRQRIRVAVIRA | SEQ ID NO 300 |
| HH301 | VRRRIRVAVIRA | SEQ ID NO 301 |
| HH302 | VRSRIRVAVIRA | SEQ ID NO 302 |
| HH303 | VRTRIRVAVIRA | SEQ ID NO 303 |
| HH304 | VRVRIRVAVIRA | SEQ ID NO 304 |
| HH305 | VRWRIRVAVIRA | SEQ ID NO 305 |
| HH306 | VRYRIRVAVIRA | SEQ ID NO 306 |
| HH307 | VRLAIRVAVIRA | SEQ ID NO 307 |
| HH308 | VRLDIRVAVIRA | SEQ ID NO 308 |
| HH309 | VRLEIRVAVIRA | SEQ ID NO 309 |
| HH310 | VRLFIRVAVIRA | SEQ ID NO 310 |
| HH311 | VRLGIRVAVIRA | SEQ ID NO 311 |
| HH312 | VRLHIRVAVIRA | SEQ ID NO 312 |
| HH313 | VRLIIRVAVIRA | SEQ ID NO 313 |
| HH314 | VRLKIRVAVIRA | SEQ ID NO 314 |
| HH315 | VRLLIRVAVIRA | SEQ ID NO 315 |
| HH316 | VRLLIRVAVIRA | SEQ ID NO 316 |
| HH317 | VRLNIRVAVIRA | SEQ ID NO 317 |
| HH318 | VRLPIRVAVIRA | SEQ ID NO 318 |
| HH319 | VRLQIRVAVIRA | SEQ ID NO 319 |
| HH320 | VRLSIRVAVIRA | SEQ ID NO 320 |
| HH321 | VRLTIRVAVIRA | SEQ ID NO 321 |
| HH322 | VRLVIRVAVIRA | SEQ ID NO 322 |
| HH323 | VRLWIRVAVIRA | SEQ ID NO 323 |
| HH324 | VRLYIRVAVIRA | SEQ ID NO 324 |
| HH325 | VRLRARVAVIRA | SEQ ID NO 325 |
| HH326 | VRLRDRVAVIRA | SEQ ID NO 326 |
| HH327 | VRLRERVAVIRA | SEQ ID NO 327 |
| HH328 | VRLRFRVAVIRA | SEQ ID NO 328 |
| HH329 | VRLRGRVAVIRA | SEQ ID NO 329 |
| HH330 | VRLRHRVAVIRA | SEQ ID NO 330 |
| HH331 | VRLRKRVAVIRA | SEQ ID NO 331 |
| HH332 | VRLRLRVAVIRA | SEQ ID NO 332 |
| HH333 | VRLRMRVAVIRA | SEQ ID NO 333 |
| HH334 | VRLRNRVAVIRA | SEQ ID NO 334 |
| HH335 | VRLRPRVAVIRA | SEQ ID NO 335 |
| HH336 | VRLRQRVAVIRA | SEQ ID NO 336 |
| HH337 | VRLRRRVAVIRA | SEQ ID NO 337 |
| HH338 | VRLRSRVAVIRA | SEQ ID NO 338 |
| HH339 | VRLRTRVAVIRA | SEQ ID NO 339 |
| HH340 | VRLRVRVAVIRA | SEQ ID NO 340 |
| HH341 | VRLRWRVAVIRA | SEQ ID NO 341 |
| HH342 | VRLRYRVAVIRA | SEQ ID NO 342 |
| HH343 | VRLRIAVAVIRA | SEQ ID NO 343 |
| HH344 | VRLRIDVAVIRA | SEQ ID NO 344 |

TABLE 2A-continued

Peptides utilized in these studies. All peptides were amidated at the C-terminus unless otherwise noted.

| Name | Sequence | ID |
|---|---|---|
| HH345 | VRLRIEVAVIRA | SEQ ID NO 345 |
| HH346 | VRLRIFVAVIRA | SEQ ID NO 346 |
| HH347 | VRLRIGVAVIRA | SEQ ID NO 347 |
| HH348 | VRLRIHVAVIRA | SEQ ID NO 348 |
| HH349 | VRLRIIVAVIRA | SEQ ID NO 349 |
| HH350 | VRLRIKVAVIRA | SEQ ID NO 350 |
| HH351 | VRLRILVAVIRA | SEQ ID NO 351 |
| HH352 | VRLRIMVAVIRA | SEQ ID NO 352 |
| HH353 | VRLRINVAVIRA | SEQ ID NO 353 |
| HH354 | VRLRIPVAVIRA | SEQ ID NO 354 |
| HH355 | VRLRIQVAVIRA | SEQ ID NO 355 |
| HH356 | VRLRISVAVIRA | SEQ ID NO 356 |
| HH357 | VRLRITVAVIRA | SEQ ID NO 357 |
| HH358 | VRLRIVVAVIRA | SEQ ID NO 358 |
| HH359 | VRLRIWVAVIRA | SEQ ID NO 359 |
| HH360 | VRLRIYVAVIRA | SEQ ID NO 360 |
| HH361 | VRLRIRAAVIRA | SEQ ID NO 361 |
| HH362 | VRLRIRDAVIRA | SEQ ID NO 362 |
| HH363 | VRLRIREAVIRA | SEQ ID NO 363 |
| HH364 | VRLRIRFAVIRA | SEQ ID NO 364 |
| HH365 | VRLRIRGAVIRA | SEQ ID NO 365 |
| HH366 | VRLRIRHAVIRA | SEQ ID NO 366 |
| HH367 | VRLRIRIAVIRA | SEQ ID NO 367 |
| HH368 | VRLRIRKAVIRA | SEQ ID NO 368 |
| HH369 | VRLRIRLAVIRA | SEQ ID NO 369 |
| HH370 | VRLRIRMAVIRA | SEQ ID NO 370 |
| HH371 | VRLRIRNAVIRA | SEQ ID NO 371 |
| HH372 | VRLRIRPAVIRA | SEQ ID NO 372 |
| HH373 | VRLRIRQAVIRA | SEQ ID NO 373 |
| HH374 | VRLRIRRAVIRA | SEQ ID NO 374 |
| HH375 | VRLRIRSAVIRA | SEQ ID NO 375 |
| HH376 | VRLRIRTAVIRA | SEQ ID NO 376 |
| HH377 | VRLRIRWAVIRA | SEQ ID NO 377 |
| HH378 | VRLRIRYAVIRA | SEQ ID NO 378 |
| HH379 | VRLRIRVDVIRA | SEQ ID NO 379 |
| HH380 | VRLRIRVEVIRA | SEQ ID NO 380 |
| HH381 | VRLRIRVFVIRA | SEQ ID NO 381 |
| HH382 | VRLRIRVGVIRA | SEQ ID NO 382 |
| HH383 | VRLRIRVHVIRA | SEQ ID NO 383 |
| HH384 | VRLRIRVIVIRA | SEQ ID NO 384 |
| HH385 | VRLRIRVKVIRA | SEQ ID NO 385 |
| HH386 | VRLRIRVLVIRA | SEQ ID NO 386 |
| HH387 | VRLRIRVMVIRA | SEQ ID NO 387 |
| HH388 | VRLRIRVNVIRA | SEQ ID NO 388 |
| HH389 | VRLRIRVPVIRA | SEQ ID NO 389 |
| HH390 | VRLRIRVQVIRA | SEQ ID NO 390 |
| HH391 | VRLRIRVRVIRA | SEQ ID NO 391 |
| HH392 | VRLRIRVSVIRA | SEQ ID NO 392 |
| HH393 | VRLRIRVTVIRA | SEQ ID NO 393 |
| HH394 | VRLRIRVVVIRA | SEQ ID NO 394 |
| HH395 | VRLRIRVWVIRA | SEQ ID NO 395 |
| HH396 | VRLRIRVYVIRA | SEQ ID NO 396 |
| HH397 | VRLRIRVAAIRA | SEQ ID NO 397 |
| HH398 | VRLRIRVADIRA | SEQ ID NO 398 |
| HH399 | VRLRIRVAEIRA | SEQ ID NO 399 |
| HH400 | VRLRIRVAFIRA | SEQ ID NO 400 |
| HH401 | VRLRIRVAGIRA | SEQ ID NO 401 |
| HH402 | VRLRIRVAHIRA | SEQ ID NO 402 |
| HH403 | VRLRIRVAIIRA | SEQ ID NO 403 |
| HH404 | VRLRIRVAKIRA | SEQ ID NO 404 |
| HH405 | VRLRIRVALIRA | SEQ ID NO 405 |
| HH406 | VRLRIRVAMIRA | SEQ ID NO 406 |
| HH407 | VRLRIRVANIRA | SEQ ID NO 407 |
| HH408 | VRLRIRVAPIRA | SEQ ID NO 408 |
| HH409 | VRLRIRVAQIRA | SEQ ID NO 409 |
| HH410 | VRLRIRVARIRA | SEQ ID NO 410 |
| HH411 | VRLRIRVAMIRA | SEQ ID NO 411 |
| HH412 | VRLRIRVATIRA | SEQ ID NO 412 |
| HH413 | VRLRIRVAWIRA | SEQ ID NO 413 |
| HH414 | VRLRIRVAYIRA | SEQ ID NO 414 |
| HH415 | VRLRIRVAVARA | SEQ ID NO 415 |
| HH416 | VRLRIRVAVDRA | SEQ ID NO 416 |
| HH417 | VRLRIRVAVERA | SEQ ID NO 417 |
| HH418 | VRLRIRVAVFRA | SEQ ID NO 418 |

TABLE 2A-continued

Peptides utilized in these studies. All peptides were amidated at the C-terminus unless otherwise noted.

| Name | Sequence | ID |
|---|---|---|
| HH419 | VRLRIRVAVGRA | SEQ ID NO 419 |
| HH420 | VRLRIRVAVHRA | SEQ ID NO 420 |
| HH421 | VRLRIRVAVKRA | SEQ ID NO 421 |
| HH422 | VRLRIRVAVLRA | SEQ ID NO 422 |
| HH423 | VRLRIRVAVMRA | SEQ ID NO 423 |
| HH424 | VRLRIRVAVNRA | SEQ ID NO 424 |
| HH425 | VRLRIRVAVPRA | SEQ ID NO 425 |
| HH426 | VRLRIRVAVQRA | SEQ ID NO 426 |
| HH427 | VRLRIRVAVRRA | SEQ ID NO 427 |
| HH428 | VRLRIRVAVSRA | SEQ ID NO 428 |
| HH429 | VRLRIRVAVTRA | SEQ ID NO 429 |
| HH430 | VRLRIRVAVVRA | SEQ ID NO 430 |
| HH431 | VRLRIRVAVWRA | SEQ ID NO 431 |
| HH432 | VRLRIRVAVYRA | SEQ ID NO 432 |
| HH433 | VRLRIRVAVIAA | SEQ ID NO 433 |
| HH434 | VRLRIRVAVIDA | SEQ ID NO 434 |
| HH435 | VRLRIRVAVIEA | SEQ ID NO 435 |
| HH436 | VRLRIRVAVIFA | SEQ ID NO 436 |
| HH437 | VRLRIRVAVIGA | SEQ ID NO 437 |
| HH438 | VRLRIRVAVIHA | SEQ ID NO 438 |
| HH439 | VRLRIRVAVIAA | SEQ ID NO 439 |
| HH440 | VRLRIRVAVIKA | SEQ ID NO 440 |
| HH441 | VRLRIRVAVILA | SEQ ID NO 441 |
| HH442 | VRLRIRVAVIMA | SEQ ID NO 442 |
| HH443 | VRLRIRVAVINA | SEQ ID NO 443 |
| HH444 | VRLRIRVAVIPA | SEQ ID NO 444 |
| HH445 | VRLRIRVAVIQA | SEQ ID NO 445 |
| HH446 | VRLRIRVAVISA | SEQ ID NO 446 |
| HH447 | VRLRIRVAVITA | SEQ ID NO 447 |
| HH448 | VRLRIRVAVIVA | SEQ ID NO 448 |
| HH449 | VRLRIRVAVIWA | SEQ ID NO 449 |
| HH450 | VRLRIRVAVIYA | SEQ ID NO 450 |
| HH451 | VRLRIRVAVIRD | SEQ ID NO 451 |
| HH452 | VRLRIRVAVIRE | SEQ ID NO 452 |
| HH453 | VRLRIRVAVIRF | SEQ ID NO 453 |
| HH454 | VRLRIRVAVIRG | SEQ ID NO 454 |
| HH455 | VRLRIRVAVIRH | SEQ ID NO 455 |
| HH456 | VRLRIRVAVIRI | SEQ ID NO 456 |
| HH457 | VRLRIRVAVIRK | SEQ ID NO 457 |
| HH458 | VRLRIRVAVIRL | SEQ ID NO 458 |
| HH459 | VRLRIRVAVIRM | SEQ ID NO 459 |
| HH460 | VRLRIRVAVIRN | SEQ ID NO 460 |
| HH461 | VRLRIRVAVIRP | SEQ ID NO 461 |
| HH462 | VRLRIRVAVIRQ | SEQ ID NO 462 |
| HH463 | VRLRIRVAVIRR | SEQ ID NO 463 |
| HH464 | VRLRIRVAVIRS | SEQ ID NO 464 |
| HH465 | VRLRIRVAVIRT | SEQ ID NO 465 |
| HH466 | VRLRIRVAVIRV | SEQ ID NO 466 |
| HH467 | VRLRIRVAVIRW | SEQ ID NO 467 |
| HH468 | VRLRIRVAVIRY | SEQ ID NO 468 |
| HH469 | RRRRVKWWR | SEQ ID NO 469 |
| HH470 | WLRKKQGRL | SEQ ID NO 470 |
| HH471 | KWVRVYLRW | SEQ ID NO 471 |
| HH472 | GKVMISIVR | SEQ ID NO 472 |
| HH473 | IKVVRWRWR | SEQ ID NO 473 |
| HH474 | RRRRWVRR | SEQ ID NO 474 |
| HH475 | HMNRFRTVY | SEQ ID NO 475 |
| HH476 | VRKRGSWRM | SEQ ID NO 476 |
| HH477 | RIIRTYKRG | SEQ ID NO 477 |
| HH478 | WWRWRLRLI | SEQ ID NO 478 |
| HH479 | WLNRLYIRL | SEQ ID NO 479 |
| HH480 | IWRWTKWFW | SEQ ID NO 480 |
| HH481 | RFKGSWKYR | SEQ ID NO 481 |
| HH482 | VWVIRKKKW | SEQ ID NO 482 |
| HH483 | RGRRVWRLF | SEQ ID NO 483 |
| HH484 | WRWRKVKQW | SEQ ID NO 484 |
| HH485 | WWKYWRKVI | SEQ ID NO 485 |
| HH486 | WLVRIRKRI | SEQ ID NO 486 |
| HH487 | WWRWWQRRW | SEQ ID NO 487 |
| HH488 | RKKWWWKIR | SEQ ID NO 488 |
| HH489 | WVRKKIRRR | SEQ ID NO 489 |
| HH490 | RYRRRWYIR | SEQ ID NO 490 |
| HH491 | LYRWVWKVG | SEQ ID NO 491 |
| HH492 | VRRRWFKWL | SEQ ID NO 492 |

TABLE 2A-continued

Peptides utilized in these studies. All peptides were amidated at the C-terminus unless otherwise noted.

| Name | Sequence | ID |
| --- | --- | --- |
| HH493 | RRLWWWKWL | SEQ ID NO 493 |
| HH494 | WRFKWTRRG | SEQ ID NO 494 |
| HH495 | KWWRHRRMW | SEQ ID NO 495 |
| HH496 | RRKRWWWRT | SEQ ID NO 496 |
| HH497 | WRRKIVRVW | SEQ ID NO 497 |
| HH498 | KLRRGSLWR | SEQ ID NO 498 |
| HH499 | RVIWWWRRK | SEQ ID NO 499 |
| HH500 | TWRVWKVRW | SEQ ID NO 500 |
| HH501 | QRGIVIWRK | SEQ ID NO 501 |
| HH502 | GKWWKWGIW | SEQ ID NO 502 |
| HH503 | RVRRWWFVR | SEQ ID NO 503 |
| HH504 | FWRRRVKWR | SEQ ID NO 504 |
| HH505 | FRRYQNIVR | SEQ ID NO 505 |
| HH506 | RFWRWIFKW | SEQ ID NO 506 |
| HH507 | KRNVKRNWK | SEQ ID NO 507 |
| HH508 | WYSLIIFKR | SEQ ID NO 508 |
| HH509 | RKNRRIRVV | SEQ ID NO 509 |
| HH510 | FFRKRRWRI | SEQ ID NO 510 |
| HH511 | WKIRKVIKW | SEQ ID NO 511 |
| HH512 | IKWYWRKKK | SEQ ID NO 512 |
| HH513 | KRGWRKRWW | SEQ ID NO 513 |
| HH514 | RKWMGRRIR | SEQ ID NO 514 |
| HH515 | WKGKKRRVI | SEQ ID NO 515 |
| HH516 | KVIRYKVYI | SEQ ID NO 516 |
| HH517 | RRTRKWILR | SEQ ID NO 517 |
| HH518 | YNWNWLRRW | SEQ ID NO 518 |
| HH519 | KWKHWRWQW | SEQ ID NO 519 |
| HH520 | RKIVVKVRV | SEQ ID NO 520 |
| HH521 | QYLGWRFKW | SEQ ID NO 521 |
| HH522 | KIKTRKVKY | SEQ ID NO 522 |
| HH523 | VWIRWRRRW | SEQ ID NO 523 |
| HH524 | WGVRVRRLI | SEQ ID NO 524 |
| HH525 | WWKRVWKFI | SEQ ID NO 525 |
| HH526 | YWIYSRLRR | SEQ ID NO 526 |
| HH527 | RRYWKFKRR | SEQ ID NO 527 |
| HH528 | IVRRVIIRV | SEQ ID NO 528 |
| HH529 | ARRGLKVW | SEQ ID NO 529 |
| HH530 | RRWVRRWWR | SEQ ID NO 530 |
| HH531 | WKWKWKWQS | SEQ ID NO 531 |
| HH532 | RWKVKQRRR | SEQ ID NO 532 |
| HH533 | YWTKFRLRI | SEQ ID NO 533 |
| HH534 | WVIKVRIRW | SEQ ID NO 534 |
| HH535 | ARVQVYKYR | SEQ ID NO 535 |
| HH536 | KWRWHWVYV | SEQ ID NO 536 |
| HH537 | KVKYKFRRW | SEQ ID NO 537 |
| HH538 | RFRKRKNRI | SEQ ID NO 538 |
| HH539 | MFRRRFIWK | SEQ ID NO 539 |
| HH540 | WRLRRFRLW | SEQ ID NO 540 |
| HH541 | WIQRIRIWV | SEQ ID NO 541 |
| HH542 | RRYHWRIYI | SEQ ID NO 542 |
| HH543 | SRFWRRWRK | SEQ ID NO 543 |
| HH544 | YRVWIIRRK | SEQ ID NO 544 |
| HH545 | WRVSWLIWR | SEQ ID NO 545 |
| HH546 | RFVKRKIVW | SEQ ID NO 546 |
| HH547 | RIYKIRWII | SEQ ID NO 547 |
| HH548 | RKFWHRGTI | SEQ ID NO 548 |
| HH549 | AWVVWRKRW | SEQ ID NO 549 |
| HH550 | WVWGKVRWG | SEQ ID NO 550 |
| HH551 | FGIRFRRMV | SEQ ID NO 551 |
| HH552 | FWIRKVFRI | SEQ ID NO 552 |
| HH553 | KRWKVRVVW | SEQ ID NO 553 |
| HH554 | KIRIWRIWV | SEQ ID NO 554 |
| HH555 | RGRWKRIKK | SEQ ID NO 555 |
| HH556 | RLWFLVLRR | SEQ ID NO 556 |
| HH557 | IIRVTRWTK | SEQ ID NO 557 |
| HH558 | AMWRWKWRK | SEQ ID NO 558 |
| HH559 | TRKYFGRFV | SEQ ID NO 559 |
| HH560 | ARRVKKKRR | SEQ ID NO 560 |
| HH561 | RWWKIWKRR | SEQ ID NO 561 |
| HH562 | RWRYKIQKW | SEQ ID NO 562 |
| HH563 | RVGIKIKMK | SEQ ID NO 563 |
| HH564 | WVLKLRYKW | SEQ ID NO 564 |
| HH565 | FRRKWIFKK | SEQ ID NO 565 |
| HH566 | WIQKLWRQR | SEQ ID NO 566 |

TABLE 2A-continued

Peptides utilized in these studies. All peptides were amidated at the C-terminus unless otherwise noted.

| Name | Sequence | ID |
| --- | --- | --- |
| HH567 | RIVRLHVRK | SEQ ID NO 567 |
| HH568 | VRIGWRRVK | SEQ ID NO 568 |
| HH569 | RRRIGIKRF | SEQ ID NO 569 |
| HH570 | RRRRKKVRI | SEQ ID NO 570 |
| HH571 | KLWRYKRWR | SEQ ID NO 571 |
| HH572 | RIRRFIKKW | SEQ ID NO 572 |
| HH573 | LWHKKKKIW | SEQ ID NO 573 |
| HH574 | LTRRFWLRR | SEQ ID NO 574 |
| HH575 | RRRYVIRRR | SEQ ID NO 575 |
| HH576 | WGWRWIWIK | SEQ ID NO 576 |
| HH577 | RWRWQRGRF | SEQ ID NO 577 |
| HH578 | RRKKWKVRI | SEQ ID NO 578 |
| HH579 | KMKLYKGSM | SEQ ID NO 579 |
| HH580 | GTIRWWRRR | SEQ ID NO 580 |
| HH581 | SLRRYIWRF | SEQ ID NO 581 |
| HH582 | GRYWKKWRR | SEQ ID NO 582 |
| HH583 | WIRQFRWKK | SEQ ID NO 583 |
| HH584 | AKVRRIKHW | SEQ ID NO 584 |
| HH585 | YSRRKTWWI | SEQ ID NO 585 |
| HH586 | RGRWWIRRQ | SEQ ID NO 586 |
| HH587 | WVFRWVWWR | SEQ ID NO 587 |
| HH588 | VYRVWWLKW | SEQ ID NO 588 |
| HH589 | WWVRRRVGW | SEQ ID NO 589 |
| HH590 | WFKIKRLYL | SEQ ID NO 590 |
| HH591 | WKMWKRGWT | SEQ ID NO 591 |
| HH592 | RWWRKSRRL | SEQ ID NO 592 |
| HH593 | FWRIRWWRW | SEQ ID NO 593 |
| HH594 | VWWFGKRTT | SEQ ID NO 594 |
| HH595 | VRIIWWIWR | SEQ ID NO 595 |
| HH596 | WWVRIWRWM | SEQ ID NO 596 |
| HH597 | RKWKKWFHR | SEQ ID NO 597 |
| HH598 | RKWKFWGYK | SEQ ID NO 598 |
| HH599 | FWYIWSKRV | SEQ ID NO 599 |
| HH600 | YWRQFRRKQ | SEQ ID NO 600 |
| HH601 | WWWKVKSRR | SEQ ID NO 601 |
| HH602 | WRLWIWWIR | SEQ ID NO 602 |
| HH603 | QFRVNRRKY | SEQ ID NO 603 |
| HH604 | RYRFWWVRR | SEQ ID NO 604 |
| HH605 | THIWLRRRR | SEQ ID NO 605 |
| HH606 | RRRFRKRRM | SEQ ID NO 606 |
| HH607 | LYTRVRRYS | SEQ ID NO 607 |
| HH608 | WSIRRLWWL | SEQ ID NO 608 |
| HH609 | YKIKRRRYG | SEQ ID NO 609 |
| HH610 | WKRIQFRRK | SEQ ID NO 610 |
| HH611 | HKKRRIWRK | SEQ ID NO 611 |
| HH612 | WRLIRWWIR | SEQ ID NO 612 |
| HH613 | LRKNWWWRR | SEQ ID NO 613 |
| HH614 | VKRIRIWML | SEQ ID NO 614 |
| HH615 | IRYRNWKWL | SEQ ID NO 615 |
| HH616 | GRILSRRWK | SEQ ID NO 616 |
| HH617 | KHWKIHVRW | SEQ ID NO 617 |
| HH618 | WIYWKVWRR | SEQ ID NO 618 |
| HH619 | KLWKVRNRR | SEQ ID NO 619 |
| HH620 | RRVYYYKWV | SEQ ID NO 620 |
| HH621 | WRWGVFRLR | SEQ ID NO 621 |
| HH622 | IWRVLKKRV | SEQ ID NO 622 |
| HH623 | AKKFWRNWI | SEQ ID NO 623 |
| HH624 | RQWRKVVKK | SEQ ID NO 624 |
| HH625 | GWKRWWVML | SEQ ID NO 625 |
| HH626 | KWRRTRRRK | SEQ ID NO 626 |
| HH627 | FRRMKRFLR | SEQ ID NO 627 |
| HH628 | RSWNWWWIR | SEQ ID NO 628 |
| HH629 | WRRRIWINR | SEQ ID NO 629 |
| HH630 | RWKWFYLKR | SEQ ID NO 630 |
| HH631 | RKRTIWRII | SEQ ID NO 631 |
| HH632 | RRRVWWRRR | SEQ ID NO 632 |
| HH633 | KWRFKWWKR | SEQ ID NO 633 |
| HH634 | KWIWGWRRW | SEQ ID NO 634 |
| HH635 | WIKRKWKMR | SEQ ID NO 635 |
| HH636 | MWKKVLRRV | SEQ ID NO 636 |
| HH637 | WRWRIFHWL | SEQ ID NO 637 |
| HH638 | KIQRWKGKR | SEQ ID NO 638 |
| HH639 | LWYKYWRWR | SEQ ID NO 639 |
| HH640 | YVRRIWKIT | SEQ ID NO 640 |

TABLE 2A-continued

Peptides utilized in these studies. All peptides were amidated at the C-terminus unless otherwise noted.

| Name | Sequence | ID |
|---|---|---|
| HH641 | RWRQYRSRW | SEQ ID NO 641 |
| HH642 | VGRWKRRRW | SEQ ID NO 642 |
| HH643 | KSSRIYILF | SEQ ID NO 643 |
| HH644 | AKWWWYRKI | SEQ ID NO 644 |
| HH645 | FYWWRWFRV | SEQ ID NO 645 |
| HH646 | RTRWLRYRR | SEQ ID NO 646 |
| HH647 | WNIIWWIRR | SEQ ID NO 647 |
| HH648 | KRGFWWWRI | SEQ ID NO 648 |
| HH649 | RRRKKYIIR | SEQ ID NO 649 |
| HH650 | VWKVGWYYR | SEQ ID NO 650 |
| HH651 | LKFSTGRVR | SEQ ID NO 651 |
| HH652 | RRVWVRRKR | SEQ ID NO 652 |
| HH653 | RFWYMWKYV | SEQ ID NO 653 |
| HH654 | WYVRWMGRR | SEQ ID NO 654 |
| HH655 | WKRRMRRRK | SEQ ID NO 655 |
| HH656 | RVLRRVSWV | SEQ ID NO 656 |
| HH657 | RRLRKKWGW | SEQ ID NO 657 |
| HH658 | WYKKIRLII | SEQ ID NO 658 |
| HH659 | IYIIIWRTK | SEQ ID NO 659 |
| HH660 | TWRMRVKVS | SEQ ID NO 660 |
| HH661 | AWWKIRWRI | SEQ ID NO 661 |
| HH662 | RVRRYRWSW | SEQ ID NO 662 |
| HH663 | IWRIRRFRI | SEQ ID NO 663 |
| HH664 | KIRRKWWWF | SEQ ID NO 664 |
| HH665 | RRFWWIKIR | SEQ ID NO 665 |
| HH666 | WYWWRVRRV | SEQ ID NO 666 |
| HH667 | WYKLWRRKV | SEQ ID NO 667 |
| HH668 | WWFSWRWRV | SEQ ID NO 668 |
| HH669 | RFKTRRGWR | SEQ ID NO 669 |
| HH670 | WIWIVRRRV | SEQ ID NO 670 |
| HH671 | RRFKKWMYW | SEQ ID NO 671 |
| HH672 | RWYRVIRWK | SEQ ID NO 672 |
| HH673 | YRWMVRWVR | SEQ ID NO 673 |
| HH674 | KVRRYNRRR | SEQ ID NO 674 |
| HH675 | WFVWNRRVV | SEQ ID NO 675 |
| HH676 | RWKWRWRWY | SEQ ID NO 676 |
| HH677 | ARWRVRKWW | SEQ ID NO 677 |
| HH678 | KIKFWIIRR | SEQ ID NO 678 |
| HH679 | WYWRVRLQW | SEQ ID NO 679 |
| HH680 | YWWWKRRRR | SEQ ID NO 680 |
| HH681 | FIKRVRRRW | SEQ ID NO 681 |
| HH682 | VSVVFRRRY | SEQ ID NO 682 |
| HH683 | KFRVMVRVL | SEQ ID NO 683 |
| HH684 | WMYYKRRRR | SEQ ID NO 684 |
| HH685 | IWIWWRWRW | SEQ ID NO 685 |
| HH686 | WKKKKIIRV | SEQ ID NO 686 |
| HH687 | RRGWRRRRR | SEQ ID NO 687 |
| HH688 | WRWRKIWKW | SEQ ID NO 688 |
| HH689 | WWRWKRRII | SEQ ID NO 689 |
| HH690 | WKVRWKIRR | SEQ ID NO 690 |
| HH691 | RFWVRGRRS | SEQ ID NO 691 |
| HH692 | RRWVLWRRR | SEQ ID NO 692 |
| HH693 | KYIWKKRRY | SEQ ID NO 693 |
| HH694 | KWQWIRKIR | SEQ ID NO 694 |
| HH695 | YWIRRRWRL | SEQ ID NO 695 |
| HH696 | RVKWIKWLH | SEQ ID NO 696 |
| HH697 | YVRQWKKRR | SEQ ID NO 697 |
| HH698 | WKIVGVFRV | SEQ ID NO 698 |
| HH699 | VIKYVRMWW | SEQ ID NO 699 |
| HH700 | RRRRVWRVR | SEQ ID NO 700 |
| HH701 | RRRKIRVYR | SEQ ID NO 701 |
| HH702 | RRNRWRRIR | SEQ ID NO 702 |
| HH703 | IRKWIWRRV | SEQ ID NO 703 |
| HH704 | QRWRVRRRY | SEQ ID NO 704 |
| HH705 | WWMIIKIRN | SEQ ID NO 705 |
| HH706 | ARRRGRRVM | SEQ ID NO 706 |
| HH707 | RRWHWRKRK | SEQ ID NO 707 |
| HH708 | KRFLRKRRF | SEQ ID NO 708 |
| HH709 | RWKGWYLRT | SEQ ID NO 709 |
| HH710 | WSWRGRRKF | SEQ ID NO 710 |
| HH711 | KIIMKRRRW | SEQ ID NO 711 |
| HH712 | VWKRFLHWR | SEQ ID NO 712 |
| HH713 | RLKRRKKWR | SEQ ID NO 713 |
| HH714 | AVRKFRRVT | SEQ ID NO 714 |

TABLE 2A-continued

Peptides utilized in these studies. All peptides were amidated at the C-terminus unless otherwise noted.

| Name | Sequence | ID |
|---|---|---|
| HH715 | IKQRFWWRT | SEQ ID NO 715 |
| HH716 | WKIVVWIIK | SEQ ID NO 716 |
| HH717 | LYRWIVWKR | SEQ ID NO 717 |
| HH718 | WWWRWRIRK | SEQ ID NO 718 |
| HH719 | RLWRKWQWN | SEQ ID NO 719 |
| HH720 | RVKLRWGWR | SEQ ID NO 720 |
| HH721 | AWRYKRRIF | SEQ ID NO 721 |
| HH722 | KRWQIRGIT | SEQ ID NO 722 |
| HH723 | KRWRWRWRW | SEQ ID NO 723 |
| HH724 | KRWVYKYRV | SEQ ID NO 724 |
| HH725 | VHWRWRFWK | SEQ ID NO 725 |
| HH726 | FVGKTKRKR | SEQ ID NO 726 |
| HH727 | RLRFGWFLF | SEQ ID NO 727 |
| HH728 | AKRWIWIQV | SEQ ID NO 728 |
| HH729 | RKYVRRWVY | SEQ ID NO 729 |
| HH730 | YRVYWWWWR | SEQ ID NO 730 |
| HH731 | KRRKKRRVR | SEQ ID NO 731 |
| HH732 | KKVRFTITW | SEQ ID NO 732 |
| HH733 | KLWYWKKVV | SEQ ID NO 733 |
| HH734 | WRWGLRWWQ | SEQ ID NO 734 |
| HH735 | AFFYRWWIR | SEQ ID NO 735 |
| HH736 | WYWRRRRLK | SEQ ID NO 736 |
| HH737 | YKFRWRIYI | SEQ ID NO 737 |
| HH738 | WLRKVWNWR | SEQ ID NO 738 |
| HH739 | RVRFKVYRV | SEQ ID NO 739 |
| HH740 | RWLSKIWKV | SEQ ID NO 740 |
| HH741 | RRRLGWRRG | SEQ ID NO 741 |
| HH742 | KKWGGGLVK | SEQ ID NO 742 |
| HH743 | YWWLWRKKR | SEQ ID NO 743 |
| HH744 | WIRLWVKWR | SEQ ID NO 744 |
| HH745 | GRRSTHWRI | SEQ ID NO 745 |
| HH746 | KKKLFINTW | SEQ ID NO 746 |
| HH747 | VYRRRVKG | SEQ ID NO 747 |
| HH748 | KGWIIWKIV | SEQ ID NO 748 |
| HH749 | VFHRIRRIK | SEQ ID NO 749 |
| HH750 | RLRLWKSKR | SEQ ID NO 750 |
| HH751 | RRKVFKLRR | SEQ ID NO 751 |
| HH752 | VWLKVYWFK | SEQ ID NO 752 |
| HH753 | VRWGRRRWV | SEQ ID NO 753 |
| HH754 | RYNWVRRKK | SEQ ID NO 754 |
| HH755 | KIRWRKYHL | SEQ ID NO 755 |
| HH756 | VIWRWRKFY | SEQ ID NO 756 |
| HH757 | RRWWKWWWR | SEQ ID NO 757 |
| HH758 | WRVKGKRSK | SEQ ID NO 758 |
| HH759 | RWRTRRNIV | SEQ ID NO 759 |
| HH760 | WWFSIRLWR | SEQ ID NO 760 |
| HH761 | YTWYIKKKR | SEQ ID NO 761 |
| HH762 | VWRKKKYWR | SEQ ID NO 762 |
| HH763 | YLTRFVKYF | SEQ ID NO 763 |
| HH764 | KRWKHIRRI | SEQ ID NO 764 |
| HH765 | WIVWIRKRI | SEQ ID NO 765 |
| HH766 | RRWVIRIYK | SEQ ID NO 766 |
| HH767 | WFWRRKMIR | SEQ ID NO 767 |
| HH768 | RYRRWVRKR | SEQ ID NO 768 |
| HH769 | RKWWKWRR | SEQ ID NO 769 |
| HH770 | RIWMFKIFR | SEQ ID NO 770 |
| HH771 | IVRVGIFRL | SEQ ID NO 771 |
| HH772 | IIRLIKWWR | SEQ ID NO 772 |
| HH773 | WVRRYQMRR | SEQ ID NO 773 |
| HH774 | WQVVMRYRR | SEQ ID NO 774 |
| HH775 | KKWKVWRFG | SEQ ID NO 775 |
| HH776 | WRYWWTRRI | SEQ ID NO 776 |
| HH777 | RIRKGWKWG | SEQ ID NO 777 |
| HH778 | KKRRGNRVR | SEQ ID NO 778 |
| HH779 | VMRKLRRRW | SEQ ID NO 779 |
| HH780 | RNRTHWWRK | SEQ ID NO 780 |
| HH781 | RFTWWWRKF | SEQ ID NO 781 |
| HH782 | KRIRYKRWH | SEQ ID NO 782 |
| HH783 | RWRRYGRVY | SEQ ID NO 783 |
| HH784 | TVVKKRVKK | SEQ ID NO 784 |
| HH785 | RKYRRRYRR | SEQ ID NO 785 |
| HH786 | YFRWWKRWI | SEQ ID NO 786 |
| HH787 | WWQWIVWRK | SEQ ID NO 787 |
| HH788 | RKRLYRWIK | SEQ ID NO 788 |

TABLE 2A-continued

Peptides utilized in these studies. All peptides were amidated at the C-terminus unless otherwise noted.

| Name | Sequence | ID |
|---|---|---|
| HH789 | GWWKNWRWW | SEQ ID NO 789 |
| HH790 | KWWWYWYRR | SEQ ID NO 790 |
| HH791 | RFKWFIRRF | SEQ ID NO 791 |
| HH792 | RIRRLWNIV | SEQ ID NO 792 |
| HH793 | ARWMWRRWR | SEQ ID NO 793 |
| HH794 | LVRWVWGKR | SEQ ID NO 794 |
| HH795 | KRWLKWWRV | SEQ ID NO 795 |
| HH796 | FVYRGWRRK | SEQ ID NO 796 |
| HH797 | RRRWKIYKW | SEQ ID NO 797 |
| HH798 | KRWWQWRWF | SEQ ID NO 798 |
| HH799 | KRVKVRWVT | SEQ ID NO 799 |
| HH800 | RFKYWRWWQ | SEQ ID NO 800 |
| HH801 | KRQWWRVFK | SEQ ID NO 801 |
| HH802 | FKIVWWRRR | SEQ ID NO 802 |
| HH803 | QWWWKYRWK | SEQ ID NO 803 |
| HH804 | RWLRIRKVY | SEQ ID NO 804 |
| HH805 | RYKRVVYRH | SEQ ID NO 805 |
| HH806 | KVRWKWWGW | SEQ ID NO 806 |
| HH807 | IWKVRIFKR | SEQ ID NO 807 |
| HH808 | AIWHKTRRL | SEQ ID NO 808 |
| HH809 | IRQRVRWRW | SEQ ID NO 809 |
| HH810 | MKVWIRWRI | SEQ ID NO 810 |
| HH811 | QRRWWGRFK | SEQ ID NO 811 |
| HH812 | NKRVWFIYR | SEQ ID NO 812 |
| HH813 | RVVNWKGGL | SEQ ID NO 813 |
| HH814 | RYRRFRVRW | SEQ ID NO 814 |
| HH815 | KKVRRVIWW | SEQ ID NO 815 |
| HH816 | WFTRWKWRW | SEQ ID NO 816 |
| HH817 | KWVWFRWRK | SEQ ID NO 817 |
| HH818 | KYLRSVIFY | SEQ ID NO 818 |
| HH819 | FKRSWVQIV | SEQ ID NO 819 |
| HH820 | RWWFIRKWW | SEQ ID NO 820 |
| HH821 | IRRWKRVWW | SEQ ID NO 821 |
| HH822 | QKWYRQRRN | SEQ ID NO 822 |
| HH823 | VWRKWYRVK | SEQ ID NO 823 |
| HH824 | KKKLWRKFR | SEQ ID NO 824 |
| HH825 | RRWWWWRFN | SEQ ID NO 825 |
| HH826 | WFFKSKVYW | SEQ ID NO 826 |
| HH827 | RVVNLNWRW | SEQ ID NO 827 |
| HH828 | RWRRNWMTK | SEQ ID NO 828 |
| HH829 | WKIWKIRWF | SEQ ID NO 829 |
| HH830 | WWFWVIRKY | SEQ ID NO 830 |
| HH831 | RYVKIRWVR | SEQ ID NO 831 |
| HH832 | RIWILSWRW | SEQ ID NO 832 |
| HH833 | KSWRKLFIW | SEQ ID NO 833 |
| HH834 | VWVRWKIWY | SEQ ID NO 834 |
| HH835 | KKRRFKRRY | SEQ ID NO 835 |
| HH836 | RFWKKIRRH | SEQ ID NO 836 |
| HH837 | RKVWWRVFY | SEQ ID NO 837 |
| HH838 | YWRRKWRRK | SEQ ID NO 838 |
| HH839 | KRIRRWKWW | SEQ ID NO 839 |
| HH840 | YWRYLWIRF | SEQ ID NO 840 |
| HH841 | IIYKWRWYW | SEQ ID NO 841 |
| HH842 | QTVYLIFRR | SEQ ID NO 842 |
| HH843 | AKKIKWLVW | SEQ ID NO 843 |
| HH844 | YRFVRRWIV | SEQ ID NO 844 |
| HH845 | VWRRYWWYR | SEQ ID NO 845 |
| HH846 | ARKWKYWRF | SEQ ID NO 846 |
| HH847 | RKRVIKRWR | SEQ ID NO 847 |
| HH848 | RSFWWMWFK | SEQ ID NO 848 |
| HH849 | WRINIFKRI | SEQ ID NO 849 |
| HH850 | RWRVLKRRK | SEQ ID NO 850 |
| HH851 | RWWVIWWWK | SEQ ID NO 851 |
| HH852 | KLIRIWWWW | SEQ ID NO 852 |
| HH853 | FKRKRWWGI | SEQ ID NO 853 |
| HH854 | VWHWWRWRW | SEQ ID NO 854 |
| HH855 | WKRWLIIGR | SEQ ID NO 855 |
| HH856 | AYRWWTRFK | SEQ ID NO 856 |
| HH857 | SWWWIWLKK | SEQ ID NO 857 |
| HH858 | FVIWKYIRV | SEQ ID NO 858 |
| HH859 | RWVRTRRRR | SEQ ID NO 859 |
| HH860 | RRSWWYKRR | SEQ ID NO 860 |
| HH861 | RKYVWWKSI | SEQ ID NO 861 |
| HH862 | WWKRYIVKK | SEQ ID NO 862 |

TABLE 2A-continued

Peptides utilized in these studies. All peptides were amidated at the C-terminus unless otherwise noted.

| Name | Sequence | ID |
|---|---|---|
| HH863 | WFIRVWRYR | SEQ ID NO 863 |
| HH864 | WKMWLRKHW | SEQ ID NO 864 |
| HH865 | RRFFWKKGI | SEQ ID NO 865 |
| HH866 | KRWTFWSRR | SEQ ID NO 866 |
| HH867 | AVQRWRWVV | SEQ ID NO 867 |
| HH868 | IWKYGWRYK | SEQ ID NO 868 |
| HH869 | IIKWWRRWR | SEQ ID NO 869 |
| HH870 | AFRKVKRWG | SEQ ID NO 870 |
| HH871 | MGFTRKWQF | SEQ ID NO 871 |
| HH872 | NWIRWRKWR | SEQ ID NO 872 |
| HH873 | RIGRKLRIR | SEQ ID NO 873 |
| HH874 | RWWRWRHVI | SEQ ID NO 874 |
| HH875 | RLVSKRRRK | SEQ ID NO 875 |
| HH876 | RRKYWKKYR | SEQ ID NO 876 |
| HH877 | IILWWYRRK | SEQ ID NO 877 |
| HH878 | IYFWWWRIR | SEQ ID NO 878 |
| HH879 | HKRKWWRFR | SEQ ID NO 879 |
| HH880 | IGRFWRRWL | SEQ ID NO 880 |
| HH881 | RIRRVLVYV | SEQ ID NO 881 |
| HH882 | WWLRGRRWL | SEQ ID NO 882 |
| HH883 | VRIRKRRWR | SEQ ID NO 883 |
| HH884 | WWRRKWWRR | SEQ ID NO 884 |
| HH885 | WWWRSFRKR | SEQ ID NO 885 |
| HH886 | VGQKWRKRT | SEQ ID NO 886 |
| HH887 | FRRRYRVYR | SEQ ID NO 887 |
| HH888 | RIRRKRKGR | SEQ ID NO 888 |
| HH889 | WKWVTRMYI | SEQ ID NO 889 |
| HH890 | KVVRKKRLR | SEQ ID NO 890 |
| HH891 | RKRRKHWRY | SEQ ID NO 891 |
| HH892 | RVTRTWQRW | SEQ ID NO 892 |
| HH893 | RRRITRKRI | SEQ ID NO 893 |
| HH894 | RLILIKKKW | SEQ ID NO 894 |
| HH895 | WKRRWSRSR | SEQ ID NO 895 |
| HH896 | MWWWFLWRR | SEQ ID NO 896 |
| HH897 | RWVRIWKKK | SEQ ID NO 897 |
| HH898 | KRRVWRMWR | SEQ ID NO 898 |
| HH899 | WHWWIRWWR | SEQ ID NO 899 |
| HH900 | WWRRLRWLV | SEQ ID NO 900 |
| HH901 | KWWIWKRRR | SEQ ID NO 901 |
| HH902 | RYGRKWMIW | SEQ ID NO 902 |
| HH903 | RVKKIKLFI | SEQ ID NO 903 |
| HH904 | RIRYIQRVW | SEQ ID NO 904 |
| HH905 | RLIRWWRKR | SEQ ID NO 905 |
| HH906 | QRGRWLRRG | SEQ ID NO 906 |
| HH907 | RRRRWIRKK | SEQ ID NO 907 |
| HH908 | LGRRWRYRR | SEQ ID NO 908 |
| HH909 | FKIVHVKVR | SEQ ID NO 909 |
| HH910 | FRKKYRVRR | SEQ ID NO 910 |
| HH911 | WKYKYRIRL | SEQ ID NO 911 |
| HH912 | HVRRWWRII | SEQ ID NO 912 |
| HH913 | RFKWWRRYW | SEQ ID NO 913 |
| HH914 | RRRRMRKKI | SEQ ID NO 914 |
| HH915 | RRIRGRVGR | SEQ ID NO 915 |
| HH916 | AFWRWIRFK | SEQ ID NO 916 |
| HH917 | VKKRKIVIY | SEQ ID NO 917 |
| HH918 | KRVKWTWRK | SEQ ID NO 918 |
| HH919 | TGVGRGYRI | SEQ ID NO 919 |
| HH920 | LSWKWWRRV | SEQ ID NO 920 |
| HH921 | IKTFIKRWR | SEQ ID NO 921 |
| HH922 | KMRLKWKRR | SEQ ID NO 922 |
| HH923 | WRWYVTRRK | SEQ ID NO 923 |
| HH924 | IYRRRKLR | SEQ ID NO 924 |
| HH925 | VWWKWWRWW | SEQ ID NO 925 |
| HH926 | KYKKGWRVV | SEQ ID NO 926 |
| HH927 | KWRRWYYWR | SEQ ID NO 927 |
| HH928 | RRWVFGRRY | SEQ ID NO 928 |
| HH929 | GFTWKKKRR | SEQ ID NO 929 |
| HH930 | YKKIRIKRR | SEQ ID NO 930 |
| HH931 | VWIRRIKRR | SEQ ID NO 931 |
| HH932 | WWKWIRKIV | SEQ ID NO 932 |
| HH933 | WRRKWWSRW | SEQ ID NO 933 |
| HH934 | VTRRRTRIK | SEQ ID NO 934 |
| HH935 | RKRWFVYIW | SEQ ID NO 935 |
| HH936 | IIKWKRIMI | SEQ ID NO 936 |

TABLE 2A-continued

Peptides utilized in these studies. All peptides were amidated at the C-terminus unless otherwise noted.

| Name | Sequence | ID |
|---|---|---|
| HH937 | FNRWWKKI | SEQ ID NO 937 |
| HH938 | RYKSRRVRR | SEQ ID NO 938 |
| HH939 | VKVIKKFVR | SEQ ID NO 939 |
| HH940 | KWKWLQGRR | SEQ ID NO 940 |
| HH941 | KVRWYNIK | SEQ ID NO 941 |
| HH942 | FWFRIRKLK | SEQ ID NO 942 |
| HH943 | KRRKQRKYR | SEQ ID NO 943 |
| HH944 | AKNSKRRLW | SEQ ID NO 944 |
| HH945 | RNRRIFRYS | SEQ ID NO 945 |
| HH946 | RWTKWFLVR | SEQ ID NO 946 |
| HH947 | RIRRTRRTR | SEQ ID NO 947 |
| HH948 | KIRWWRISI | SEQ ID NO 948 |
| HH949 | YKGRWGRRW | SEQ ID NO 949 |
| HH950 | MYYRIKQKW | SEQ ID NO 950 |
| HH951 | WRIQRWRWQ | SEQ ID NO 951 |
| HH952 | IRRWSYRRW | SEQ ID NO 952 |
| HH953 | VRIWKIIWW | SEQ ID NO 953 |
| HH954 | RWRWWWLWK | SEQ ID NO 954 |
| HH955 | TKRRWIWIT | SEQ ID NO 955 |
| HH956 | RRWHYWKGW | SEQ ID NO 956 |
| HH957 | WRIRKWWMR | SEQ ID NO 957 |
| HH958 | KRRTRWWVR | SEQ ID NO 958 |
| HH959 | RKWRVWKRR | SEQ ID NO 959 |
| HH960 | WRVWKIRVR | SEQ ID NO 960 |
| HH961 | KYWGIGGWR | SEQ ID NO 961 |
| HH962 | RLISRRRKK | SEQ ID NO 962 |
| HH963 | VSRRIVRRM | SEQ ID NO 963 |
| HH964 | ITKWWRKRR | SEQ ID NO 964 |
| HH965 | KWKIQLWKI | SEQ ID NO 965 |
| HH966 | KKWTWWYVI | SEQ ID NO 966 |
| HH967 | SWKKNRKIW | SEQ ID NO 967 |
| HH968 | HKRQYRKWF | SEQ ID NO 968 |
| HH969 | IFKWFYRRK | SEQ ID NO 969 |
| Bac2A | RLARIVVIRVAR | SEQ ID NO 970 |
| Indolicidin | ILPWKWPWWPWRR | SEQ ID NO 971 |
| Scrambled | VRLRIRVAVIRA | SEQ ID NO 972 |
| HH970 | ILKWKWPWWKWRR | SEQ ID NO 973 |
| HH971 | ILPWKWRWWKWRR | SEQ ID NO 974 |
| HH972 | FLPKKFRWWKYRK | SEQ ID NO 975 |
| HH973 | FIKWKFRWWKWRK | SEQ ID NO 976 |
| HH974 | KWPWWPWRR | SEQ ID NO 977 |
| HH975 | KWPWWPWRK | SEQ ID NO 978 |
| HH976 | KFPWWPWRR | SEQ ID NO 979 |
| HH977 | KKPWWPWRR | SEQ ID NO 980 |
| HH978 | KWRWWPWRR | SEQ ID NO 981 |
| HH979 | KWPKWPWRR | SEQ ID NO 982 |
| HH980 | KWPWKPWRR | SEQ ID NO 983 |
| HH981 | KWPWWKWRR | SEQ ID NO 984 |
| HH982 | KWPWWPKRR | SEQ ID NO 985 |
| HH983 | KWPWWPWRR | SEQ ID NO 986 |
| HH984 | KFRWWPWRR | SEQ ID NO 987 |
| HH985 | KFRWWKWRR | SEQ ID NO 988 |
| HH986 | KWRWWKKRR | SEQ ID NO 989 |
| HH987 | KKKWWKWRR | SEQ ID NO 990 |
| HH988 | KFHWWIWRK | SEQ ID NO 991 |
| HH989 | KFHWWKWRK | SEQ ID NO 992 |
| HH990 | KFKWWKYRK | SEQ ID NO 993 |
| HH991 | KFKFFKYRK | SEQ ID NO 994 |
| HH992 | KFKFFKFRK | SEQ ID NO 995 |
| HH993 | PWWPWRR | SEQ ID NO 996 |
| HH994 | KWWPWRR | SEQ ID NO 997 |
| HH995 | PWKWRR | SEQ ID NO 998 |
| HH996 | RWWPWRR | SEQ ID NO 999 |
| HH997 | PKWPWRR | SEQ ID NO 1000 |
| HH998 | PWKPWRR | SEQ ID NO 1001 |
| HH999 | PWWKWRR | SEQ ID NO 1002 |
| HH1000 | PWWPKRR | SEQ ID NO 1003 |
| HH1001 | PWWPWRK | SEQ ID NO 1004 |
| HH1002 | RWWKWRR | SEQ ID NO 1005 |
| HH1003 | RWWKWRK | SEQ ID NO 1006 |
| HH1004 | RFWKWRR | SEQ ID NO 1007 |
| HH1005 | RWWIKRR | SEQ ID NO 1008 |
| HH1006 | RWWIYRR | SEQ ID NO 1009 |
| HH1007 | RFFKFRR | SEQ ID NO 1010 |

TABLE 2A-continued

Peptides utilized in these studies. All peptides were amidated at the C-terminus unless otherwise noted.

| Name | Sequence | ID |
|---|---|---|
| HH1008 | KWWKWKK | SEQ ID NO 1011 |
| HH1009 | KFFKFKK | SEQ ID NO 1012 |
| HHC1 | RWRWKRWWW | SEQ ID NO 1013 |
| HHC2 | RWRRWKWWW | SEQ ID NO 1014 |
| HHC3 | RWWRWRKWW | SEQ ID NO 1015 |
| HHC4 | RWRRKWWWW | SEQ ID NO 1016 |
| HHC5 | RWRWWKRWY | SEQ ID NO 1017 |
| HHC6 | RRKRWWWWW | SEQ ID NO 1018 |
| HHC7 | RWRIKRWWW | SEQ ID NO 1019 |
| HHC8 | KIWWWWRKR | SEQ ID NO 1020 |
| HHC9 | RWRRWKWWL | SEQ ID NO 1021 |
| HHC10 | KRWWKWIRW | SEQ ID NO 1022 |
| HHC11 | KRWWWWWKR | SEQ ID NO 1023 |
| HHC12 | IRWWKRWWR | SEQ ID NO 1024 |
| HHC13 | IKRWRWWR | SEQ ID NO 1025 |
| HHC14 | RRKWWWRWW | SEQ ID NO 1026 |
| HHC15 | RKWWRWWRW | SEQ ID NO 1027 |
| HHC16 | KRWWWWRFR | SEQ ID NO 1028 |
| HHC17 | IKRWWWRRW | SEQ ID NO 1029 |
| HHC18 | KRWWWWWKR | SEQ ID NO 1030 |
| HHC19 | KWRRWKRWW | SEQ ID NO 1031 |
| HHC20 | WRWWKIWKR | SEQ ID NO 1032 |
| HHC21 | WRWRWWKRW | SEQ ID NO 1033 |
| HHC22 | WKRWKWWKR | SEQ ID NO 1034 |
| HHC23 | RIKRWWWWR | SEQ ID NO 1035 |
| HHC24 | IWKRWWRRW | SEQ ID NO 1036 |
| HHC25 | KWWKIWWKR | SEQ ID NO 1037 |
| HHC26 | RKRWLWRWW | SEQ ID NO 1038 |
| HHC27 | KRWRWWRWW | SEQ ID NO 1039 |
| HHC28 | KKRWLWWWR | SEQ ID NO 1040 |
| HHC29 | RWWRKWWIR | SEQ ID NO 1041 |
| HHC30 | KWWRWWRKW | SEQ ID NO 1042 |
| HHC31 | KRWWIRWWR | SEQ ID NO 1043 |
| HHC32 | KIWWWWRRR | SEQ ID NO 1044 |
| HHC33 | RRRKWWIWW | SEQ ID NO 1045 |
| HHC34 | RRRWWWWWW | SEQ ID NO 1046 |
| HHC35 | RWWIRKWWR | SEQ ID NO 1047 |
| HHC36 | KRWWKWWRR | SEQ ID NO 1048 |
| HHC37 | KRWWRKWWR | SEQ ID NO 1049 |
| HHC38 | RRIWRWWWW | SEQ ID NO 1050 |
| HHC39 | IRRRKWWWW | SEQ ID NO 1051 |
| HHC40 | KRKIWWWIR | SEQ ID NO 1052 |
| HHC41 | RKIWWWRIR | SEQ ID NO 1053 |
| HHC42 | KRWIWRIR | SEQ ID NO 1054 |
| HHC43 | RWFRWWKRW | SEQ ID NO 1055 |
| HHC44 | WRWWKKWR | SEQ ID NO 1056 |
| HHC45 | WKRWWKKWR | SEQ ID NO 1057 |
| HHC46 | WKRWRWIRW | SEQ ID NO 1058 |
| HHC47 | WRWWKWWRR | SEQ ID NO 1059 |
| HHC48 | WKKWWKRRW | SEQ ID NO 1060 |
| HHC49 | WRWYWWKKR | SEQ ID NO 1061 |
| HHC50 | WRRWWKWWR | SEQ ID NO 1062 |
| HHC51 | IRMWVKRWR | SEQ ID NO 1063 |
| HHC52 | RIWYWYKRW | SEQ ID NO 1064 |
| HHC53 | FRRWWKWFK | SEQ ID NO 1065 |
| HHC54 | RVRWWKKRW | SEQ ID NO 1066 |
| HHC55 | RLKKVRWWW | SEQ ID NO 1067 |
| HHC56 | RWWLKIRKW | SEQ ID NO 1068 |
| HHC57 | LRWWWIKRI | SEQ ID NO 1069 |
| HHC58 | TRKVWWWRW | SEQ ID NO 1070 |
| HHC59 | KRFWIWFWR | SEQ ID NO 1071 |
| HHC60 | KKRWVWVIR | SEQ ID NO 1072 |
| HHC61 | KRWVWYRYW | SEQ ID NO 1073 |
| HHC62 | IRKWRRWWK | SEQ ID NO 1074 |
| HHC63 | RHWKTWWKR | SEQ ID NO 1075 |
| HHC64 | RRFKKWYWY | SEQ ID NO 1076 |
| HHC65 | RIKVIWWWR | SEQ ID NO 1077 |
| HHC66 | RKRLKWWIY | SEQ ID NO 1078 |
| HHC67 | LVFRKYWKR | SEQ ID NO 1079 |
| HHC68 | RRRWWWIIV | SEQ ID NO 1080 |
| HHC69 | KKRWVWIRY | SEQ ID NO 1081 |
| HHC70 | RWRIKFKRW | SEQ ID NO 1082 |
| HHC71 | KWKIFRRWW | SEQ ID NO 1083 |
| HHC72 | IWKRWRKRL | SEQ ID NO 1084 |

TABLE 2A-continued

Peptides utilized in these studies. All peptides were amidated at the C-terminus unless otherwise noted.

| Name | Sequence | ID |
|---|---|---|
| HHC73 | RRRKWWIWG | SEQ ID NO 1085 |
| HHC74 | RWLVLRKRW | SEQ ID NO 1086 |
| HHC75 | RKWIWRWFL | SEQ ID NO 1087 |
| HHC76 | KRRRIWWWK | SEQ ID NO 1088 |
| HHC77 | IWWKWRRWV | SEQ ID NO 1089 |
| HHC78 | LRWRWWKIK | SEQ ID NO 1090 |
| HHC79 | RWKMWWRWV | SEQ ID NO 1091 |
| HHC80 | VKRYYWRWR | SEQ ID NO 1092 |
| HHC81 | RWYRKRWSW | SEQ ID NO 1093 |
| HHC82 | KRKLIRWWW | SEQ ID NO 1094 |
| HHC83 | RWRWWIKII | SEQ ID NO 1095 |
| HHC84 | KFRKRVWWW | SEQ ID NO 1096 |
| HHC85 | IWIWRKLRW | SEQ ID NO 1097 |
| HHC86 | LRFILWWKR | SEQ ID NO 1098 |
| HHC87 | RVWFKRRWW | SEQ ID NO 1099 |
| HHC88 | RRWFVKWWY | SEQ ID NO 1100 |
| HHC89 | KWWLVWKRK | SEQ ID NO 1101 |
| HHC90 | RWILWWWRI | SEQ ID NO 1102 |
| HHC91 | KRWLTWRFR | SEQ ID NO 1103 |
| HHC92 | RKWRWRWLK | SEQ ID NO 1104 |
| HHC93 | IRRRWWWIV | SEQ ID NO 1105 |
| HHC94 | IKWWWRMRI | SEQ ID NO 1106 |
| HHC95 | RWKIFIRWW | SEQ ID NO 1107 |
| HHC96 | IRQWWRRWW | SEQ ID NO 1108 |
| HHC97 | RRRKTWYWW | SEQ ID NO 1109 |
| HHC98 | RRWWHLWRK | SEQ ID NO 1110 |
| HHC99 | RRWWMRWWV | SEQ ID NO 1111 |
| HHC100 | RRFKFIRWW | SEQ ID NO 1112 |
| HHC101 | INRKRRLRW | SEQ ID NO 1113 |
| HHC102 | RRMKKLRRK | SEQ ID NO 1114 |
| HHC103 | RKVRWKIRV | SEQ ID NO 1115 |
| HHC104 | VRIVRVRIR | SEQ ID NO 1116 |
| HHC105 | IKRVKRRKR | SEQ ID NO 1117 |
| HHC106 | RVKTWRVRT | SEQ ID NO 1118 |
| HHC107 | RVFVKIRMK | SEQ ID NO 1119 |
| HHC108 | IRGRIIFWV | SEQ ID NO 1120 |
| HHC109 | ATWIWVFRR | SEQ ID NO 1121 |
| HHC110 | KKSKQLWKR | SEQ ID NO 1122 |
| HHC111 | MINRVRLRW | SEQ ID NO 1123 |
| HHC112 | GGIRRLRWY | SEQ ID NO 1124 |
| HHC113 | RLVHWIRRV | SEQ ID NO 1125 |
| HHC114 | AWKIKKGRI | SEQ ID NO 1126 |
| HHC115 | FVVMKRIVW | SEQ ID NO 1127 |
| HHC116 | GIKWRSRRW | SEQ ID NO 1128 |
| HHC117 | RWMVSKIWY | SEQ ID NO 1129 |
| HHC118 | IVVRVWVVR | SEQ ID NO 1130 |
| HHC119 | RWIGVIIKY | SEQ ID NO 1131 |
| HHC120 | WIRKRSRIF | SEQ ID NO 1132 |
| HHC121 | GWKILRKRK | SEQ ID NO 1133 |
| HHC122 | YQRLFVRIR | SEQ ID NO 1134 |
| HHC123 | AVWKFVKRV | SEQ ID NO 1135 |
| HHC124 | IRKKRRRWT | SEQ ID NO 1136 |
| HHC125 | ILRVISKRR | SEQ ID NO 1137 |
| HHC126 | AWRFKNIRK | SEQ ID NO 1138 |
| HHC127 | HYKFQRWIK | SEQ ID NO 1139 |
| HHC128 | RRIRRVRWG | SEQ ID NO 1140 |
| HHC129 | VLVKKRRRR | SEQ ID NO 1141 |
| HHC130 | RWRGIVHIR | SEQ ID NO 1142 |
| HHC131 | WRNRKVVWR | SEQ ID NO 1143 |
| HHC132 | KFWWWNYLK | SEQ ID NO 1144 |
| HHC133 | KRIMKLKMR | SEQ ID NO 1145 |
| HHC134 | IRRRKKRIK | SEQ ID NO 1146 |
| HHC135 | RKWMGRFLM | SEQ ID NO 1147 |
| HHC136 | RRVQRGKWW | SEQ ID NO 1148 |
| HHC137 | WHGVRWWKW | SEQ ID NO 1149 |
| HHC138 | WVRFVYRYW | SEQ ID NO 1150 |
| HHC139 | RKRTKVTWI | SEQ ID NO 1151 |
| HHC140 | IRRIVRRKI | SEQ ID NO 1152 |
| HHC141 | KIRRKVRWG | SEQ ID NO 1153 |
| HHC142 | AIRRWRIRK | SEQ ID NO 1154 |
| HHC143 | WRFKVLRQR | SEQ ID NO 1155 |
| HHC144 | RSGKKRWRR | SEQ ID NO 1156 |
| HHC145 | FMWVYRYKK | SEQ ID NO 1157 |
| HHC146 | RGKYIRWRK | SEQ ID NO 1158 |

TABLE 2A-continued

Peptides utilized in these studies. All peptides were amidated at the C-terminus unless otherwise noted.

| Name | Sequence | ID |
|---|---|---|
| HHC147 | WVKVWKYTW | SEQ ID NO 1159 |
| HHC148 | VVLKIVRRF | SEQ ID NO 1160 |
| HHC149 | GKFYKVWVR | SEQ ID NO 1161 |
| HHC150 | SWYRTRKRV | SEQ ID NO 1162 |
| HHC151 | KNRGRWFSH | SEQ ID NO 1163 |
| HHC152 | AFRGSRHRM | SEQ ID NO 1164 |
| HHC153 | GRNGWYRIN | SEQ ID NO 1165 |
| HHC154 | AGGMRKRTR | SEQ ID NO 1166 |
| HHC155 | ATRKGYSKF | SEQ ID NO 1167 |
| HHC156 | SSGVRWSWR | SEQ ID NO 1168 |
| HHC157 | RVWRNGYSR | SEQ ID NO 1169 |
| HHC158 | WGRTRWSSR | SEQ ID NO 1170 |
| HHC159 | GKRVWGRGR | SEQ ID NO 1171 |
| HHC160 | SFNWKRSGK | SEQ ID NO 1172 |
| HHC161 | WGRGGWTNR | SEQ ID NO 1173 |
| HHC162 | ANRWGRGIR | SEQ ID NO 1174 |
| HHC163 | WGGHKRRGW | SEQ ID NO 1175 |
| HHC164 | WHGGQKWRK | SEQ ID NO 1176 |
| HHC165 | FVWQKGTNR | SEQ ID NO 1177 |
| HHC166 | HGVWGNRKR | SEQ ID NO 1178 |
| HHC167 | TRGWSLGTR | SEQ ID NO 1179 |
| HHC168 | GRRVMNQKR | SEQ ID NO 1180 |
| HHC169 | RNKFGGNWR | SEQ ID NO 1181 |
| HHC170 | GVRVQRNSK | SEQ ID NO 1182 |
| HHC171 | NQKWSGRRR | SEQ ID NO 1183 |
| HHC172 | RQNGVWRVF | SEQ ID NO 1184 |
| HHC173 | GRMRLWNGR | SEQ ID NO 1185 |
| HHC174 | WHYRSQVGR | SEQ ID NO 1186 |
| HHC175 | GWNTMGRRW | SEQ ID NO 1187 |
| HHC176 | RRMGNGGFR | SEQ ID NO 1188 |
| HHC177 | SKNVRTWRQ | SEQ ID NO 1189 |
| HHC178 | ARGRWINGR | SEQ ID NO 1190 |
| HHC179 | GSRRSVWVF | SEQ ID NO 1191 |
| HHC180 | WSQNVRTRI | SEQ ID NO 1192 |
| HHC181 | GMRRWRGKN | SEQ ID NO 1193 |
| HHC182 | RGRTSNWKM | SEQ ID NO 1194 |
| HHC183 | GRRWGMGVR | SEQ ID NO 1195 |
| HHC184 | WGKRRGWNT | SEQ ID NO 1196 |
| HHC185 | AMLGGRQWR | SEQ ID NO 1197 |
| HHC186 | QRNKGLRHH | SEQ ID NO 1198 |
| HHC187 | ARGKSIKNR | SEQ ID NO 1199 |
| HHC188 | NRRNGQMRR | SEQ ID NO 1200 |
| HHC189 | RGRRQIGKF | SEQ ID NO 1201 |
| HHC190 | ASKRVGVRN | SEQ ID NO 1202 |
| HHC191 | GRIGGKNVR | SEQ ID NO 1203 |
| HHC192 | NKTGYRWRN | SEQ ID NO 1204 |
| HHC193 | VSGNWRGSR | SEQ ID NO 1205 |
| HHC194 | GWGGKRRNF | SEQ ID NO 1206 |
| HHC195 | KNNRRWQGR | SEQ ID NO 1207 |
| HHC196 | GRTMGNGRW | SEQ ID NO 1208 |
| HHC197 | GRQISWGRT | SEQ ID NO 1209 |
| HHC198 | GGRGTRWHG | SEQ ID NO 1210 |
| HHC199 | GVRSWSQRT | SEQ ID NO 1211 |
| HHC200 | GSRRFGWNR | SEQ ID NO 1212 |
| 1001 | LVRAIQVRAVIR | SEQ ID NO 1213 |
| 1002 | VQRWLIVWRIRK | SEQ ID NO 1214 |
| 1003 | IVWKIKRWWVGR | SEQ ID NO 1215 |
| 1004 | RFWKVRVKYIRF | SEQ ID NO 1216 |
| 1005 | VQLRIRVAV | SEQ ID NO 1217 |
| 1006 | VQLRIWVRR | SEQ ID NO 1218 |
| 1007 | WNRVKWIRR | SEQ ID NO 1219 |
| 1008 | RIKWIVRFR | SEQ ID NO 1220 |
| 1009 | AIRVVRARLVRR | SEQ ID NO 1221 |
| 1010 | IRWRIRVWVRRI | SEQ ID NO 1222 |
| 1011 | RRWVVWRIVQRR | SEQ ID NO 1223 |
| 1012 | IFWRRIVIVKKF | SEQ ID NO 1224 |
| 1013 | VRLRIRVAV | SEQ ID NO 1225 |
| 1014 | RQVIVRRW | SEQ ID NO 1226 |
| 1015 | VLIRWNGKK | SEQ ID NO 1227 |
| 1016 | LRIRWIFKR | SEQ ID NO 1228 |
| 1017 | KRIVRRLVARIV | SEQ ID NO 1229 |
| 1018 | VRLIVAVRIWRR | SEQ ID NO 1230 |
| 1019 | IVVWRRQLVKNK | SEQ ID NO 1231 |
| 1020 | VRLRIRWWVLRK | SEQ ID NO 1232 |

TABLE 2A-continued

Peptides utilized in these studies. All peptides were amidated at the C-terminus unless otherwise noted.

| Name   | Sequence        | ID              |
|--------|-----------------|-----------------|
| 1021   | VRLRIRVAV       | SEQ ID NO 1233  |
| 1022   | LRIRVIVWR       | SEQ ID NO 1234  |
| 1023   | IRVWVLRQR       | SEQ ID NO 1235  |
| 1024   | RIRVIVLKK       | SEQ ID NO 1236  |
| 1025   | RRIVKKFQIVRR    | SEQ ID NO 1237  |
| 1026   | VQWRIRVRVIKK    | SEQ ID NO 1238  |
| 1027   | KKQVSRVKVWRK    | SEQ ID NO 1239  |
| 1028   | LIQRIRVRNIVK    | SEQ ID NO 1240  |
| 1029   | KQFRIRVRV       | SEQ ID NO 1241  |
| 1030   | FRIRVRVIR       | SEQ ID NO 1242  |
| 1031   | WRWRVRVWR       | SEQ ID NO 1243  |
| 1032   | IRVRVIWRK       | SEQ ID NO 1244  |
| 1033   | RRVIVKKFRIRR    | SEQ ID NO 1245  |
| 1034   | KQFRNRLRIVKK    | SEQ ID NO 1246  |
| 1035   | KRWRWIVRNIRR    | SEQ ID NO 1247  |
| 1036   | VQFRIRVIVIRK    | SEQ ID NO 1248  |
| 1037   | KRFRIRVRV       | SEQ ID NO 1249  |
| 1038   | IVVRRVIRK       | SEQ ID NO 1250  |
| 1039   | IWVIRRVWR       | SEQ ID NO 1251  |
| 1040   | FQVVKIKVR       | SEQ ID NO 1252  |
| 1041   | VIWIRWR         | SEQ ID NO 1253  |
| 1042   | IVWIWRR         | SEQ ID NO 1254  |
| 1043   | WIVIWRR         | SEQ ID NO 1255  |
| 1044   | RRWIVWI         | SEQ ID NO 1256  |
| 1045   | RWWRIVI         | SEQ ID NO 1257  |
| 1046   | WIRVIRW         | SEQ ID NO 1258  |
| 1047   | IIRRWWV         | SEQ ID NO 1259  |
| 1048   | IRWVIRW         | SEQ ID NO 1260  |
| HH1010 | ILRWKWRWWRWRR   | SEQ ID NO 1261  |
| HH1011 | RWRWWRWRR       | SEQ ID NO 1262  |
| HH1012 | KWKWWKWKK       | SEQ ID NO 1263  |
| HH1013 | RWWRWRR         | SEQ ID NO 1264  |

Minimal inhibitory concentration (MIC) determination. The MIC of the peptides were measured using a modified broth microdilution method in Mueller Hinton (MH) medium (Wu M, Hancock R E W. 1999. Interaction of the cyclic antimicrobial cationic peptide bactenecin with the outer and cytoplasmic membrane. J Biol Chem 274, 29-35). Briefly, the peptides were dissolved and stored in glass vials. The assay was performed in sterile 96-well polypropylene microtitre plates were used. Serial dilutions of the peptides to be assayed were performed in 0.01% acetic acid (Fisher) containing 0.2% bovine serum albumin (Boehringer Mannheim GmbH) at 10× the desired final concentration. Ten microlitres of the 10× peptides were added to each well of a 96-well polypropylene plate containing 90 µl of MH media per well. Bacteria were added to the plate from an overnight culture at 2-7×10⁵ colony forming units/ml and incubated over night at 37° C. The MIC was taken as the concentration at which no growth was observed.

Luminescence-based MIC assay for the non-cleaved peptides on cellulose membranes. The method followed was as previously described (Hilpert K, Volkmer-Engert R, Walter T, Hancock R E W. High-throughput generation of small antibacterial peptides with improved activity. Nature Biotech 23:1008-1012, 2005). Peptides were robotically synthesized on cellulose sheets and then the peptide spots were punched out and transferred to a 96 well microtiter plate with a clear polystyrene bottom and opaque white polypropylene sides (PerkinElmer, Boston, USA). The spots were washed two times with 100% ethanol for 5 min and afterwards equilibrated five times with 100 mM Tris buffer pH 7.3 for 5 min. An overnight culture of *Pseudomonas aeruginosa* strain H1001 fliC::luxCDABE was diluted 1:50 in new MH medium and incubated at 37° C. to an OD600 of 0.35. This bacterial culture was diluted 1:25 into 100 mM Tris-HCl buffer, pH 7.3 containing 20 mM glucose. Fifty µl of this culture was added to all wells of the microtiter plate and incubated at 37° C. The luminescence of the strain produced by the FMN-dependent luciferase system was detected in a time dependent manner using a Tecan Spectra Fluor plus (Tecan, Austria). At the end of the experiment, the membranes were cleaned by washing the spots two times with 100% ethanol for five minutes. After removing the ethanol the membrane was air-dried.

Assay for the cleaved peptides from cellulose support. The peptides were cleaved from the dried membrane in an ammonia atmosphere overnight, resulting in free peptides with an amidated C-terminus. The free peptides contained two β-alanines at the C-terminus, in addition to being amidated due to the linker between the cellulose membrane and the peptide sequence. The peptide spots were punched out and transferred in a 96-well microtiter plate. Serial dilutions were carried out from the membrane spots. Four rows were filled with four controls including 2×Bac2A and 2× an unrelated peptide. The other eight rows were used for serial dilution steps of the peptide variants. An overnight culture of *Pseudomonas aeruginosa* strain H1001 was diluted 1:500 using either LB media or 100 mM Tris buffer pH 7.3, 20 mM glucose and was added to the wells (100 µl/well) containing the peptide spots. In all other wells 50 µl were added. The microtiter plate was incubated for 30 min at 37° C. to release the peptides from the membrane. Subsequently, a dilution series were performed and the plate was incubated at 37° C. The luminescence produced by the FMN dependent luciferase system were detected in a time dependent manner using a Tecan Spectra Fluor plus.

Cytotoxicity and TNFα suppression assay. THP1 cells were cultured in RPMI 1640 medium (supplemented with 10% (v/v) FCS, 1% L-glutamine, and 1 nM sodium pyruvate) in E-toxa-clean (Sigma-Aldrich, Oakville, Ontario, Canada)-washed, endotoxin-free bottle. THP1 cells were counted and 250 µl per well of 2-4 10⁴ cells/ml were transferred into a 96 well tissue cultured treated polystyrene microtiterplate (Beckton Dickinson, Franklin Lakes, USA). In addition PMA were added (1.3 nM) and the cells were incubated for three days. After three days the medium were exchanged and *Pseudomonas aeruginosa* LPS and the peptides were added. The incubation time was four hours and the supernatant was frozen at −20° C. The cells were stained with Tryphan Blue for 2 minutes and washed with PBS two times. The viability of the cells was determined by counting the stained cells over the unstained. The supernatent was used to measure the TNFα production by an ELISA (eBioscience, San Diego, USA) following the manufactures protocol.

Strains. For the killing assay a mini-Tn5-lux mutant in *Pseudomonas aeruginosa* H103 was used. The strain is called H1001 and contains a fliC::luxCDABE transcriptional fusion resulting in constitutive expression of luciferase. The bacterial strains used for the antimicrobial activity assays included *Escherichia coli* UB1005 (F—, nalA37, metB1), a wild-type *Salmonella enterica* ssp. *typhimurium* (*S. typhimurium*), wild-type *Pseudomonas aeruginosa* PAO1 strain H103, *Enterococcus faecalis* ATCC29212, *Staphylococcus aureus* ATCC25923, and a clinical isolate of *Staphylococcus epidermidis* obtained from Dr. D. Speert (Department of Medicine, University of British Columbia). Antifungal activity was tested using a lab isolate of *Candida albicans* obtained from Dr. B. Dill (Department of Microbiology and Immunology, University of British Columbia).

Example 2

12-mer Peptides

Bactenecin is a short peptide of 12 amino acids with a maximal length of about 55 Å. This peptide can kill both Gram positive and Gram negative bacteria. We previously made many scrambled and single amino acid substitution mutants of this peptide. A complete substitution analysis of a scrambled variant of Bac2A, SEQ ID NO 972 was synthesized (FIG. 2) identifying peptides that had distinct advantages over their parent peptide and positionally defining advantageous substitutions. The most favoured residues were:

$AA_1$=all except D and E
$AA_2$=F, H, K, L, Q, R, S, T, V, Y
$AA_3$=F, W
$AA_4$=K, R
$AA_5$=F, L, M, V, W
$AA_6$=K, R
$AA_7$=V, I
$AA_8$=H, K, N, Q, R, S, Y
$AA_9$=V, M
$AA_{10}$=I, K, R
$AA_{11}$=K, R, H
$AA_{12}$=H, K, N, R, T It is clear that some amino acids particularly R, K and W were often preferred to the parent residue. In contrast, some residues were usually detrimental to activity, namely the acidic amino acids D and E. Overall substitutions were rarely conservative and predictable just from the obvious substitution of e.g. one hydrophobic residue for another. Some positions were particularly rich candidates for substitution, namely positions 2, 5, 8 and 12 while others were very difficult to improve especially the charged residues and isoleucin and valin in the core region. Regarding unfavourable substitutions, the least favourable substitutions were:

$AA_1$=D, E
$AA_2$=D, E
$AA_3$=D, E
$AA_4$=D, E, F, G, I, Y
$AA_5$=all except F, L, M, V, W, Y
$AA_6$=all except K, R
$AA_7$=all except F, I, L, M, R, V, W, Y
$AA_8$=D, E, P
$AA_9$=D, E, G, P, Q
$AA_{10}$=none
$AA_{11}$=D, E, F, I, L, M, Q, T, V, W
$AA_{12}$=none A range of novel peptides that are very distinct but possess thematic similarities to linear bactenecin (Bac2A) were synthesized and tested for activity (Table 3).

TABLE 3

Determination of the minimal inhibitory concentrations (MIC) in Mueller-Hinton media for 6 different bacteria and the yeast *Candida albicans*.

| Sequence (all C-terminally amidated) | Name | MIC (µg/ml)[a] | | | | | | |
|---|---|---|---|---|---|---|---|---|
| | | P. aerug. | E. coli | S. typhi | S. aureus | S. epi. | E. faecalis | C. albicans |
| RLARIVVIRVAR | Bac2A | 50 | 17 | 34 | 17 | 4 | 17 | 9 |
| QRLRIRVAVIRA | HH1 | 50 | 6 | 25 | 50 | 12 | 50 | 25 |
| VQLRIRVAVIRA | HH2 | >50 | 6 | 12 | 50 | 12 | 50 | 25 |
| VRFRIRVAVIRA | HH3 | 6 | 1.6 | 6 | 12 | 1.6 | 25 | 6 |
| VRWRIRVAVIRA | HH4 | 6 | 1.6 | 6 | 12 | 1.6 | 12 | 12 |
| VRLWIRVAVIRA | HH5 | >50 | 6 | >50 | 50 | 3 | 25 | 50 |
| VRLRIRVWVIRA | HH6 | 12 | 3 | 12 | 6 | 1.6 | 6 | 25 |

TABLE 3-continued

Determination of the minimal inhibitory concentrations (MIC) in Mueller-Hinton media for 6 different bacteria and the yeast *Candida albicans*.

| Sequence (all C-terminally amidated) | Name | MIC (µg/ml)[a] | | | | | | |
|---|---|---|---|---|---|---|---|---|
| | | P. aerug. | E. coli | S. typhi | S. aureus | S. epi. | E. faecalis | C. albicans |
| VRLRIRVAVRRA | HH7 | 12 | 6 | 6 | 12 | 1.6 | 25 | 6 |
| VRLRIRVAVIRK | HH8 | 6 | 3 | 6 | 6 | 1.6 | 12 | 3 |
| VQLRIRVRVIRK | HH9 | 6 | 3 | 6 | 12 | 1.6 | 12 | 6 |
| KRFRIRVAVRRA | HH10 | 25 | 6 | >50 | 25 | 3.1 | >50 | 12 |
| VRLRIRVRVIRK | HH11 | 3 | 1.6 | 6 | 6 | 0.8 | 12 | 3 |
| KQFRIRVRVIRK | HH12 | 6 | 3 | 6 | 12 | 1.6 | 25 | 6 |
| HQFRFRFRVRRK | HH13 | 50 | 25 | 12 | 12 | 6 | >50 | >50 |
| HQWRIRVAVRRH | HH14 | 50 | 6 | 25 | 25 | 12 | >50 | 25 |
| KRFRIRVRVIRK | HH15 | 6 | 1.6 | 3 | 6 | 0.8 | 25 | 12 |
| KRWRIRVRVIRK | HH16 | 3 | 1.6 | 3 | 3 | 0.8 | 12 | 6 |
| KIWVRWK-NH2 | HH17 | >50 | 50 | >50 | >50 | >50 | >50 | >50 |
| IWVIWRR-NH2 | HH18 | 50 | 6 | 12.5 | 25 | 6 | 25 | 25 |

The values are averages of three independent measurements. Sequences = SEQ ID NOS: 970 and 1-18, respectively.

As can be seen from Table 3, each of the peptides, except HH17, represents an improvement on the parent peptide. Some, in particular HH8, HH9, HH11, HH12, HH15 and HH16, have excellent broad spectrum antimicrobial activity. For example HH8 and HH11 represent two of the best anti-Candidal peptides ever identified. HH3, HH4, HH15 and HH16 have excellent activity against the major nosocomial Gram negative pathogen *E. coli*. These results thus show that it is possible to further optimize scrambled peptides and therefore gain peptides with totally different sequences as the original peptide Bac2A.

Example 3

Complete Substitution Analysis of Indolicidin

Peptide synthesis on cellulose is a very effective and inexpensive way to investigate many different peptide variants for one particular activity. However, one of the problems of this technique is the low peptide amount synthesized on the membrane, about 280 nmol per cm$^2$. An average peptide spot used for the experiments presented is about 0.3 cm$^2$. Therefore, an assay had to be developed that was sensitive enough to show activity with this amount of peptides. *P. aeruginosa* H1001 has a luciferase gene cassette incorporated into the bacterial chromosome in a gene fliC (involved in flagellar biosynthesis) that is constitutively expressed. It will thus produce light if FMN is present. When this strain is killed, e.g. by peptides, the amount of light produced will decrease due to a decrease in FMN levels in the killed cells. This action can thus be monitored by detecting luminescence in a microtiter plate luminescence reader over time. The volume and amount of cells per well were optimized for this assay. After screening, we were able to monitor the killing action with small amounts of the parent peptide Bac2A (2 µg/ml of free peptide). Control experiments demonstrated that the decrease in luminescence reflected bacterial death as assessed by the loss of colony forming ability.

Figure 3A:
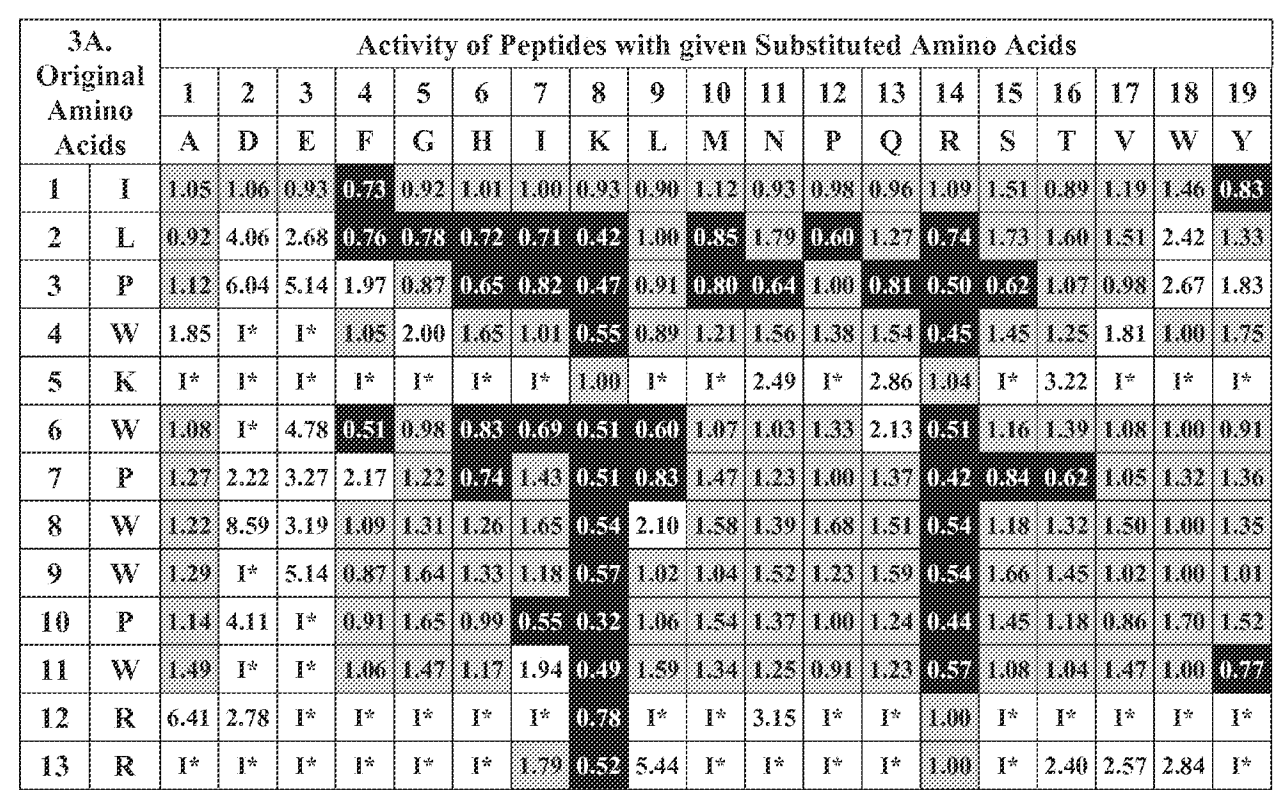

To analyze the positional importance of the specific amino acids in the bovine peptide indolicidin, each amino acid was changed to the other 19 amino acids one-by-one, creating a total of 247 unique peptides. Activity was assessed in the lux-based assay (FIG. 3). The results revealed definite positional specificity of particular amino acids and many substitutions that improved the activity of indolicidin. The most favoured residues were:

$AA_1$=F, Y
$AA_2$=F, G, H, I, K, M, P, R
$AA_3$=H, I, K, M, N, Q, R, S
$AA_4$=K, R
$AA_5$=no improvement on K $AA_6$=F, H, I, K, L, R
$AA_7$=H, K, L, R, S, T
$AA_8$=K, R
$AA_9$=K, R
$AA_{10}$=I, K, R
$AA_{11}$=K, R, Y amino acid could only be improved by changing the basic residue utilized.

The activity of these peptides was confirmed by synthesizing selected examples of single and multiple substitutions (Table 3). The majority of these had superior activity to the parent peptide indolicidin.

TABLE 4

Antimicrobial activity of single and multiple substitution variants of indolicidin (substituted amino acids are indicated in bold in column 1).

| Sequence | Name | MIC (µg/ml)[a] | | | | | | |
|---|---|---|---|---|---|---|---|---|
| | | P. aerug. | E. coli | S. typhi | S. aureus | S. epi. | E. faecalis | C. albicans |
| ILPWKWPWWPWRR | Indolicidin | 62 | 8 | 31 | 16 | 8 | 31 | 16 |
| ILPWKFPWWPWRR | HH63 | 62 | 16 | 31 | 8 | 4 | 31 | 16 |
| ILKWKWPWWPWRR | HH111 | 16 | 8 | 31 | 8 | 4 | 31 | 8 |
| ILPWKKPWWPWRR | HH113 | 31 | 31 | 62 | 31 | 8 | 125 | 62 |
| ILPWKWPWWKWRR | HH117 | 16 | 8 | 31 | 8 | 2 | 31 | 16 |
| ILPWWWPWWPWRR | HH235 | >84 | >84 | >84 | 20 | 5 | 84 | 84 |
| ILKWKWPWWKWRR | HH970 | 16 | 8 | 16 | 8 | 2 | 31 | 16 |
| ILPWKRWWKWRR | HH971 | 16 | 8 | 16 | 8 | 2 | 31 | 8 |
| FLPKKFRWWKYRK | HH972 | 31 | 16 | 31 | 31 | 8 | >125 | 31 |
| FIKWKFRWWKWR | HH973 | 8 | 4 | 8 | 4 | 2 | 8 | 8 |

Sequences = SEQ ID NOS: 971, 63, 111, 113, 117, 235 and 973-976, respectively.

$AA_{12}$=K
$AA_{13}$=K

It is clear that some amino acids particularly R and K are often preferred to the parent residue. In contrast, some residues were usually detrimental to indolicidin activity, namely the acidic amino acids D and E, while others never led to an improvement in activity, namely A, V and W. Overall substitutions were rarely conservative and predictable just from the obvious substitution of e.g. one hydrophobic residue for another. Some positions were particularly rich candidates for substitution, namely positions 2, 3, 6 and 7 while others were very difficult to improve especially the charged residues.

Regarding unfavourable substitutions, the least favourable substitutions were:
$AA_1$=none
$AA_2$=D, E, W
$AA_3$=D, E, F, W, Y
$AA_4$=A, D, E, G, V
$AA_5$=all except K and R
$AA_6$=D, E, Q
$AA_7$=D, E, F
$AA_8$=D, E, L
$AA_9$=D, E
$AA_{10}$=D, E
$AA_{11}$=D, E, I
$AA_{12}$=all except K and R
$AA_{13}$=all except K, R and I Generally speaking those positions with the most favourable substitutions ($AA_2$, $AA_3$, $AA_6$, and $AA_7$) were the most flexible and had few unfavourable substitutions. Three positions with charged residues did not readily accept substitutions namely $AA_5$, $AA_{12}$, and $AA_{13}$, and for these the parent This was used to synthesize a series of 9 and 7 amino acid peptides and activity was tested by the luciferase method (Table 5). All synthesized 9-mers were active whereas peptides as small as 7 amino acids also had excellent antimicrobial activity.

TABLE 5

Antimicrobial activity of selected 9 amino acid and 7 amino acid peptides.

| Name | ID | Peptide sequence | Antimicrobial activity* |
|---|---|---|---|
| HH974 | SEQ ID NO 977 | KWPWWPWRR | +/++ |
| HH975 | SEQ ID NO 978 | KWPWWPWRK | + |
| HH976 | SEQ ID NO 979 | KFPWWPWRR | + |
| HH977 | SEQ ID NO 980 | KKPWWPWRR | + |
| HH978 | SEQ ID NO 981 | KWRWWPWRR | ++ |
| HH979 | SEQ ID NO 982 | KWPKWPWRR | + |
| HH980 | SEQ ID NO 983 | KWPWKPWRR | + |
| HH981 | SEQ ID NO 984 | KWPWWKWRR | ++ |
| HH982 | SEQ ID NO 985 | KWPWWPKRR | + |
| HH983 | SEQ ID NO 986 | KWPWWPWRR | +/++ |
| HH984 | SEQ ID NO 987 | KFRWWPWRR | ++ |
| HH985 | SEQ ID NO 988 | KFRWWKWRR | ++ |
| HH986 | SEQ ID NO 989 | KWRWWKKRR | ++ |

TABLE 5-continued

Antimicrobial activity of selected 9 amino acid and 7 amino acid peptides.

| Name | ID | Peptide sequence | Antimicrobial activity* |
|---|---|---|---|
| HH987 | SEQ ID NO 990 | KKKWWKWRR | ++ |
| HH988 | SEQ ID NO 991 | KFHWWIWRK | ++ |
| HH989 | SEQ ID NO 992 | KFHWWKWRK | ++ |
| HH990 | SEQ ID NO 993 | KFKWWKYRK | ++ |
| HH991 | SEQ ID NO 994 | KFKFFKYRK | + |
| HH992 | SEQ ID NO 995 | KFKFFKFRK | + |
| HH993 | SEQ ID NO 996 | PWWPWRR | + |
| HH994 | SEQ ID NO 997 | KWWPWRR | + |
| HH995 | SEQ ID NO 998 | PWWKWRR | +/++ |
| HH996 | SEQ ID NO 999 | RWWPWRR | + |
| HH997 | SEQ ID NO 1000 | PKWPWRR | - |
| HH998 | SEQ ID NO 1001 | PWKPWRR | - |
| HH999 | SEQ ID NO 1002 | PWWKWRR | + |
| HH1000 | SEQ ID NO 1003 | PWWPKRR | - |
| HH1001 | SEQ ID NO 1004 | PWWPWRK | - |
| HH1002 | SEQ ID NO 1005 | RWWKWRR | ++ |
| HH1003 | SEQ ID NO 1006 | RWWKWRK | +/++ |
| HH1004 | SEQ ID NO 1007 | RFWKWRR | + |
| HH1005 | SEQ ID NO 1008 | RWWIKRR | +/++ |
| HH1006 | SEQ ID NO 1009 | RWWIYRR | + |
| HH1007 | SEQ ID NO 1010 | RFFKFRR | - |
| HH1008 | SEQ ID NO 1011 | KWWKWKK | + |
| HH1009 | SEQ ID NO 1012 | KFFKFKK | - |

*Antimicrobial activity against P. aeruginosa strain H1001 was determined after 4 hours incubation time with the peptide using luminescence as an indicator (method described above). The antimicrobial activity was ranked using the following symbols, - for minimal or no activity, + for weak activity, +/++ for intermediate activity, ++ strong activity.

Example 4

Figure 4:
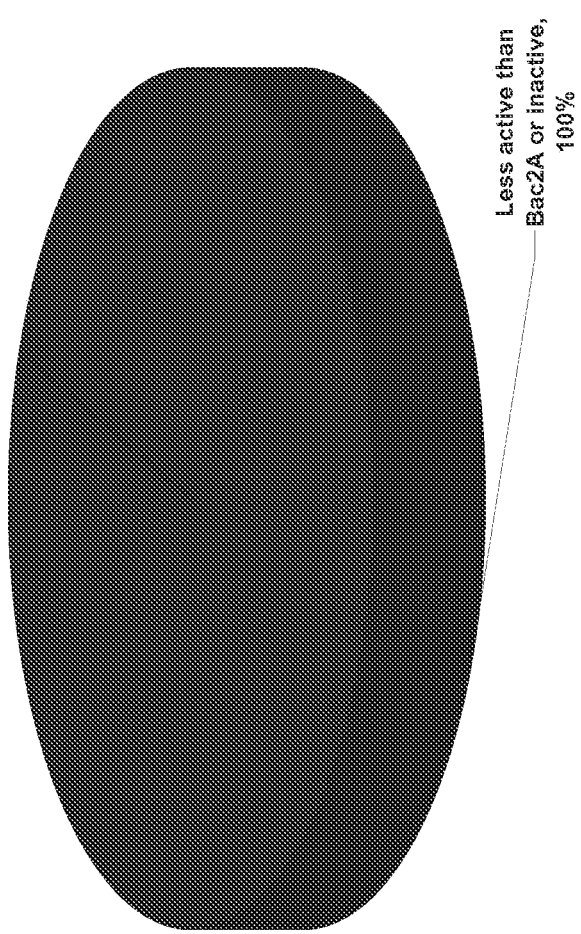
FIG. 4. Antimicrobial activity of 200 random peptides. All peptides were categorized into the activity class "less active than the control peptide Bac2A or inactive".

Development of Semi-Random Peptide Libraries with Enriched Antimicrobial Activities Semi-random peptide libraries are a simple, powerful tool to create novel peptide sequences. These novel peptides can be screened for the desired biological activity. This approach is independent of knowledge of naturally occurring peptides, and can create sequences from the full sequence space of all possible peptides. In our first attempts we created 200 random 9 amino acid (9-mer) peptides de novo [sequences not included with this patent as they are inactive]. For this peptide set cysteine was excluded to avoid the potential for formation of peptide dimers. All peptides were synthesized on cellulose and tested for their ability to kill P. aeruginaosa, using the lux assay and luminescent strain H1001. After 4 hours incubation time of H1001 with the peptides no antimicrobial activity was detected (FIG. 4).

Figure 5:
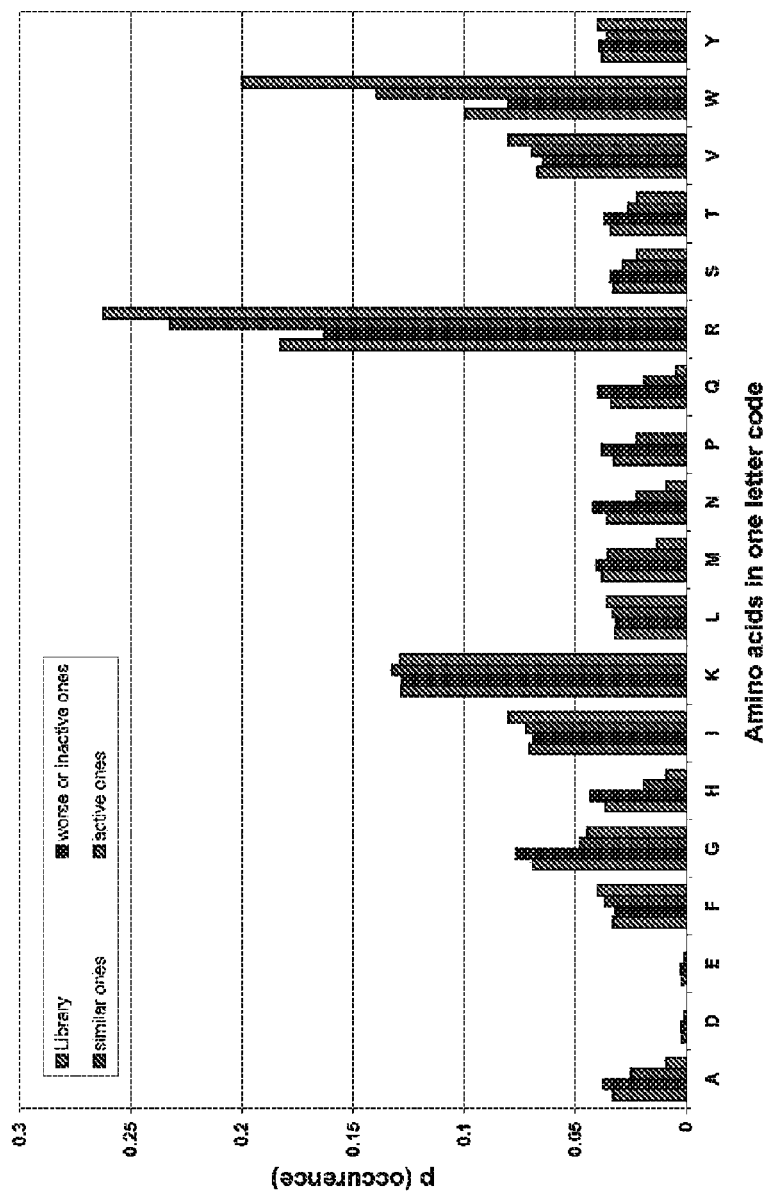
FIG. 5. Occurrence of amino acids in the new semi-random peptide library. The amino acids are given as the one letter code. After assessment of antimicrobial activity using the Lux assay, the occurrence of amino acids in each activity group, except superior (not enough members), was compared to the occurrence of the semi random library setting.

Thus a totally random peptide library resulted in essentially no active antimicrobial peptides, and this demonstrates that it is not feasible to screen thousands of random peptides to find a few with antimicrobial activity. To improve the chances of finding active antimicrobial peptides, the information gained from previous Bac2A peptide libraries (Hilpert, K., M. R. Elliott, R. Volkmer-Engert, P. Henklein, O. Donini, Q. Zhou, D. F. H. Winkler and R. E. W. Hancock. 2006. Sequence requirements and a novel optimization strategy for short antimicrobial peptides. Chem Biol. 13:1101-1107) was used to design new parameters related to input amino acid composition to create a semi-random approach. Thus instead of using the same occurrence for each amino acid, the occurrence was changed for certain amino acids, according to their occurrence in peptides with good activity, as presented in FIG. 5.

Using these new occurrence settings 943 peptide were semi-randomly designed and synthesised on cellulose. Twenty eight percent of peptides demonstrated similar activity to the control while 2% were more active, and 0.3% demonstrated superior activity. These assessments were repeated with 152 of these peptides from the semi-random peptide library and 96% of the activities could be confirmed. Further MIC studies with a random selection of peptides indicated that the active peptides within the semi-random library are suitable to use as lead structures for drug design.

Figure 6:
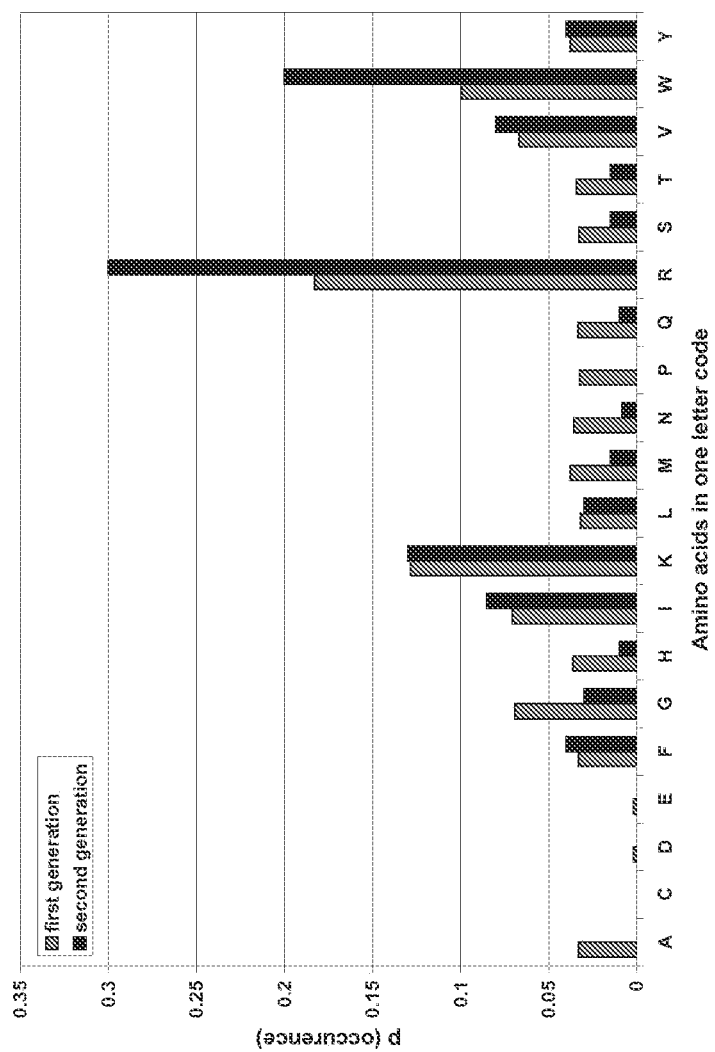
FIG. 6. Occurrence (proportion of total) of amino acids in both (first and second generation) semi-random peptide libraries.

To further improve the library design, the different activity groups found within the first semi-random library were compared with the setting used to design the first semi random library. The comparison is presented in FIG. 5. The more active group showed lower usage of the amino acids A, D, E, G, H, M, N, P, Q, S and T compared to the library settings. On the other hand the amino acids I, R, V and W were used more often compared to the library settings. Using this information, a second generation semi-random peptide library was designed. The new settings are presented as a comparison between the first and second library settings in FIG. 6.

Figure 7:
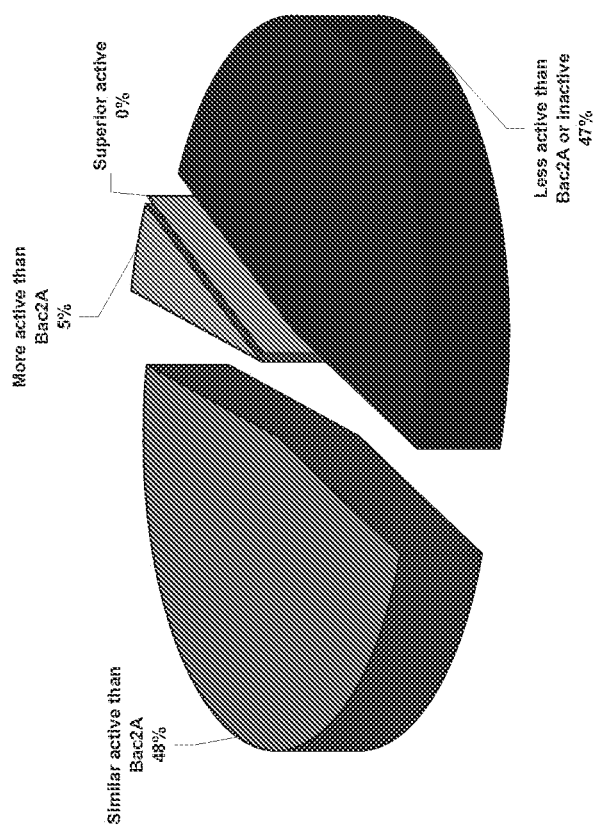
FIG. 7. Antimicrobial activity of 500 semi-random peptides. The peptides were categorized into activity classes corresponding to their antimicrobial activity vs. *P. aeruginosa* in comparison to the control peptide Bac2A. Four activity classes were used: "less active than control or inactive", "similarly active to control", "more active than control" and "superior activity". The number of peptides in each class is expressed as a percentage of the total number of peptides in the library.

By using these settings 500 new peptides were designed and synthesized on cellulose (HH469-HH969), and their antimicrobial activities were tested against H1001. The result of this screen is given in FIG. 7.

Thus the chances of finding an antimicrobial peptide, with activity against P. aeruginosa that was comparable to Bac2A or better, using this second generation library setting, was greater than 50%. The library features could most probably still be optimized since a comparison of the amino acid occurrences in the different peptide classes still showed that there was room for improvement. Thus we used the settings of the second generation library adopted combined with a QSAR approach that utilized our peptide libraries as training sets for the QSAR analysis and designed 100,000 peptides.

Example 5

QSAR Analysis as a Route to Predicting New Peptides

The method of Artificial Neural Networks represents one of the most broadly used machine-learning techniques that utilize basic principles of brain organization and memory mechanisms. The structure of a Neural Network mimics three main components of a neural cell and consists of an input layer where information is entered, one or more hidden layers where signals are conducted and processed, and an output layer where the result of the calculation ends up. Such data flow resembles the passage of an electric signal between neural cells. In short, a dendrite body of a cell receives multiple input signals from other neurons, and depending on the intensity of the accumulated input, the activation signal can be passed to the axon and, hence, along the downstream connections. Just like a complex biological network of connected neurons, the Artificial Neural Networks model can learn by example. During the learning phase, it defines the relationship between n input variables Input_nodeij and a known dependent value Output_nodei by recursive adjustments of the weights attributes wij assigned to each network node. In particular, a set of inputs multiplied by each neuron's weights are summed up for each of m hidden node:

$$\text{Output\_node} = \sum_{i=1}^{m} (\text{Hidden\_node}_i * w_{ij} + const_0 * w_0)$$

Then, the transformed sums for the hidden units are multiplied by the output weights:

$$\text{Hidden\_node}_i = \tanh\left[\sum_{i=1}^{n} (\text{Input\_node}_i * w_{ij} + const_0 * w_0)\right]$$

where they are summed a final time and transformed with the learning function $$\frac{1}{1+e^{-x}}$$

that resembles a sigmoid electric potential occurring between a neuron and dendrite cell. With a trained network, the independent arguments (QSAR descriptors) of an unknown entry (untested peptide) can be passed though the input nodes and transformed through the pre-defined network connections into the output signal (predicted activity). The output values can then be interpreted as active of inactive prediction by its respective proximity to 1.0 or 0.0 thresholds.

The common and 'inductive' QSAR descriptors described in Table 6 were used.

TABLE 6

'Inductive' and conventional molecular descriptors utilized in the QSAR modeling of antimicrobial activity of short cationic peptides.

| QSAR parameter | Description |
|---|---|
| Electronegativity-based | |
| EO_Equalized | Iteratively equalized electronegativity of a molecule |
| Average_EO_Pos | Arithmetic mean of electronegativities of atoms with positive partial charge |
| Average_EO_Neg | Arithmetic mean of electronegativities of atoms with negative partial charge |
| Hardness-based | |
| Sum_Hardness | Sum of hardnesses of atoms of a molecule |
| Sum_Neg_Hardness | Sum of hardnesses of atoms with negative partial charge |

TABLE 6-continued

'Inductive' and conventional molecular descriptors utilized in the QSAR modeling of antimicrobial activity of short cationic peptides.

| QSAR parameter | Description |
|---|---|
| Average_Hardness | Arithmetic mean of hardnesses of all atoms of a molecule |
| Average_Pos_Hardness | Arithmetic mean of hardnesses of atoms with positive partial charge |
| Average_Neg_Hardness | Arithmetic mean of hardnesses of atoms with negative partial charge |
| Smallest_Pos_Hardness | Smallest atomic hardness among values for positively charged atoms |
| Smallest_Neg_Hardness | Smallest atomic hardness among values for negatively charged atoms |
| Largest_Pos_Hardness | Largest atomic hardness among values for positively charged atoms |
| Largest_Neg_Hardness | Largest atomic hardness among values for negatively charged atoms |
| Hardness_of_Most_Pos | Atomic hardness of an atom with the most positive charge |
| Hardness_of_Most_Neg | Atomic hardness of an atom with the most negative charge |
| Softness based | |
| Total_Neg_Softness | Sum of softnesses of atoms with negative partial charge |
| Average_Neg_Softness | Arithmetic mean of softnesses of atoms with negative partial charge |
| Charge-based | |
| Average_Pos_Charge | Arithmetic mean of positive partial charges on atoms of a molecule |
| Average_Neg_Charge | Arithmetic mean of negative partial charges on atoms of a molecule |
| Descriptors based on inductive substituent constants | |
| Total_Sigma_mol_i | Sum of inductive parameters sigma (molecule→atom) for all atoms within a molecule |
| Most_Pos_Sigma_mol_i | Largest positive group inductive parameter sigma (molecule→atom) for atoms in a molecule |
| Most_Neg_Sigma_mol_i | Largest (by absolute value) negative group inductive parameter sigma (molecule→atom) for atoms in a molecule |
| Sum_Pos_Sigma_mol_i | Sum of all positive group inductive parameters sigma (molecule→atom) within a molecule |
| Sum_Neg_Sigma_mol_i | Sum of all negative group inductive parameters sigma (molecule→atom) within a molecule |
| Descriptors based on steric substituent constants | |
| Smallest_Rs_mol_i | Smallest value of group steric influence Rs(molecule→atom) in a molecule |
| Largest_Rs_i_mol | Largest value of atomic steric influence Rs(atom→molecule) in a molecule |
| Most_Neg_Rs_mol_i | Steric influence Rs(molecule→atom) ON the most negatively charged atom in a molecule |
| Most_Neg_Rs_i_mol | Steric influence Rs(atom→molecule) OF the most negatively charged atom to the rest of a molecule |
| Conventional QSAR descriptors implemented by the Molecular Operational Environment (MOE) v. 2006.05 software, Chemical Computation Group Inc., Montreal, Canada. | |
| a_acc | Number of hydrogen bond acceptor atoms |
| a_don | Number of hydrogen bond donor atoms |
| ASA | Water accessible surface area |
| ASA_H | Water accessible surface area of all hydrophobic atoms |
| ASA_P | Water accessible surface area of all polar atoms |
| ASA− | Water accessible surface area of all atoms with negative partial charge |
| ASA+ | Water accessible surface area of all atoms with positive partial charge |

TABLE 6-continued

'Inductive' and conventional molecular descriptors utilized
in the QSAR modeling
of antimicrobial activity of short cationic peptides.

| QSAR parameter | Description |
|---|---|
| FCharge | Total charge of the molecule |
| logP(o/w) | Log of the octanol/water partition coefficient |
| logS | Log of the aqueous solubility |
| PC− | Total negative partial charge |
| PC+ | Total positive partial charge |
| RPC+ | Relative positive partial charge |
| vdw_area | van der Waals surface area calculated using a connection table approximation |
| vsa_acc | Approximation to the sum of VDW surface areas of pure hydrogen bond acceptors |
| vsa_acid | Approximation to the sum of VDW surface areas of acidic atoms |
| vsa_hyd | Approximation to the sum of VDW surface areas of basic atoms |
| Weight | Molecular weight |

The conventional QSAR descriptors were calculated for the training set and external set compounds using the default setting of the MOE package, while the 'inductive' parameters have been calculated by customized SVL scripts (a specialized language of the MOE) using the fundamental equations found in FIG. 8) for steric effect parameters, parameters of inductive influence, 'inductive' partial charge, group 'inductive' electronegativity and 'inductive' analogues of local and global chemical hardness and softness. The linear character of these equations made the inductive descriptors in FIG. 8 readily computable and suitable for sizable databases and positions them as appropriate parameters for large-scale QSAR models.

The interatomic distances were calculated for all evaluated peptides using their three-dimensional structures optimized with MMFF94 force-field. The atomic types have been assigned according to the name, valent state and a formal charge of atoms as it is defined within the MOE.

The QSAR descriptors used in the study have been normalized into the range [0.0÷1.0] and the non-overlapping training and testing sets have been randomly drawn by the customized Java scripts. The training and testing of the neural networks has been conducted using the Stuttgart Neural Network Simulator. The training was performed through the feed-forward back-propagation algorithm with the weight decay and pattern shuffling. The values of initial rates were randomly assigned in a range [0.0÷1.0], the learning rate has been set to 0.8 with the threshold 0.10. The external set of 100,000 peptide candidates designed using the second generation library parameters described in FIG. 6 was created using customized SVL scripts.

Example 6

Prediction of Novel Peptides

To relate QSAR descriptors to known antimicrobial activity of previously studied peptides, as described in Example 5, the method of Artificial Neural Networks, one of the most effective pattern recognition techniques that is ranked very highly among machine learning approaches, was employed. Two training datasets of 943 peptides (Hilpert K, and R E W Hancock, unpublished) and 500 peptides (FIG. 7) were dealt with separately, since they were assayed at different times under slightly different conditions, and in combined collection of 933+500=1433 substances and consequently trained three independent Neural Network models respectively based on the training sets 'A', 'B' and 'A+B'.

Within each of those training sets, an output value of 1.0 was assigned for the most active (top 5%) of the peptides and 0.0 values were used for all others. With this, multiple training runs of the Neural Networks were carried out, while changing the number of their hidden nodes. As the result, it was established that the most optimal performance by the Network-based solutions was achieved with 10 nodes in the hidden layer. Using this optimized 44-10-1 configuration of the Neural Network QSAR solutions were trained using 10-folds cross-validation technique. In particular, for each training set 'A', 'B' and 'A+B', 10 independent models were created, each derived from a 90% portion of the training set. Every solution was then applied to the remaining 10% of data that had been excluded from the training process. Thus, for every peptide in the training sets 'A', 'B' and 'A+B' 10 predictions were computed and these were further averaged as arithmetic means. The averaged outputs were then interpreted as active/inactive predictions by applying the previously utilized top 5% (most active peptides) criterion. Finally, the predicted outcomes were compared with experimental peptide activities (also separated into the top 5% vs. remaining 95%) to produce confusion matrices. The resulting parameters of Specificity, Sensitivity, Accuracy and the Positive Predictive Value observed when delineating the top 5, 10 or 25% of peptides as the "most active" are presented in Table 7.

TABLE 7

Parameters characterizing the ability of the Neural Networks to recognize
the most active peptides in training sets A, B and 'A + B' containing
known antimicrobial peptides.

| Training set | Top % as "most actives" | Accuracy | Specificity | Sensitivity | Positive Predictive Value |
|---|---|---|---|---|---|
| A | 5% | 0.96 | 0.98 | 0.62 | 0.58 |
|   | 10% | 0.93 | 0.94 | 0.76 | 0.39 |
|   | 25% | 0.78 | 0.78 | 0.85 | 0.17 |
| B | 5% | 0.94 | 0.97 | 0.33 | 0.30 |
|   | 10% | 0.88 | 0.90 | 0.33 | 0.12 |
|   | 25% | 0.77 | 0.77 | 0.80 | 0.12 |
| A + B | 5% | 0.95 | 0.97 | 0.47 | 0.47 |
|   | 10% | 0.91 | 0.92 | 0.54 | 0.27 |
|   | 25% | 0.76 | 0.77 | 0.66 | 0.13 |

In addition, all three developed QSAR models were assessed using the Receiver Operating Characteristics curves (plotting average true positive rates as a function of average false positive rates. The computed 'area under the curve' values of Training set A=0.87, B=0.83 and A+B=0.80 confirmed the accuracy of these QSAR models and demonstrated that the selected set of 44 QSAR descriptors can adequately capture structural properties of peptides that are relevant for their antibacterial activities.

In silico interrogation of designed peptide libraries. To utilize the developed QSAR solutions further, 100,000 virtual variants of 9-amino acid long peptides were created using the favorable proportions of amino acids utilized for the second generation library as described in FIG. 6.

At the next step we calculated 44 QSAR parameters for each virtual peptide and scored all 100,000 of them with 30 neural network-based QSAR solutions created with the training sets 'A', 'B' and 'A+B' and described in the previous section. Thus, for every hypothetical peptide we produced 30 independent network outputs representing hypothetical antimicrobial potentials, but instead of averaging, they were subjected to a binary voting system. In particular, after sorting 30 sets of predicted activities, the cumulative votes were computed for ~100,000 peptides, whereby each peptide would receive a vote of 1 for every top 5% ranking (thus, the maximal possible value was set to 30). In addition, the cumulative ranks of peptides were also computed. The activity prediction for the 100,000 peptides is summarized in Table 7 (see appendix) and assorted according to quartiles (Most active predicted quartile to least active).

To test the accuracy of predictions, fifty peptides were taken from the boundaries of each quartile (total of 200 peptides) and resynthesized on cellulose arrays and tested for antimicrobial activity using the luminescence assay described above, see Table 7. Results were as follows:

For the first 50 (representing the first quartile), 47 of them (94%) were more active than the control Bac2A, with only 3 peptide being as active as the control.

For the second 50 (representing the second quartile) 32 of them (64%) were more active than the control, while 17 peptides were similar or worse than control and 1 peptide was inactive.

For the third 50 (representing the third quartile) Only 8 (16%) similar to or better than the control, 38 were worse than the control and 4 were inactive For the bottom 50 (representing the fourth quartile with lowest predicted activity) 44 were worse than control and 6 were inactive.

Figure 20:
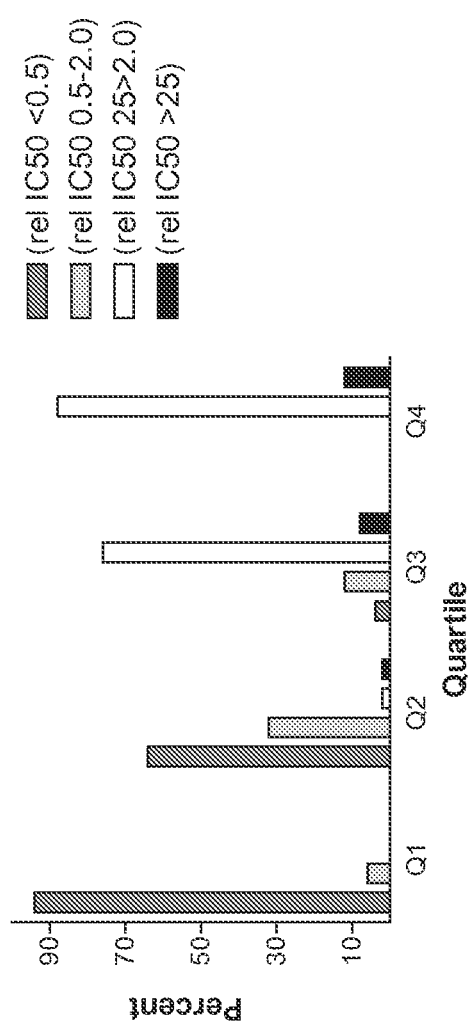
FIG. 20. Activities of 200 peptides from the 100 k test set. Q1: top of $1^{st}$ quartile; Q2: Top of $2^{nd}$ Quartile; Q3: Bottom of $3^{rd}$ Quartile; Q4: Bottom of $4^{th}$ Quartile. relIC$_{50}$ is the relative IC$_{50}$, the ratio of the IC$_{50}$ for the experimental peptide to the IC$_{50}$ of Bac2A. Peptides where the highest concentration failed to reduce the luminescence by at least 50% were identified as inactive.

Thus it is quite clear that the QSAR-derived model was very accurate in predicting peptides with excellent antimicrobial activity. See FIG. 20.

TABLE 8

Selected peptides (SEQ ID NOS: 1013-1212) from the 100,000 peptide set. The predicted activities are given in activity quartiles, where the most active predicted peptide quartile (top 25,000 peptides) is Quartile 1, Quartiles 2 and 3 are predicted to be successively less active and the least active is predicted to be Quartile 4.

| Name | Sequence | Predicted activity (in Quartiles) | Measured activity ($IC_{50}$) |
|---|---|---|---|
| HHC1 | RWRWKRWWW | 1 | 0.25 |
| HHC2 | RWRRWKWWW | 1 | 0.40 |
| HHC3 | RWWRWRKWW | 1 | 0.28 |
| HHC4 | RWRRKWWWW | 1 | 0.39 |
| HHC5 | RWRWWKRWY | 1 | 0.20 |
| HHC6 | RRKRWWWWW | 1 | 0.43 |
| HHC7 | RWRIKRWWW | 1 | 0.12 |
| HHC8 | KIWWWWRKR | 1 | 0.13 |
| HHC9 | RWRRWKWWL | 1 | 0.078 |
| HHC10 | KRWWKWIRW | 1 | 0.037 |
| HHC11 | KRWWWWWKR | 1 | 0.22 |
| HHC12 | IRWWKRWWR | 1 | 0.21 |
| HHC13 | IKRWWRWWR | 1 | 0.23 |
| HHC14 | RRKWWWRWW | 1 | 0.27 |
| HHC15 | RKWWRWWRW | 1 | 0.31 |
| HHC16 | KRWWWWRFR | 1 | 0.24 |
| HHC17 | IKRWWWRRW | 1 | 0.22 |
| HHC18 | KRWWVWKR | 1 | 0.36 |
| HHC19 | KWRRWKRWW | 1 | 0.15 |
| HHC20 | WRWWKIWKR | 1 | 0.14 |
| HHC21 | WRWRWWKRW | 1 | 0.28 |
| HHC22 | WKRWKWWKR | 1 | 0.25 |
| HHC23 | RIKRWWWWR | 1 | 0.31 |
| HHC24 | IWKRWWRRW | 1 | 0.24 |
| HHC25 | KWWKIWWKR | 1 | 0.20 |
| HHC26 | RKRWLWRWW | 1 | 0.25 |
| HHC27 | KRWRWWRWW | 1 | 0.28 |
| HHC28 | KKRWLWWWR | 1 | 0.30 |
| HHC29 | RWWRKWWIR | 1 | 0.24 |
| HHC30 | KWWRWWRKW | 1 | 0.20 |
| HHC31 | KRWWIRWWR | 1 | 0.21 |
| HHC32 | KIWWWWRRR | 1 | 0.21 |
| HHC33 | RRRKWWIWW | 1 | 0.18 |
| HHC34 | RRRWWWWWW | 1 | 1.8 |
| HHC35 | RWWIRKWWR | 1 | 0.21 |
| HHC36 | KRWWKWWRR | 1 | 0.13 |
| HHC37 | KRWWRKWWR | 1 | 0.15 |
| HHC38 | RRIWRWWWW | 1 | 0.68 |
| HHC39 | IRRRKWWWW | 1 | 0.21 |
| HHC40 | KRKIWWWIR | 1 | 0.28 |
| HHC41 | RKIWWWRIR | 1 | 0.59 |
| HHC42 | KRWWIWRIR | 1 | 0.35 |
| HHC43 | RWFRWWKRW | 1 | 0.26 |
| HHC44 | WRWWWKKWR | 1 | 0.19 |
| HHC45 | WKRWWKKWR | 1 | 0.20 |
| HHC46 | WKRWRWIRW | 1 | 0.28 |
| HHC47 | WRWWKWWRR | 1 | 0.23 |

TABLE 8-continued

Selected peptides (SEQ ID NOS: 1013-1212) from the 100,000 peptide set. The predicted activities are given in activity quartiles, where the most active predicted peptide quartile (top 25,000 peptides) is Quartile 1, Quartiles 2 and 3 are predicted to be successively less active and the least active is predicted to be Quartile 4.

| Name | Sequence | Predicted activity (in Quartiles) | Measured activity ($IC_{50}$) |
|---|---|---|---|
| HHC48 | WKKWWKRRW | 1 | 0.19 |
| HHC49 | WRWYWWKKR | 1 | 0.22 |
| HHC50 | WRRWWKWWR | 1 | 0.23 |
| HHC51 | IRMWVKRWR | 2 | 0.61 |
| HHC52 | RIWYWYKRW | 2 | 0.36 |
| HHC53 | FRRWWKWFK | 2 | 0.12 |
| HHC54 | RVRWWKKRW | 2 | 0.27 |
| HHC55 | RLKKVRWWW | 2 | 0.34 |
| HHC56 | RWWLKIRKW | 2 | 0.18 |
| HHC57 | LRWWWIKRI | 2 | 0.33 |
| HHC58 | TRKVWWWRW | 2 | 0.76 |
| HHC59 | KRFWIWFWR | 2 | 3.0 |
| HHC60 | KKRWVWVIR | 2 | 0.35 |
| HHC61 | KRWVWYRYW | 2 | 0.54 |
| HHC62 | IRKWRRWWK | 2 | 0.41 |
| HHC63 | RHWKTWWKR | 2 | 0.95 |
| HHC64 | RRFKKWYWY | 2 | 0.26 |
| HHC65 | RIKVIWWWR | 2 | 0.51 |
| HHC66 | RKRLKWWIY | 2 | 0.18 |
| HHC67 | LVFRKYWKR | 2 | 0.99 |
| HHC68 | RRRWWWIIV | 2 | 0.85 |
| HHC69 | KKRWVWIRY | 2 | 0.22 |
| HHC70 | RWRIKFKRW | 2 | 0.26 |
| HHC71 | KWKIFRRWW | 2 | 0.16 |
| HHC72 | IWKRWRKRL | 2 | 0.33 |
| HHC73 | RRRKWWIWG | 2 | 0.57 |
| HHC74 | RWLVLRKRW | 2 | 0.53 |
| HHC75 | RKWIWRWFL | 2 | 0.15 |
| HHC76 | KRRRIWWWK | 2 | 0.40 |
| HHC77 | IWWKWRRWV | 2 | 0.29 |
| HHC78 | LRWRWWKIK | 2 | 0.26 |
| HHC79 | RWKMWWRWV | 2 | 0.24 |
| HHC80 | VKRYYWRWR | 2 | 1.2 |
| HHC81 | RWYRKRWSW | 2 | 0.70 |
| HHC82 | KRKLIRWWW | 2 | 0.23 |
| HHC83 | RWRWWIKII | 2 | 0.46 |
| HHC84 | KFRKRVWWW | 2 | 0.30 |
| HHC85 | IWIWRKLRW | 2 | 0.46 |
| HHC86 | LRFILWWKR | 2 | 0.88 |
| HHC87 | RVWFKRRWW | 2 | 0.26 |
| HHC88 | RRWFVKWWY | 2 | 0.52 |
| HHC89 | KWWLVWKRK | 2 | 0.23 |
| HHC90 | RWILWWWRI | 2 | 25 |
| HHC91 | KRWLTWRFR | 2 | 0.54 |
| HHC92 | RKWRWRWLK | 2 | 0.31 |
| HHC93 | IRRRWWWIV | 2 | 0.23 |
| HHC94 | IKWWWRMRI | 2 | 0.39 |
| HHC95 | RWKIFIRWW | 2 | 1.8 |
| HHC96 | IRQWWRRWW | 2 | 0.50 |
| HHC97 | RRRKTWYWW | 2 | 0.32 |
| HHC98 | RRWWHLWRK | 2 | 0.38 |
| HHC99 | RRWWMRWWV | 2 | 0.33 |
| HHC100 | RRFKFIRWW | 2 | 0.24 |
| HHC101 | INRKRRLRW | 3 | 4.2 |
| HHC102 | RRMKKLRRK | 3 | 4.2 |
| HHC103 | RKVRWKIRV | 3 | 0.32 |
| HHC104 | VRIVRVRIR | 3 | 2.2 |
| HHC105 | IKRVKRRKR | 3 | 2.9 |
| HHC106 | RVKTWRVRT | 3 | 5.7 |
| HHC107 | RVFVKIRMK | 3 | 0.72 |
| HHC108 | IRGRIIFWV | 3 | 0.44 |
| HHC109 | ATWIWVFRR | 3 | 4.9 |
| HHC110 | KKSKQLWKR | 3 | 3.2 |
| HHC111 | MINRVRLRW | 3 | 2.8 |
| HHC112 | GGIRRLRWY | 3 | 1.2 |
| HHC113 | RLVHWIRRV | 3 | 2.6 |
| HHC114 | AWKIKKGRI | 3 | 3.6 |

TABLE 8-continued

Selected peptides (SEQ ID NOS: 1013-1212) from the 100,000 peptide set. The predicted activities are given in activity quartiles, where the most active predicted peptide quartile (top 25,000 peptides) is Quartile 1, Quartiles 2 and 3 are predicted to be successively less active and the least active is predicted to be Quartile 4.

| Name | Sequence | Predicted activity (in Quartiles) | Measured activity (IC$_{50}$) |
|---|---|---|---|
| HHC115 | FVVMKRIVW | 3 | 5.4 |
| HHC116 | GIKWRSRRW | 3 | 1.1 |
| HHC117 | RWMVSKIWY | 3 | 25 |
| HHC118 | IVVRVWVVR | 3 | 3.5 |
| HHC119 | RWIGVIIKY | 3 | 2.2 |
| HHC120 | WIRKRSRIF | 3 | 3.4 |
| HHC121 | GWKILRKRK | 3 | 2.7 |
| HHC122 | YQRLFVRIR | 3 | 25 |
| HHC123 | AVWKFVKRV | 3 | 8.2 |
| HHC124 | IRKKRRRWT | 3 | 6.6 |
| HHC125 | ILRVISKRR | 3 | 25 |
| HHC126 | AWRFKNIRK | 3 | 9.2 |
| HHC127 | HYKFQRWIK | 3 | 2.8 |
| HHC128 | RRIRRVRWG | 3 | 8.2 |
| HHC129 | VLVKKRRRR | 3 | 12 |
| HHC130 | RWRGIVHIR | 3 | 4.9 |
| HHC131 | WRNRKVVWR | 3 | 6.8 |
| HHC132 | KFWWWNYLK | 3 | 1.8 |
| HHC133 | KRIMKLKMR | 3 | 6.5 |
| HHC134 | IRRRKKRIK | 3 | 6.4 |
| HHC135 | RKWMGRFLM | 3 | 4.4 |
| HHC136 | RRVQRGKWW | 3 | 6.3 |
| HHC137 | WHGVRWWKW | 3 | 2.5 |
| HHC138 | WVRFVYRYW | 3 | 2.1 |
| HHC139 | RKRTKVTWI | 3 | 5.1 |
| HHC140 | IRRIVRRKI | 3 | 11.1 |
| HHC141 | KIRRKVRWG | 3 | 10.6 |
| HHC142 | AIRRWRIRK | 3 | 4.6 |
| HHC143 | WRFKVLRQR | 3 | 7.1 |
| HHC144 | RSGKKRWRR | 3 | 6.5 |
| HHC145 | FMWVYRYKK | 3 | 1.5 |
| HHC146 | RGKYIRWRK | 3 | 3.8 |
| HHC147 | WVKVWKYTW | 3 | 5.6 |
| HHC148 | VVLKIVRRF | 3 | 25 |
| HHC149 | GKFYKVWVR | 3 | 1.2 |
| HHC150 | SWYRTRKRV | 3 | 6.7 |
| HHC151 | KNRGRWFSH | 4 | 9.8 |
| HHC152 | AFRGSRHRM | 4 | 11 |
| HHC153 | GRNGWYRIN | 4 | 11 |
| HHC154 | AGGMRKRTR | 4 | 25 |
| HHC155 | ATRKGYSKF | 4 | 25 |
| HHC156 | SSGVRWSWR | 4 | 8.2 |
| HHC157 | RVWRNGYSR | 4 | 10 |
| HHC158 | WGRTRWSSR | 4 | 9.6 |
| HHC159 | GKRVWGRGR | 4 | 8.2 |
| HHC160 | SFNWKRSGK | 4 | 25 |
| HHC161 | WGRGGWTNR | 4 | 25 |
| HHC162 | ANRWGRGIR | 4 | 11 |
| HHC163 | WGGHKRRGW | 4 | 6.2 |
| HHC164 | WHGGQKWRK | 4 | 8.5 |
| HHC165 | FVWQKGTNR | 4 | 11 |
| HHC166 | HGVWGNRKR | 4 | 7.9 |
| HHC167 | TRGWSLGTR | 4 | 12 |
| HHC168 | GRRVMNQKR | 4 | 9.8 |
| HHC169 | RNKFGGNWR | 4 | 25 |
| HHC170 | GVRVQRNSK | 4 | 25 |
| HHC171 | NQKWSGRRR | 4 | 8.0 |
| HHC172 | RQNGVWRVF | 4 | 8.3 |
| HHC173 | GRMRLWNGR | 4 | 7.9 |
| HHC174 | WHYRSQVGR | 4 | 6.6 |
| HHC175 | GWNTMGRRW | 4 | 6.3 |
| HHC176 | RRMGNGGFR | 4 | 8.7 |
| HHC177 | SKNVRTWRQ | 4 | 7.6 |
| HHC178 | ARGRWINGR | 4 | 7.2 |
| HHC179 | GSRRSVWVF | 4 | 2.3 |
| HHC180 | WSQNVRTRI | 4 | 5.7 |
| HHC181 | GMRRWRGKN | 4 | 6.0 |

TABLE 8-continued

Selected peptides (SEQ ID NOS: 1013-1212) from the 100,000 peptide set. The predicted activities are given in activity quartiles, where the most active predicted peptide quartile (top 25,000 peptides) is Quartile 1, Quartiles 2 and 3 are predicted to be successively less active and the least active is predicted to be Quartile 4.

| Name | Sequence | Predicted activity (in Quartiles) | Measured activity ($IC_{50}$) |
|---|---|---|---|
| HHC182 | RGRTSNWKM | 4 | 7.1 |
| HHC183 | GRRWGMGVR | 4 | 7.7 |
| HHC184 | WGKRRGWNT | 4 | 7.9 |
| HHC185 | AMLGGRQWR | 4 | 6.7 |
| HHC186 | QRNKGLRHH | 4 | 8.8 |
| HHC187 | ARGKSIKNR | 4 | 8.3 |
| HHC188 | NRRNGQMRR | 4 | 8.4 |
| HHC189 | RGRRQIGKF | 4 | 8.5 |
| HHC190 | ASKRVGVRN | 4 | 8.2 |
| HHC191 | GRIGGKNVR | 4 | 9.1 |
| HHC192 | NKTGYRWRN | 4 | 8.3 |
| HHC193 | VSGNWRGSR | 4 | 8.5 |
| HHC194 | GWGGKRRNF | 4 | 7.3 |
| HHC195 | KNNRRWQGR | 4 | 6.4 |
| HHC196 | GRTMGNGRW | 4 | 6.9 |
| HHC197 | GRQISWGRT | 4 | 8.0 |
| HHC198 | GGRGTRWHG | 4 | 8.6 |
| HHC199 | GVRSWSQRT | 4 | 8.5 |
| HHC200 | GSRRFGWNR | 4 | 8.1 |

The antimicrobial activity of these peptides was determined by the luminescence assay. The activity was determined by graphing the luminescence values as a function of peptide concentration. The highest peptide concentration was set to 1. As a consequence, the determined $IC_{50}$ values, rounded to 2 significant figures, are relative (Hilpert, K., and R. E. W. Hancock, Use of luminescent bacteria for rapid screening and characterization of short cationic antimicrobial peptides synthesized on cellulose using peptide array technology, Nature Protocols, 2007, vol. 2, pp. 1652-1660).

To further evaluate the accuracy of the developed structure-activity models 25 peptide candidates (Table 9) were selected at random from the above-described 200 peptides and representing the entire range of predicted activities. Thus five to eight sequences were selected from each quartile of the 100,000 predicted peptides sorted by their cumulative votes and ranking Thus, the collection of 25 selected peptides was expected to contain high-, median-, low- and completely inactive entries (roughly corresponding to the quartiles).

The selected peptides were synthesized and assayed against several major antibiotic-resistant pathogens. Initially, the peptides were screened against the laboratory strain of *P. aeruginosa* PAO1 to compare the results with the training data. It was confirmed that peptide candidates selected from the 'fourth quartile' did not posses any antimicrobial activity, as had been forecasted by the QSAR (HHC-152, HHC-183, HHC-186, HHC-189, and HHC-190). The antibacterial activity in the form of minimal inhibitory concentration (MIC) of the other studied peptides was assessed in greater depth (Table 9) against many highly antibiotic resistant pathogens.

TABLE 9

MIC activity values for the QSAR-designed peptides. (SEQ ID NOS: 970, 1020-1022, 1032, 1048, 1057, 1060, 1065, 1069, 1078, 1081, 1083, 1087, 1089, 1112, 1135, 1138, 1145, 1154, 1160, 1164, 1195, 1198, 1201 qand 1202, respectively).

| Peptide | Sequence | MIC (µM) | | | | | | | |
|---|---|---|---|---|---|---|---|---|---|
| | | PA | A | B | C | D | E | F | G |
| Bac2A | RLARIVVIRVAR | 35 | 48 | 192 | 95 | 12 | 3 | 24 | 24 |
| HHC-8 | KIWWWWRKR | 5 | 6 | 47 | 24 | 5.9 | 3 | 94 | 6 |
| HHC-9 | RWRRWKWWL | 37 | 3 | 12 | 12 | 0.3 | 0.7 | 6 | 3 |
| HHC-10 | KRWWKWIRW | 1.4 | 0.8 | 6 | 1.5 | 0.8 | 0.4 | 3 | 1.5 |
| HHC-20 | WRWWKIWKR | 5 | 6 | 24 | 24 | 1.5 | 0.8 | 12 | 6 |
| HHC-36 | KRWWKWWRR | 4 | 0.7 | 5.7 | 1.4 | 0.3 | 1.4 | 11 | 3 |
| HHC-45 | WKRWWKKWR | 7 | 23 | 46 | 46 | 6 | 1.4 | 93 | 3 |
| HHC-48 | WKKWWKRRW | 7 | 23 | 46 | 46 | 6 | 1.4 | 23 | 3 |

TABLE 9-continued

MIC activity values for the QSAR-designed peptides. (SEQ ID NOS: 970, 1020-1022, 1032, 1048, 1057, 1060, 1065, 1069, 1078, 1081, 1083, 1087, 1089, 1112, 1135, 1138, 1145, 1154, 1160, 1164, 1195, 1198, 1201 qand 1202, respectively).

| Peptide | Sequence | | | | | | | |
|---|---|---|---|---|---|---|---|---|
| HHC-53 | FRRWWKWFK | 4.2 | 1.5 | 12 | 3.0 | 1.5 | 0.8 | 24 | 6 |
| HHC-57 | LRWWWIKRI | 12 | 13 | 50 | 25 | 6 | 3 | 50 | 13 |
| HHC-66 | RKRLKWWIY | 7 | 25 | 50 | 50 | 6 | 3 | 13 | 6 |
| HHC-69 | KKRWVWIRY | 8 | 25 | 51 | 25 | 3 | 1.6 | 25 | 13 |
| HHC-71 | KWKIFRRWW | 6 | 12 | 24 | 24 | 3 | 1.5 | 6 | 12 |
| HHC-75 | RKWIWRWFL | 5 | 6 | 12 | 3 | 1.5 | 1.5 | 3 | 1.5 |
| HHC-77 | IWWKWRRWV | 10 | 6 | 48 | 12 | 6 | 1.5 | 6 | 6 |
| HHC-100 | RRFKFIRWW | 9 | 6 | 24 | 49 | 3 | 0.8 | 12 | 12 |
| HHC-123 | AVWKFVKRV | 360 | >240 | >240 | 240 | 120 | 60 | >240 | 120 |
| HHC-126 | AWRFKNIRK | 376 | >223 | >223 | >223 | 111 | >223 | >223 | 223 |
| HHC-133 | KRIMKLKMR | 269 | >226 | >226 | >226 | >226 | >226 | >226 | >226 |
| HHC-142 | AIRRWRIRK | 184 | >217 | >217 | >217 | 217 | 108 | 108 | 108 |
| HHC-148 | VVLKIVRRF | 1104 | >241 | >241 | >241 | 241 | 60 | 241 | 241 |
| HHC-152 | AFRGSRHRM | 506 | NT | NT | NT | NT | NT | NT | NT |
| HHC-183 | GRRWGMGVR | 360 | NT | NT | NT | NT | NT | NT | NT |
| HHC-186 | QRNKGLRHH | 381 | NT | NT | NT | NT | NT | NT | NT |
| HHC-189 | RGRRQIGKF | 379 | NT | NT | NT | NT | NT | NT | NT |
| HHC-190 | ASKRVGVRN | 413 | NT | NT | NT | NT | NT | NT | NT |

| | | MIC (μM) | | | | | | | |
|---|---|---|---|---|---|---|---|---|---|
| Peptide | Sequence | H | I | J | K | L | M | N | O |
| Bac2A | RLARIVVIRVAR | 192 | 24 | 24 | 12 | 48 | 12 | 3 | 48 |
| HHC-8 | KIWWWWRKR | 47 | 6 | 6 | 24 | 94 | 6 | 1.5 | 94 |
| HHC-9 | RWRRWKWWL | 11 | 3 | 3 | 23 | 92 | 6 | 1.4 | 92 |
| HHC-10 | KRWWKWIRW | 6 | 3 | 1.5 | 12 | 99 | 3 | 1.5 | 49 |
| HHC-20 | WRWWKIWKR | 24 | 3 | 3 | 24 | 94 | 6 | 1.5 | 94 |
| HHC-36 | KRWKWWRR | 22 | 3 | 1.4 | 43 | >174 | 11 | 1.3 | 174 |
| HHC-45 | WKRWWKKWR | 46 | 68 | 6 | 93 | >186 | 23 | 6 | >186 |
| HHC-48 | WKKWWKRRW | 46 | 1.4 | 39 | 93 | >186 | 12 | 6 | >186 |
| HHC-53 | FRRWWKWFK | 24 | 1.5 | 3 | 24 | 195 | 6 | 6 | 97 |
| HHC-57 | LRWWWIKRI | 50 | 6 | 63 | 13 | 50 | 6 | 1.5 | 25 |
| HHC-66 | RKRLKWWIY | 50 | 6 | 6 | 50 | >202 | 13 | 3 | 202 |
| HHC-69 | KKRWVWIRY | 51 | 13 | 13 | 25 | 102 | 6 | 6 | 102 |
| HHC-71 | KWKIFRRWW | 97 | 3 | 3 | 24 | 97 | 24 | 6 | 97 |
| HHC-75 | RKWIWRWFL | 3.1 | 31 | 3 | 6 | 24 | 3 | 3 | 24 |
| HHC-77 | IWWKWRRWV | 12 | 3 | 3 | 24 | 48 | 6 | 3 | 48 |
| HHC-100 | RRFKFIRWW | 49 | 6 | 6 | 12 | 98 | 6 | 6 | 49 |
| HHC-123 | AVWKFVKRV | >240 | 240 | 240 | >240 | >240 | 120 | 120 | >240 |
| HHC-126 | AWRFKNIRK | >223 | 223 | >223 | >223 | >223 | >223 | 223 | >223 |

TABLE 9-continued

MIC activity values for the QSAR-designed peptides. (SEQ ID NOS: 970, 1020-1022, 1032, 1048, 1057, 1060, 1065, 1069, 1078, 1081, 1083, 1087, 1089, 1112, 1135, 1138, 1145, 1154, 1160, 1164, 1195, 1198, 1201 qand 1202, respectively).

| | | | | | | | | | |
|---|---|---|---|---|---|---|---|---|---|
| HHC-133 | KRIMKLKMR | >226 | >226 | >226 | >226 | >226 | >226 | >226 | >226 |
| HHC-142 | AIRRWRIRK | >217 | 54 | 54 | >217 | >217 | 108 | 14 | >217 |
| HHC-148 | VVLKIVRRF | >241 | 241 | 241 | 241 | >241 | 241 | 60 | >241 |
| HHC-152 | AFRGSRHRM | NT | NT | NT | NT | NT | NT | NT | NT |
| HHC-183 | GRRWGMGVR | NT | NT | NT | NT | NT | NT | NT | NT |
| HHC-186 | QRNKGLRHH | NT | NT | NT | NT | NT | NT | NT | NT |
| HHC-189 | RGRRQIGKF | NT | NT | NT | NT | NT | NT | NT | NT |
| HHC-190 | ASKRVGVRN | NT | NT | NT | NT | NT | NT | NT | NT |

Column legends: PA01, *P. aeruginosa*
Lab strain; A, *P. aeruginosa* wild type strain H103; B, C, *P. aeruginosa* multidrug resistant strains from Brazil strain H9 and H123; D, *P. aeruginosa* multidrug resistant Liverpool epidemic strains H1031, H1030, and H1027 respectively; E, multidrug resistant *Pseudomonas maltophilia* ATCC13637; F, Extended-Spectrum β-lactamase-producing β-lactam resistant (ESBL) *Enterobacter cloacae* strain C601. G, ESBL *E. coli* clinical strain 64771; H, ESBL *Klebsiella pneumonia* clinical strain 63575; I, *S. aureus* ATCC25923; J, Methicillin resistant *S. aureus* (MRSA) strain C623; K, *Enterococcus faecalis* ATCC29212; L, M, VRE Vancomycin resistant *Enterococcus faecalis* clinical isolates w61950 (VanA) and f43559 (VanB);
N, O, VRE Vancomycin resistant *Enterococcus faecium* clinical isolates mic80 (VanA) and t62764 (VanB).

All of the peptides in Table 9 had similar physical properties. These experimental results unambiguously demonstrated that the QSAR approach is able to be utilized for accurately forecasting the antimicrobial activity of de novo designed peptides. Thus, all 7 'first-quartile' derivatives demonstrated very significant activity against *P. aeruginosa* PAO1 with the corresponding MIC parameters ranging from 1.4 µM to 6.8 µM. Moreover, 2 out of 7 'first-quartile' peptides (HHC-8, HHC-9, HHC-10, HHC-20, HHC-36, HHC-45, and HHC-48), actually outperformed the most active lead from the training 'set A' (with MIC=3.29 µM). Interestingly enough, there were only 6 peptides with MIC <7 µM could be found in the entire 'set A'. In another pre-designed training 'set B' only 1 out of 500 entries demonstrated an MIC <6 µM. Importantly, peptides selected from the 'second quartile' also demonstrated substantial antimicrobial activity in that their MIC values ranged between 4 µM and 12 µM (HHC-53, HHC-57, HHC-66, HHC-69, HHC-71, HHC-75, HHC-77, and HHC-100). As predicted by the QSAR, the third quartile selection (HHC-123, HHC-126, HHC-133, HHC-142, HHC-148) did not return any generally active substances, while the fourth quartile peptides were all virtually completely inactive.

Figure 9:
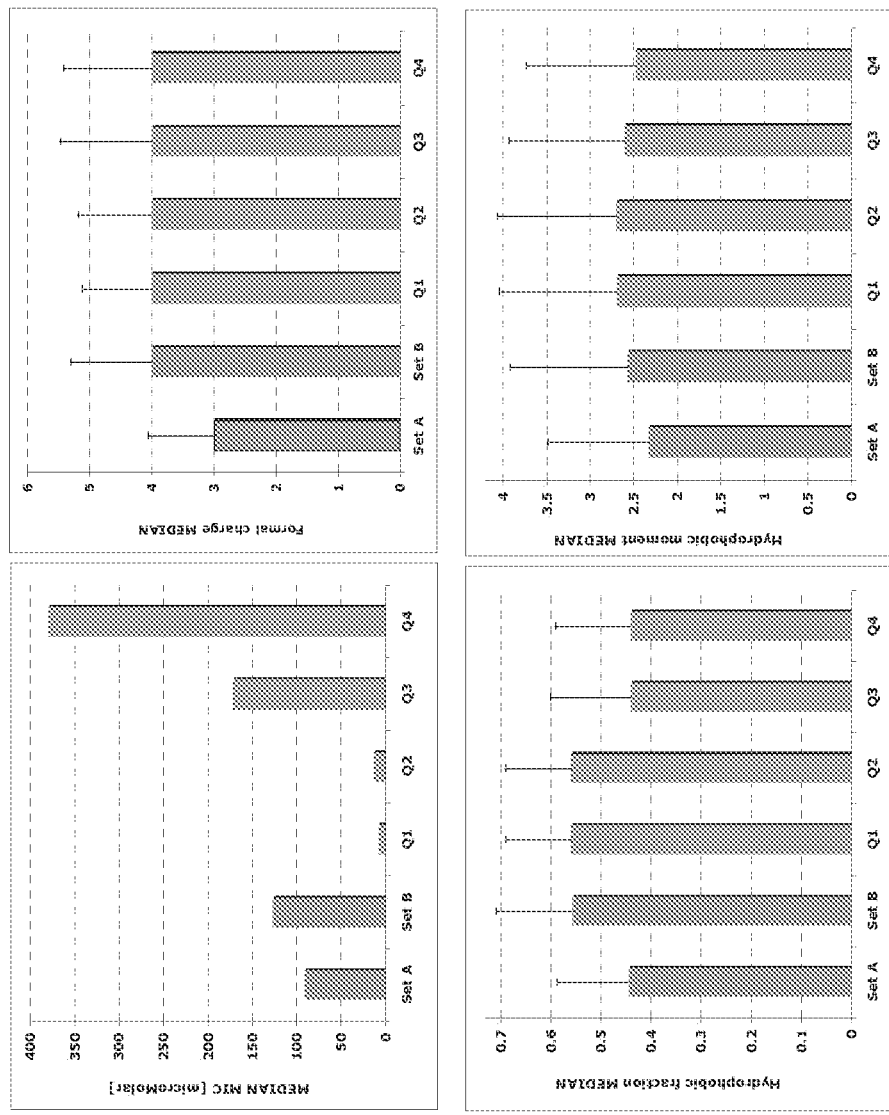
FIG. 9. Similar physical properties of the 4 predicted-activity-based quartiles of peptides. Panel A: Median MIC, against *P. aeruginosa* PAO1, of known antimicrobial peptides from training sets A and B (measured) and the corresponding median values for 25 experimentally tested peptides separated into activity quartiles. Panels B-D: Median values of charge (Q), hydrophobicity (P) and amphipathicity/hydrophobic moment (HM).

These results clearly illustrate that the QSAR approach can accurately predict the antimicrobial activity of peptides and permit the development of structure-activity models that create lists of drug candidates. To illustrate that important observation, we derived median MICs for *P. aeruginosa* PAO1 for the training sets A (91 µM) and B (127 µM) compared to the corresponding median MICs for the experimentally tested peptides from the $1^{st}$, $2^{nd}$, $3^{rd}$, and $4^{th}$ quartiles (7, 13, 172 and 379 µM respectively). Thus, these results demonstrated the superior performance of atom-based QSAR approach compared to conventional peptide design strategies traditionally relying on charge, hydrophobicity and/or amphipathicity properties of isolated aminoacids. To illustrate this notion further, median values of formal charge, hydrophobic fraction and hydrophobic moment were computed for peptides present in the training sets A and B as well as for all 100,000 predicted candidates populating the quartiles (FIG. 9).

This chart clearly demonstrates that there was very limited variation in charge (Q), hydrophobicity (P) and hydrophobic moments (HM) of peptides in the 4 activity quartiles, while their antimicrobial activities varied tremendously. Thus adequate modeling of antimicrobial activity of cationic peptides demands substantially more refined structure-activity approaches including a detailed, atomic-level of consideration of molecular structures, rather than simplistic consideration of the polar and hydrophobic characteristics of constituent aminoacids.

All peptides derived from the $1^{st}$, $2^{nd}$, and $3^{rd}$ quartiles were further evaluated for their antibacterial activities against several highly antibiotic resistant pathogens (Table 3). These included clinical isolates of MRSA, ESBL *E. cloacae*, and multidrug resistant *Pseudomonas* strains including Brazilian clinical isolates of *P. aeruginosa* that are resistant to meropenem, ceftazidime, piperacillin/tazobactam, ciprofloxacin, cefepime and polymyxin B, and the Liverpool Epidemic Strains. All 15 peptides from the $1^{st}$ and $2^{nd}$ quartiles demonstrated significant activity against resistant strains, and effectively inhibited bacterial growth at low µM concentrations. Some candidates such as HHC-9, HHC-10, HHC-36 and HHC-75 exhibited 1-10 µM activity against nearly all tested superbugs. Such results characterize the developed peptides as excellent antibiotic candidates, providing new means for treating most dangerous and severe forms of human infections.

Figure 10:
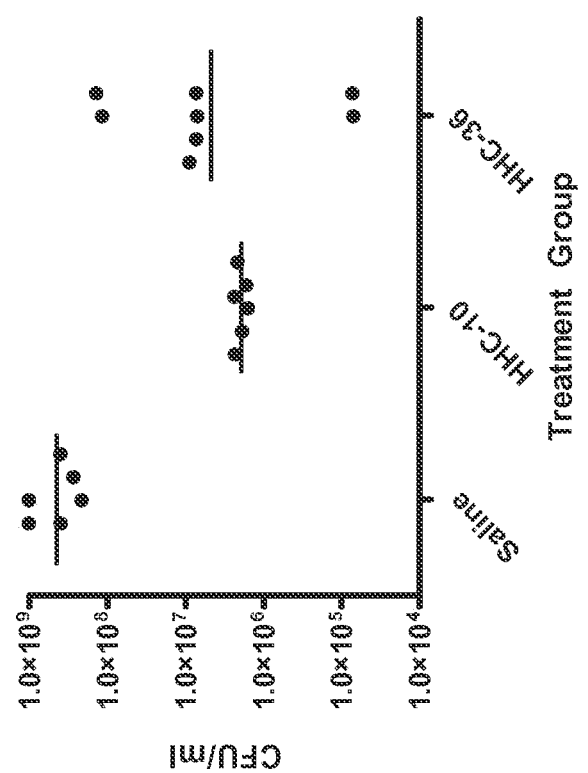
FIG. 10. Ability of new antimicrobial peptides HHC-10 and HHC-36 to protect mice against *Staph aureus* infections. Bacterial loads in the peritoneal lavage from individual mice after 24 hours of infection are shown (solid circles). Dead animals were assigned the highest colony forming unit (CFU) count obtained in the experiment. The solid line represents the arithmetic mean for each group.

To further confirm this, a mouse model of aggressive bacterial infection, widely used to assess antibiotic efficacy, was utilized. Mice were treated with $1.6 \times 10^{10}$ CFU IP. Four hours post infection they received a dose of 4 mg/kg peptide IP. The infection was allowed to progress for 20 more hours, for a total infection time of 24 hours. Control mice injected with just saline demonstrated 100% death; in contrast HHC-10 protected 40% of mice while HHC-36 protected 60% of mice. A second experiment with administration of $1.4 \times 10^{10}$ IP resulted in significant reduction in the number of bacteria in the animals given peptide (FIG. 10).

Figure 11:
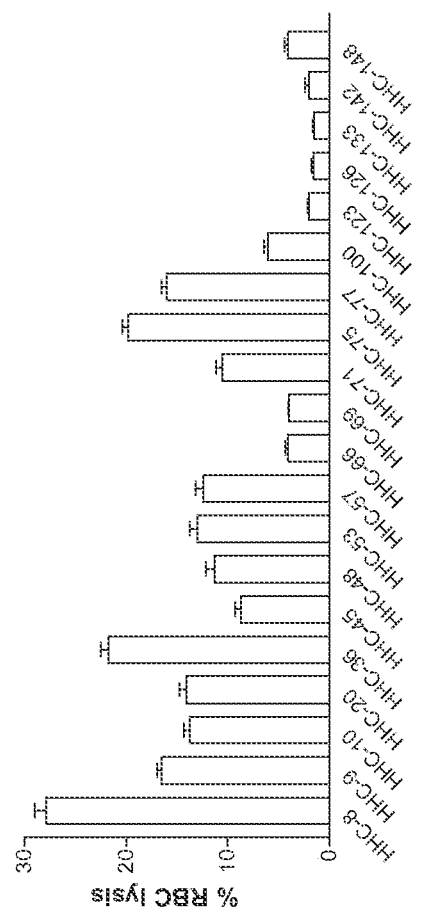
FIG. 11. The lack of hemolytic activity (at 375 µg/ml) of 20 antimicrobial peptides that demonstrated antibacterial activity. In addition to this modest effect at this very high concentration there was no hemolytic activity at 100 µg/ml.

To assess possible host toxicity of the developed compounds we also tested 20 peptides for their hemolytic activity (FIG. 11) demonstrating that the developed antibiotics do not affect host cells.

Amongst the preferred nine amino acid antimicrobial peptides, a clear pattern of related peptides were found that obviously represented minor substitutions, deletions or additions to a base sequence represented by SEQ ID NO: 1022. Thus these peptides have a clear unitary relationship. In the following sequence alignments bolded letters represent amino acids that are identical or represent conservative substitutions (i.e., hydrophobic amino acid substitutions A, L, V, W, I, or F; or charge substitutions R or K).

| | | |
|---|---|---|
| HHC-10 | KRWWK-WIRW | SEQ ID NO: 1022 |
| HHC-36 | KRWWK-WWRR | SEQ ID NO: 1048 |
| HHC-8 | KIWWW-W-RKR | SEQ ID NO: 1020 |
| HHC-20 | WRWWKIWKR | SEQ ID NO: 1032 |
| HHC-45 | WKRWWKKW-R | SEQ ID NO: 1057 |
| HHC-48 | WKKWWKR-RW | SEQ ID NO: 1060 |

Example 7

Anti-Septic Impact on Innate Immunity

It is well known that cationic antimicrobial peptides have the ability to boost immunity while suppressing septic responses to bacterial pathogen associated molecular pattern molecules like lipopolysaccharide and lipoteichoic acids as well as reducing inflammation and endotoxaemia (Finlay, B. B., and R. E. W. Hancock. 2004. Can innate immunity be enhanced to treat infections? Nature Microbiol. Rev. 2:497-504).

Figure 12:
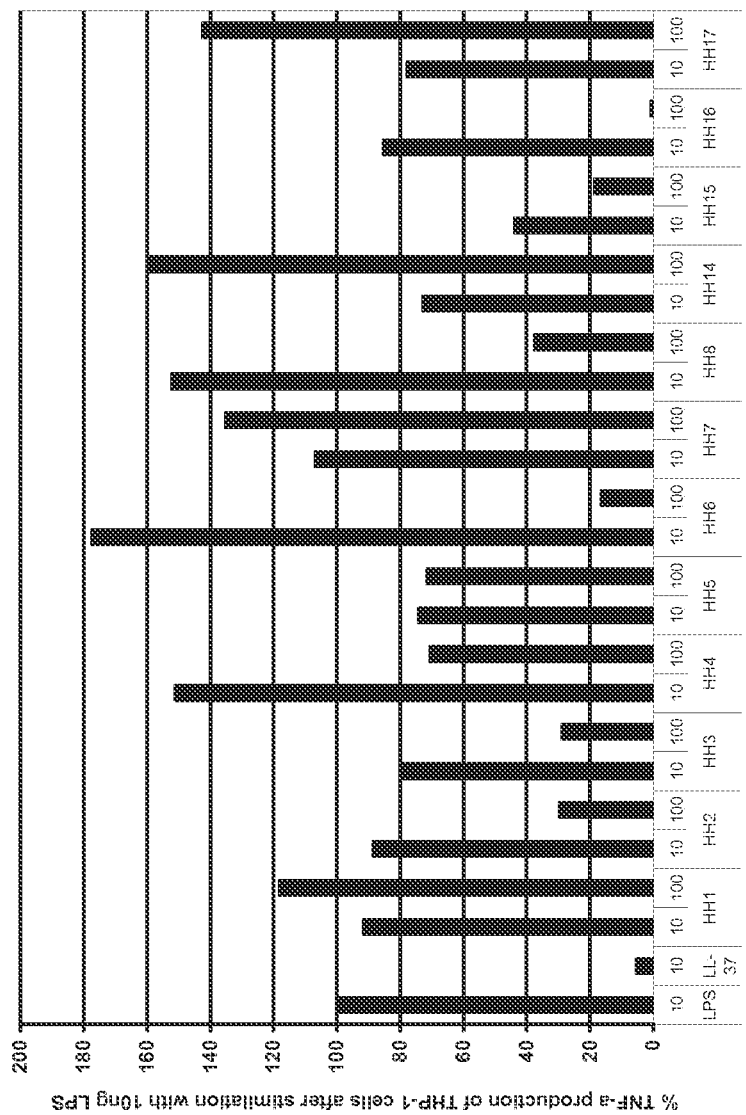
FIG. 12. Assessment of the ability of peptides to suppress *P. aeruginosa* LPS (10 ng/ml)-stimulated TNFα production in THP1 cells. Presented results are the mean values for 4 wells performed on 2 separate occasions. The x-axis number labeling is the amount of each peptide in µg/ml for the corresponding peptides.

Small 12-mer peptides like Bac2A and 13-mer peptides like indolicidin have been previously shown in our laboratory to have rather modest anti-endotoxic activity, which can be assessed by measuring the ability of the peptide to suppress the LPS-stimulated production of TNFα by macrophages. It is well known for other cationic antimicrobial peptides that this corresponds to anti-endotoxic activity in reversing lethal endotoxaemia in animal models (Gough M, Hancock R E W, and Kelly N M. 1996. Anti-endotoxic potential of cationic peptide antimicrobials. Infect. Immun. 64, 4922-4927). In contrast LL-37 is known to have excellent anti-endotoxic activity in vitro, as assessed by its ability to suppress the LPS-mediated induction of TNFα in monocytic cells and this is reflected by its ability to both reduce endotoxin mediated TNFα induction and lethality in a mouse model (Scott, M. G., D. J. Davidson, M. R. Gold, D. Bowdish, and R. E. W. Hancock. 2002. The human antimicrobial peptide, LL-37, is a multifunctional modulator of innate immune responses. J. Immunol. 169:3883-3891). A selection of peptides were tested and some of these indeed had excellent anti-endotoxic activity (FIG. 12).

Only three of the peptides showed any evidence of cytotoxicity toward THP-1 cells, and this was only evident at 100 µg/ml of peptide (Table 10). In addition the following peptides were tested for LDH release: 1002, 1005, 1012, 1010, 1013, 1018, 1020, 1026, 1028, 1032, 1033, 1035, and 1037. None showed any LDH release even at 200 µg/ml.

TABLE 10

Cytotoxicity of peptides against THP-1 cells tested at 10 and 100 µg/ml.

| Name | Cytotoxicity |
|---|---|
| HH1 | No cytotoxicity observed |
| HH2 | No cytotoxicity observed |
| HH3 | No cytotoxicity observed |
| HH4 | No cytotoxicity observed |
| HH5 | 50-60% at 100 µg/ml |
| HH6 | No cytotoxicity observed |
| HH7 | No cytotoxicity observed |
| HH8 | No cytotoxicity observed |
| HH14 | No cytotoxicity observed |
| HH15 | 25% at 100 µg/ml |
| HH16 | 80% at 100 µg/ml |
| HH17 | No cytotoxicity observed |

LPS from *P. aeruginosa* strain H103 was highly purified free of proteins and lipids using the Darveau-Hancock method. Briefly, *P. aeruginosa* was grown overnight in LB broth at 37° C. Cells were collected and washed and the isolated LPS pellets were extracted with a 2:1 chloroform: methanol solution to remove contaminating lipids. Purified LPS samples were quantitated using an assay for the specific sugar 2-keto-3-deoxyoctosonic acid (KDO assay) and then resuspended in endotoxin-free water (Sigma-Aldrich).

Human monocytic cells, THP-1, were obtained from American type culture collection, ATCC® (TIB-202) and were grown in suspension in RPMI-1640 media (Gibco®, Invitrogen™ Life technologies, Burlington, ON), supplemented with 10% (v/v) heat inactivated fetal bovine serum (FBS), 2 mM L-glutamine and 1 mM sodium pyruvate (all from Invitrogen Life Technologies). Cultures were maintained at 37° C. in a humidified 5% (v/v) $CO_2$ incubator up to a maximum of six passages. THP-1 cells at a density of $1 \times 10^6$ cells/ml were treated with 0.3 µg/ml phorbol 12-myristate 13-acetate (PMA; Sigma-Aldrich Canada, Oakville ON) for 24 hours, inducing plastic-adherent cells that were further rested in complete RPMI-1640 medium for an additional 24 hours prior to stimulation with various treatments including *P. aeruginosa* LPS (10 ng/ml) with or without peptides for 24 hours after which supernatants were collected and TNFα assessed by ELISA.

THP-1 cells were stimulated with LPS (10 ng/ml) with or without peptide (10 or 100 µg/ml) for 4 hours as indicated in the results section. Following incubation of the cells under various treatment regimens, the tissue culture supernatants were centrifuged at 1000×g for 5 min, then at 10,000×g for 2 min to obtain cell-free samples. Supernatants were aliquoted and then stored at −20° C. prior to assay for various cytokines TNFα secretion was detected with a capture ELISA (eBioscience and BioSource International Inc., CA, USA respectively).

The data in FIG. 12 demonstrated that LPS as expected induced large levels of TNFα. This was strongly suppressed by the control peptide LL-37, as well as by the novel peptides HH2, HH3, HH6, HH8, HH15 and HH16. In addition several of the remaining peptides, including HH1, HH5, and HH17 caused no significant increase in TNFα production.

Figure 13:
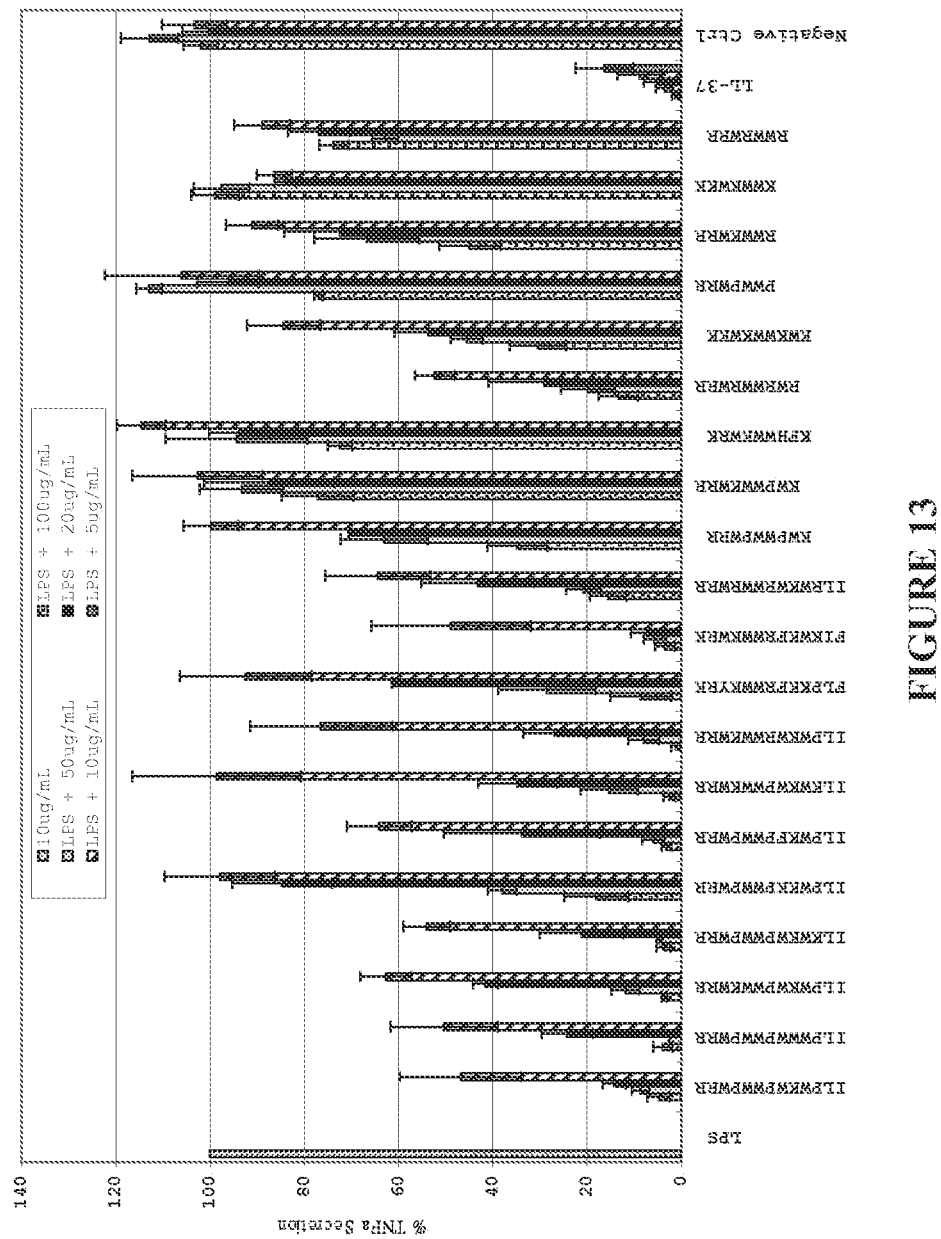
FIG. 13. Suppression of inflammatory responses by peptides. Monocyte/macrophage-like adherent THP-1 cells were stimulated with 10 ng/ml *P. aeruginosa* LPS and the resulting TNFα response measured. Peptides (SEQ ID NOS: 971, 235, 117, 111, 113, 63, 973-976, 1261, 977, 984, 992, 1262, 1263, 996, 1005, 1011 and 1264, respectively) were added at 10, 20 and 50 µg/ml. The observed TNF-release was measured by ELISA and related to the 100% value of the untreated (without peptide) cells.

Anti-endotoxin effects of peptides derived from indolicidin. Some smaller peptides, like indolicidin (Bowdish D M, Davidson D J, Scott M G, Hancock R E W. Immunomodulatory activities of small host defense peptides. Antimicrobial Agents Chemotherapy 49:1727-32, 2005), are known to be able to inhibit the production of proinflammatory cytokines like TNFα in response to endotoxin. Therefore a variety of peptides derived from indolicidin were tested for their ability to inhibit TNFα responses after challenge with *P. aeruginosa* LPS. The results are presented in FIG. 13. Basically we were able to demonstrate that the following peptides HH63, HH111, HH117, HH235, HH973, HH1010 and HH1011 were slightly better or equivalent than indolicidin.

Example 8

Enhancement of Innate Immunity

The natural human peptide LL-37 is able to protect against bacterial infections despite having no antimicrobial activity under physiological conditions (Bowdish, D. M. E., D. J. Davidson, Y. E. Lau, K. Lee, M. G. Scott, and R. E. W. Hancock. 2005. Impact of LL-37 on anti-infective immunity. J. Leukocyte Biol. 77:451-459). It appears to manifest this activity due to its ability to induce the production of certain chemokines which are able to recruit subsets of cells of innate immunity to infected tissues. Therefore we tested if the novel peptides described here had the ability to induce chemokine production in human peripheral blood mononuclear cells.

Venous blood (20 ml) from healthy volunteers was collected in Vacutainer® collection tubes containing sodium heparin as an anticoagulant (Becton Dickinson, Mississauga, ON) in accordance with UBC ethical approval and guidelines. Blood was diluted 1:1 with complete RPMI 1640 medium and separated by centrifugation over a Ficoll-Paque® Plus (Amersham Biosciences, Piscataway, N.J., USA) density gradient. White blood cells were isolated from the buffy coat, washed twice in RPMI 1640 complete medium, and the number of peripheral blood mononuclear cells (PBMC) was determined by trypan blue exclusion. PBMC ($5 \times 10^5$) were seeded into 12-well tissue culture dishes (Falcon; Becton Dickinson) at 0.75 to $1 \times 10^6$ cells/ml at 37° C. in 5% $CO_2$. The above conditions were chosen to mimic conditions for circulating blood monocytes entering tissues at the site of infection via extravasation.

Following incubation of the cells under various treatment regimens, the tissue culture supernatants were centrifuged at 1000×g for 5 min, then at 10,000×g for 2 min to obtain cell-free samples. Supernatants were aliquoted and then stored at −20° C. prior to assay for various chemokines by capture ELISA (eBioscience and BioSource International Inc., CA, USA respectively)

Figure 14:
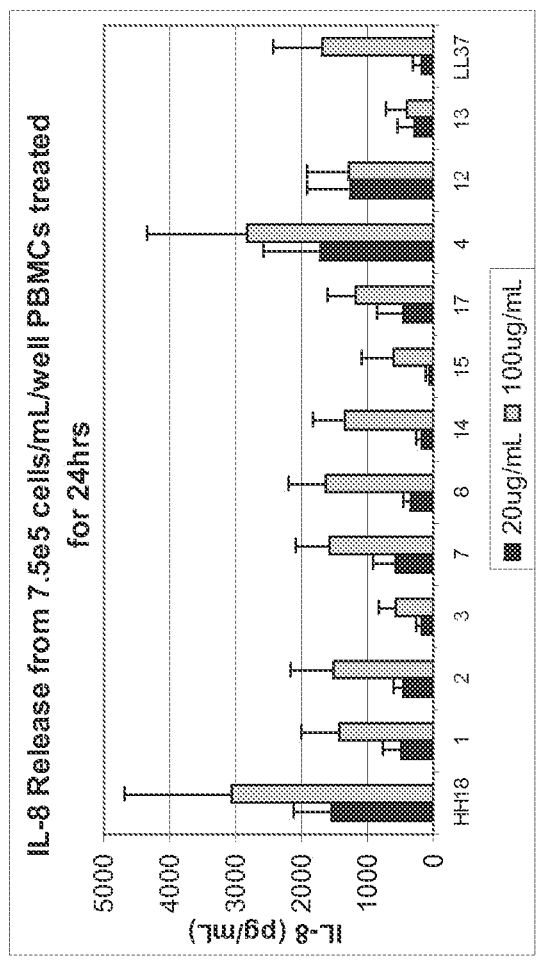
FIG. 14. Induction of IL8 release by $7.5 \times 10^5$ human PBMC in response to treatment with 20 or 100 µg/ml of different peptides for 24 hours.

As shown in FIG. 14, most of the peptides stimulated the expression of the neutrophils chemokine IL8 even at the lowest peptide concentration utilized (20 µg/ml). Peptides HH2, HH4, HH7, HH8, HH13, HH7, HH14, and HH18 appeared to have the strongest abilities to induce this chemokine.

Figure 15:
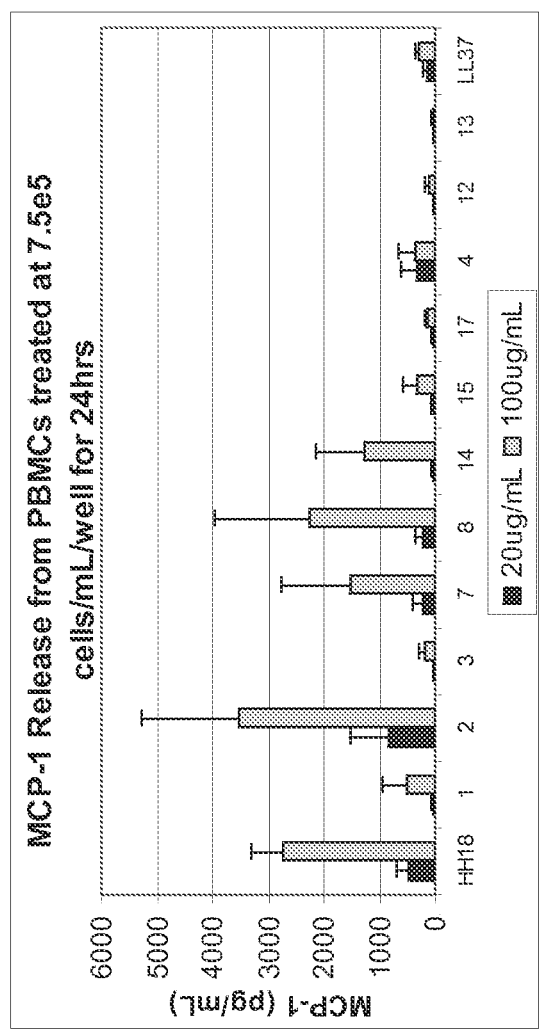
FIG. 15. Induction of MCP-1 release by $7.5 \times 10^5$ human PBMC in response to treatment with 20 or 100 µg/ml of different peptides for 24 hours.
Figure 16:
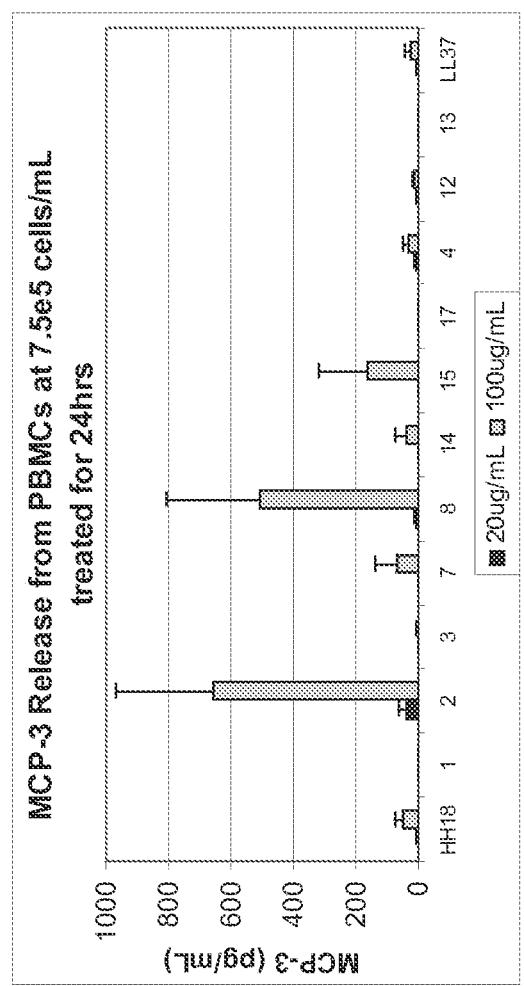
FIG. 16. Induction of MCP3 release by $7.5 \times 10^5$ human PBMC in response to treatment with 20 or 100 µg/ml of different peptides for 24 hours.
Figure 17:
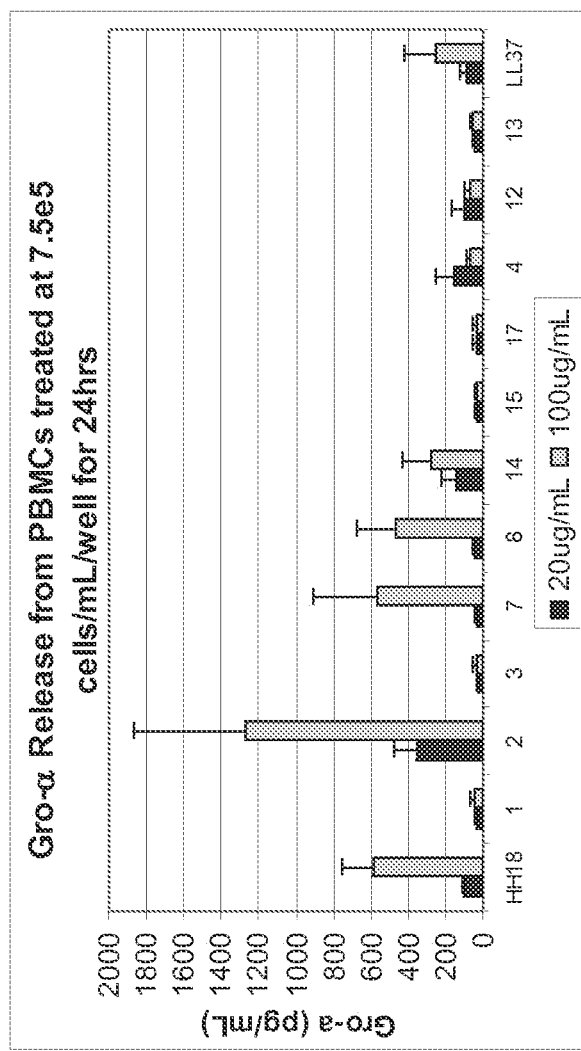
FIG. 17. Induction of CXCL1 (Gro-α) release by $7.5 \times 10^5$ human PBMC in response to treatment with 20 or 100 µg/ml of different peptides for 24 hours.

The monocyte chemokine MCP1 (FIG. 15) was also induced by a subset of the peptides including especially, HH1, HH2, HH4, HH7, HH8, HH14, and HH18. A similar result was obtained for experiments investigating release of the macrophage chemokine MCP3 (FIG. 16) and neutrophils chemokine Gro-α (FIG. 17), although HH1 was not active in this assay.

Based on these results new peptides were iteratively designed from the best peptides by substitution and/or scrambling of peptide sequences. Screening of these peptides for chemokine induction in human PBMC gave the results presented in Table 11.

TABLE 11

Chemokine induction (pg/ml) by new peptides in human PBMC. Chemokine induction (pg/ml) by the given concentrations of peptide

| Name | Sequence | MCP-1 | | MCP-3 | | Gro-α | |
|---|---|---|---|---|---|---|---|
| | | 20 µg/ml | 100 µg/ml | 20 µg/ml | 100 µg/ml | 20 µg/ml | 100 µg/ml |
| Background | No peptide | 204 | | 6 | | 196 | |
| Bac2a | RLARIVVIRVAR | 316 | 442 | 2 | 2 | 9 | 8 |
| HH2 | VQLRIRVAVIRA | 4882 | 10235 | 86 | 283 | 867 | 2693 |
| 1001 | LVRAIQVRAVIR | 516 | 2491 | 0 | 40 | 88 | 850 |
| 1002 | VQRWLIVWRIRK | 2472 | 5566 | 13 | 141 | 1032 | 2117 |
| 1003 | IVWKIKRWWVGR | 31 | 1361 | 0 | 5 | 65 | 170 |
| 1004 | RFWKVRVKYIRF | 300 | 1680 | 1 | 30 | 55 | 336 |
| 1005 | VQLRIRVAV | 1228 | 4555 | 23 | 126 | 332 | 2247 |
| 1006 | VQLRIWVRR | 392 | 3004 | 0 | 58 | 65 | 1245 |
| 1007 | WNRVKWIRR | 103 | 247 | 7 | 28 | 65 | 170 |
| 1008 | RIKWIVRFR | 633 | 1775 | 1 | 22 | 109 | 869 |
| HH7 | VRLRIRVAVRRA | 894 | 1197 | 11 | 14 | 122 | 152 |

TABLE 11-continued

Chemokine induction (pg/ml) by new peptides in human PBMC.
Chemokine induction (pg/ml) by the given concentrations of peptide

| Name | Sequence | MCP-1 20 µg/ml | MCP-1 100 µg/ml | MCP-3 20 µg/ml | MCP-3 100 µg/ml | Gro-α 20 µg/ml | Gro-α 100 µg/ml |
|---|---|---|---|---|---|---|---|
| 1009 | AIRVVRARLVRR | 634 | 1093 | 6 | 6 | 230 | 377 |
| 1010 | IRWRIRVWVRRI | 706 | 5662 | 3 | 604 | 149 | 1384 |
| 1011 | RRWVVWRIVQRR | 579 | 2282 | 1 | 35 | 46 | 308 |
| 1012 | IFWRRIVIVKKF | 11475 | 30148 | 1103 | 3303 | 3873 | 7542 |
| 1013 | VRLRIRVAV | 1914 | 4734 | 22 | 214 | 609 | 2101 |
| 1014 | RQVIVRRW | 83 | 175 | 0 | 1 | 6 | 15 |
| 1015 | VLIRWNGKK | 113 | 644 | 0 | 10 | 42 | 178 |
| 1016 | LRIRWIFKR | 269 | 819 | 1 | 27 | 26 | 247 |
| HH8 | VRLRIRVAVIRK | 194 | 180 | 1 | 3 | 7 | 4 |
| 1017 | KRIVRRLVARIV | 585 | 1019 | 0 | 0 | 56 | 250 |
| 1018 | VRLIVAVRIWRR | 8774 | 13041 | 156 | 604 | 826 | 2692 |
| 1019 | IVVWRRQLVKNK | 27 | 438 | 0 | 0 | 5 | 43 |
| 1020 | VRLRIRWWVLRK | 2485 | 2813 | 82 | 35 | 760 | 370 |
| 1021 | VRLRIRVAV | 158 | 276 | 3 | 10 | 29 | 112 |
| 1022 | LRIRVIVWR | 52 | 983 | 0 | 1 | 10 | 64 |
| 1023 | IRVWVLRQR | 250 | 712 | 0 | 1 | 36 | 38 |
| 1024 | RIRVIVLKK | 285 | 81 | 1 | 0 | 20 | −21 |
| HH12 | KQFRIRVRVIRK | 1649 | 635 | 91 | 21 | 773 | 172 |
| 1025 | RRIVKKFQIVRR | 109 | 284 | 1 | 3 | −3 | 32 |
| 1026 | VQWRIRVRVIKK | 403 | 4717 | 1 | 430 | 77 | 2124 |
| 1027 | KKQVSRVKVWRK | 54 | 1466 | 0 | 14 | 8 | 204 |
| 1028 | LIQRIRVRNIVK | 41 | 385 | 0 | 7 | −17 | 34 |
| 1029 | KQFRIRVRV | 296 | 205 | 3 | 3 | 49 | 60 |
| 1030 | FRIRVRVIR | 139 | 2075 | 1 | 35 | 10 | 674 |
| 1031 | WRWRVRVWR | 875 | 552 | 9 | 9 | 172 | 112 |
| 1032 | IRVRVIWRK | 896 | 203 | 21 | 3 | 297 | 12 |
| HH15 | KRFRIRVRVIRK | 61 | 303 | 0 | 5 | 17 | 17 |
| 1033 | RRIVKKFRIRR | 1747 | 301 | 61 | 6 | 359 | 6 |
| 1034 | KQFRNRLRIVKK | 434 | 796 | 0 | 4 | 60 | 61 |
| 1035 | KRWRWIVRNIRR | 15 | 75 | 0 | 1 | 10 | 27 |

TABLE 11-continued

Chemokine induction (pg/ml) by new peptides in human PBMC.
Chemokine induction (pg/ml) by the
given concentrations of peptide

| Name | Sequence | MCP-1 | | MCP-3 | | Gro-α | |
|---|---|---|---|---|---|---|---|
| | | 20 µg/ml | 100 µg/ml | 20 µg/ml | 100 µg/ml | 20 µg/ml | 100 µg/ml |
| 1036 | VQFRIRVIVIRK | 601 | 968 | 1 | 39 | 51 | 137 |
| 1037 | KRFRIRVRV | 50 | 33 | 0 | 0 | -12 | -21 |
| 1038 | IVVRRVIRK | 25 | 1552 | 0 | 41 | 12 | 518 |
| 1039 | IWVIRRVWR | 603 | 2420 | 13 | 67 | 469 | 1717 |
| 1040 | FQVVKIKVR | 74 | 1143 | 0 | 9 | 2 | 264 |
| HH18 | IWVIWRR | 1111 | 9608 | 32 | 431 | 865 | 2964 |
| 1041 | VIWIRWR | 146 | 1218 | 7 | 53 | 110 | 450 |
| 1042 | IVWIWRR | -7 | 12 | 3 | 3 | 44 | 9 |
| 1043 | WIVIWRR | 98 | 1998 | 0 | 21 | 26 | 881 |
| 1044 | RRWIVWI | 1561 | 5024 | 115 | 261 | 1963 | 1545 |
| 1045 | RWWRIVI | -2 | 989 | 0 | 31 | 13 | 435 |
| 1046 | WIRVIRW | 46 | 449 | 1 | 4 | 38 | 147 |
| 1047 | IIRRWWV | 8 | 130 | 0 | 0 | -1 | -3 |
| 1048 | IRWVIRW | 96 | 38 | 0 | 0 | 7 | -11 |
| HH1 | QRLRIRVAVIRA | 0 | 2 | 35 | 49 | 45 | 516 |
| HH3 | VRFRIRVAVIRA | 0 | 2 | 26 | 38 | 19 | 179 |
| HH4 | VRWRIRVAVIRA | 7 | 30 | 157 | 62 | 333 | 370 |
| HH13 | HQFRFRFRVRRK | 1 | 0 | 40 | 54 | 15 | 42 |
| HH14 | HQWRIRVAVRRH | 0 | 39 | 140 | 273 | 53 | 1279 |
| HH17 | KIWVRWK | 0 | 0 | 37 | 36 | 48 | 132 |
| HHC-8 | KIWWWWRKR | 68 | 835 | 1 | 4 | 9 | -11 |
| HHC-9 | RWRRWKWWL | 9 | 4493 | -1 | 48 | -25 | 5 |
| HHC-10 | KRWWKWIRW | 48 | 3210 | -1 | 49 | -11 | 2 |
| HHC-20 | WRWWKIWKR | 290 | 974 | 8 | 12 | 169 | 33 |
| HHC-36 | KRWWKWWRR | 38 | 168 | 1 | 1 | 19 | -8 |
| HHC-45 | WKRWWKKWR | -9 | 161 | -2 | -2 | -15 | -32 |
| HHC-48 | WKKWWKRRW | 2 | 12 | -1 | -1 | -8 | -10 |
| HHC-53 | FRRWKWFK | -26 | 391 | -1 | 5 | -23 | 2 |
| HHC-57 | LRWWIKRI | 146 | 1364 | 0 | 9 | 21 | 18 |
| HHC-66 | RKRLKWWIY | 351 | 355 | 0 | 0 | -12 | -23 |
| HHC-69 | KKRWVWIRY | 440 | 245 | 1 | 0 | 17 | -3 |
| HHC-71 | KWKIFRRWW | -6 | 99 | 0 | 2 | -17 | 1 |
| HHC-75 | RKWIWRWFL | 1313 | 6140 | 34 | 322 | 554 | 1683 |
| HHC-77 | IWWKWRRWV | 98 | 4548 | 0 | 23 | -22 | 50 |

TABLE 11-continued

Chemokine induction (pg/ml) by new peptides in human PBMC.

| | | Chemokine induction (pg/ml) by the given concentrations of peptide | | | | | |
|---|---|---|---|---|---|---|---|
| | | MCP-1 | | MCP-3 | | Gro-α | |
| Name | Sequence | 20 µg/ml | 100 µg/ml | 20 µg/ml | 100 µg/ml | 20 µg/ml | 100 µg/ml |
| HHC-100 | RRFKFIRWW | 179 | 197 | -1 | 0 | -18 | -43 |
| HHC-123 | AVWKFVKRV | 46 | 204 | 0 | 3 | -25 | 17 |
| HHC-126 | AWRFKNIRK | 314 | 104 | 3 | 0 | 75 | -2 |
| HHC-133 | KRIMKLKMR | 195 | 444 | 0 | 2 | 15 | 81 |
| HHC-142 | AIRRWRIRK | 67 | -16 | 1 | 0 | 59 | 22 |
| HHC-148 | VVLKIVRRF | 25 | 210 | 1 | 3 | 55 | 60 |

Experiments were performed 2-4 times. Background values on average of 204 (MCP-1), 6 (MCP-3) and 196 (Gro-α) were subtracted. Bold numbers represent significant upregulation ($p < 0.05$). Sequences = SEQ ID NOS: 970, 2, 1213-1220, 7, 1221-1228, 8, 1229-1236, 12, 1237-1244, 15, 1245-1252, 18, 1253-1260, 1, 3, 4, 13, 14, 17, 1020-1022, 1032, 1048, 1057, 1060, 1065, 1069, 1078, 1081, 1083, 1087, 1089, 1112, 1135, 1138, 1145, 1154 and 1160, respectively.

Figure 18:
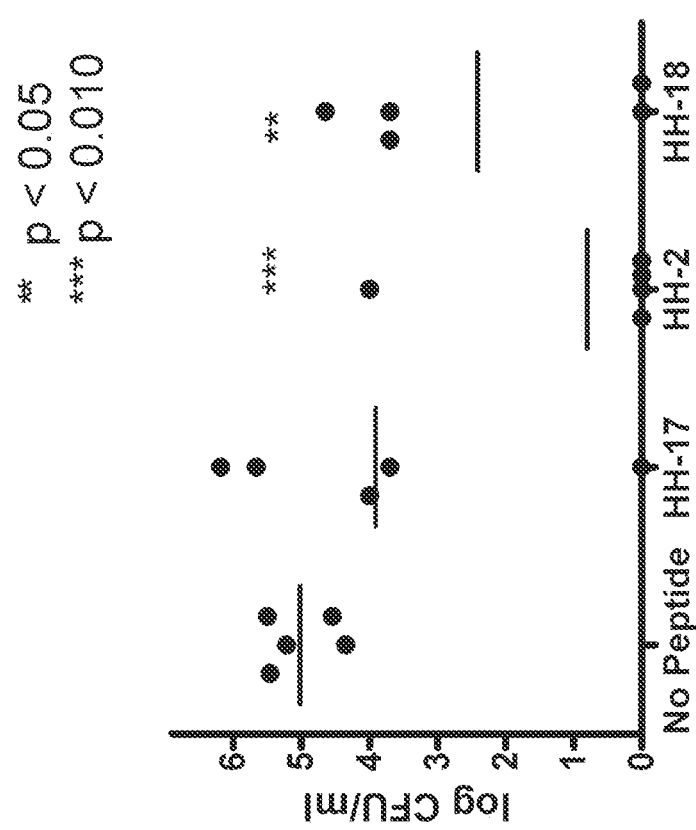
FIG. 18. Protection of mice from *S. aureus* infections by peptides HH-2 and HH-18 compared to negative control peptide HH-17. Mice were treated with $1.6 \times 10^{10}$ CFU of *S. aureus* intraperitoneally. Four hours post infection they received a dose of 8 mg/kg peptide IP. The infection was allowed to progress for 4 or 24 hours after which mice were euthanaised and plate counts of staphylococci surviving in the peritoneum were determined. Bacterial loads in the peritoneal lavage from individual mice after 24 hours of infection are shown (solid circles). The solid line represents the arithmetic mean for each group.
Figure 19:
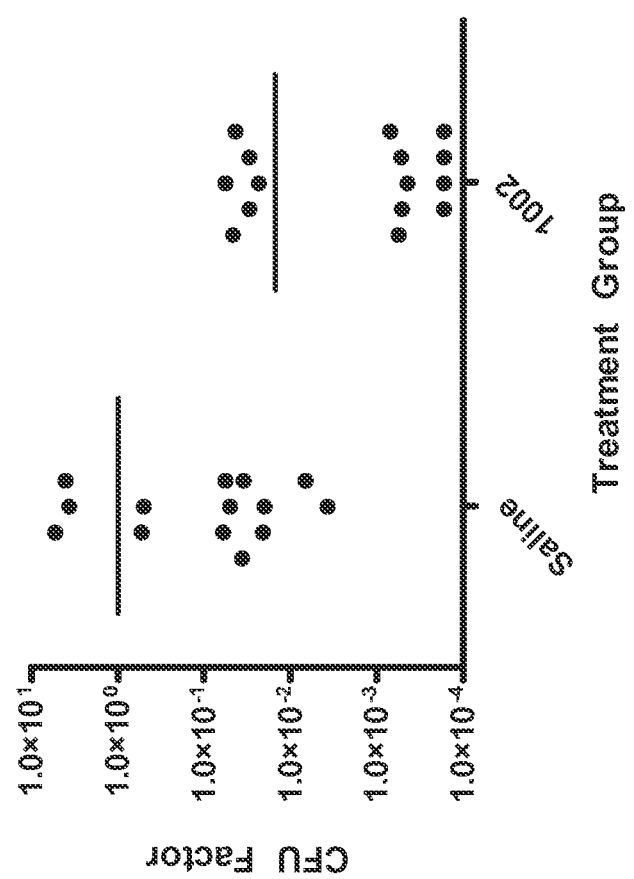
FIG. 19. Protection of mice from *S. aureus* infections by peptide 1002. Mice were treated with $1.6 \times 10^{10}$ CFU of *S. aureus* intraperitoneally. Four hours post infection they received a dose of 8 mg/kg peptide IP. The infection was allowed to progress for 4 or 24 hours after which mice were euthanaised and plate counts of staphylococci surviving in the peritoneum were determined. Bacterial loads in the peritoneal lavage from individual mice after 24 hours of infection are shown (solid circles). The solid line represents the arithmetic mean for each group.

These immunomodulatory activities led to protection against infections by *S. aureus*. Briefly a mouse model of aggressive bacterial infection, widely used to assess antibiotic efficacy, was utilized. Mice were treated with $1.6 \times 10^{10}$ CFU of *S. aureus* intraperitoneally as described previously (Scott, M. G. et al., 2007. An anti-infective peptide that selectively modulates the innate immune response. Nature Biotechnology 25: 465-472). Four hours post infection they received a dose of 4 mg/kg peptide IP. The infection was allowed to progress for 4 or 24 hours after which mice were euthanaised and plate counts of staphylococci surviving in the peritoneum were determined. FIG. 18 shows results for peptides HH2, HH18 and HH17, while FIG. 19 shows results for 1002 and 1012.

Amongst the preferred twelve amino acid immunomodulatory peptides, a clear pattern of related peptides were found that obviously represented minor substitutions, deletions or additions to a base sequence represented by SEQ ID NO: 2. Thus these peptides have a clear unitary relationship. In the following sequence alignments bolded letters represent amino acids that are identical or represent conservative substitutions (i.e., hydrophobic amino acid substitutions A, L, V, W, I, or F or charge substitutions R or K).

| HH2 | VQLR-IRV-AVIRA | SEQ ID NO: 2 |
| 1001 | LV--RAIQVRAVIR | SEQ ID NO: 1213 |
| 1002 | VQ-RWLIV-WRIRK | SEQ ID NO: 1214 |
| 1010 | IRWR-IRVW-VRRI | SEQ ID NO: 1222 |
| 1012 | IFWRRI-V-IVKKF | SEQ ID NO: 1224 |
| 1018 | VRLI-VAVR-IWRR | SEQ ID NO: 1230 |
| 1020 | VRLR-IR-WWVLRK | SEQ ID NO: 1232 |
| HH12 | KQFR-IRVR-VIRK | SEQ ID NO: 12 |
| 1026 | VQWR-IRVR-VIKK | SEQ ID NO: 1238 |

Amongst the preferred nine amino acid immunomodulatory peptides, a clear pattern of related peptides were found that obviously represented minor substitutions, deletions or additions to a base sequence represented by SEQ ID NO: 1225. Thus these peptides have a clear unitary relationship. In the following sequence alignments bolded letters represent amino acids that are identical or represent conservative substitutions (i.e, hydrophobic amino acid substitutions A, L, V, W, I, or F; or charge substitutions R or K).

| 1013 | VRLRIRVAV | SEQ ID NO: 1225 |
| 1005 | VQLRIRVAV | SEQ ID NO: 1217 |
| 1006 | VQLRIWVRR | SEQ ID NO: 1218 |
| 1030 | FRIRVRVIR | SEQ ID NO: 1242 |
| 1031 | WRWRVRVWR | SEQ ID NO: 1243 |
| 1032 | IRVRV-IWRK | SEQ ID NO: 1244 |

Amongst the preferred seven amino acid immunomodulatory peptides, a clear pattern of related peptides were found that obviously represented minor substitutions, deletions or additions to a base sequence represented by SEQ ID NO: 18. Thus these peptides have a clear unitary relationship. In the following sequence alignments bolded letters represent amino acids that are identical or represent conservative substitutions (i.e., hydrophobic amino acid substitutions A, L, V, W, I, or F; or charge substitutions R or K).

| HH18 | IWVIWRR | SEQ ID NO: 18 |
| 1041 | VIWIRWR | SEQ ID NO: 1253 |
| 1043 | WIVIWRR | SEQ ID NO: 1255 |

Example 9

Adjuvanticity as a Result of Enhancement of Innate Immunity

It is well accepted that vaccine immunization is best achieved by co-administration of an adjuvant. The precise mechanism by which these adjuvants work has eluded immunologists but appears to work in part by upregulating elements of innate immunity that smooth the transition to adaptive (antigen-specific) immunity (Bendelac A and R. Medzhitov. 2002. Adjuvants of immunity: Harnessing innate immunity to promote adaptive immunity J. Exp. Med. 195:F19-F23). Within this concept there are several possible avenues by which adjuvants might work including the attraction of immune cells into the site at which a particular antigen is injected, through e.g., upregulation of chemokines, the appropriate activation of cells when they reach that site, which can be caused by local cell or tissue damage releasing endogenous adjuvants or through specific cell activation by the adjuvants, and the compartmentalization of immune responses to the site of immunization (the so-called "depot" effect). Due to their ability to selectively modulate cell responses, including induction of chemokine expression, cationic host defence peptides such as human LL-37 and defensins, have been examined for adjuvant activity and demonstrated to enhance adaptive immune responses to a variety of antigens (Bowdish D M, D J Davidson, R E W Hancock. 2006. Immunomodulatory properties of defensins and cathelicidins. Curr Top Microbiol Immunol 2006:27-66). Therefore we studies the ability of our small host defence peptides to upregulate adjuvant responses in both human PBMC and cord blood mononuclear cells (CBMC) (representing the responses of blood cells from neonates), both alone (Table 10 and 11) and in combination with other proposed adjuvant agents that might work through other mechanisms such as CpG oligodeoxy ribonucleotides (TLR9 agonists that activate cells through interaction with TLR9 and fit into 3 different classes A=molecule 2336, B=10103 and C=2395), and polyphosphazene P6 (which induces a depot effect). The results demonstrate a variety of peptides that lead to upregulation of chemokine production (Table 10), and most of these are either additively enhancing chemokine induction in the presence of CpG or the combination of CpG and P6 (Table 12), or actually demonstrate significant synergy (bolded in Table 12). In particular HH2 showed excellent ability to upregulate chemokine production, significant synergy with CpG (particularly CpG-B) in PBMC and CBMC, and an ability to enhance antigen specific responses in mose model experiments using pertussis toxin as an adjuvant.

TABLE 12

Potential adjuvant properties (ability to induce cytokines and chemokines) of peptides in combination with polyphosphazines (P6) and CpG oligonucleotides of classes A-C.

|  | Treatment | Gro-α | MCP-3 | MCP-1 | IL-8 | IL-6 | TNF-α |
|---|---|---|---|---|---|---|---|
| Control PBMC | Background | 28 | 6 | 13 | 81 | 13 | 0 |
| Peptide alone | HH2 | 21 | 0 | 54 | 624 | 23 | 0 |
| (20 ug/mL) | HH3 | 8 | 0 | 8 | 490 | 7 | 0 |
|  | HH18 | 143 | 3 | 64 | 2558 | 180 | 56 |
|  | HH17 | 0 | 3 | 91 | 146 | 0 | 7 |
| CpG alone | CpG-A (2336) | 101 | 66 | 462 | 41 | −2 | 26 |
| (5 ug/mL) | CpG-B (10103) | 73 | 32 | 250 | 447 | −3 | 12 |
|  | CpG-C (2395) | 123 | 71 | 350 | 174 | −5 | 24 |
| HH2 + CpG | HH2 + CpG-A | 152 | 90 | 570 | 393 | 16 | 48 |
|  | HH2 + CpG-B | 280 | 453 | 772 | 344 | 7 | 56 |
|  | HH2 + CpG-C | 274 | 352 | 705 | 267 | 10 | 73 |
| HH3 + CpG | HH3 + CpG-A | 110 | 47 | 593 | 292 | −3 | 25 |
|  | HH3 + CpG-B | 198 | 207 | 683 | 522 | 0 | 36 |
|  | HH3 + CpG-C | 181 | 158 | 587 | 823 | 1 | 22 |
| HH18 + CpG | HH18 + CpG-A | 138 | 163 | 466 | 900 | 18 | 53 |
|  | HH18 + CpG-B | 138 | 368 | 614 | 2850 | 72 | 35 |
|  | HH18 + CpG-C | 119 | 339 | 534 | 1391 | 28 | 46 |
| HH17+ CpG | HH17 + CpG-A | 76 | 38 | 315 | 227 | −2 | 40 |
|  | HH17 + CpG-B | 95 | 33 | 285 | 1323 | 1 | 26 |
|  | HH17 + CpG-C | 100 | 93 | 524 | 678 | 0 | 22 |
| Control PBMC | Background | 5 | ND | ND | 9 | ND | 210 |
| Peptide alone | 1012 | 26 | ND | ND | 8 | ND | −90 |
| (5 ug/mL) | 1002 | 8 | ND | ND | 10 | ND | 282 |
| Polyphosphazene | P6 5 ug/mL | 0 | ND | ND | −1 | ND | 83 |
| P6 | P6 10 ug/mL | 0 | ND | ND | 1 | ND | 35 |
| CpG (5 ug/mL) | CpG-B(10103) | 205 | ND | ND | 18 | ND | 968 |
| Combination | 1012 + P6 + CpG-B | 240 | ND | ND | 48 | ND | 1478 |
| 5 ug/mL | 1002 + P6 + CpG-B | 16 | ND | ND | 23 | ND | 971 |
| P6 10 ug/mL, CpG | 1002 + P6 + CpG-B | 73 | ND | ND | 26 | ND | 373 |
| and peptide at 5 ug/mL | 1012 + P6 + CpG-B | 77 | ND | ND | 53 | ND | 1170 |
| Control CBMC | Background | 25 | 110 | 121 | 413 | 20 | 8 |
| CBMC Peptide | HH2 | 45 | −40 | 131 | 104 | 11 | −4 |
| alone (20 ug/mL) | HH3 | 37 | −43 | 249 | 471 | 14 | −8 |
|  | HH18 | 55 | −24 | 54 | 372 | 7 | −4 |
|  | HH17 | 12 | −41 | 25 | 41 | −2 | −8 |
| CBMC | CpG-A (2336) | −4 | 30 | 165 | 473 | 311 | 2 |
| CpG alone | CpG-B (10103) | 133 | 99 | 204 | 674 | 289 | 15 |
| (5 ug/mL) | CpG-C (2395) | 96 | 134 | 202 | 908 | 259 | 10 |
| CBMC | HH2 + CpG-A | 75 | 164 | 410 | 406 | 353 | 12 |
| HH2 + CpG | HH2 + CpG-B | 149 | 347 | 489 | 433 | 873 | 26 |
|  | HH2 + CpG-C | 52 | 221 | 504 | 734 | 722 | 21 |
| CBMC | HH3 + CpG-A | 50 | 149 | 539 | 427 | 408 | 6 |
| HH3 + CpG | HH3 + CpG-B | 126 | 182 | 583 | 704 | 725 | 14 |
|  | HH3 + CpG-C | 40 | 159 | 551 | 840 | 697 | 26 |
| CBMC | HH18 + CpG-A | 81 | 89 | 308 | 688 | 469 | 5 |

TABLE 12-continued

Potential adjuvant properties (ability to induce cytokines and chemokines) of peptides in combination with polyphosphazines (P6) and CpG oligonucleotides of classes A-C.

| | | Cytokines induced (pg/ml) | | | | | |
|---|---|---|---|---|---|---|---|
| | Treatment | Gro-α | MCP-3 | MCP-1 | IL-8 | IL-6 | TNF-α |
| HH18 + CpG | HH18 + CpG-B | 171 | 146 | 363 | 998 | 461 | 6 |
| | HH18 + CpG-C | 122 | 126 | 371 | 1248 | 559 | 5 |
| CBMC | HH17 + CpG-A | 17 | −8 | 393 | −38 | 412 | −1 |
| HH17 + CpG | HH17 + CpG-B | 94 | 91 | 339 | 1804 | 241 | 3 |
| | HH17 + CpG-C | 86 | 97 | 385 | 2012 | 405 | 5 |

All experiments were performed with human PBMC except those indicated as having been done with CBMC. The indicated backgrounds were subtracted from the measurements with different adjuvants alone and in combination. Bolded numbers represent apparently synergistic combinations.
ND = Not done.

APPENDIX

Non-Natural Amino Acids
Tryptophan Variants
2. DL-7-azatryptophan
3. β-(3-benzothienyl)-L-alanine
4. β-(3-benzothienyl)-D-alanine
5. 5-benzyloxy-DL-tryptophan
6. 7-benzyloxy-DL-tryptophan
7. 5-bromo-DL-tryptophan
8. 5-fluoro-DL-tryptophan
9. 6-fluoro-DL-tryptophan
10. 5-hydroxy-L-tryptophan
11. 5-hydroxy-DL-tryptophan
12. 5-methoxy-DL-tryptophan
13. α-methyl-DL-tryptophan
14. 1-methyl-DL-tryptophan
15. 5-methyl-DL-tryptophan
16. 6-methyl-DL-tryptophan
17. 7-methyl-DL-tryptophan
18. D-1,2,3,4-tetrahydronorharman-3-carboxylic acid
19. DL-6-methoxy-1,2,3,4-tetrahydronorharman-1-carboxylic acid
20. 5-Hydroxytryptophan: 2-Amino 3-[5-hydroxyindolyl]-propionic acid
21. L-Neo-Tryptophan
22. D-Neo-Tryptophan
Phenylalanine and Tyrosine Variants
24. 4-aminomethyl-L-phenylalanine
25. 4-aminomethyl-D-phenylalanine
26. 4-amino-L-phenylalanine
27. 4-amino-D-phenylalanine
28. 3-amino-L-tyrosine
29. 4-bromo-L-phenylalanine
30. 4-bromo-D-phenylalanine
31. 4-bis(2-chloroethyl)amino-L-phenylalanine
32. 2-chloro-L-phenylalanine
33. 2-chloro-D-phenylalanine
34. 4-chloro-L-phenylalanine
35. 4-chloro-D-phenylalanine
36. 3-chloro-L-tyrosine
37. 3,4-dichloro-L-phenylalanine
38. 3,4-dichloro-D-phenylalanine
39. 3,4-difluoro-L-phenylalanine
40. 3,4-difluoro-D-phenylalanine
41. 3,4-dihydroxy-L-phenylalanine
42. 3,5-diiodo-L-thyronine
43. 3,5-diiodo-D-tyrosine
44. 3,4-dimethoxy-L-phenylalanine
45. 3,4-dimethoxy-DL-phenylalanine
46. O-ethyl-L-tyrosine
47. O-ethyl-D-tyrosine
48. 2-fluoro-L-phenylalanine
49. 2-fluoro-D-phenylalanine
50. 4-fluoro-L-phenylalanine
51. 4-fluoro-D-phenylalanine
52. 3-fluoro-DL-tyrosine
53. L-homophenylalanine
54. D-homophenylalanine
55. 2-hydroxy-3-methyl-L-phenylalanine
56. 2-hydroxy-3-methyl-D-phenylalanine
57. 2-hydroxy-3-methyl-DL-phenylalanine
58. 2-hydroxy-4-methyl-L-phenylalanine
59. 2-hydroxy-4-methyl-D-phenylalanine
60. 2-hydroxy-4-methyl-DL-phenylalanine
61. 2-hydroxy-5-methyl-L-phenylalanine
62. 2-hydroxy-5-methyl-D-phenylalanine
63. 2-hydroxy-5-methyl-DL-phenylalanine
64. β-hydroxy-DL-phenylalanine (DL-threo-3-phenylserine)
65. 7-hydroxy-(S)-1,2,3,4-tetrahydroisoquinoline-3-carboxylic acid (hydroxy-Tic-OH)
66. 7-hydroxy-(R)-1,2,3,4-tetrahydroisoquinoline-3-carboxylic acid (hydroxy-D-Tic-OH)
67. 4-iodo-L-phenylalanine
68. 4-iodo-D-phenylalanine
69. 3-iodo-L-tyrosine
70. α-methyl-3-methoxy-DL-phenylalanine
71. α-methyl-4-methoxy-L-phenylalanine
72. α-methyl-4-methoxy-DL-phenylalanine
73. α-methyl-L-phenylalanine
74. α-methyl-D-phenylalanine
75. β-methyl-DL-phenylalanine
76. α-methyl-DL-tyrosine
77. O-methyl-L-tyrosine
78. O-methyl-D-tyrosine
79. 4-nitro-L-phenylalanine
80. 4-nitro-D-phenylalanine
81. 3-nitro-L-tyrosine
82. (S)-1,2,3,4-tetrahydroisoquinoline-3-carboxylic acid (L-Tic-OH)
83. (R)-1,2,3,4-tetrahydroisoquinoline-3-carboxylic acid (D-Tic-OH)
84. L-thyronine
85. DL-thyronine
86. L-thyroxine
87. D-thyroxine
88. 2,4,5-trihydroxy-DL-phenylalanine
89. 3,5,3'-triiodo-L-thyronine
90. DL-m-tyrosine 91. DL-o-tyrosine
92. 2-(trifluoromethyl)-L-phenylalanine
93. 2-(trifluoromethyl)-D-phenylalanine
94. 2-cyano-L-phenylalanine
95. 2-cyano-D-phenylalanine
96. 2-methyl-L-phenylalanine
97. 2-methyl-D-phenylalanine
98. 3-(trifluoromethyl)-L-phenylalanine
99. 3-(trifluoromethyl)-D-phenylalanine
100. 3-cyano-L-phenylalanine
101. 3-cyano-D-phenylalanine
102. 3-fluoro-L-phenylalanine
103. fluoro-D-phenylalanine
104. 3-methyl-L-phenylalanine
105. 3-methyl-D-phenylalanine
106. 4-benzoyl-L-phenylalanine
107. 4-benzoyl-D-phenylalanine
108. 4-(trifluoromethyl)-L-phenylalanine
109. 4-(trifluoromethyl)-D-phenylalanine
110. 4-cyano-L-phenylalanine
111. 4-cyano-D-phenylalanine
112. 4-methyl-L-phenylalanine
113. 4-methyl-D-phenylalanine
114. 2,4-dichloro-L-phenylalanine
115. 2,4-dichloro-D-phenylalanine
116. 3,5-diiodo-L-tyrosine OSu Arginine and Lysine Variants
118. L-2-amino-3-guanidinopropionic acid
119. L-2-amino-3-ureidopropionic acid (Albizziin)
120. L-citrulline
121. DL-citrulline
122. 2,6-diaminoheptanedioic acid (mixture of isomers)
123. N-ω,ω-dimethyl-L-arginine (symmetrical)
124. N-ε,ε-dimethyl-L-lysine hydrochloride salt
125. α-methyl-DL-ornithine
126. N-ω-nitro-L-arginine
127. N-ω-nitro-D-arginine
128. N-δ-benzyloxycarbonyl-L-ornithine
129. (N-δ-)-L-ornithine
130. (N-δ-)-D-ornithine
131. (N-δ-1-(4,4-dimethyl-2,6-dioxocyclohex-1-ylidene)ethyl)-D-ornithine (D-Orn-(Dde)-OH)
132. L-ornithine (Orn( )-OH)
133. (N-d-4-methyltrityl)-L-ornithine (Orn(Mtt)-OH)
134. (N-d-4-methyltrityl)-D-ornithine (D-Orn(Mtt)-OH)

Proline Variants
136. cis-4-amino-L-proline methyl ester hydrochloride salt
137. trans-4-amino-L-proline methyl ester hydrochloride salt
138. (S)-azetidine-2-carboxylic acid
139. trans-4-cyano-L-proline
140. cis-4-cyano-L-proline methyl ester
141. trans-4-cyano-L-proline methyl ester
142. 3,4-dehydro-L-proline
143. (R)-5,5-dimethylthiazolidine-4-carboxylic acid
144. (4S,2RS)-2-ethylthiazolidine-4-carboxylic acid
145. trans-4-fluoro-L-proline
146. (2S,3S)-3-hydroxypyrrolidine-2-carboxylic acid (trans-3-hydroxy-L-proline)
147. (2S,4S)-(–)-4-hydroxypyrrolidine-2-carboxylic acid (cis-4-hydroxy-L-proline)
148. (2S,4R)-(–)-4-hydroxypyrrolidine-2-carboxylic acid (trans-4-hydroxy-L-proline)
149. (2R,4R)-(+)-4-hydroxypyrrolidine-2-carboxylic acid (cis-4-hydroxy-D-proline)
150. (2S,4R)-(–)-4-t-butoxypyrrolidine-2-carboxylic acid (trans-4-t-butoxy-L-proline)
151. (2S,5RS)-5-methylpyrrolidine-2-carboxylic acid
152. (4S,2RS)-2-methylthiazolidine-4-carboxylic acid
153. (2S,3R)-3-phenylpyrrolidine-2-carboxylic acid
154. (4S,2RS)-2-phenylthiazolidine-4-carboxylic acid
155. (S)-thiazolidine-2-carboxylic acid
156. (R)-thiazolidine-2-carboxylic acid
157. (S)-thiazolidine-4-carboxylic acid
158. (R)-thiazolidine-4-carboxylic acid (L-thioproline)
159. α-allyl-DL-proline
160. α-benzyl-DL-proline
161. α-(2-bromobenzyl)-DL-proline
162. α-(4-bromobenzyl)-DL-proline
163. α-(2-chlorobenzyl)-DL-proline
164. α-(3-chlorobenzyl)-DL-proline
165. α-(diphenylmethyl)-DL-proline
166. α-(4-fluorobenzyl)-DL-proline
167. α-methyl-DL-proline
168. α-(4-methylbenzyl)-DL-proline
169. α-(1-naphthylmethyl)-DL-proline
170. α-propyl-DL-proline
171. 4-benzyl-L-pyroglutamic
172. 4-(2-bromobenzyl)-L-pyroglutamic acid benzyl ester
173. 4-(4-bromobenzyl)-L-pyroglutamic acid benzyl ester
174. 4-(4-methylbenzyl)-L-pyroglutamic acid benzyl ester Miscellaneous Heterocyclic Amino Acids
176. α-amino-3-chloro-4,5-dihydro-5-isoxazoleacetic acid
177. 2-amino-α-(methoxyimino)-4-thiazoleacetic acid (predominantly syn)
178. 5-aminoorotic acid
179. 2-aminopyridyl-3-carboxylic acid (2-aminonicotinic acid)
180. 6-aminopyridyl-3-carboxylic acid (6-aminonicotinic acid)
181. 2-aminothiazole-4-acetic acid
182. (S)-azetidine-2-carboxylic acid
183. azetidine-3-carboxylic acid
184. 4-carboxymethylpiperazine
185. 4-carboxymethylpiperazine
186. 2-carboxypiperazine
187. 3-carboxypiperidine
188. indoline-2-carboxylic acid
189. L-mimosine
190. 4-phenylpiperidine-4-carboxylic acid
191. (S)-(–)-piperidine-2-carboxylic acid (L-(–)-pipecolic acid)
192. (R)-(+)-piperidine-2-carboxylic acid (D-(+)-pipecolic acid)
193. (RS)-piperidine-2-carboxylic acid (DL-pipecolic acid)
194. piperidine-4-carboxylic acid (isonipecotic acid)

Analogs of Alanine, Glycine, Valine, and Leucine
196. 3-(2-furyl)-D-Ala-OH
197. 3-cyclopentyl-DL-Ala-OH
198. 3-(4-quinolyl)-DL-Ala-OH
199. 3-(4-quinolyl)-DL-Ala-OH dihydrochloride dihydrate
200. 3-(2-quinolyl)-DL-Ala-OH
201. 3-(2-quinoxalyl)-DL-Ala-OH
202. α-allyl-L-alanine
203. L-allylglycine
204. L-allylglycine dicyclohexylammonium salt
205. D-allylglycine
206. D-allylglycine dicyclohexylammonium salt
207. L-α-aminobutyric acid (Abu-OH)
208. D-α-aminobutyric acid (D-Abu-OH)
209. DL-β-aminobutyric acid (DL-β-Abu-OH)
210. γ-aminobutyric acid (γ-Abu-OH)
211. α-aminoisobutyric acid (Aib-OH)
212. DL-β-aminoisobutyric acid (DL-β-Aib-OH)

213. Di-N-α-aminomethyl-L-alanine
214. 2-amino-4,4,4-trifluorobutyric acid
215. 3-amino-4,4,4-trifluorobutyric acid
216. β-(3-benzothienyl)-L-alanine
217. β-(3-benzothienyl)-D-alanine
218. t-butyl-L-alanine
219. t-butyl-D-alanine
220. L-t-butylglycine
221. D-t-butylglycine
222. β-cyano-L-alanine
223. β-cyclohexyl-L-alanine (Cha-OH)
224. β-cyclohexyl-D-alanine (D-Cha-OH)
225. L-cyclohexylglycine (Chg-OH)
226. D-cyclohexylglycine (D-Chg-OH)
227. β-cyclopentyl-DL-alanine
228. β-cyclopenten-1-yl-DL-alanine
229. β-cyclopropyl-L-alanine
230. cyclopropyl-DL-phenylglycine
231. DL-dehydroarmentomycin
232. 4,5-dehydro-L-leucine
233. L-α,γ-diaminobutyric acid (Dab-OH)
234. D-α,γ-diaminobutyric acid (D-Dab-OH)
235. Di-L-α,γ-diaminobutyric acid (Dab( )-OH)
236. Di-D-α,γ-diaminobutyric acid (D-Dab( )-OH)
237. (N-γ-allyloxycarbonyl)-L-α,γ-diaminobutyric acid (Dab(Aloc)-OH)
238. (N-γ-)-L-α,γ-diaminobutyric acid (Dab( )-OH)
239. (N-γ-1-(4,4-dimethyl-2,6-dioxocyclohex-1-ylidene)ethyl)-L-α,γ-diaminobutyric acid (Dab(Dde)-OH)
240. (N-γ-4-methyltrityl)-L-α,γ-diaminobutyric acid (Dab(Mtt)-OH)
241. (N-γ-)-D-α,γ-diaminobutyric acid (D-Dab( )-OH)
242. (N-γ-1-(4,4-dimethyl-2,6-dioxocyclohex-1-ylidene)ethyl)-D-α,γ-diaminobutyric acid (D-Dab(Dde)-OH)
243. (N-γ-4-methyltrityl)-D-α,γ-diaminobutyric acid (D-Dab(Mtt)-OH)
244. L-α,β-diaminopropionic acid (Dap-OH)
245. D-α,β-diaminopropionic acid (D-Dap-OH)
246. Di-L-α,β-diaminopropionic acid (Dap( )-OH)
247. Di-D-α,β-diaminopropionic acid (D-Dap( )-OH)
248. (N-β-allyloxycarbonyl)-L-α,β-diaminopropionic acid (Dap(Aloc)-OH)
249. (N-β-)-L-α,β-diaminopropionic acid (Dap( )-OH)
250. β-(1-naphthyl)-D-alanine (D-1-Nal-OH)
251. β-(2-naphthyl)-L-alanine (2-Nal-OH)
252. β-(2-naphthyl)-D-alanine (D-2-Nal-OH)
253. L-phenylglycine (Phg-OH)
254. D-phenylglycine (D-Phg-OH)
255. L-propargylglycine
256. L-propargylglycine dicyclohexylammonium salt
257. D-propargylglycine
258. D-propargylglycine dicyclohexylammonium salt
259. β-(2-pyridyl)-L-alanine (L-2-pyridylalanine)
260. β-(2-pyridyl)-D-alanine (D-2-pyridylalanine)
261. β-(3-pyridyl)-L-alanine (L-3-pyridylalanine)
262. β-(3-pyridyl)-D-alanine (D-3-pyridylalanine)
263. β-(4-pyridyl)-L-alanine (L-4-pyridylalanine)
264. β-(4-pyridyl)-D-alanine (D-4-pyridylalanine)
265. β-(2-thienyl)-L-alanine (Thi-OH)
266. β-(2-thienyl)-D-alanine (D-Thi-OH)
267. L-(2-thienyl)glycine
268. D-(2-thienyl)glycine
269. L-(3-thienyl)glycine
270. D-(3-thienyl)glycine
271. 5,5,5-trifluoro-DL-leucine
272. 4,4,4-trifluoro-DL-valine
273. L-2-amino-3-(dimethylamino)propionic acid (aza-L-leucine)
274. DL-2-amino-3-(dimethylamino)propionic acid (aza-DL-leucine)
275. (N-β-1-(4,4-dimethyl-2,6-dioxocyclohex-1-ylidene)ethyl)-L-α,β-diaminopropionic acid (Dap(Dde)-OH)
276. (N-β-(2,4-dinitrophenyl))-L-α,β-diaminopropionic acid (Dap(Dnp)-OH)
277. (N-β-4-methyltrityl)-L-α,β-diaminopropionic acid (Dap(Mtt)-OH)
278. (N-β-)-L-α,β-diaminopropionic acid (Dap( )-OH)
279. (N-β-)-D-α,β-diaminopropionic acid (D-Dap( )-OH)
280. (N-β-1-(4,4-dimethyl-2,6-dioxocyclohex-1-ylidene)ethyl)-D-α,β-diaminopropionic acid (D-Dap(Dde)-OH)
281. 2,5-dihydro-D-phenylglycine
282. 2,4-dinitro-DL-phenylglycine
283. 2-fluoro-DL-phenylglycine
284. 4-fluoro-L-phenylglycine
285. 4-fluoro-D-phenylglycine
286. 3-fluoro-DL-valine
287. 4-hydroxy-D-phenylglycine
288. α-methyl-DL-leucine
289. β-(1-naphthyl)-L-alanine (1-Nal-OH)
290. β-(1-naphthyl)-D-alanine (D-1-Nal-OH)
Analogs of Benzoic Acid
292. 2-amino-4-fluorobenzoic acid
293. 2-amino-5-fluorobenzoic acid
294. 2-amino-6-fluorobenzoic acid
295. 2-amino-5-iodobenzoic acid
296. 2-amino-3-methoxybenzoic acid
297. 2-amino-5-methoxybenzoic acid
298. 3-amino-4-methoxybenzoic acid
299. 4-amino-3-methoxybenzoic acid
300. 2-amino-3-methylbenzoic acid
301. 2-amino-5-methylbenzoic acid
302. 2-amino-6-methylbenzoic acid
303. 3-amino-2-methylbenzoic acid
304. 3-amino-4-methylbenzoic acid
305. 4-amino-3-methylbenzoic acid
306. 3-aminomethylbenzoic acid (Mamb-OH)
307. 4-aminomethylbenzoic acid (Pamb-OH)
308. 2-amino-3,4,5-trimethoxybenzoic acid
309. Di-3,4-diaminobenzoic acid
310. Di-3,5-diaminobenzoic acid
311. 4-methylaminobenzoic acid
312. 5-acetamido-2-aminobenzoic acid (5-acetamidoanthranilic acid)
313. 2-aminobenzene-1,4-dicarboxylic acid
314. 3-aminobenzene-1,2-dicarboxylic acid
315. 2-aminobenzoic acid (2-Abz-OH)
316. 3-aminobenzoic acid (3-Abz-OH)
317. 4-aminobenzoic acid (4-Abz-OH)
318. 2-(2-aminobenzoyl)benzoic acid
319. 2-amino-5-bromobenzoic acid
320. 2-amino-4-chlorobenzoic acid
321. 2-amino-5-chlorobenzoic acid
322. 2-amino-6-chlorobenzoic acid
323. 3-amino-4-chlorobenzoic acid
324. 4-amino-2-chlorobenzoic acid
325. 5-amino-2-chlorobenzoic acid
326. 2-amino-4,5-dimethoxybenzoic acid
327. 2-amino-3,5-dimethylbenzoic acid
328. 2-amino-4-fluorobenzoic acid
Miscellaneous Aromatic Amino Acids
330. Di-2-amino-3-(2-aminobenzoyl)propionic acid
331. 4-aminocinnamic acid (predominantly trans)
332. 4-aminohippuric acid 333. 3-amino-2-naphthoic acid
334. 4-aminooxanilic acid
335. (3-aminophenyl)acetic acid
336. (4-aminophenyl)acetic acid
337. 4-(4-aminophenyl)butanoic acid
338. 3-amino-3-phenylpropionic acid
339. (4-aminophenylthio)acetic acid
340. (2R,3S)-2-amino-3-(phenylthio)butanoic acid
341. Analogs of Cysteine and Methionine
342. S-acetamidomethyl-L-penicillamine
343. S-acetamidomethyl-D-penicillamine
344. S-(2-aminoethyl)-L-cysteine
345. S-benzyl-L-cysteine
346. S-benzyl-D-cysteine
347. S-benzyl-DL-homocysteine
348. L-buthionine
349. L-buthioninesulfoximine
350. DL-buthioninesulfoximine
351. S-n-butyl-L-cysteine
352. S-t-butyl-L-cysteine
353. S-t-butyl-D-cysteine
354. S-carbamoyl-L-cysteine
355. S-carboxyethyl-L-cysteine
356. S-carboxymethyl-L-cysteine
357. L-cysteic acid
358. S-diphenylmethyl-L-cysteine
359. L-ethionine (2-amino-4-(ethyl(thio)butyric acid)
360. D-ethionine (D-2-amino-4-(ethyl(thio)butyric acid)
361. S-ethyl-L-cysteine
362. S-trityl-L-homocysteine
363. Di-L-homocystine
364. DL-methionine methylsulfonium chloride
365. S-4-methoxybenzyl-L-penicillamine
366. S-4-methoxybenzyl-L-penicillamine (Pen(4-MeOBzl)-OH)
367. S-4-methylbenzyl-L-penicillamine dicyclohexylammonium salt (Pen(4-MeBzl)-OH.DCHA)
368. S-methyl-L-cysteine
369. α-methyl-DL-methionine
370. S-(2-(4-pyridyl)ethyl)-L-cysteine
371. S-(2-(4-pyridyl)ethyl)-DL-penicillamine
372. Di-seleno-L-cystine
373. L-selenomethionine
374. DL-selenomethionine
375. S-trityl-L-penicillamine
376. S-trityl-D-penicillamine
377. Di-L-cystathion
378. Di-DL-cystathionine
Analogs of Serine, Threonine, and Statine
380. 2-amino-3-methoxypropionic acid
381. L-α-methylserine
382. D-α-methylserine
383. (S)-2-amino-4-trityloxybutanoic acid (Hse(Trt)-OH)
384. (RS)-2-amino-4-trityloxybutanoic acid (DL-Hse(Trt)-OH)
385. (S)-2-amino-3-benzyloxypropionic acid
386. (R)-2-amino-3-benzyloxypropionic acid
387. (2S,3S)-2-amino-3-ethoxybutanoic acid
388. 2-amino-3-ethoxybutanoic acid
389. 2-amino-3-ethoxypropionic acid
390. 4-amino-3-hydroxybutanoic acid
391. (R)-2-amino-3-hydroxy-3-methylbutanoic acid
392. (S)-2-amino-3-hydroxy-3-methylbutanoic acid
393. (RS)-2-amino-3-hydroxy-3-methylbutanoic acid
394. (3S,4S)-4-amino-3-hydroxy-6-methylheptanoic acid (Sta-OH)
395. (2R,3R)-3-amino-2-hydroxy-5-methylhexanoic acid
396. (2R,3S)-3-amino-2-hydroxy-5-methylhexanoic acid
397. (2S,3R)-3-amino-2-hydroxy-5-methylhexanoic acid
398. (2S,3S)-3-amino-2-hydroxy-5-methylhexanoic acid
399. (2S,3R)-2-amino-3-hydroxy-4-methylpentanoic acid
400. (2R,3S)-2-amino-3-hydroxy-4-methylpentanoic acid
401. (2S,3RS)-2-amino-3-hydroxy-4-methylpentanoic acid
402. 2-amino-3-hydroxypentanoic acid
403. (2S,3R)-3-amino-2-hydroxy-4-phenylbutanoic acid
404. (2R,3R)-3-amino-2-hydroxy-4-phenylbutanoic acid
405. (2S,3S)-2-amino-3-methoxybutanoic acid
406. 2-amino-3-methoxybutanoic acid
407. (S)-2-amino-3-methoxypropionic acid
Miscellaneous Aliphatic Amino Acids
409. α-amino-1-adamantanepropionic acid
410. 2-aminobicyclo[2.2.1]heptane-2-carboxylic acid (mixture of isomers)
411. 3-endo-aminobicyclo[2.2.1]heptane-2-endo-carboxylic acid
412. 3-endo-aminobicyclo[2.2.1]heptane-2-endo-carboxylic acid
413. 3-endo-aminobicyclo[2.2.1]hept-5-ene-2-endo-carboxylic acid
414. 1-aminocyclobutane-1-carboxylic acid
415. 5-amino-1,3-cyclohexadiene-1-carboxylic acid
416. 1-aminocyclohexane-1-carboxylic acid
417. (±)-cis-2-aminocyclohexane-1-carboxylic acid
418. (±)-trans-2-aminocyclohexane-1-carboxylic acid
419. trans-4-aminocyclohexane-1-carboxylic acid
420. (±)-cis-3-aminocyclohexane-1-carboxylic acid
421. cis-4-aminocyclohexane-1-carboxylic acid
422. (±)-cis-2-aminocyclohex-4-ene-1-carboxylic acid
423. (±)-trans-2-aminocyclohex-4-ene-1-carboxylic acid
424. cis-4-aminocyclohexane-1-acetic acid
425. 1-aminocyclopentane-1-carboxylic acid
426. (±)-cis-2-aminocyclopentane-1-carboxylic acid
427. 1-aminocyclopropane-1-carboxylic acid
428. 2-aminoheptanoic acid
429. 7-aminoheptanoic acid
430. 6-aminohexanoic acid (6-aminocaproic acid)
431. 5-aminolevulinic acid
432. trans-4-(aminomethyl)cyclohexane-1-carboxylic acid
433. 2-aminooctanoic acid
434. 8-aminooctanoic acid (8-Aminocaprylic acid)
435. 3-(aminooxy)acetic acid
436. 5-aminopentanoic acid
437. 11-aminoundecanoic acid
β-Amino Acids
439. β-alanine (β-Ala-OH)
440. L-β-homoalanine (β-homoAla-OH)
441. (S)—N-ω-2,2,4,6,7-pentamethyldihydrobenzofuran-5-sulfonyl-L-β-homoarginine (β-homoArg(Pbf)-OH)
442. N-ω-tosyl-L-β-homoarginine (β-homoArg(Tos)-OH)
443. γ-trityl-L-β-homoasparagine (β-homoAsn(Trt)-OH)
444. L-β-homoaspartic acid γ-t-butyl ester (β-homoAsp(OtBu)-OH)
445. L-β-homoaspartic acid γ-benzyl ester (β-homoAsp(OBzl)-OH)
446. L-β-homoglutamic acid δ-t-butyl ester (β-homoGlu(OtBu)-OH)
447. L-β-homoglutamic acid δ-benzyl ester (β-homoGlu(OBzl)-OH)
448. N-δ-trityl-L-β-homoglutamine (β-homoGln(Trt)-OH)
449. β-t-butyl-L-β-homohydroxyproline (β-homoHyp(tBu)-OH)
450. L-β-homoisoleucine (β-homoIle-OH)
451. DL-β-leucine (DL-β-Leu-OH)
452. L-β-homoleucine (β-homoLeu-OH)

453. L-N-ω-β-homolysine (β-homoLys( )-OH)
454. L-N-ω-2-benzyloxycarbonyl-β-homolysine (β-homoLys(Z)—OH)
455. L-β-homomethionine (β-homoMet-OH)
456. L-β-phenylalanine (β-Phe-OH)
457. D-β-phenylalanine (D-β-Phe-OH)
458. L-β-homophenylalanine (β-homoPhe-OH)
459. L-β-homoproline (β-homoPro-OH)
460. β-t-butyl-L-β-homoserine (β-homoSer(tBu)-OH)
461. O-benzyl-L-β-homoserine (β-homoSer(Bzl)-OH)
462. O-benzyl-L-β-homothreonine (β-homoThr(Bzl)-OH)
463. L-β-homotryptophan (β-homoTrp-OH)
464. O-t-butyl-L-β-homotyrosine (β-homoTyr(tBu)-OH)
465. L-β-homovaline (β-homoVal-OH)
466. (R)-3-amino-4-(3-benzothienyl)butyric acid
467. (S)-3-amino-4-(3-benzothienyl)butyric acid
468. 3-aminobicyclo[2.2.2]octane-2-carboxylic acid (mixture of isomers)
469. (R)-3-amino-4-(4-bromophenyl)butyric acid
470. (S)-3-amino-4-(4-bromophenyl)butyric acid
471. (R)-3-amino-4-(2-chlorophenyl)butyric acid
472. (S)-3-amino-4-(2-chlorophenyl)butyric acid
473. (R)-3-amino-4-(3-chlorophenyl)butyric acid
474. (S)-3-amino-4-(3-chlorophenyl)butyric acid
475. (R)-3-amino-4-(4-chlorophenyl)butyric acid
476. (S)-3-amino-4-(4-chlorophenyl)butyric acid
477. 3-amino-3-(4-chlorophenyl)propionic acid
478. (R)-3-amino-4-(2-cyanophenyl)butyric acid
479. (S)-3-amino-4-(2-cyanophenyl)butyric acid
480. (R)-3-amino-4-(3-cyanophenyl)butyric acid
481. (S)-3-amino-4-(3-cyanophenyl)butyric acid
482. (R)-3-amino-4-(4-cyanophenyl)butyric acid
483. (S)-3-amino-4-(4-cyanophenyl)butyric acid
484. (R)-3-amino-4-(2,4-dichlorophenyl)butyric acid
485. (S)-3-amino-4-(2,4-dichlorophenyl)butyric acid
486. (R)-3-amino-4-(3,4-dichlorophenyl)butyric acid
487. (S)-3-amino-4-(3,4-dichlorophenyl)butyric acid
488. (R)-3-amino-4-(3,4-difluorophenyl)butyric acid
489. (S)-3-amino-4-(3,4-difluorophenyl)butyric acid
490. (R)-3-amino-4-(2-fluorophenyl)butyric acid
491. (S)-3-amino-4-(2-fluorophenyl)butyric acid
492. (R)-3-amino-4-(3-fluorophenyl)butyric acid
493. (S)-3-amino-4-(3-fluorophenyl)butyric acid
494. (R)-3-amino-4-(4-fluorophenyl)butyric acid
495. (S)-3-amino-4-(4-fluorophenyl)butyric acid
496. (R)-3-amino-4-(2-furyl)butyric acid
497. (S)-3-amino-4-(2-furyl)butyric acid
498. (R)-3-amino-5-hexenoic acid
499. (S)-3-amino-5-hexenoic acid
500. (R)-3-amino-5-hexynoic acid
501. (S)-3-amino-5-hexynoic acid
502. (R)-3-amino-4-(4-iodophenyl)butyric acid
503. (S)-3-amino-4-(4-iodophenyl)butyric acid
504. (R)-3-amino-4-(2-methylphenyl)butyric acid
505. (S)-3-amino-4-(2-methylphenyl)butyric acid
506. (R)-3-amino-4-(3-methylphenyl)butyric acid
507. (S)-3-amino-4-(3-methylphenyl)butyric acid
508. (R)-3-amino-4-(4-methylphenyl)butyric acid
509. (S)-3-amino-4-(4-methylphenyl)butyric acid
510. (R)-3-amino-4-(1-naphthyl)butyric acid
511. (S)-3-amino-4-(1-naphthyl)butyric acid
512. (R)-3-amino-4-(2-naphthyl)butyric acid
513. (S)-3-amino-4-(2-naphthyl)butyric acid
514. (R)-3-amino-4-(4-nitrophenyl)butyric acid
515. (S)-3-amino-4-(4-nitrophenyl)butyric acid
516. (R)-3-amino-4-pentafluorophenylbutyric acid
517. (S)-3-amino-4-pentafluorophenylbutyric acid
518. (R)-3-amino-6-phenyl-5-hexenoic acid
519. (S)-3-amino-6-phenyl-5-hexenoic acid
520. (R)-3-amino-5-phenylpentanoic acid
521. (S)-3-amino-5-phenylpentanoic acid
522. (R)-3-amino-4-(3-pyridyl)butyric acid
523. (S)-3-amino-4-(3-pyridyl)butyric acid
524. (R)-3-amino-4-(4-pyridyl)butyric acid
525. (S)-3-amino-4-(4-pyridyl)butyric acid
526. (R)-3-amino-4-(2-thienyl)butyric acid
527. (S)-3-amino-4-(2-thienyl)butyric acid
528. (R)-3-amino-4-(3-thienyl)butyric acid
529. (S)-3-amino-4-(3-thienyl)butyric acid
530. 3-amino-3-(2-thienyl)propionic acid
531. 3-amino-4,4,4-trifluorobutyric acid
532. (R)-3-amino-4-(2-trifluoromethylphenyl)butyric acid
533. (S)-3-amino-4-(2-trifluoromethylphenyl)butyric acid
534. (R)-3-amino-4-(3-trifluoromethylphenyl)butyric acid
535. (S)-3-amino-4-(3-trifluoromethylphenyl)butyric acid
536. (R)-3-amino-4-(4-trifluoromethylphenyl)butyric acid
537. (S)-3-amino-4-(4-trifluoromethylphenyl)butyric acid
538. (R)-1,2,3,4-tetrahydroisoquinoline-3-acetic acid
539. (S)-1,2,3,4-tetrahydroisoquinoline-3-acetic acid
540. 1,2,5,6-tetrahydropyridine-3-carboxylic acid (guvacine)
541. H-L-β-Homopro-OH HCl(S)-2-(2-Pyrrolidinyl) acetic acid hydrochloride
542. H-DL-β-Leu-OH (1)-3-Amino-4-methylpentanoic acid
543. H-DL-β-Homoleu-OH (1)-3-Amino-5-methylcaproic acid
544. H-DL-β-Phe-OH (1)-3-Amino-3-phenylpropionic acid
545. L-Homophe-OEt HCl
546. D-Homophe-OEt HCl
547. N-Benzyl-L-Homophe-OEt HCl
548. N-Benzyl-D-Homophe-OEt HCl
549. (1)-3-(amino)-4-(4-biphenylyl)butyric acid
550. (1)-3-Amino-4-(4-biphenylyl)butyric acid hydrochloride
551. (+)-Ethyl (S)-2-amino-4-cyclohexylbutyrate hydrochloride
552. (−)-Ethyl (R)-2-amino-4-cyclohexylbutyrate hydrochloride N-α-Methyl Amino Acids
554. N-α-methyl-L-alanine (MeAla-OH)
555. N-α-methyl-D-alanine (D-MeAla-OH)
556. N-α-methyl-L-alloisoleucine (MeAlloIle-OH)
557. N-α-methyl-D-alloisoleucine (D-MeAlloIle-OH)
558. N-α-methyl-N-ω-tosyl-L-arginine (MeArg(Tos)-OH)
559. N-α-methyl-N-ω-2,2,4,6,7-pentamethyldihydrobenzofuran-5-sulfonyl-D-arginine (D-MeArg(Pbf)-OH)
560. N-α-methyl-N-ω-tosyl-D-arginine (D-MeArg(Tos)-OH)
561. N-α-methyl-L-aspartic acid
562. N-α-methyl-L-aspartic acid β-t-butyl ester (MeAsp(OtBu)-OH)
563. N-α-methyl-D-aspartic acid
564. N-α-methyl-D-aspartic acid β-t-butyl ester (D-MeAsp(OtBu)-OH)
565. N-α-methyl-4-chloro-L-phenylalanine (Me(4-Cl-Phe)-OH)
566. N-α-methyl-4-chloro-D-phenylalanine (D-Me(4-Cl-Phe)-OH)
567. N-α-methyl-L-glutamic acid γ-t-butyl ester (MeGlu(OtBu)-OH)
568. N-α-methyl-D-glutamic acid γ-t-butyl ester (D-MeGlu(OtBu)-OH)
569. N-α-methylglycine (sarcosine; Sar-OH)
570. N-α-methyl-N-im-trityl-L-histidine (MeHis(Trt)-OH)

571. N-α-methyl-N-im-trityl-D-histidine (D-MeHis(Trt)-OH)
572. N-α-methyl-trans-L-4-hydroxyproline
573. N-α-methyl-L-isoleucine (MeIle-OH)
574. N-α-methyl-L-leucine (MeLeu-OH)
575. N-α-methyl-D-leucine (D-MeLeu-OH)
576. N-α-methyl-N-ε-t-L-lysine (MeLys( )-OH)
577. N-α-methyl-N-ε-2-chlorobenzyloxycarbonyl-L-lysine (MeLys(2-Cl—Z)—OH)
578. N-α-methyl-4-nitro-L-phenylalanine (MePhe(4-NO2)-OH)
579. N-α-methyl-L-norleucine (MeNle-OH)
580. N-α-methyl-L-norvaline (MeNva-OH)
581. N-α-methyl-L-phenylalanine (MePhe-OH)
582. N-α-methyl-D-phenylalanine (D-MePhe-OH)
583. N-α-methyl-L-phenylglycine (MePhg-OH)
584. N-α-methyl-L-proline
585. N-α-methyl-O-benzyl-L-serine (MeSer(Bzl)-OH)
586. N-α-methyl-O-benzyl-L-serine dicyclohexylammonium salt (MeSer(Bzl)-OH.DCHA)
587. N-α-methyl-O-t-butyl-L-serine (MeSer(tBu)-OH)
588. N-α-methyl-O-t-butyl-L-threonine (MeThr(tBu)-OH)
589. N-α-methyl-L-tryptophan (MeTrp-OH)
590. N-α-methyl-DL-tryptophan (DL-MeTrp-OH)
591. N-α-methyl-O-benzyl-L-tyrosine (MeTyr(Bzl)-OH)
592. N-α-methyl-O-t-butyl-L-tyrosine (MeTyr(tBu)-OH)
593. N-α-methyl-O-methyl-L-tyrosine (MeTyr(Me)-OH)
594. N-α-methyl-O-benzyl-D-tyrosine (D-MeTyr(Bzl)-OH)
595. N-α-methyl-L-valine (MeVal-OH)
596. N-α-methyl-D-valine (D-MeVal-OH)
Amino Alcohols
598. L-alaninol
599. D-alaninol
600. 2-aminobenzylalcohol
601. 3-aminobenzylalcohol
602. 4-aminobenzylalcohol
603. (R)-(−)-2-aminobutanol
604. (S)-(+)-2-aminobutanol
605. 4-aminobutanol
606. 4-amino-2-butanol
607. 2-amino-5-chlorobenzylalcohol
608. (±)-cis-2-aminocyclohexanol
609. (±)-trans-2-aminocyclohexanol
610. trans-4-aminocyclohexanol
611. (1R,2S)-(−)-2-amino-1,2-diphenylethanol
612. (1S,2R)-(+)-2-amino-1,2-diphenylethanol
613. 2-(2-aminoethoxyl)ethanol
614. α-(1-aminoethyl)-4-hydroxybenzyl alcohol
615. 2-amino-2-ethyl-1,3-propanediol
616. 6-aminohexanol
617. 1-amino-4-(2-hydroxyethyl)piperazine
618. (1R,2S)-(+)-cis-1-amino-2-indanol
619. (1S,2R)-(−)-cis-1-amino-2-indanol
620. (1S,2R)-(+)-2-amino-3-methoxyphenylpropanol
621. (±)-cis-2-aminomethylcycloheptanol
622. (±)-1-aminomethylcyclohexanol
623. (±)-cis-2-aminomethylcyclohexanol
624. (±)-trans-2-aminomethylcyclohexanol
625. (±)-cis-2-aminomethylcyclooctanol
626. 6-amino-2-methyl-2-heptanol (heptaminol)
627. α-aminomethyl-3-hydroxybenzyl alcohol (norphenylephrine)
628. α-aminomethyl-4-hydroxybenzyl alcohol (octopamine)
629. α-aminomethyl-4-hydroxy-3-methoxybenzyl alcohol (normetaephrine)
630. 2-amino-2-methyl-1,3-propanediol
631. 2-amino-2-methylpropanol (β-aminoisobutanol)
632. (1R,2R)-(−)-2-amino-1-(4-nitrophenyl)-1,3-propanediol
633. (1S,2S)-(+)-2-amino-1-(4-nitrophenyl)-1,3-propanediol
634. 5-aminopentanol
635. 1-amino-3-phenoxy-2-propanol
636. (R)-(−)-2-amino-1-phenylethanol
637. (S)-(+)-2-amino-1-phenylethanol
638. 2-(4-aminophenyl)ethanol
639. (1R,2R)-(−)-2-amino-1-phenyl-1,3-propanediol
640. (1S,2S)-(+)-2-amino-1-phenyl-1,3-propanediol
641. 3-amino-3-phenylpropanol
642. (RS)-3-amino-1,2-propanediol
643. (S)-(+)-3-amino-1,2-propanediol
644. (R)-(−)-1-amino-2-propanol
645. (S)-(+)-1-amino-2-propanol
646. 3-amino-1-propanol
647. N-ω-2,2,4,6,7-pentamethyldihydrobenzofuran-5-sulfonyl-L-argininol (Arg(Pbf)-ol)
648. N-ω-tosyl-L-argininol
649. N-β-trityl-L-asparaginol (Asn(Trt)-ol)
650. L-asparaginol (Asn-ol)
651. N-β-trityl-D-asparaginol (D-Asn(Trt)-ol)
652. D-asparaginol (D-Asn-ol)
653. L-aspartimol β-t-butyl ester (Asp(OtBu)-ol)
654. D-aspartimol β-t-butyl ester (D-Asp(OtBu)-ol)
655. DL-4-chlorophenylalaninol
656. β-cyclohexyl-L-alaninol
657. S-t-butyl-L-cysteinol (Cys(tBu)-ol)
658. S-t-butyl-D-cysteinol (D-Cys(tBu)-ol)
659. 1,1-diphenyl-L-alaninol
660. L-glutaminol (Gln-ol)
661. N-γ-trityl-L-glutaminol (Gln(Trt)-ol)
662. L-glutamol γ-t-butyl ester (Glu(OtBu)-ol)
663. L-glutamol γ-benzyl ester (Glu(OBzl)-ol)
664. D-glutamol γ-t-butyl ester (D-Glu(OtBu)-ol)
665. D-glutamol γ-benzyl ester (D-Glu(OtBu)-ol)
666. ethanolamine (Gly-ol)
667. N-im-t-L-histidinol
668. N-im-trityl-L-histidinol
669. N-im-benzyl-L-histidinol
670. 1-hydroxyethylethoxypiperazine
671. N-(2-hydroxyethyl)piperazine
672. N-(2-hydroxyethyl)-1,3-propanediamine
673. 3-endo-hydroxymethylbicyclo[2.2.1]hept-5-enyl-2-endo-amine
674. (±)-cis-2-hydroxymethyl-4-cyclohexenyl-1-amine
675. (±)-cis-2-hydroxymethyl-1-cyclohexylamine
676. (±)-trans-2-hydroxymethyl-1-cyclohexylamine
677. (±)-cis-2-hydroxymethyl-trans-4-phenyl-1-cyclohexylamine
678. 3-hydroxypiperidine
679. 4-hydroxypiperidine
680. L-isoleucinol (Ile-ol)
681. L-leucinol (leu-ol)
682. D-leucinol (D-leu-ol)
683. L-tert-leucinol((S)-(−)-2-amino-3,3-dimethyl-1-butanol)
684. N-ε-t-L-lysinol (Lys( )-ol)
685. N-ε-benzyloxycarbonyl-L-lysinol (Lys(Z)-ol)
686. N-ε-2-cholorobenzyloxycarbonyl-L-lysinol (Lys(2-Cl—Z)-ol)
687. N-ε-t-D-lysinol (D-Lys( )-ol)
688. N-ε-benzyloxycarbonyl-D-lysinol (D-Lys(Z)-ol)
689. N-ε-2-cholorobenzyloxycarbonyl-D-lysinol (D-Lys(2-Cl—Z)-ol)

690. L-methioninol (Met-ol)
691. D-methioninol (D-Met-ol)
692. (1R,2S)-(−)-norephedrine
693. (1S,2R)-(+)-norephedrine
694. L-norleucinol
695. L-norvalinol
696. L-phenylalaninol
697. D-phenylalaninol (D-Phe-ol)
698. L-phenylglycinol (Phg-ol)
699. D-phenylglycinol (D-Phg-ol)
700. 2-(2-piperidyl)ethanol
701. 2-(4-piperidyl)ethanol
702. 2-piperidylmethanol
703. L-prolinol (Pro-ol)
704. D-prolinol (D-Pro-ol)
705. O-benzyl-L-serinol (Ser(Bzl)-ol)
706. O-t-butyl-L-serinol (Ser(tBu)-ol)
707. O-benzyl-D-serinol (D-Ser(Bzl)-ol)
708. O-t-butyl-D-serinol (D-Ser(tBu)-ol)
709. O-butyl-L-threoninol (Thr(tBu)-ol)
710. O-t-butyl-D-threoninol (Thr(tBu)-ol)
711. O-butyl-D-threoninol (Thr(tBu)-ol)
712. L-tryptophanol (Trp-ol)
713. D-tryptophanol (D-Trp-ol)
714. O-benzyl-L-tyrosinol (Tyr(Bzl)-ol)
715. O-t-butyl-L-tyrosinol (Tyr(tBu)-ol)
716. O-benzyl-D-tyrosinol (D-Tyr(Bzl)-ol)
717. L-valinol (Val-ol)
718. D-valinol (D-Val-ol)
Others
720. Norleucine
721. Ethionine
722. Ornithine
723. Thi-OH (−)-(R)-4-thiazolidine-carboxylic acid
724. 2-phosphonoglycine trimethyl ester
725. iminodiacetic acid
726. (1)-2-Aminoheptanedioic acid
727. (1)-2-Aminopimelic acid
728. 2-[2-(amino)ethoxy]ethoxy}acetic acid
729. 8-(amino)-3,6-dioxaoctanoic acid
730. 1-azetidine-3-carboxylic acid
731. (1R,4S)-(+)-4-(amino)-2-cyclopentene-1-carboxylic acid
732. cycloleucine
733. homocycloleucine
734. Freidinger's lactam
735. 1,2,3,4-tetrahydronorharman-3-carboxylic acid
736. 4-(aminomethyl)benzoic acid
737. 3-(aminomethyl)benzoic acid
738. 4-Abz-OH 4-(amino)benzoic acid
739. 3-Abz-OH 3-(amino)benzoic acid
740. 2-Abz-OH 2-(amino)benzoic acid
741. 2-(amino)isobutyric acid
742. 12-(amino)dodecanoic acid
743. 8-(amino)caprylic acid
744. 7-(amino)enanthic acid
745. 6-(amino)caproic acid
746. 5-(amino)pentanoic acid
747. 4-(amino)butyric acid
748. N'-diaminoacetic acid
749. L-2,3-diaminopropionic acid
750. N-β-L-2,3-diaminopropionic acid
751. (R)-4-(amino)-3-(Z-amino)butyric acid
752. (S)-4-(amino)-3-(Z-amino)butyric acid
753. 1,6-hexanediamine HCl
754. 1,5-pentanediamine
755. N-p-phenylenediamine
756. N-1,4-butanediamine
757. N-1,3-propanediamine
758. N-ethylenediamine
759. N—N-methylethylenediamine
760. 1-piperazine
761. 1-homopiperazine

What is claimed:

1. An isolated immunomodulatory peptide comprising the amino acid sequence set forth in SEQ ID NO: 1214, or a variant thereof comprising an Ile, Arg or Val at position 5, or an amino acid sequence having at least 90% identity thereto.

2. The isolated immunomodulatory peptide of claim 1 wherein the variant comprises an Ile at position 5, or an amino acid sequence having at least 90% identity thereto.

3. An isolated immunomodulatory peptide comprising the amino acid sequence set forth in SEQ ID NO: 1214, or a variant thereof comprising an Ile, Arg or Val at position 5.

4. The isolated immunomodulatory peptide of claim 3 wherein the variant comprises an Ile at position 5.

* * * * *

SEQUENCE LISTING

```
<160> NUMBER OF SEQ ID NOS: 1268

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Gln Arg Leu Arg Ile Arg Val Ala Val Ile Arg Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic construct

<400> SEQUENCE: 2

Val Gln Leu Arg Ile Arg Val Ala Val Ile Arg Ala
1               5                   10

<210> SEQ ID NO 3
<211> LENGTH: 12
<212> TYPE: PRT
```

<213> ORGANISM: Artificial Sequence
<220> FEATURE:
<223> OTHER INFORMATION: Synthetic construct

<400> SEQUENCE: 3

Val Arg Phe Arg Ile Arg Val Ala Val Ile Arg Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic construct

<400> SEQUENCE: 4

Val Arg Trp Arg Ile Arg Val Ala Val Ile Arg Ala
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic construct

<400> SEQUENCE: 5

Val Arg Leu Trp Ile Arg Val Ala Val Ile Arg Ala
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic construct

<400> SEQUENCE: 6

Val Arg Leu Arg Ile Arg Val Trp Val Ile Arg Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic construct

<400> SEQUENCE: 7

Val Arg Leu Arg Ile Arg Val Ala Val Arg Arg Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic construct

<400> SEQUENCE: 8

Val Arg Leu Arg Ile Arg Val Ala Val Ile Arg Lys
1               5                   10

<210> SEQ ID NO 9
<211> LENGTH: 12
<212> TYPE: PRT
<213> ORGANISM: Artificial Sequence

```
<220> FEATURE:
<223> OTHER INFORMATION: Synthetic construct

<400> SEQUENCE: 9

Val Gln Leu Arg Ile Arg Val Arg Val Ile Arg Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic construct

<400> SEQUENCE: 10

Lys Arg Phe Arg Ile Arg Val Ala Val Arg Arg Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic construct

<400> SEQUENCE: 11

Val Arg Leu Arg Ile Arg Val Arg Val Ile Arg Lys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Lys Gln Phe Arg Ile Arg Val Arg Val Ile Arg Lys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic construct

<400> SEQUENCE: 13

His Gln Phe Arg Phe Arg Phe Arg Val Arg Arg Lys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic construct

<400> SEQUENCE: 14

His Gln Trp Arg Ile Arg Val Ala Val Arg Arg His
1               5                   10

<210> SEQ ID NO 15
<211> LENGTH: 12
<212> TYPE: PRT
<213> ORGANISM: Artificial Sequence
<220> FEATURE:
```

<223> OTHER INFORMATION: Synthetic construct

<400> SEQUENCE: 15

Lys Arg Phe Arg Ile Arg Val Arg Val Ile Arg Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic construct

<400> SEQUENCE: 16

Lys Arg Trp Arg Ile Arg Val Arg Val Ile Arg Lys
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic construct

<400> SEQUENCE: 17

Lys Ile Trp Val Arg Trp Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic construct

<400> SEQUENCE: 18

Ile Trp Val Ile Trp Arg Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic construct

<400> SEQUENCE: 19

Ala Leu Pro Trp Lys Trp Pro Trp Trp Pro Trp Arg Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic construct

<400> SEQUENCE: 20

Ile Ala Pro Trp Lys Trp Pro Trp Trp Pro Trp Arg Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic construct

```
<400> SEQUENCE: 21

Ile Leu Ala Trp Lys Trp Pro Trp Trp Pro Trp Arg Arg
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic construct

<400> SEQUENCE: 22

Ile Leu Pro Ala Lys Trp Pro Trp Trp Pro Trp Arg Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic construct

<400> SEQUENCE: 23

Ile Leu Pro Trp Ala Trp Pro Trp Trp Pro Trp Arg Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic construct

<400> SEQUENCE: 24

Ile Leu Pro Trp Lys Ala Pro Trp Trp Pro Trp Arg Arg
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic construct

<400> SEQUENCE: 25

Ile Leu Pro Trp Lys Trp Ala Trp Trp Pro Trp Arg Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic construct

<400> SEQUENCE: 26

Ile Leu Pro Trp Lys Trp Pro Ala Trp Pro Trp Arg Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic construct
```

```
<400> SEQUENCE: 27

Ile Leu Pro Trp Lys Trp Pro Trp Ala Pro Trp Arg Arg
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic construct

<400> SEQUENCE: 28

Ile Leu Pro Trp Lys Trp Pro Trp Trp Ala Trp Arg Arg
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic construct

<400> SEQUENCE: 29

Ile Leu Pro Trp Lys Trp Pro Trp Trp Pro Ala Arg Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic construct

<400> SEQUENCE: 30

Ile Leu Pro Trp Lys Trp Pro Trp Trp Pro Trp Ala Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic construct

<400> SEQUENCE: 31

Ile Leu Pro Trp Lys Trp Pro Trp Trp Pro Trp Arg Ala
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic construct

<400> SEQUENCE: 32

Asp Leu Pro Trp Lys Trp Pro Trp Trp Pro Trp Arg Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic construct

<400> SEQUENCE: 33
```

```
Ile Asp Pro Trp Lys Trp Pro Trp Trp Pro Trp Arg Arg
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: Synthetic construct

<400> SEQUENCE: 34

```
Ile Leu Asp Trp Lys Trp Pro Trp Trp Pro Trp Arg Arg
1               5                   10
```

<210> SEQ ID NO 35
<211> LENGTH: 13
<212> TYPE: PRT
<213> ORGANISM: Artificial Sequence
<220> FEATURE:
<223> OTHER INFORMATION: Synthetic construct

<400> SEQUENCE: 35

```
Ile Leu Pro Asp Lys Trp Pro Trp Trp Pro Trp Arg Arg
1               5                   10
```

<210> SEQ ID NO 36
<211> LENGTH: 13
<212> TYPE: PRT
<213> ORGANISM: Artificial Sequence
<220> FEATURE:
<223> OTHER INFORMATION: Synthetic construct

<400> SEQUENCE: 36

```
Ile Leu Pro Trp Asp Trp Pro Trp Trp Pro Trp Arg Arg
1               5                   10
```

<210> SEQ ID NO 37
<211> LENGTH: 13
<212> TYPE: PRT
<213> ORGANISM: Artificial Sequence
<220> FEATURE:
<223> OTHER INFORMATION: Synthetic construct

<400> SEQUENCE: 37

```
Ile Leu Pro Trp Lys Asp Pro Trp Trp Pro Trp Arg Arg
1               5                   10
```

<210> SEQ ID NO 38
<211> LENGTH: 13
<212> TYPE: PRT
<213> ORGANISM: Artificial Sequence
<220> FEATURE:
<223> OTHER INFORMATION: Synthetic construct

<400> SEQUENCE: 38

```
Ile Leu Pro Trp Lys Trp Asp Trp Trp Pro Trp Arg Arg
1               5                   10
```

<210> SEQ ID NO 39
<211> LENGTH: 13
<212> TYPE: PRT
<213> ORGANISM: Artificial Sequence
<220> FEATURE:
<223> OTHER INFORMATION: Synthetic construct

<400> SEQUENCE: 39

Ile Leu Pro Trp Lys Trp Pro Asp Trp Pro Trp Arg Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic construct

<400> SEQUENCE: 40

Ile Leu Pro Trp Lys Trp Pro Trp Asp Pro Trp Arg Arg
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic construct

<400> SEQUENCE: 41

Ile Leu Pro Trp Lys Trp Pro Trp Trp Asp Trp Arg Arg
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic construct

<400> SEQUENCE: 42

Ile Leu Pro Trp Lys Trp Pro Trp Trp Pro Asp Arg Arg
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic construct

<400> SEQUENCE: 43

Ile Leu Pro Trp Lys Trp Pro Trp Trp Pro Trp Asp Arg
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic construct

<400> SEQUENCE: 44

Ile Leu Pro Trp Lys Trp Pro Trp Trp Pro Trp Arg Asp
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic construct

<400> SEQUENCE: 45

Glu Leu Pro Trp Lys Trp Pro Trp Trp Pro Trp Arg Arg

```
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic construct

<400> SEQUENCE: 46

Ile Glu Pro Trp Lys Trp Pro Trp Trp Pro Trp Arg Arg
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic construct

<400> SEQUENCE: 47

Ile Leu Glu Trp Lys Trp Pro Trp Trp Pro Trp Arg Arg
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic construct

<400> SEQUENCE: 48

Ile Leu Pro Glu Lys Trp Pro Trp Trp Pro Trp Arg Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic construct

<400> SEQUENCE: 49

Ile Leu Pro Trp Glu Trp Pro Trp Trp Pro Trp Arg Arg
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic construct

<400> SEQUENCE: 50

Ile Leu Pro Trp Lys Glu Pro Trp Trp Pro Trp Arg Arg
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic construct

<400> SEQUENCE: 51

Ile Leu Pro Trp Lys Trp Glu Trp Trp Pro Trp Arg Arg
1               5                   10
```

<210> SEQ ID NO 52
<211> LENGTH: 13
<212> TYPE: PRT
<213> ORGANISM: Artificial Sequence
<220> FEATURE:
<223> OTHER INFORMATION: Synthetic construct

<400> SEQUENCE: 52

Ile Leu Pro Trp Lys Trp Pro Glu Trp Pro Trp Arg Arg
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic construct

<400> SEQUENCE: 53

Ile Leu Pro Trp Lys Trp Pro Trp Glu Pro Trp Arg Arg
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic construct

<400> SEQUENCE: 54

Ile Leu Pro Trp Lys Trp Pro Trp Trp Glu Trp Arg Arg
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic construct

<400> SEQUENCE: 55

Ile Leu Pro Trp Lys Trp Pro Trp Trp Pro Glu Arg Arg
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic construct

<400> SEQUENCE: 56

Ile Leu Pro Trp Lys Trp Pro Trp Trp Pro Trp Glu Arg
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic construct

<400> SEQUENCE: 57

Ile Leu Pro Trp Lys Trp Pro Trp Trp Pro Trp Arg Glu
1               5                   10

```
<210> SEQ ID NO 58
<211> LENGTH: 13
<212> TYPE: PRT
<213> ORGANISM: Artificial Sequence
<220> FEATURE:
<223> OTHER INFORMATION: Synthetic construct

<400> SEQUENCE: 58

Phe Leu Pro Trp Lys Trp Pro Trp Trp Pro Trp Arg Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic construct

<400> SEQUENCE: 59

Ile Phe Pro Trp Lys Trp Pro Trp Trp Pro Trp Arg Arg
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic construct

<400> SEQUENCE: 60

Ile Leu Phe Trp Lys Trp Pro Trp Trp Pro Trp Arg Arg
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic construct

<400> SEQUENCE: 61

Ile Leu Pro Phe Lys Trp Pro Trp Trp Pro Trp Arg Arg
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic construct

<400> SEQUENCE: 62

Ile Leu Pro Trp Phe Trp Pro Trp Trp Pro Trp Arg Arg
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic construct

<400> SEQUENCE: 63

Ile Leu Pro Trp Lys Phe Pro Trp Trp Pro Trp Arg Arg
1               5                   10
```

```
<210> SEQ ID NO 64
<211> LENGTH: 13
<212> TYPE: PRT
<213> ORGANISM: Artificial Sequence
<220> FEATURE:
<223> OTHER INFORMATION: Synthetic construct

<400> SEQUENCE: 64

Ile Leu Pro Trp Lys Trp Phe Trp Trp Pro Trp Arg Arg
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic construct

<400> SEQUENCE: 65

Ile Leu Pro Trp Lys Trp Pro Phe Trp Pro Trp Arg Arg
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic construct

<400> SEQUENCE: 66

Ile Leu Pro Trp Lys Trp Pro Trp Phe Pro Trp Arg Arg
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic construct

<400> SEQUENCE: 67

Ile Leu Pro Trp Lys Trp Pro Trp Trp Phe Trp Arg Arg
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic construct

<400> SEQUENCE: 68

Ile Leu Pro Trp Lys Trp Pro Trp Trp Pro Phe Arg Arg
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic construct

<400> SEQUENCE: 69

Ile Leu Pro Trp Lys Trp Pro Trp Trp Pro Trp Phe Arg
1               5                   10

<210> SEQ ID NO 70
```

```
<211> LENGTH: 13
<212> TYPE: PRT
<213> ORGANISM: Artificial Sequence
<220> FEATURE:
<223> OTHER INFORMATION: Synthetic construct

<400> SEQUENCE: 70

Ile Leu Pro Trp Lys Trp Pro Trp Trp Pro Trp Arg Phe
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic construct

<400> SEQUENCE: 71

Gly Leu Pro Trp Lys Trp Pro Trp Trp Pro Trp Arg Arg
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetic construct

<400> SEQUENCE: 72

Ile Gly Pro Trp Lys Trp Pro Trp Trp Pro Trp Arg Arg
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic construct

<400> SEQUENCE: 73

Ile Leu Gly Trp Lys Trp Pro Trp Trp Pro Trp Arg Arg
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic construct

<400> SEQUENCE: 74

Ile Leu Pro Gly Lys Trp Pro Trp Trp Pro Trp Arg Arg
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic construct

<400> SEQUENCE: 75

Ile Leu Pro Trp Gly Trp Pro Trp Trp Pro Trp Arg Arg
1               5                   10

<210> SEQ ID NO 76
<211> LENGTH: 13
```

```
<212> TYPE: PRT
<213> ORGANISM: Artificial Sequence
<220> FEATURE:
<223> OTHER INFORMATION: Synthetic construct

<400> SEQUENCE: 76

Ile Leu Pro Trp Lys Gly Pro Trp Trp Pro Trp Arg Arg
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic construct

<400> SEQUENCE: 77

Ile Leu Pro Trp Lys Trp Gly Trp Trp Pro Trp Arg Arg
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic construct

<400> SEQUENCE: 78

Ile Leu Pro Trp Lys Trp Pro Gly Trp Pro Trp Arg Arg
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic construct

<400> SEQUENCE: 79

Ile Leu Pro Trp Lys Trp Pro Trp Gly Pro Trp Arg Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic construct

<400> SEQUENCE: 80

Ile Leu Pro Trp Lys Trp Pro Trp Trp Gly Trp Arg Arg
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic construct

<400> SEQUENCE: 81

Ile Leu Pro Trp Lys Trp Pro Trp Trp Pro Gly Arg Arg
1               5                   10

<210> SEQ ID NO 82
<211> LENGTH: 13
<212> TYPE: PRT
```

```
<213> ORGANISM: Artificial Sequence
<220> FEATURE:
<223> OTHER INFORMATION: Synthetic construct

<400> SEQUENCE: 82

Ile Leu Pro Trp Lys Trp Pro Trp Trp Pro Trp Gly Arg
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic construct

<400> SEQUENCE: 83

Ile Leu Pro Trp Lys Trp Pro Trp Trp Pro Trp Arg Gly
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic construct

<400> SEQUENCE: 84

His Leu Pro Trp Lys Trp Pro Trp Trp Pro Trp Arg Arg
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic construct

<400> SEQUENCE: 85

Ile His Pro Trp Lys Trp Pro Trp Trp Pro Trp Arg Arg
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic construct

<400> SEQUENCE: 86

Ile Leu His Trp Lys Trp Pro Trp Trp Pro Trp Arg Arg
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Synthetic construct

<400> SEQUENCE: 87

Ile Leu Pro His Lys Trp Pro Trp Trp Pro Trp Arg Arg
1               5                   10

<210> SEQ ID NO 88
<211> LENGTH: 13
<212> TYPE: PRT
<213> ORGANISM: Artificial Sequence
```

```
<220> FEATURE:
<223> OTHER INFORMATION: Synthetic construct

<400> SEQUENCE: 88

Ile Leu Pro Trp His Trp Pro Trp Trp Pro Trp Arg Arg
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic construct

<400> SEQUENCE: 89

Ile Leu Pro Trp Lys His Pro Trp Trp Pro Trp Arg Arg
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthetic construct

<400> SEQUENCE: 90

Ile Leu Pro Trp Lys Trp His Trp Trp Pro Trp Arg Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic construct

<400> SEQUENCE: 91

Ile Leu Pro Trp Lys Trp Pro His Trp Pro Trp Arg Arg
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic construct

<400> SEQUENCE: 92

Ile Leu Pro Trp Lys Trp Pro Trp His Pro Trp Arg Arg
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic construct

<400> SEQUENCE: 93

Ile Leu Pro Trp Lys Trp Pro Trp Trp His Trp Arg Arg
1               5                   10

<210> SEQ ID NO 94
<211> LENGTH: 13
<212> TYPE: PRT
<213> ORGANISM: Artificial Sequence
<220> FEATURE:
```

-continued

```
<223> OTHER INFORMATION: Synthetic construct

<400> SEQUENCE: 94

Ile Leu Pro Trp Lys Trp Pro Trp Trp Pro His Arg Arg
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic construct

<400> SEQUENCE: 95

Ile Leu Pro Trp Lys Trp Pro Trp Trp Pro Trp His Arg
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic construct

<400> SEQUENCE: 96

Ile Leu Pro Trp Lys Trp Pro Trp Trp Pro Trp Arg His
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetic construct

<400> SEQUENCE: 97

Ile Ile Pro Trp Lys Trp Pro Trp Trp Pro Trp Arg Arg
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic construct

<400> SEQUENCE: 98

Ile Leu Ile Trp Lys Trp Pro Trp Trp Pro Trp Arg Arg
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic construct

<400> SEQUENCE: 99

Ile Leu Pro Ile Lys Trp Pro Trp Trp Pro Trp Arg Arg
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic construct
```

<400> SEQUENCE: 100

Ile Leu Pro Trp Ile Trp Pro Trp Trp Pro Trp Arg Arg
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic construct

<400> SEQUENCE: 101

Ile Leu Pro Trp Lys Ile Pro Trp Trp Pro Trp Arg Arg
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Synthetic construct

<400> SEQUENCE: 102

Ile Leu Pro Trp Lys Trp Ile Trp Trp Pro Trp Arg Arg
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Synthetic construct

<400> SEQUENCE: 103

Ile Leu Pro Trp Lys Trp Pro Ile Trp Pro Trp Arg Arg
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic construct

<400> SEQUENCE: 104

Ile Leu Pro Trp Lys Trp Pro Trp Ile Pro Trp Arg Arg
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Synthetic construct

<400> SEQUENCE: 105

Ile Leu Pro Trp Lys Trp Pro Trp Trp Ile Trp Arg Arg
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Synthetic construct

```
<400> SEQUENCE: 106

Ile Leu Pro Trp Lys Trp Pro Trp Trp Pro Ile Arg Arg
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic construct

<400> SEQUENCE: 107

Ile Leu Pro Trp Lys Trp Pro Trp Trp Pro Trp Ile Arg
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic construct

<400> SEQUENCE: 108

Ile Leu Pro Trp Lys Trp Pro Trp Trp Pro Trp Arg Ile
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic construct

<400> SEQUENCE: 109

Lys Leu Pro Trp Lys Trp Pro Trp Trp Pro Trp Arg Arg
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic construct

<400> SEQUENCE: 110

Ile Lys Pro Trp Lys Trp Pro Trp Trp Pro Trp Arg Arg
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic construct

<400> SEQUENCE: 111

Ile Leu Lys Trp Lys Trp Pro Trp Trp Pro Trp Arg Arg
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic construct

<400> SEQUENCE: 112
```

Ile Leu Pro Lys Lys Trp Pro Trp Trp Pro Trp Arg Arg
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Synthetic construct

<400> SEQUENCE: 113

Ile Leu Pro Trp Lys Lys Pro Trp Trp Pro Trp Arg Arg
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic construct

<400> SEQUENCE: 114

Ile Leu Pro Trp Lys Trp Lys Trp Trp Pro Trp Arg Arg
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic construct

<400> SEQUENCE: 115

Ile Leu Pro Trp Lys Trp Pro Lys Trp Pro Trp Arg Arg
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Synthetic construct

<400> SEQUENCE: 116

Ile Leu Pro Trp Lys Trp Pro Trp Lys Pro Trp Arg Arg
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic construct

<400> SEQUENCE: 117

Ile Leu Pro Trp Lys Trp Pro Trp Trp Lys Trp Arg Arg
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic construct

<400> SEQUENCE: 118

```
Ile Leu Pro Trp Lys Trp Pro Trp Trp Pro Lys Arg Arg
1               5                   10
```

<210> SEQ ID NO 119
<211> LENGTH: 13
<212> TYPE: PRT
<213> ORGANISM: Artificial Sequence
<220> FEATURE:
<223> OTHER INFORMATION: Synthetic construct

<400> SEQUENCE: 119

```
Ile Leu Pro Trp Lys Trp Pro Trp Trp Pro Trp Lys Arg
1               5                   10
```

<210> SEQ ID NO 120
<211> LENGTH: 13
<212> TYPE: PRT
<213> ORGANISM: Artificial Sequence
<220> FEATURE:
<223> OTHER INFORMATION: Synthetic construct

<400> SEQUENCE: 120

```
Ile Leu Pro Trp Lys Trp Pro Trp Trp Pro Trp Arg Lys
1               5                   10
```

<210> SEQ ID NO 121
<211> LENGTH: 13
<212> TYPE: PRT
<213> ORGANISM: Artificial Sequence
<220> FEATURE:
<223> OTHER INFORMATION: Synthetic construct

<400> SEQUENCE: 121

```
Leu Leu Pro Trp Lys Trp Pro Trp Trp Pro Trp Arg Arg
1               5                   10
```

<210> SEQ ID NO 122
<211> LENGTH: 13
<212> TYPE: PRT
<213> ORGANISM: Artificial Sequence
<220> FEATURE:
<223> OTHER INFORMATION: Synthetic construct

<400> SEQUENCE: 122

```
Ile Leu Leu Trp Lys Trp Pro Trp Trp Pro Trp Arg Arg
1               5                   10
```

<210> SEQ ID NO 123
<211> LENGTH: 13
<212> TYPE: PRT
<213> ORGANISM: Artificial Sequence
<220> FEATURE:
<223> OTHER INFORMATION: Synthetic construct

<400> SEQUENCE: 123

```
Ile Leu Pro Leu Lys Trp Pro Trp Trp Pro Trp Arg Arg
1               5                   10
```

<210> SEQ ID NO 124
<211> LENGTH: 13
<212> TYPE: PRT
<213> ORGANISM: Artificial Sequence
<220> FEATURE:
<223> OTHER INFORMATION: Synthetic construct

<400> SEQUENCE: 124

```
Ile Leu Pro Trp Leu Trp Pro Trp Trp Pro Trp Arg Arg
```

```
1               5                   10
```

<210> SEQ ID NO 125
<211> LENGTH: 13
<212> TYPE: PRT
<213> ORGANISM: Artificial Sequence
<220> FEATURE:
<223> OTHER INFORMATION: Synthetic construct

<400> SEQUENCE: 125

```
Ile Leu Pro Trp Lys Leu Pro Trp Trp Pro Trp Arg Arg
1               5                   10
```

<210> SEQ ID NO 126
<211> LENGTH: 13
<212> TYPE: PRT
<213> ORGANISM: Artificial Sequence
<220> FEATURE:
<223> OTHER INFORMATION: Synthetic construct

<400> SEQUENCE: 126

```
Ile Leu Pro Trp Lys Trp Leu Trp Trp Pro Trp Arg Arg
1               5                   10
```

<210> SEQ ID NO 127
<211> LENGTH: 13
<212> TYPE: PRT
<213> ORGANISM: Artificial Sequence
<220> FEATURE:
<223> OTHER INFORMATION: Synthetic construct

<400> SEQUENCE: 127

```
Ile Leu Pro Trp Lys Trp Pro Leu Trp Pro Trp Arg Arg
1               5                   10
```

<210> SEQ ID NO 128
<211> LENGTH: 13
<212> TYPE: PRT
<213> ORGANISM: Artificial Sequence
<220> FEATURE:
<223> OTHER INFORMATION: Synthetic construct

<400> SEQUENCE: 128

```
Ile Leu Pro Trp Lys Trp Pro Trp Leu Pro Trp Arg Arg
1               5                   10
```

<210> SEQ ID NO 129
<211> LENGTH: 13
<212> TYPE: PRT
<213> ORGANISM: Artificial Sequence
<220> FEATURE:
<223> OTHER INFORMATION: Synthetic construct

<400> SEQUENCE: 129

```
Ile Leu Pro Trp Lys Trp Pro Trp Trp Leu Trp Arg Arg
1               5                   10
```

<210> SEQ ID NO 130
<211> LENGTH: 13
<212> TYPE: PRT
<213> ORGANISM: Artificial Sequence
<220> FEATURE:
<223> OTHER INFORMATION: Synthetic construct

<400> SEQUENCE: 130

```
Ile Leu Pro Trp Lys Trp Pro Trp Trp Pro Leu Arg Arg
1               5                   10
```

<210> SEQ ID NO 131
<211> LENGTH: 13
<212> TYPE: PRT
<213> ORGANISM: Artificial Sequence
<220> FEATURE:
<223> OTHER INFORMATION: Synthetic construct

<400> SEQUENCE: 131

Ile Leu Pro Trp Lys Trp Pro Trp Trp Pro Trp Leu Arg
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Synthetic construct

<400> SEQUENCE: 132

Ile Leu Pro Trp Lys Trp Pro Trp Trp Pro Trp Arg Leu
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Synthetic construct

<400> SEQUENCE: 133

Met Leu Pro Trp Lys Trp Pro Trp Trp Pro Trp Arg Arg
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Synthetic construct

<400> SEQUENCE: 134

Ile Met Pro Trp Lys Trp Pro Trp Trp Pro Trp Arg Arg
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthetic construct

<400> SEQUENCE: 135

Ile Leu Met Trp Lys Trp Pro Trp Pro Trp Arg Arg
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Synthetic construct

<400> SEQUENCE: 136

Ile Leu Pro Met Lys Trp Pro Trp Trp Pro Trp Arg Arg
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Synthetic construct

<400> SEQUENCE: 137

Ile Leu Pro Trp Met Trp Pro Trp Trp Pro Trp Arg Arg
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic construct

<400> SEQUENCE: 138

Ile Leu Pro Trp Lys Met Pro Trp Trp Pro Trp Arg Arg
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Synthetic construct

<400> SEQUENCE: 139

Ile Leu Pro Trp Lys Trp Met Trp Trp Pro Trp Arg Arg
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic construct

<400> SEQUENCE: 140

Ile Leu Pro Trp Lys Trp Pro Met Trp Pro Trp Arg Arg
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic construct

<400> SEQUENCE: 141

Ile Leu Pro Trp Lys Trp Pro Trp Met Pro Trp Arg Arg
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic construct

<400> SEQUENCE: 142

Ile Leu Pro Trp Lys Trp Pro Trp Trp Met Trp Arg Arg
1               5                   10

```
<210> SEQ ID NO 143
<211> LENGTH: 13
<212> TYPE: PRT
<213> ORGANISM: Artificial Sequence
<220> FEATURE:
<223> OTHER INFORMATION: Synthetic construct

<400> SEQUENCE: 143

Ile Leu Pro Trp Lys Trp Pro Trp Trp Pro Met Arg Arg
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Synthetic construct

<400> SEQUENCE: 144

Ile Leu Pro Trp Lys Trp Pro Trp Trp Pro Trp Met Arg
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Synthetic construct

<400> SEQUENCE: 145

Ile Leu Pro Trp Lys Trp Pro Trp Trp Pro Trp Arg Met
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Synthetic construct

<400> SEQUENCE: 146

Asn Leu Pro Trp Lys Trp Pro Trp Trp Pro Trp Arg Arg
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Synthetic construct

<400> SEQUENCE: 147

Ile Asn Pro Trp Lys Trp Pro Trp Trp Pro Trp Arg Arg
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic construct

<400> SEQUENCE: 148

Ile Leu Asn Trp Lys Trp Pro Trp Trp Pro Trp Arg Arg
1               5                   10

<210> SEQ ID NO 149
```

```
<211> LENGTH: 13
<212> TYPE: PRT
<213> ORGANISM: Artificial Sequence
<220> FEATURE:
<223> OTHER INFORMATION: Synthetic construct

<400> SEQUENCE: 149

Ile Leu Pro Asn Lys Trp Pro Trp Trp Pro Trp Arg Arg
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Synthetic construct

<400> SEQUENCE: 150

Ile Leu Pro Trp Asn Trp Pro Trp Trp Pro Trp Arg Arg
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Synthetic construct

<400> SEQUENCE: 151

Ile Leu Pro Trp Lys Asn Pro Trp Trp Pro Trp Arg Arg
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic construct

<400> SEQUENCE: 152

Ile Leu Pro Trp Lys Trp Asn Trp Trp Pro Trp Arg Arg
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Synthetic construct

<400> SEQUENCE: 153

Ile Leu Pro Trp Lys Trp Pro Asn Trp Pro Trp Arg Arg
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Synthetic construct

<400> SEQUENCE: 154

Ile Leu Pro Trp Lys Trp Pro Trp Asn Pro Trp Arg Arg
1               5                   10

<210> SEQ ID NO 155
<211> LENGTH: 13
```

```
<212> TYPE: PRT
<213> ORGANISM: Artificial Sequence
<220> FEATURE:
<223> OTHER INFORMATION: Synthetic construct

<400> SEQUENCE: 155

Ile Leu Pro Trp Lys Trp Pro Trp Trp Asn Trp Arg Arg
1               5                   10

<210> SEQ ID NO 156
<211> LENGTH: 13
<212> TYPE: PRT
<213> ORGANISM: Artificial Sequence
<220> FEATURE:
<223> OTHER INFORMATION: Synthetic construct

<400> SEQUENCE: 156

Ile Leu Pro Trp Lys Trp Pro Trp Trp Pro Asn Arg Arg
1               5                   10

<210> SEQ ID NO 157
<211> LENGTH: 13
<212> TYPE: PRT
<213> ORGANISM: Artificial Sequence
<220> FEATURE:
<223> OTHER INFORMATION: Synthetic construct

<400> SEQUENCE: 157

Ile Leu Pro Trp Lys Trp Pro Trp Trp Pro Trp Asn Arg
1               5                   10

<210> SEQ ID NO 158
<211> LENGTH: 13
<212> TYPE: PRT
<213> ORGANISM: Artificial Sequence
<220> FEATURE:
<223> OTHER INFORMATION: Synthetic construct

<400> SEQUENCE: 158

Ile Leu Pro Trp Lys Trp Pro Trp Trp Pro Trp Arg Asn
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic construct

<400> SEQUENCE: 159

Pro Leu Pro Trp Lys Trp Pro Trp Trp Pro Trp Arg Arg
1               5                   10

<210> SEQ ID NO 160
<211> LENGTH: 13
<212> TYPE: PRT
<213> ORGANISM: Artificial Sequence
<220> FEATURE:
<223> OTHER INFORMATION: Synthetic construct

<400> SEQUENCE: 160

Ile Pro Pro Trp Lys Trp Pro Trp Trp Pro Trp Arg Arg
1               5                   10

<210> SEQ ID NO 161
<211> LENGTH: 13
<212> TYPE: PRT
```

```
<213> ORGANISM: Artificial Sequence
<220> FEATURE:
<223> OTHER INFORMATION: Synthetic construct

<400> SEQUENCE: 161

Ile Leu Pro Pro Lys Trp Pro Trp Trp Pro Trp Arg Arg
1               5                   10

<210> SEQ ID NO 162
<211> LENGTH: 13
<212> TYPE: PRT
<213> ORGANISM: Artificial Sequence
<220> FEATURE:
<223> OTHER INFORMATION: Synthetic construct

<400> SEQUENCE: 162

Ile Leu Pro Trp Pro Trp Pro Trp Trp Pro Trp Arg Arg
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Synthetic construct

<400> SEQUENCE: 163

Ile Leu Pro Trp Lys Pro Pro Trp Trp Pro Trp Arg Arg
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Synthetic construct

<400> SEQUENCE: 164

Ile Leu Pro Trp Lys Trp Pro Pro Trp Pro Trp Arg Arg
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Synthetic construct

<400> SEQUENCE: 165

Ile Leu Pro Trp Lys Trp Pro Trp Pro Pro Trp Arg Arg
1               5                   10

<210> SEQ ID NO 166
<211> LENGTH: 13
<212> TYPE: PRT
<213> ORGANISM: Artificial Sequence
<220> FEATURE:
<223> OTHER INFORMATION: Synthetic construct

<400> SEQUENCE: 166

Ile Leu Pro Trp Lys Trp Pro Trp Trp Pro Pro Arg Arg
1               5                   10

<210> SEQ ID NO 167
<211> LENGTH: 13
<212> TYPE: PRT
<213> ORGANISM: Artificial Sequence
```

```
<220> FEATURE:
<223> OTHER INFORMATION: Synthetic construct

<400> SEQUENCE: 167

Ile Leu Pro Trp Lys Trp Pro Trp Trp Pro Trp Pro Arg
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Synthetic construct

<400> SEQUENCE: 168

Ile Leu Pro Trp Lys Trp Pro Trp Trp Pro Trp Arg Pro
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Synthetic construct

<400> SEQUENCE: 169

Gln Leu Pro Trp Lys Trp Pro Trp Trp Pro Trp Arg Arg
1               5                   10

<210> SEQ ID NO 170
<211> LENGTH: 13
<212> TYPE: PRT
<213> ORGANISM: Artificial Sequence
<220> FEATURE:
<223> OTHER INFORMATION: Synthetic construct

<400> SEQUENCE: 170

Ile Gln Pro Trp Lys Trp Pro Trp Trp Pro Trp Arg Arg
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Synthetic construct

<400> SEQUENCE: 171

Ile Leu Gln Trp Lys Trp Pro Trp Trp Pro Trp Arg Arg
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Synthetic construct

<400> SEQUENCE: 172

Ile Leu Pro Gln Lys Trp Pro Trp Trp Pro Trp Arg Arg
1               5                   10

<210> SEQ ID NO 173
<211> LENGTH: 13
<212> TYPE: PRT
<213> ORGANISM: Artificial Sequence
<220> FEATURE:
```

<223> OTHER INFORMATION: Synthetic construct

<400> SEQUENCE: 173

Ile Leu Pro Trp Gln Trp Pro Trp Trp Pro Trp Arg Arg
1               5                   10

<210> SEQ ID NO 174
<211> LENGTH: 13
<212> TYPE: PRT
<213> ORGANISM: Artificial Sequence
<220> FEATURE:
<223> OTHER INFORMATION: Synthetic construct

<400> SEQUENCE: 174

Ile Leu Pro Trp Lys Gln Pro Trp Trp Pro Trp Arg Arg
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Synthetic construct

<400> SEQUENCE: 175

Ile Leu Pro Trp Lys Trp Gln Trp Trp Pro Trp Arg Arg
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Synthetic construct

<400> SEQUENCE: 176

Ile Leu Pro Trp Lys Trp Pro Gln Trp Pro Trp Arg Arg
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Synthetic construct

<400> SEQUENCE: 177

Ile Leu Pro Trp Lys Trp Pro Trp Gln Pro Trp Arg Arg
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Synthetic construct

<400> SEQUENCE: 178

Ile Leu Pro Trp Lys Trp Pro Trp Trp Gln Trp Arg Arg
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Synthetic construct

```
<400> SEQUENCE: 179

Ile Leu Pro Trp Lys Trp Pro Trp Trp Pro Gln Arg Arg
1               5                   10

<210> SEQ ID NO 180
<211> LENGTH: 13
<212> TYPE: PRT
<213> ORGANISM: Artificial Sequence
<220> FEATURE:
<223> OTHER INFORMATION: Synthetic construct

<400> SEQUENCE: 180

Ile Leu Pro Trp Lys Trp Pro Trp Trp Pro Trp Gln Arg
1               5                   10

<210> SEQ ID NO 181
<211> LENGTH: 13
<212> TYPE: PRT
<213> ORGANISM: Artificial Sequence
<220> FEATURE:
<223> OTHER INFORMATION: Synthetic construct

<400> SEQUENCE: 181

Ile Leu Pro Trp Lys Trp Pro Trp Trp Pro Trp Arg Gln
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Synthetic construct

<400> SEQUENCE: 182

Arg Leu Pro Trp Lys Trp Pro Trp Trp Pro Trp Arg Arg
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Synthetic construct

<400> SEQUENCE: 183

Ile Arg Pro Trp Lys Trp Pro Trp Trp Pro Trp Arg Arg
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Synthetic construct

<400> SEQUENCE: 184

Ile Leu Arg Trp Lys Trp Pro Trp Trp Pro Trp Arg Arg
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Synthetic construct
```

```
<400> SEQUENCE: 185

Ile Leu Pro Arg Lys Trp Pro Trp Trp Pro Trp Arg Arg
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Synthetic construct

<400> SEQUENCE: 186

Ile Leu Pro Trp Arg Trp Pro Trp Trp Pro Trp Arg Arg
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Synthetic construct

<400> SEQUENCE: 187

Ile Leu Pro Trp Lys Arg Pro Trp Trp Pro Trp Arg Arg
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Synthetic construct

<400> SEQUENCE: 188

Ile Leu Pro Trp Lys Trp Arg Trp Trp Pro Trp Arg Arg
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Synthetic construct

<400> SEQUENCE: 189

Ile Leu Pro Trp Lys Trp Pro Arg Trp Pro Trp Arg Arg
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Synthetic construct

<400> SEQUENCE: 190

Ile Leu Pro Trp Lys Trp Pro Trp Arg Pro Trp Arg Arg
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Synthetic construct

<400> SEQUENCE: 191
```

```
Ile Leu Pro Trp Lys Trp Pro Trp Trp Arg Trp Arg Arg
1               5                   10
```

<210> SEQ ID NO 192
<211> LENGTH: 13
<212> TYPE: PRT
<213> ORGANISM: Artificial Sequence
<220> FEATURE:
<223> OTHER INFORMATION: Synthetic construct

<400> SEQUENCE: 192

```
Ile Leu Pro Trp Lys Trp Pro Trp Trp Pro Arg Arg Arg
1               5                   10
```

<210> SEQ ID NO 193
<211> LENGTH: 13
<212> TYPE: PRT
<213> ORGANISM: Artificial Sequence
<220> FEATURE:
<223> OTHER INFORMATION: Synthetic construct

<400> SEQUENCE: 193

```
Ser Leu Pro Trp Lys Trp Pro Trp Trp Pro Trp Arg Arg
1               5                   10
```

<210> SEQ ID NO 194
<211> LENGTH: 13
<212> TYPE: PRT
<213> ORGANISM: Artificial Sequence
<220> FEATURE:
<223> OTHER INFORMATION: Synthetic construct

<400> SEQUENCE: 194

```
Ile Ser Pro Trp Lys Trp Pro Trp Trp Pro Trp Arg Arg
1               5                   10
```

<210> SEQ ID NO 195
<211> LENGTH: 13
<212> TYPE: PRT
<213> ORGANISM: Artificial Sequence
<220> FEATURE:
<223> OTHER INFORMATION: Synthetic construct

<400> SEQUENCE: 195

```
Ile Leu Ser Trp Lys Trp Pro Trp Trp Pro Trp Arg Arg
1               5                   10
```

<210> SEQ ID NO 196
<211> LENGTH: 13
<212> TYPE: PRT
<213> ORGANISM: Artificial Sequence
<220> FEATURE:
<223> OTHER INFORMATION: Synthetic construct

<400> SEQUENCE: 196

```
Ile Leu Pro Ser Lys Trp Pro Trp Trp Pro Trp Arg Arg
1               5                   10
```

<210> SEQ ID NO 197
<211> LENGTH: 13
<212> TYPE: PRT
<213> ORGANISM: Artificial Sequence
<220> FEATURE:
<223> OTHER INFORMATION: Synthetic construct

<400> SEQUENCE: 197

```
Ile Leu Pro Trp Ser Trp Pro Trp Trp Pro Trp Arg Arg
1               5                   10
```

<210> SEQ ID NO 198
<211> LENGTH: 13
<212> TYPE: PRT
<213> ORGANISM: Artificial Sequence
<220> FEATURE:
<223> OTHER INFORMATION: Synthetic construct

<400> SEQUENCE: 198

```
Ile Leu Pro Trp Lys Ser Pro Trp Trp Pro Trp Arg Arg
1               5                   10
```

<210> SEQ ID NO 199
<211> LENGTH: 13
<212> TYPE: PRT
<213> ORGANISM: Artificial Sequence
<220> FEATURE:
<223> OTHER INFORMATION: Synthetic construct

<400> SEQUENCE: 199

```
Ile Leu Pro Trp Lys Trp Ser Trp Trp Pro Trp Arg Arg
1               5                   10
```

<210> SEQ ID NO 200
<211> LENGTH: 13
<212> TYPE: PRT
<213> ORGANISM: Artificial Sequence
<220> FEATURE:
<223> OTHER INFORMATION: Synthetic construct

<400> SEQUENCE: 200

```
Ile Leu Pro Trp Lys Trp Pro Ser Trp Pro Trp Arg Arg
1               5                   10
```

<210> SEQ ID NO 201
<211> LENGTH: 13
<212> TYPE: PRT
<213> ORGANISM: Artificial Sequence
<220> FEATURE:
<223> OTHER INFORMATION: Synthetic construct

<400> SEQUENCE: 201

```
Ile Leu Pro Trp Lys Trp Pro Trp Ser Pro Trp Arg Arg
1               5                   10
```

<210> SEQ ID NO 202
<211> LENGTH: 13
<212> TYPE: PRT
<213> ORGANISM: Artificial Sequence
<220> FEATURE:
<223> OTHER INFORMATION: Synthetic construct

<400> SEQUENCE: 202

```
Ile Leu Pro Trp Lys Trp Pro Trp Trp Ser Trp Arg Arg
1               5                   10
```

<210> SEQ ID NO 203
<211> LENGTH: 13
<212> TYPE: PRT
<213> ORGANISM: Artificial Sequence
<220> FEATURE:
<223> OTHER INFORMATION: Synthetic construct

<400> SEQUENCE: 203

Ile Leu Pro Trp Lys Trp Pro Trp Trp Pro Ser Arg Arg

```
<210> SEQ ID NO 204
<211> LENGTH: 13
<212> TYPE: PRT
<213> ORGANISM: Artificial Sequence
<220> FEATURE:
<223> OTHER INFORMATION: Synthetic construct

<400> SEQUENCE: 204

Ile Leu Pro Trp Lys Trp Pro Trp Trp Pro Trp Ser Arg
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Synthetic construct

<400> SEQUENCE: 205

Ile Leu Pro Trp Lys Trp Pro Trp Trp Pro Trp Arg Ser
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Synthetic construct

<400> SEQUENCE: 206

Thr Leu Pro Trp Lys Trp Pro Trp Trp Pro Trp Arg Arg
1               5                   10

<210> SEQ ID NO 207
<211> LENGTH: 13
<212> TYPE: PRT
<213> ORGANISM: Artificial Sequence
<220> FEATURE:
<223> OTHER INFORMATION: Synthetic construct

<400> SEQUENCE: 207

Ile Thr Pro Trp Lys Trp Pro Trp Trp Pro Trp Arg Arg
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthetic construct

<400> SEQUENCE: 208

Ile Leu Thr Trp Lys Trp Pro Trp Trp Pro Trp Arg Arg
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Synthetic construct

<400> SEQUENCE: 209

Ile Leu Pro Thr Lys Trp Pro Trp Trp Pro Trp Arg Arg
1               5                   10
```

<210> SEQ ID NO 210
<211> LENGTH: 13
<212> TYPE: PRT
<213> ORGANISM: Artificial Sequence
<220> FEATURE:
<223> OTHER INFORMATION: Synthetic construct

<400> SEQUENCE: 210

Ile Leu Pro Trp Thr Trp Pro Trp Trp Pro Trp Arg Arg
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Synthetic construct

<400> SEQUENCE: 211

Ile Leu Pro Trp Lys Thr Pro Trp Trp Pro Trp Arg Arg
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Synthetic construct

<400> SEQUENCE: 212

Ile Leu Pro Trp Lys Trp Thr Trp Trp Pro Trp Arg Arg
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Synthetic construct

<400> SEQUENCE: 213

Ile Leu Pro Trp Lys Trp Pro Thr Trp Pro Trp Arg Arg
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Synthetic construct

<400> SEQUENCE: 214

Ile Leu Pro Trp Lys Trp Pro Trp Thr Pro Trp Arg Arg
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Synthetic construct

<400> SEQUENCE: 215

Ile Leu Pro Trp Lys Trp Pro Trp Trp Thr Trp Arg Arg
1               5                   10

```
<210> SEQ ID NO 216
<211> LENGTH: 13
<212> TYPE: PRT
<213> ORGANISM: Artificial Sequence
<220> FEATURE:
<223> OTHER INFORMATION: Synthetic construct

<400> SEQUENCE: 216

Ile Leu Pro Trp Lys Trp Pro Trp Trp Pro Thr Arg Arg
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Synthetic construct

<400> SEQUENCE: 217

Ile Leu Pro Trp Lys Trp Pro Trp Trp Pro Trp Thr Arg
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Synthetic construct

<400> SEQUENCE: 218

Ile Leu Pro Trp Lys Trp Pro Trp Trp Pro Trp Arg Thr
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Synthetic construct

<400> SEQUENCE: 219

Val Leu Pro Trp Lys Trp Pro Trp Trp Pro Trp Arg Arg
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Synthetic construct

<400> SEQUENCE: 220

Ile Val Pro Trp Lys Trp Pro Trp Trp Pro Trp Arg Arg
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Synthetic construct

<400> SEQUENCE: 221

Ile Leu Val Trp Lys Trp Pro Trp Trp Pro Trp Arg Arg
1               5                   10
```

```
<210> SEQ ID NO 222
<211> LENGTH: 13
<212> TYPE: PRT
<213> ORGANISM: Artificial Sequence
<220> FEATURE:
<223> OTHER INFORMATION: Synthetic construct

<400> SEQUENCE: 222

Ile Leu Pro Val Lys Trp Pro Trp Trp Pro Trp Arg Arg
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Synthetic construct

<400> SEQUENCE: 223

Ile Leu Pro Trp Val Trp Pro Trp Trp Pro Trp Arg Arg
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Synthetic construct

<400> SEQUENCE: 224

Ile Leu Pro Trp Lys Val Pro Trp Trp Pro Trp Arg Arg
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Synthetic construct

<400> SEQUENCE: 225

Ile Leu Pro Trp Lys Trp Val Trp Trp Pro Trp Arg Arg
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Synthetic construct

<400> SEQUENCE: 226

Ile Leu Pro Trp Lys Trp Pro Val Trp Pro Trp Arg Arg
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Synthetic construct

<400> SEQUENCE: 227

Ile Leu Pro Trp Lys Trp Pro Trp Val Pro Trp Arg Arg
1               5                   10

<210> SEQ ID NO 228
```

```
<211> LENGTH: 13
<212> TYPE: PRT
<213> ORGANISM: Artificial Sequence
<220> FEATURE:
<223> OTHER INFORMATION: Synthetic construct

<400> SEQUENCE: 228

Ile Leu Pro Trp Lys Trp Pro Trp Trp Val Trp Arg Arg
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Synthetic construct

<400> SEQUENCE: 229

Ile Leu Pro Trp Lys Trp Pro Trp Trp Pro Val Arg Arg
1               5                   10

<210> SEQ ID NO 230
<211> LENGTH: 13
<212> TYPE: PRT
<213> ORGANISM: Artificial Sequence
<220> FEATURE:
<223> OTHER INFORMATION: Synthetic construct

<400> SEQUENCE: 230

Ile Leu Pro Trp Lys Trp Pro Trp Trp Pro Trp Val Arg
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Synthetic construct

<400> SEQUENCE: 231

Ile Leu Pro Trp Lys Trp Pro Trp Trp Pro Trp Arg Val
1               5                   10

<210> SEQ ID NO 232
<211> LENGTH: 13
<212> TYPE: PRT
<213> ORGANISM: Artificial Sequence
<220> FEATURE:
<223> OTHER INFORMATION: Synthetic construct

<400> SEQUENCE: 232

Trp Leu Pro Trp Lys Trp Pro Trp Trp Pro Trp Arg Arg
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Synthetic construct

<400> SEQUENCE: 233

Ile Trp Pro Trp Lys Trp Pro Trp Trp Pro Trp Arg Arg
1               5                   10

<210> SEQ ID NO 234
<211> LENGTH: 13
```

```
<212> TYPE: PRT
<213> ORGANISM: Artificial Sequence
<220> FEATURE:
<223> OTHER INFORMATION: Synthetic construct

<400> SEQUENCE: 234

Ile Leu Trp Trp Lys Trp Pro Trp Trp Pro Trp Arg Arg
1               5                   10

<210> SEQ ID NO 235
<211> LENGTH: 13
<212> TYPE: PRT
<213> ORGANISM: Artificial Sequence
<220> FEATURE:
<223> OTHER INFORMATION: Synthetic construct

<400> SEQUENCE: 235

Ile Leu Pro Trp Trp Trp Pro Trp Trp Pro Trp Arg Arg
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Synthetic construct

<400> SEQUENCE: 236

Ile Leu Pro Trp Lys Trp Trp Trp Trp Pro Trp Arg Arg
1               5                   10

<210> SEQ ID NO 237
<211> LENGTH: 13
<212> TYPE: PRT
<213> ORGANISM: Artificial Sequence
<220> FEATURE:
<223> OTHER INFORMATION: Synthetic construct

<400> SEQUENCE: 237

Ile Leu Pro Trp Lys Trp Pro Trp Trp Trp Trp Arg Arg
1               5                   10

<210> SEQ ID NO 238
<211> LENGTH: 13
<212> TYPE: PRT
<213> ORGANISM: Artificial Sequence
<220> FEATURE:
<223> OTHER INFORMATION: Synthetic construct

<400> SEQUENCE: 238

Ile Leu Pro Trp Lys Trp Pro Trp Trp Pro Trp Trp Arg
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Synthetic construct

<400> SEQUENCE: 239

Ile Leu Pro Trp Lys Trp Pro Trp Trp Pro Trp Arg Trp
1               5                   10

<210> SEQ ID NO 240
<211> LENGTH: 13
<212> TYPE: PRT
```

```
<213> ORGANISM: Artificial Sequence
<220> FEATURE:
<223> OTHER INFORMATION: Synthetic construct

<400> SEQUENCE: 240

Tyr Leu Pro Trp Lys Trp Pro Trp Trp Pro Trp Arg Arg
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Synthetic construct

<400> SEQUENCE: 241

Ile Tyr Pro Trp Lys Trp Pro Trp Trp Pro Trp Arg Arg
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Synthetic construct

<400> SEQUENCE: 242

Ile Leu Tyr Trp Lys Trp Pro Trp Trp Pro Trp Arg Arg
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Synthetic construct

<400> SEQUENCE: 243

Ile Leu Pro Tyr Lys Trp Pro Trp Trp Pro Trp Arg Arg
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Synthetic construct

<400> SEQUENCE: 244

Ile Leu Pro Trp Tyr Trp Pro Trp Trp Pro Trp Arg Arg
1               5                   10

<210> SEQ ID NO 245
<211> LENGTH: 13
<212> TYPE: PRT
<213> ORGANISM: Artificial Sequence
<220> FEATURE:
<223> OTHER INFORMATION: Synthetic construct

<400> SEQUENCE: 245

Ile Leu Pro Trp Lys Tyr Pro Trp Trp Pro Trp Arg Arg
1               5                   10

<210> SEQ ID NO 246
<211> LENGTH: 13
<212> TYPE: PRT
<213> ORGANISM: Artificial Sequence
```

```
<220> FEATURE:
<223> OTHER INFORMATION: Synthetic construct

<400> SEQUENCE: 246

Ile Leu Pro Trp Lys Trp Tyr Trp Trp Pro Trp Arg Arg
1               5                   10

<210> SEQ ID NO 247
<211> LENGTH: 13
<212> TYPE: PRT
<213> ORGANISM: Artificial Sequence
<220> FEATURE:
<223> OTHER INFORMATION: Synthetic construct

<400> SEQUENCE: 247

Ile Leu Pro Trp Lys Trp Pro Tyr Trp Pro Trp Arg Arg
1               5                   10

<210> SEQ ID NO 248
<211> LENGTH: 13
<212> TYPE: PRT
<213> ORGANISM: Artificial Sequence
<220> FEATURE:
<223> OTHER INFORMATION: Synthetic construct

<400> SEQUENCE: 248

Ile Leu Pro Trp Lys Trp Pro Trp Tyr Pro Trp Arg Arg
1               5                   10

<210> SEQ ID NO 249
<211> LENGTH: 13
<212> TYPE: PRT
<213> ORGANISM: Artificial Sequence
<220> FEATURE:
<223> OTHER INFORMATION: Synthetic construct

<400> SEQUENCE: 249

Ile Leu Pro Trp Lys Trp Pro Trp Trp Tyr Trp Arg Arg
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Synthetic construct

<400> SEQUENCE: 250

Ile Leu Pro Trp Lys Trp Pro Trp Trp Pro Tyr Arg Arg
1               5                   10

<210> SEQ ID NO 251
<211> LENGTH: 13
<212> TYPE: PRT
<213> ORGANISM: Artificial Sequence
<220> FEATURE:
<223> OTHER INFORMATION: Synthetic construct

<400> SEQUENCE: 251

Ile Leu Pro Trp Lys Trp Pro Trp Trp Pro Trp Tyr Arg
1               5                   10

<210> SEQ ID NO 252
<211> LENGTH: 13
<212> TYPE: PRT
<213> ORGANISM: Artificial Sequence
<220> FEATURE:
```

```
<223> OTHER INFORMATION: Synthetic construct

<400> SEQUENCE: 252

Ile Leu Pro Trp Lys Trp Pro Trp Trp Pro Trp Arg Tyr
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Synthetic construct

<400> SEQUENCE: 253

Ala Arg Leu Arg Ile Arg Val Ala Val Ile Arg Ala
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Synthetic construct

<400> SEQUENCE: 254

Asp Arg Leu Arg Ile Arg Val Ala Val Ile Arg Ala
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Synthetic construct

<400> SEQUENCE: 255

Glu Arg Leu Arg Ile Arg Val Ala Val Ile Arg Ala
1               5                   10

<210> SEQ ID NO 256
<211> LENGTH: 12
<212> TYPE: PRT
<213> ORGANISM: Artificial Sequence
<220> FEATURE:
<223> OTHER INFORMATION: Synthetic construct

<400> SEQUENCE: 256

Phe Arg Leu Arg Ile Arg Val Ala Val Ile Arg Ala
1               5                   10

<210> SEQ ID NO 257
<211> LENGTH: 12
<212> TYPE: PRT
<213> ORGANISM: Artificial Sequence
<220> FEATURE:
<223> OTHER INFORMATION: Synthetic construct

<400> SEQUENCE: 257

Gly Arg Leu Arg Ile Arg Val Ala Val Ile Arg Ala
1               5                   10

<210> SEQ ID NO 258
<211> LENGTH: 12
<212> TYPE: PRT
<213> ORGANISM: Artificial Sequence
<220> FEATURE:
<223> OTHER INFORMATION: Synthetic construct
```

<400> SEQUENCE: 258

His Arg Leu Arg Ile Arg Val Ala Val Ile Arg Ala
1               5                   10

<210> SEQ ID NO 259
<211> LENGTH: 12
<212> TYPE: PRT
<213> ORGANISM: Artificial Sequence
<220> FEATURE:
<223> OTHER INFORMATION: Synthetic construct

<400> SEQUENCE: 259

Ile Arg Leu Arg Ile Arg Val Ala Val Ile Arg Ala
1               5                   10

<210> SEQ ID NO 260
<211> LENGTH: 12
<212> TYPE: PRT
<213> ORGANISM: Artificial Sequence
<220> FEATURE:
<223> OTHER INFORMATION: Synthetic construct

<400> SEQUENCE: 260

Lys Arg Leu Arg Ile Arg Val Ala Val Ile Arg Ala
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Synthetic construct

<400> SEQUENCE: 261

Leu Arg Leu Arg Ile Arg Val Ala Val Ile Arg Ala
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Synthetic construct

<400> SEQUENCE: 262

Met Arg Leu Arg Ile Arg Val Ala Val Ile Arg Ala
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Synthetic construct

<400> SEQUENCE: 263

Asn Arg Leu Arg Ile Arg Val Ala Val Ile Arg Ala
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Synthetic construct

```
<400> SEQUENCE: 264

Pro Arg Leu Arg Ile Arg Val Ala Val Ile Arg Ala
1               5                   10

<210> SEQ ID NO 265

<400> SEQUENCE: 265

000

<210> SEQ ID NO 266
<211> LENGTH: 12
<212> TYPE: PRT
<213> ORGANISM: Artificial Sequence
<220> FEATURE:
<223> OTHER INFORMATION: Synthetic construct

<400> SEQUENCE: 266

Arg Arg Leu Arg Ile Arg Val Ala Val Ile Arg Ala
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Synthetic construct

<400> SEQUENCE: 267

Ser Arg Leu Arg Ile Arg Val Ala Val Ile Arg Ala
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Synthetic construct

<400> SEQUENCE: 268

Thr Arg Leu Arg Ile Arg Val Ala Val Ile Arg Ala
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Synthetic construct

<400> SEQUENCE: 269

Trp Arg Leu Arg Ile Arg Val Ala Val Ile Arg Ala
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Synthetic construct

<400> SEQUENCE: 270

Tyr Arg Leu Arg Ile Arg Val Ala Val Ile Arg Ala
1               5                   10

<210> SEQ ID NO 271
```

```
<211> LENGTH: 12
<212> TYPE: PRT
<213> ORGANISM: Artificial Sequence
<220> FEATURE:
<223> OTHER INFORMATION: Synthetic construct

<400> SEQUENCE: 271

Val Ala Leu Arg Ile Arg Val Ala Val Ile Arg Ala
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Synthetic construct

<400> SEQUENCE: 272

Val Asp Leu Arg Ile Arg Val Ala Val Ile Arg Ala
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Synthetic construct

<400> SEQUENCE: 273

Val Glu Leu Arg Ile Arg Val Ala Val Ile Arg Ala
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Synthetic construct

<400> SEQUENCE: 274

Val Phe Leu Arg Ile Arg Val Ala Val Ile Arg Ala
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Synthetic construct

<400> SEQUENCE: 275

Val Gly Leu Arg Ile Arg Val Ala Val Ile Arg Ala
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Synthetic construct

<400> SEQUENCE: 276

Val His Leu Arg Ile Arg Val Ala Val Ile Arg Ala
1               5                   10

<210> SEQ ID NO 277
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 277

Val Ile Leu Arg Ile Arg Val Ala Val Ile Arg Ala
1               5                   10

<210> SEQ ID NO 278
<211> LENGTH: 12
<212> TYPE: PRT
<213> ORGANISM: Artificial Sequence
<220> FEATURE:
<223> OTHER INFORMATION: Synthetic construct

<400> SEQUENCE: 278

Val Lys Leu Arg Ile Arg Val Ala Val Ile Arg Ala
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Synthetic construct

<400> SEQUENCE: 279

Val Leu Leu Arg Ile Arg Val Ala Val Ile Arg Ala
1               5                   10

<210> SEQ ID NO 280
<211> LENGTH: 12
<212> TYPE: PRT
<213> ORGANISM: Artificial Sequence
<220> FEATURE:
<223> OTHER INFORMATION: Synthetic construct

<400> SEQUENCE: 280

Val Met Leu Arg Ile Arg Val Ala Val Ile Arg Ala
1               5                   10

<210> SEQ ID NO 281
<211> LENGTH: 12
<212> TYPE: PRT
<213> ORGANISM: Artificial Sequence
<220> FEATURE:
<223> OTHER INFORMATION: Synthetic construct

<400> SEQUENCE: 281

Val Asn Leu Arg Ile Arg Val Ala Val Ile Arg Ala
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Synthetic construct

<400> SEQUENCE: 282

Val Pro Leu Arg Ile Arg Val Ala Val Ile Arg Ala
1               5                   10

<210> SEQ ID NO 283

<400> SEQUENCE: 283
```

000

<210> SEQ ID NO 284
<211> LENGTH: 12
<212> TYPE: PRT
<213> ORGANISM: Artificial Sequence
<220> FEATURE:
<223> OTHER INFORMATION: Synthetic construct

<400> SEQUENCE: 284

Val Ser Leu Arg Ile Arg Val Ala Val Ile Arg Ala
1               5                   10

<210> SEQ ID NO 285
<211> LENGTH: 12
<212> TYPE: PRT
<213> ORGANISM: Artificial Sequence
<220> FEATURE:
<223> OTHER INFORMATION: Synthetic construct

<400> SEQUENCE: 285

Val Thr Leu Arg Ile Arg Val Ala Val Ile Arg Ala
1               5                   10

<210> SEQ ID NO 286
<211> LENGTH: 12
<212> TYPE: PRT
<213> ORGANISM: Artificial Sequence
<220> FEATURE:
<223> OTHER INFORMATION: Synthetic construct

<400> SEQUENCE: 286

Val Val Leu Arg Ile Arg Val Ala Val Ile Arg Ala
1               5                   10

<210> SEQ ID NO 287
<211> LENGTH: 12
<212> TYPE: PRT
<213> ORGANISM: Artificial Sequence
<220> FEATURE:
<223> OTHER INFORMATION: Synthetic construct

<400> SEQUENCE: 287

Val Trp Leu Arg Ile Arg Val Ala Val Ile Arg Ala
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Synthetic construct

<400> SEQUENCE: 288

Val Tyr Leu Arg Ile Arg Val Ala Val Ile Arg Ala
1               5                   10

<210> SEQ ID NO 289
<211> LENGTH: 12
<212> TYPE: PRT
<213> ORGANISM: Artificial Sequence
<220> FEATURE:
<223> OTHER INFORMATION: Synthetic construct

<400> SEQUENCE: 289

Val Arg Ala Arg Ile Arg Val Ala Val Ile Arg Ala

<210> SEQ ID NO 290
<211> LENGTH: 12
<212> TYPE: PRT
<213> ORGANISM: Artificial Sequence
<220> FEATURE:
<223> OTHER INFORMATION: Synthetic construct

<400> SEQUENCE: 290

Val Arg Asp Arg Ile Arg Val Ala Val Ile Arg Ala
1               5                   10

<210> SEQ ID NO 291
<211> LENGTH: 12
<212> TYPE: PRT
<213> ORGANISM: Artificial Sequence
<220> FEATURE:
<223> OTHER INFORMATION: Synthetic construct

<400> SEQUENCE: 291

Val Arg Glu Arg Ile Arg Val Ala Val Ile Arg Ala
1               5                   10

<210> SEQ ID NO 292

<400> SEQUENCE: 292

000

<210> SEQ ID NO 293
<211> LENGTH: 12
<212> TYPE: PRT
<213> ORGANISM: Artificial Sequence
<220> FEATURE:
<223> OTHER INFORMATION: Synthetic construct

<400> SEQUENCE: 293

Val Arg Gly Arg Ile Arg Val Ala Val Ile Arg Ala
1               5                   10

<210> SEQ ID NO 294
<211> LENGTH: 12
<212> TYPE: PRT
<213> ORGANISM: Artificial Sequence
<220> FEATURE:
<223> OTHER INFORMATION: Synthetic construct

<400> SEQUENCE: 294

Val Arg His Arg Ile Arg Val Ala Val Ile Arg Ala
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Synthetic construct

<400> SEQUENCE: 295

Val Arg Ile Arg Ile Arg Val Ala Val Ile Arg Ala
1               5                   10

<210> SEQ ID NO 296
<211> LENGTH: 12
<212> TYPE: PRT
<213> ORGANISM: Artificial Sequence

```
<220> FEATURE:
<223> OTHER INFORMATION: Synthetic construct

<400> SEQUENCE: 296

Val Arg Lys Arg Ile Arg Val Ala Val Ile Arg Ala
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Synthetic construct

<400> SEQUENCE: 297

Val Arg Met Arg Ile Arg Val Ala Val Ile Arg Ala
1               5                   10

<210> SEQ ID NO 298
<211> LENGTH: 12
<212> TYPE: PRT
<213> ORGANISM: Artificial Sequence
<220> FEATURE:
<223> OTHER INFORMATION: Synthetic construct

<400> SEQUENCE: 298

Val Arg Asn Arg Ile Arg Val Ala Val Ile Arg Ala
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Synthetic construct

<400> SEQUENCE: 299

Val Arg Pro Arg Ile Arg Val Ala Val Ile Arg Ala
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Synthetic construct

<400> SEQUENCE: 300

Val Arg Gln Arg Ile Arg Val Ala Val Ile Arg Ala
1               5                   10

<210> SEQ ID NO 301
<211> LENGTH: 12
<212> TYPE: PRT
<213> ORGANISM: Artificial Sequence
<220> FEATURE:
<223> OTHER INFORMATION: Synthetic construct

<400> SEQUENCE: 301

Val Arg Arg Arg Ile Arg Val Ala Val Ile Arg Ala
1               5                   10

<210> SEQ ID NO 302
<211> LENGTH: 12
<212> TYPE: PRT
<213> ORGANISM: Artificial Sequence
<220> FEATURE:
```

<223> OTHER INFORMATION: Synthetic construct

<400> SEQUENCE: 302

Val Arg Ser Arg Ile Arg Val Ala Val Ile Arg Ala
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Synthetic construct

<400> SEQUENCE: 303

Val Arg Thr Arg Ile Arg Val Ala Val Ile Arg Ala
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Synthetic construct

<400> SEQUENCE: 304

Val Arg Val Arg Ile Arg Val Ala Val Ile Arg Ala
1               5                   10

<210> SEQ ID NO 305

<400> SEQUENCE: 305

000

<210> SEQ ID NO 306
<211> LENGTH: 12
<212> TYPE: PRT
<213> ORGANISM: Artificial Sequence
<220> FEATURE:
<223> OTHER INFORMATION: Synthetic construct

<400> SEQUENCE: 306

Val Arg Tyr Arg Ile Arg Val Ala Val Ile Arg Ala
1               5                   10

<210> SEQ ID NO 307
<211> LENGTH: 12
<212> TYPE: PRT
<213> ORGANISM: Artificial Sequence
<220> FEATURE:
<223> OTHER INFORMATION: Synthetic construct

<400> SEQUENCE: 307

Val Arg Leu Ala Ile Arg Val Ala Val Ile Arg Ala
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Synthetic construct

<400> SEQUENCE: 308

Val Arg Leu Asp Ile Arg Val Ala Val Ile Arg Ala
1               5                   10

<210> SEQ ID NO 309
<211> LENGTH: 12
<212> TYPE: PRT
<213> ORGANISM: Artificial Sequence
<220> FEATURE:
<223> OTHER INFORMATION: Synthetic construct

<400> SEQUENCE: 309

Val Arg Leu Glu Ile Arg Val Ala Val Ile Arg Ala
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Synthetic construct

<400> SEQUENCE: 310

Val Arg Leu Phe Ile Arg Val Ala Val Ile Arg Ala
1               5                   10

<210> SEQ ID NO 311
<211> LENGTH: 12
<212> TYPE: PRT
<213> ORGANISM: Artificial Sequence
<220> FEATURE:
<223> OTHER INFORMATION: Synthetic construct

<400> SEQUENCE: 311

Val Arg Leu Gly Ile Arg Val Ala Val Ile Arg Ala
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Synthetic construct

<400> SEQUENCE: 312

Val Arg Leu His Ile Arg Val Ala Val Ile Arg Ala
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Synthetic construct

<400> SEQUENCE: 313

Val Arg Leu Ile Ile Arg Val Ala Val Ile Arg Ala
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Synthetic construct

<400> SEQUENCE: 314

Val Arg Leu Lys Ile Arg Val Ala Val Ile Arg Ala
1               5                   10

```
<210> SEQ ID NO 315
<211> LENGTH: 12
<212> TYPE: PRT
<213> ORGANISM: Artificial Sequence
<220> FEATURE:
<223> OTHER INFORMATION: Synthetic construct

<400> SEQUENCE: 315

Val Arg Leu Leu Ile Arg Val Ala Val Ile Arg Ala
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Synthetic construct

<400> SEQUENCE: 316

Val Arg Leu Met Ile Arg Val Ala Val Ile Arg Ala
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Synthetic construct

<400> SEQUENCE: 317

Val Arg Leu Asn Ile Arg Val Ala Val Ile Arg Ala
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Synthetic construct

<400> SEQUENCE: 318

Val Arg Leu Pro Ile Arg Val Ala Val Ile Arg Ala
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Synthetic construct

<400> SEQUENCE: 319

Val Arg Leu Gln Ile Arg Val Ala Val Ile Arg Ala
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Synthetic construct

<400> SEQUENCE: 320

Val Arg Leu Ser Ile Arg Val Ala Val Ile Arg Ala
1               5                   10

<210> SEQ ID NO 321
```

```
<211> LENGTH: 12
<212> TYPE: PRT
<213> ORGANISM: Artificial Sequence
<220> FEATURE:
<223> OTHER INFORMATION: Synthetic construct

<400> SEQUENCE: 321

Val Arg Leu Thr Ile Arg Val Ala Val Ile Arg Ala
1               5                   10

<210> SEQ ID NO 322
<211> LENGTH: 12
<212> TYPE: PRT
<213> ORGANISM: Artificial Sequence
<220> FEATURE:
<223> OTHER INFORMATION: Synthetic construct

<400> SEQUENCE: 322

Val Arg Leu Val Ile Arg Val Ala Val Ile Arg Ala
1               5                   10

<210> SEQ ID NO 323

<400> SEQUENCE: 323

000

<210> SEQ ID NO 324
<211> LENGTH: 12
<212> TYPE: PRT
<213> ORGANISM: Artificial Sequence
<220> FEATURE:
<223> OTHER INFORMATION: Synthetic construct

<400> SEQUENCE: 324

Val Arg Leu Tyr Ile Arg Val Ala Val Ile Arg Ala
1               5                   10

<210> SEQ ID NO 325
<211> LENGTH: 12
<212> TYPE: PRT
<213> ORGANISM: Artificial Sequence
<220> FEATURE:
<223> OTHER INFORMATION: Synthetic construct

<400> SEQUENCE: 325

Val Arg Leu Arg Ala Arg Val Ala Val Ile Arg Ala
1               5                   10

<210> SEQ ID NO 326
<211> LENGTH: 12
<212> TYPE: PRT
<213> ORGANISM: Artificial Sequence
<220> FEATURE:
<223> OTHER INFORMATION: Synthetic construct

<400> SEQUENCE: 326

Val Arg Leu Arg Asp Arg Val Ala Val Ile Arg Ala
1               5                   10

<210> SEQ ID NO 327
<211> LENGTH: 12
<212> TYPE: PRT
<213> ORGANISM: Artificial Sequence
<220> FEATURE:
<223> OTHER INFORMATION: Synthetic construct

<400> SEQUENCE: 327
```

```
Val Arg Leu Arg Glu Arg Val Ala Val Ile Arg Ala
1               5                   10

<210> SEQ ID NO 328
<211> LENGTH: 12
<212> TYPE: PRT
<213> ORGANISM: Artificial Sequence
<220> FEATURE:
<223> OTHER INFORMATION: Synthetic construct

<400> SEQUENCE: 328

Val Arg Leu Arg Phe Arg Val Ala Val Ile Arg Ala
1               5                   10

<210> SEQ ID NO 329
<211> LENGTH: 12
<212> TYPE: PRT
<213> ORGANISM: Artificial Sequence
<220> FEATURE:
<223> OTHER INFORMATION: Synthetic construct

<400> SEQUENCE: 329

Val Arg Leu Arg Gly Arg Val Ala Val Ile Arg Ala
1               5                   10

<210> SEQ ID NO 330
<211> LENGTH: 12
<212> TYPE: PRT
<213> ORGANISM: Artificial Sequence
<220> FEATURE:
<223> OTHER INFORMATION: Synthetic construct

<400> SEQUENCE: 330

Val Arg Leu Arg His Arg Val Ala Val Ile Arg Ala
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Synthetic construct

<400> SEQUENCE: 331

Val Arg Leu Arg Lys Arg Val Ala Val Ile Arg Ala
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Synthetic construct

<400> SEQUENCE: 332

Val Arg Leu Arg Leu Arg Val Ala Val Ile Arg Ala
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Synthetic construct

<400> SEQUENCE: 333
```

```
Val Arg Leu Arg Met Arg Val Ala Val Ile Arg Ala
1               5                   10
```

<210> SEQ ID NO 334
<211> LENGTH: 12
<212> TYPE: PRT
<213> ORGANISM: Artificial Sequence
<220> FEATURE:
<223> OTHER INFORMATION: Synthetic construct

<400> SEQUENCE: 334

```
Val Arg Leu Arg Asn Arg Val Ala Val Ile Arg Ala
1               5                   10
```

<210> SEQ ID NO 335
<211> LENGTH: 12
<212> TYPE: PRT
<213> ORGANISM: Artificial Sequence
<220> FEATURE:
<223> OTHER INFORMATION: Synthetic construct

<400> SEQUENCE: 335

```
Val Arg Leu Arg Pro Arg Val Ala Val Ile Arg Ala
1               5                   10
```

<210> SEQ ID NO 336
<211> LENGTH: 12
<212> TYPE: PRT
<213> ORGANISM: Artificial Sequence
<220> FEATURE:
<223> OTHER INFORMATION: Synthetic construct

<400> SEQUENCE: 336

```
Val Arg Leu Arg Gln Arg Val Ala Val Ile Arg Ala
1               5                   10
```

<210> SEQ ID NO 337
<211> LENGTH: 12
<212> TYPE: PRT
<213> ORGANISM: Artificial Sequence
<220> FEATURE:
<223> OTHER INFORMATION: Synthetic construct

<400> SEQUENCE: 337

```
Val Arg Leu Arg Arg Arg Val Ala Val Ile Arg Ala
1               5                   10
```

<210> SEQ ID NO 338
<211> LENGTH: 12
<212> TYPE: PRT
<213> ORGANISM: Artificial Sequence
<220> FEATURE:
<223> OTHER INFORMATION: Synthetic construct

<400> SEQUENCE: 338

```
Val Arg Leu Arg Ser Arg Val Ala Val Ile Arg Ala
1               5                   10
```

<210> SEQ ID NO 339
<211> LENGTH: 12
<212> TYPE: PRT
<213> ORGANISM: Artificial Sequence
<220> FEATURE:
<223> OTHER INFORMATION: Synthetic construct

<400> SEQUENCE: 339

```
Val Arg Leu Arg Thr Arg Val Ala Val Ile Arg Ala
```

```
1               5                   10

<210> SEQ ID NO 340
<211> LENGTH: 12
<212> TYPE: PRT
<213> ORGANISM: Artificial Sequence
<220> FEATURE:
<223> OTHER INFORMATION: Synthetic construct

<400> SEQUENCE: 340

Val Arg Leu Arg Val Arg Val Ala Val Ile Arg Ala
1               5                   10

<210> SEQ ID NO 341
<211> LENGTH: 12
<212> TYPE: PRT
<213> ORGANISM: Artificial Sequence
<220> FEATURE:
<223> OTHER INFORMATION: Synthetic construct

<400> SEQUENCE: 341

Val Arg Leu Arg Trp Arg Val Ala Val Ile Arg Ala
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Synthetic construct

<400> SEQUENCE: 342

Val Arg Leu Arg Tyr Arg Val Ala Val Ile Arg Ala
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Synthetic construct

<400> SEQUENCE: 343

Val Arg Leu Arg Ile Ala Val Ala Val Ile Arg Ala
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Synthetic construct

<400> SEQUENCE: 344

Val Arg Leu Arg Ile Asp Val Ala Val Ile Arg Ala
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Synthetic construct

<400> SEQUENCE: 345

Val Arg Leu Arg Ile Glu Val Ala Val Ile Arg Ala
1               5                   10
```

```
<210> SEQ ID NO 346
<211> LENGTH: 12
<212> TYPE: PRT
<213> ORGANISM: Artificial Sequence
<220> FEATURE:
<223> OTHER INFORMATION: Synthetic construct

<400> SEQUENCE: 346

Val Arg Leu Arg Ile Phe Val Ala Val Ile Arg Ala
1               5                   10

<210> SEQ ID NO 347
<211> LENGTH: 12
<212> TYPE: PRT
<213> ORGANISM: Artificial Sequence
<220> FEATURE:
<223> OTHER INFORMATION: Synthetic construct

<400> SEQUENCE: 347

Val Arg Leu Arg Ile Gly Val Ala Val Ile Arg Ala
1               5                   10

<210> SEQ ID NO 348
<211> LENGTH: 12
<212> TYPE: PRT
<213> ORGANISM: Artificial Sequence
<220> FEATURE:
<223> OTHER INFORMATION: Synthetic construct

<400> SEQUENCE: 348

Val Arg Leu Arg Ile His Val Ala Val Ile Arg Ala
1               5                   10

<210> SEQ ID NO 349
<211> LENGTH: 12
<212> TYPE: PRT
<213> ORGANISM: Artificial Sequence
<220> FEATURE:
<223> OTHER INFORMATION: Synthetic construct

<400> SEQUENCE: 349

Val Arg Leu Arg Ile Ile Val Ala Val Ile Arg Ala
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Synthetic construct

<400> SEQUENCE: 350

Val Arg Leu Arg Ile Lys Val Ala Val Ile Arg Ala
1               5                   10

<210> SEQ ID NO 351
<211> LENGTH: 12
<212> TYPE: PRT
<213> ORGANISM: Artificial Sequence
<220> FEATURE:
<223> OTHER INFORMATION: Synthetic construct

<400> SEQUENCE: 351

Val Arg Leu Arg Ile Leu Val Ala Val Ile Arg Ala
1               5                   10
```

<210> SEQ ID NO 352
<211> LENGTH: 12
<212> TYPE: PRT
<213> ORGANISM: Artificial Sequence
<220> FEATURE:
<223> OTHER INFORMATION: Synthetic construct

<400> SEQUENCE: 352

Val Arg Leu Arg Ile Met Val Ala Val Ile Arg Ala
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Synthetic construct

<400> SEQUENCE: 353

Val Arg Leu Arg Ile Asn Val Ala Val Ile Arg Ala
1               5                   10

<210> SEQ ID NO 354
<211> LENGTH: 12
<212> TYPE: PRT
<213> ORGANISM: Artificial Sequence
<220> FEATURE:
<223> OTHER INFORMATION: Synthetic construct

<400> SEQUENCE: 354

Val Arg Leu Arg Ile Pro Val Ala Val Ile Arg Ala
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Synthetic construct

<400> SEQUENCE: 355

Val Arg Leu Arg Ile Gln Val Ala Val Ile Arg Ala
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Synthetic construct

<400> SEQUENCE: 356

Val Arg Leu Arg Ile Ser Val Ala Val Ile Arg Ala
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Synthetic construct

<400> SEQUENCE: 357

Val Arg Leu Arg Ile Thr Val Ala Val Ile Arg Ala
1               5                   10

```
<210> SEQ ID NO 358
<211> LENGTH: 12
<212> TYPE: PRT
<213> ORGANISM: Artificial Sequence
<220> FEATURE:
<223> OTHER INFORMATION: Synthetic construct

<400> SEQUENCE: 358

Val Arg Leu Arg Ile Val Val Ala Val Ile Arg Ala
1               5                   10

<210> SEQ ID NO 359
<211> LENGTH: 12
<212> TYPE: PRT
<213> ORGANISM: Artificial Sequence
<220> FEATURE:
<223> OTHER INFORMATION: Synthetic construct

<400> SEQUENCE: 359

Val Arg Leu Arg Ile Trp Val Ala Val Ile Arg Ala
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Synthetic construct

<400> SEQUENCE: 360

Val Arg Leu Arg Ile Tyr Val Ala Val Ile Arg Ala
1               5                   10

<210> SEQ ID NO 361
<211> LENGTH: 12
<212> TYPE: PRT
<213> ORGANISM: Artificial Sequence
<220> FEATURE:
<223> OTHER INFORMATION: Synthetic construct

<400> SEQUENCE: 361

Val Arg Leu Arg Ile Arg Ala Ala Val Ile Arg Ala
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Synthetic construct

<400> SEQUENCE: 362

Val Arg Leu Arg Ile Arg Asp Ala Val Ile Arg Ala
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Synthetic construct

<400> SEQUENCE: 363

Val Arg Leu Arg Ile Arg Glu Ala Val Ile Arg Ala
1               5                   10

<210> SEQ ID NO 364
```

<211> LENGTH: 12
<212> TYPE: PRT
<213> ORGANISM: Artificial Sequence
<220> FEATURE:
<223> OTHER INFORMATION: Synthetic construct

<400> SEQUENCE: 364

Val Arg Leu Arg Ile Arg Phe Ala Val Ile Arg Ala
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Synthetic construct

<400> SEQUENCE: 365

Val Arg Leu Arg Ile Arg Gly Ala Val Ile Arg Ala
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Synthetic construct

<400> SEQUENCE: 366

Val Arg Leu Arg Ile Arg His Ala Val Ile Arg Ala
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Synthetic construct

<400> SEQUENCE: 367

Val Arg Leu Arg Ile Arg Ile Ala Val Ile Arg Ala
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Synthetic construct

<400> SEQUENCE: 368

Val Arg Leu Arg Ile Arg Lys Ala Val Ile Arg Ala
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Synthetic construct

<400> SEQUENCE: 369

Val Arg Leu Arg Ile Arg Leu Ala Val Ile Arg Ala
1               5                   10

<210> SEQ ID NO 370
<211> LENGTH: 12

```
<212> TYPE: PRT
<213> ORGANISM: Artificial Sequence
<220> FEATURE:
<223> OTHER INFORMATION: Synthetic construct

<400> SEQUENCE: 370

Val Arg Leu Arg Ile Arg Met Ala Val Ile Arg Ala
1               5                   10

<210> SEQ ID NO 371
<211> LENGTH: 12
<212> TYPE: PRT
<213> ORGANISM: Artificial Sequence
<220> FEATURE:
<223> OTHER INFORMATION: Synthetic construct

<400> SEQUENCE: 371

Val Arg Leu Arg Ile Arg Asn Ala Val Ile Arg Ala
1               5                   10

<210> SEQ ID NO 372
<211> LENGTH: 12
<212> TYPE: PRT
<213> ORGANISM: Artificial Sequence
<220> FEATURE:
<223> OTHER INFORMATION: Synthetic construct

<400> SEQUENCE: 372

Val Arg Leu Arg Ile Arg Pro Ala Val Ile Arg Ala
1               5                   10

<210> SEQ ID NO 373
<211> LENGTH: 12
<212> TYPE: PRT
<213> ORGANISM: Artificial Sequence
<220> FEATURE:
<223> OTHER INFORMATION: Synthetic construct

<400> SEQUENCE: 373

Val Arg Leu Arg Ile Arg Gln Ala Val Ile Arg Ala
1               5                   10

<210> SEQ ID NO 374
<211> LENGTH: 12
<212> TYPE: PRT
<213> ORGANISM: Artificial Sequence
<220> FEATURE:
<223> OTHER INFORMATION: Synthetic construct

<400> SEQUENCE: 374

Val Arg Leu Arg Ile Arg Arg Ala Val Ile Arg Ala
1               5                   10

<210> SEQ ID NO 375
<211> LENGTH: 12
<212> TYPE: PRT
<213> ORGANISM: Artificial Sequence
<220> FEATURE:
<223> OTHER INFORMATION: Synthetic construct

<400> SEQUENCE: 375

Val Arg Leu Arg Ile Arg Ser Ala Val Ile Arg Ala
1               5                   10

<210> SEQ ID NO 376
<211> LENGTH: 12
<212> TYPE: PRT
```

```
<213> ORGANISM: Artificial Sequence
<220> FEATURE:
<223> OTHER INFORMATION: Synthetic construct

<400> SEQUENCE: 376

Val Arg Leu Arg Ile Arg Thr Ala Val Ile Arg Ala
1               5                   10

<210> SEQ ID NO 377
<211> LENGTH: 12
<212> TYPE: PRT
<213> ORGANISM: Artificial Sequence
<220> FEATURE:
<223> OTHER INFORMATION: Synthetic construct

<400> SEQUENCE: 377

Val Arg Leu Arg Ile Arg Trp Ala Val Ile Arg Ala
1               5                   10

<210> SEQ ID NO 378
<211> LENGTH: 12
<212> TYPE: PRT
<213> ORGANISM: Artificial Sequence
<220> FEATURE:
<223> OTHER INFORMATION: Synthetic construct

<400> SEQUENCE: 378

Val Arg Leu Arg Ile Arg Tyr Ala Val Ile Arg Ala
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Synthetic construct

<400> SEQUENCE: 379

Val Arg Leu Arg Ile Arg Val Asp Val Ile Arg Ala
1               5                   10

<210> SEQ ID NO 380
<211> LENGTH: 12
<212> TYPE: PRT
<213> ORGANISM: Artificial Sequence
<220> FEATURE:
<223> OTHER INFORMATION: Synthetic construct

<400> SEQUENCE: 380

Val Arg Leu Arg Ile Arg Val Glu Val Ile Arg Ala
1               5                   10

<210> SEQ ID NO 381
<211> LENGTH: 12
<212> TYPE: PRT
<213> ORGANISM: Artificial Sequence
<220> FEATURE:
<223> OTHER INFORMATION: Synthetic construct

<400> SEQUENCE: 381

Val Arg Leu Arg Ile Arg Val Phe Val Ile Arg Ala
1               5                   10

<210> SEQ ID NO 382
<211> LENGTH: 12
<212> TYPE: PRT
<213> ORGANISM: Artificial Sequence
```

<220> FEATURE:
<223> OTHER INFORMATION: Synthetic construct

<400> SEQUENCE: 382

Val Arg Leu Arg Ile Arg Val Gly Val Ile Arg Ala
1               5                   10

<210> SEQ ID NO 383
<211> LENGTH: 12
<212> TYPE: PRT
<213> ORGANISM: Artificial Sequence
<220> FEATURE:
<223> OTHER INFORMATION: Synthetic construct

<400> SEQUENCE: 383

Val Arg Leu Arg Ile Arg Val His Val Ile Arg Ala
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Synthetic construct

<400> SEQUENCE: 384

Val Arg Leu Arg Ile Arg Val Ile Val Ile Arg Ala
1               5                   10

<210> SEQ ID NO 385
<211> LENGTH: 12
<212> TYPE: PRT
<213> ORGANISM: Artificial Sequence
<220> FEATURE:
<223> OTHER INFORMATION: Synthetic construct

<400> SEQUENCE: 385

Val Arg Leu Arg Ile Arg Val Lys Val Ile Arg Ala
1               5                   10

<210> SEQ ID NO 386
<211> LENGTH: 12
<212> TYPE: PRT
<213> ORGANISM: Artificial Sequence
<220> FEATURE:
<223> OTHER INFORMATION: Synthetic construct

<400> SEQUENCE: 386

Val Arg Leu Arg Ile Arg Val Leu Val Ile Arg Ala
1               5                   10

<210> SEQ ID NO 387
<211> LENGTH: 12
<212> TYPE: PRT
<213> ORGANISM: Artificial Sequence
<220> FEATURE:
<223> OTHER INFORMATION: Synthetic construct

<400> SEQUENCE: 387

Val Arg Leu Arg Ile Arg Val Met Val Ile Arg Ala
1               5                   10

<210> SEQ ID NO 388
<211> LENGTH: 12
<212> TYPE: PRT
<213> ORGANISM: Artificial Sequence
<220> FEATURE:

-continued

<223> OTHER INFORMATION: Synthetic construct

<400> SEQUENCE: 388

Val Arg Leu Arg Ile Arg Val Asn Val Ile Arg Ala
1               5                   10

<210> SEQ ID NO 389
<211> LENGTH: 12
<212> TYPE: PRT
<213> ORGANISM: Artificial Sequence
<220> FEATURE:
<223> OTHER INFORMATION: Synthetic construct

<400> SEQUENCE: 389

Val Arg Leu Arg Ile Arg Val Pro Val Ile Arg Ala
1               5                   10

<210> SEQ ID NO 390
<211> LENGTH: 12
<212> TYPE: PRT
<213> ORGANISM: Artificial Sequence
<220> FEATURE:
<223> OTHER INFORMATION: Synthetic construct

<400> SEQUENCE: 390

Val Arg Leu Arg Ile Arg Val Gln Val Ile Arg Ala
1               5                   10

<210> SEQ ID NO 391
<211> LENGTH: 12
<212> TYPE: PRT
<213> ORGANISM: Artificial Sequence
<220> FEATURE:
<223> OTHER INFORMATION: Synthetic construct

<400> SEQUENCE: 391

Val Arg Leu Arg Ile Arg Val Arg Val Ile Arg Ala
1               5                   10

<210> SEQ ID NO 392
<211> LENGTH: 12
<212> TYPE: PRT
<213> ORGANISM: Artificial Sequence
<220> FEATURE:
<223> OTHER INFORMATION: Synthetic construct

<400> SEQUENCE: 392

Val Arg Leu Arg Ile Arg Val Ser Val Ile Arg Ala
1               5                   10

<210> SEQ ID NO 393
<211> LENGTH: 12
<212> TYPE: PRT
<213> ORGANISM: Artificial Sequence
<220> FEATURE:
<223> OTHER INFORMATION: Synthetic construct

<400> SEQUENCE: 393

Val Arg Leu Arg Ile Arg Val Thr Val Ile Arg Ala
1               5                   10

<210> SEQ ID NO 394
<211> LENGTH: 12
<212> TYPE: PRT
<213> ORGANISM: Artificial Sequence
<220> FEATURE:
<223> OTHER INFORMATION: Synthetic construct

<400> SEQUENCE: 394

Val Arg Leu Arg Ile Arg Val Val Val Ile Arg Ala
1               5                   10

<210> SEQ ID NO 395

<400> SEQUENCE: 395

000

<210> SEQ ID NO 396
<211> LENGTH: 12
<212> TYPE: PRT
<213> ORGANISM: Artificial Sequence
<220> FEATURE:
<223> OTHER INFORMATION: Synthetic construct

<400> SEQUENCE: 396

Val Arg Leu Arg Ile Arg Val Tyr Val Ile Arg Ala
1               5                   10

<210> SEQ ID NO 397
<211> LENGTH: 12
<212> TYPE: PRT
<213> ORGANISM: Artificial Sequence
<220> FEATURE:
<223> OTHER INFORMATION: Synthetic construct

<400> SEQUENCE: 397

Val Arg Leu Arg Ile Arg Val Ala Ala Ile Arg Ala
1               5                   10

<210> SEQ ID NO 398
<211> LENGTH: 12
<212> TYPE: PRT
<213> ORGANISM: Artificial Sequence
<220> FEATURE:
<223> OTHER INFORMATION: Synthetic construct

<400> SEQUENCE: 398

Val Arg Leu Arg Ile Arg Val Ala Asp Ile Arg Ala
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Synthetic construct

<400> SEQUENCE: 399

Val Arg Leu Arg Ile Arg Val Ala Glu Ile Arg Ala
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Synthetic construct

<400> SEQUENCE: 400

Val Arg Leu Arg Ile Arg Val Ala Phe Ile Arg Ala
1               5                   10

```
<210> SEQ ID NO 401
<211> LENGTH: 12
<212> TYPE: PRT
<213> ORGANISM: Artificial Sequence
<220> FEATURE:
<223> OTHER INFORMATION: Synthetic construct

<400> SEQUENCE: 401

Val Arg Leu Arg Ile Arg Val Ala Gly Ile Arg Ala
1               5                   10

<210> SEQ ID NO 402
<211> LENGTH: 12
<212> TYPE: PRT
<213> ORGANISM: Artificial Sequence
<220> FEATURE:
<223> OTHER INFORMATION: Synthetic construct

<400> SEQUENCE: 402

Val Arg Leu Arg Ile Arg Val Ala His Ile Arg Ala
1               5                   10

<210> SEQ ID NO 403
<211> LENGTH: 12
<212> TYPE: PRT
<213> ORGANISM: Artificial Sequence
<220> FEATURE:
<223> OTHER INFORMATION: Synthetic construct

<400> SEQUENCE: 403

Val Arg Leu Arg Ile Arg Val Ala Ile Ile Arg Ala
1               5                   10

<210> SEQ ID NO 404
<211> LENGTH: 12
<212> TYPE: PRT
<213> ORGANISM: Artificial Sequence
<220> FEATURE:
<223> OTHER INFORMATION: Synthetic construct

<400> SEQUENCE: 404

Val Arg Leu Arg Ile Arg Val Ala Lys Ile Arg Ala
1               5                   10

<210> SEQ ID NO 405
<211> LENGTH: 12
<212> TYPE: PRT
<213> ORGANISM: Artificial Sequence
<220> FEATURE:
<223> OTHER INFORMATION: Synthetic construct

<400> SEQUENCE: 405

Val Arg Leu Arg Ile Arg Val Ala Lys Ile Arg Ala
1               5                   10

<210> SEQ ID NO 406
<211> LENGTH: 12
<212> TYPE: PRT
<213> ORGANISM: Artificial Sequence
<220> FEATURE:
<223> OTHER INFORMATION: Synthetic construct

<400> SEQUENCE: 406

Val Arg Leu Arg Ile Arg Val Ala Lys Ile Arg Ala
1               5                   10

<210> SEQ ID NO 407
```

```
<211> LENGTH: 12
<212> TYPE: PRT
<213> ORGANISM: Artificial Sequence
<220> FEATURE:
<223> OTHER INFORMATION: Synthetic construct

<400> SEQUENCE: 407

Val Arg Leu Arg Ile Arg Val Ala Asn Ile Arg Ala
1               5                   10

<210> SEQ ID NO 408
<211> LENGTH: 12
<212> TYPE: PRT
<213> ORGANISM: Artificial Sequence
<220> FEATURE:
<223> OTHER INFORMATION: Synthetic construct

<400> SEQUENCE: 408

Val Arg Leu Arg Ile Arg Val Ala Pro Ile Arg Ala
1               5                   10

<210> SEQ ID NO 409
<211> LENGTH: 12
<212> TYPE: PRT
<213> ORGANISM: Artificial Sequence
<220> FEATURE:
<223> OTHER INFORMATION: Synthetic construct

<400> SEQUENCE: 409

Val Arg Leu Arg Ile Arg Val Ala Gln Ile Arg Ala
1               5                   10

<210> SEQ ID NO 410
<211> LENGTH: 12
<212> TYPE: PRT
<213> ORGANISM: Artificial Sequence
<220> FEATURE:
<223> OTHER INFORMATION: Synthetic construct

<400> SEQUENCE: 410

Val Arg Leu Arg Ile Arg Val Ala Arg Ile Arg Ala
1               5                   10

<210> SEQ ID NO 411
<211> LENGTH: 12
<212> TYPE: PRT
<213> ORGANISM: Artificial Sequence
<220> FEATURE:
<223> OTHER INFORMATION: Synthetic construct

<400> SEQUENCE: 411

Val Arg Leu Arg Ile Arg Val Ala Ser Ile Arg Ala
1               5                   10

<210> SEQ ID NO 412
<211> LENGTH: 12
<212> TYPE: PRT
<213> ORGANISM: Artificial Sequence
<220> FEATURE:
<223> OTHER INFORMATION: Synthetic construct

<400> SEQUENCE: 412

Val Arg Leu Arg Ile Arg Val Ala Thr Ile Arg Ala
1               5                   10

<210> SEQ ID NO 413
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 413

Val Arg Leu Arg Ile Arg Val Ala Trp Ile Arg Ala
1               5                   10

<210> SEQ ID NO 414
<211> LENGTH: 12
<212> TYPE: PRT
<213> ORGANISM: Artificial Sequence
<220> FEATURE:
<223> OTHER INFORMATION: Synthetic construct

<400> SEQUENCE: 414

Val Arg Leu Arg Ile Arg Val Ala Tyr Ile Arg Ala
1               5                   10

<210> SEQ ID NO 415
<211> LENGTH: 12
<212> TYPE: PRT
<213> ORGANISM: Artificial Sequence
<220> FEATURE:
<223> OTHER INFORMATION: Synthetic construct

<400> SEQUENCE: 415

Val Arg Leu Arg Ile Arg Val Ala Val Ala Arg Ala
1               5                   10

<210> SEQ ID NO 416
<211> LENGTH: 12
<212> TYPE: PRT
<213> ORGANISM: Artificial Sequence
<220> FEATURE:
<223> OTHER INFORMATION: Synthetic construct

<400> SEQUENCE: 416

Val Arg Leu Arg Ile Arg Val Ala Val Asp Arg Ala
1               5                   10

<210> SEQ ID NO 417
<211> LENGTH: 12
<212> TYPE: PRT
<213> ORGANISM: Artificial Sequence
<220> FEATURE:
<223> OTHER INFORMATION: Synthetic construct

<400> SEQUENCE: 417

Val Arg Leu Arg Ile Arg Val Ala Val Glu Arg Ala
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Synthetic construct

<400> SEQUENCE: 418

Val Arg Leu Arg Ile Arg Val Ala Val Phe Arg Ala
1               5                   10

<210> SEQ ID NO 419
<211> LENGTH: 12
<212> TYPE: PRT
```

<213> ORGANISM: Artificial Sequence
<220> FEATURE:
<223> OTHER INFORMATION: Synthetic construct

<400> SEQUENCE: 419

Val Arg Leu Arg Ile Arg Val Ala Val Gly Arg Ala
1               5                   10

<210> SEQ ID NO 420
<211> LENGTH: 12
<212> TYPE: PRT
<213> ORGANISM: Artificial Sequence
<220> FEATURE:
<223> OTHER INFORMATION: Synthetic construct

<400> SEQUENCE: 420

Val Arg Leu Arg Ile Arg Val Ala Val His Arg Ala
1               5                   10

<210> SEQ ID NO 421
<211> LENGTH: 12
<212> TYPE: PRT
<213> ORGANISM: Artificial Sequence
<220> FEATURE:
<223> OTHER INFORMATION: Synthetic construct

<400> SEQUENCE: 421

Val Arg Leu Arg Ile Arg Val Ala Val Lys Arg Ala
1               5                   10

<210> SEQ ID NO 422
<211> LENGTH: 12
<212> TYPE: PRT
<213> ORGANISM: Artificial Sequence
<220> FEATURE:
<223> OTHER INFORMATION: Synthetic construct

<400> SEQUENCE: 422

Val Arg Leu Arg Ile Arg Val Ala Val Leu Arg Ala
1               5                   10

<210> SEQ ID NO 423
<211> LENGTH: 12
<212> TYPE: PRT
<213> ORGANISM: Artificial Sequence
<220> FEATURE:
<223> OTHER INFORMATION: Synthetic construct

<400> SEQUENCE: 423

Val Arg Leu Arg Ile Arg Val Ala Val Met Arg Ala
1               5                   10

<210> SEQ ID NO 424
<211> LENGTH: 12
<212> TYPE: PRT
<213> ORGANISM: Artificial Sequence
<220> FEATURE:
<223> OTHER INFORMATION: Synthetic construct

<400> SEQUENCE: 424

Val Arg Leu Arg Ile Arg Val Ala Val Asn Arg Ala
1               5                   10

<210> SEQ ID NO 425
<211> LENGTH: 12
<212> TYPE: PRT
<213> ORGANISM: Artificial Sequence

```
<220> FEATURE:
<223> OTHER INFORMATION: Synthetic construct

<400> SEQUENCE: 425

Val Arg Leu Arg Ile Arg Val Ala Val Pro Arg Ala
1               5                   10

<210> SEQ ID NO 426
<211> LENGTH: 12
<212> TYPE: PRT
<213> ORGANISM: Artificial Sequence
<220> FEATURE:
<223> OTHER INFORMATION: Synthetic construct

<400> SEQUENCE: 426

Val Arg Leu Arg Ile Arg Val Ala Val Gln Arg Ala
1               5                   10

<210> SEQ ID NO 427

<400> SEQUENCE: 427

000

<210> SEQ ID NO 428
<211> LENGTH: 12
<212> TYPE: PRT
<213> ORGANISM: Artificial Sequence
<220> FEATURE:
<223> OTHER INFORMATION: Synthetic construct

<400> SEQUENCE: 428

Val Arg Leu Arg Ile Arg Val Ala Val Ser Arg Ala
1               5                   10

<210> SEQ ID NO 429
<211> LENGTH: 12
<212> TYPE: PRT
<213> ORGANISM: Artificial Sequence
<220> FEATURE:
<223> OTHER INFORMATION: Synthetic construct

<400> SEQUENCE: 429

Val Arg Leu Arg Ile Arg Val Ala Val Thr Arg Ala
1               5                   10

<210> SEQ ID NO 430
<211> LENGTH: 12
<212> TYPE: PRT
<213> ORGANISM: Artificial Sequence
<220> FEATURE:
<223> OTHER INFORMATION: Synthetic construct

<400> SEQUENCE: 430

Val Arg Leu Arg Ile Arg Val Ala Val Val Arg Ala
1               5                   10

<210> SEQ ID NO 431
<211> LENGTH: 12
<212> TYPE: PRT
<213> ORGANISM: Artificial Sequence
<220> FEATURE:
<223> OTHER INFORMATION: Synthetic construct

<400> SEQUENCE: 431

Val Arg Leu Arg Ile Arg Val Ala Val Trp Arg Ala
1               5                   10
```

-continued

```
<210> SEQ ID NO 432
<211> LENGTH: 12
<212> TYPE: PRT
<213> ORGANISM: Artificial Sequence
<220> FEATURE:
<223> OTHER INFORMATION: Synthetic construct

<400> SEQUENCE: 432

Val Arg Leu Arg Ile Arg Val Ala Val Tyr Arg Ala
1               5                   10

<210> SEQ ID NO 433
<211> LENGTH: 12
<212> TYPE: PRT
<213> ORGANISM: Artificial Sequence
<220> FEATURE:
<223> OTHER INFORMATION: Synthetic construct

<400> SEQUENCE: 433

Val Arg Leu Arg Ile Arg Val Ala Val Ile Ala Ala
1               5                   10

<210> SEQ ID NO 434
<211> LENGTH: 12
<212> TYPE: PRT
<213> ORGANISM: Artificial Sequence
<220> FEATURE:
<223> OTHER INFORMATION: Synthetic construct

<400> SEQUENCE: 434

Val Arg Leu Arg Ile Arg Val Ala Val Ile Asp Ala
1               5                   10

<210> SEQ ID NO 435
<211> LENGTH: 12
<212> TYPE: PRT
<213> ORGANISM: Artificial Sequence
<220> FEATURE:
<223> OTHER INFORMATION: Synthetic construct

<400> SEQUENCE: 435

Val Arg Leu Arg Ile Arg Val Ala Val Ile Glu Ala
1               5                   10

<210> SEQ ID NO 436
<211> LENGTH: 12
<212> TYPE: PRT
<213> ORGANISM: Artificial Sequence
<220> FEATURE:
<223> OTHER INFORMATION: Synthetic construct

<400> SEQUENCE: 436

Val Arg Leu Arg Ile Arg Val Ala Val Ile Phe Ala
1               5                   10

<210> SEQ ID NO 437
<211> LENGTH: 12
<212> TYPE: PRT
<213> ORGANISM: Artificial Sequence
<220> FEATURE:
<223> OTHER INFORMATION: Synthetic construct

<400> SEQUENCE: 437

Val Arg Leu Arg Ile Arg Val Ala Val Ile Gly Ala
1               5                   10
```

```
<210> SEQ ID NO 438
<211> LENGTH: 12
<212> TYPE: PRT
<213> ORGANISM: Artificial Sequence
<220> FEATURE:
<223> OTHER INFORMATION: Synthetic construct

<400> SEQUENCE: 438

Val Arg Leu Arg Ile Arg Val Ala Val Ile His Ala
1               5                   10

<210> SEQ ID NO 439
<211> LENGTH: 12
<212> TYPE: PRT
<213> ORGANISM: Artificial Sequence
<220> FEATURE:
<223> OTHER INFORMATION: Synthetic construct

<400> SEQUENCE: 439

Val Arg Leu Arg Ile Arg Val Ala Val Ile Ile Ala
1               5                   10

<210> SEQ ID NO 440
<211> LENGTH: 12
<212> TYPE: PRT
<213> ORGANISM: Artificial Sequence
<220> FEATURE:
<223> OTHER INFORMATION: Synthetic construct

<400> SEQUENCE: 440

Val Arg Leu Arg Ile Arg Val Ala Val Ile Lys Ala
1               5                   10

<210> SEQ ID NO 441
<211> LENGTH: 12
<212> TYPE: PRT
<213> ORGANISM: Artificial Sequence
<220> FEATURE:
<223> OTHER INFORMATION: Synthetic construct

<400> SEQUENCE: 441

Val Arg Leu Arg Ile Arg Val Ala Val Ile Leu Ala
1               5                   10

<210> SEQ ID NO 442
<211> LENGTH: 12
<212> TYPE: PRT
<213> ORGANISM: Artificial Sequence
<220> FEATURE:
<223> OTHER INFORMATION: Synthetic construct

<400> SEQUENCE: 442

Val Arg Leu Arg Ile Arg Val Ala Val Ile Met Ala
1               5                   10

<210> SEQ ID NO 443
<211> LENGTH: 12
<212> TYPE: PRT
<213> ORGANISM: Artificial Sequence
<220> FEATURE:
<223> OTHER INFORMATION: Synthetic construct

<400> SEQUENCE: 443

Val Arg Leu Arg Ile Arg Val Ala Val Ile Asn Ala
1               5                   10
```

```
<210> SEQ ID NO 444
<211> LENGTH: 12
<212> TYPE: PRT
<213> ORGANISM: Artificial Sequence
<220> FEATURE:
<223> OTHER INFORMATION: Synthetic construct

<400> SEQUENCE: 444

Val Arg Leu Arg Ile Arg Val Ala Val Ile Pro Ala
1               5                   10

<210> SEQ ID NO 445
<211> LENGTH: 12
<212> TYPE: PRT
<213> ORGANISM: Artificial Sequence
<220> FEATURE:
<223> OTHER INFORMATION: Synthetic construct

<400> SEQUENCE: 445

Val Arg Leu Arg Ile Arg Val Ala Val Ile Gln Ala
1               5                   10

<210> SEQ ID NO 446
<211> LENGTH: 12
<212> TYPE: PRT
<213> ORGANISM: Artificial Sequence
<220> FEATURE:
<223> OTHER INFORMATION: Synthetic construct

<400> SEQUENCE: 446

Val Arg Leu Arg Ile Arg Val Ala Val Ile Ser Ala
1               5                   10

<210> SEQ ID NO 447
<211> LENGTH: 12
<212> TYPE: PRT
<213> ORGANISM: Artificial Sequence
<220> FEATURE:
<223> OTHER INFORMATION: Synthetic construct

<400> SEQUENCE: 447

Val Arg Leu Arg Ile Arg Val Ala Val Ile Thr Ala
1               5                   10

<210> SEQ ID NO 448
<211> LENGTH: 12
<212> TYPE: PRT
<213> ORGANISM: Artificial Sequence
<220> FEATURE:
<223> OTHER INFORMATION: Synthetic construct

<400> SEQUENCE: 448

Val Arg Leu Arg Ile Arg Val Ala Val Ile Val Ala
1               5                   10

<210> SEQ ID NO 449
<211> LENGTH: 12
<212> TYPE: PRT
<213> ORGANISM: Artificial Sequence
<220> FEATURE:
<223> OTHER INFORMATION: Synthetic construct

<400> SEQUENCE: 449

Val Arg Leu Arg Ile Arg Val Ala Val Ile Trp Ala
1               5                   10

<210> SEQ ID NO 450
```

```
<211> LENGTH: 12
<212> TYPE: PRT
<213> ORGANISM: Artificial Sequence
<220> FEATURE:
<223> OTHER INFORMATION: Synthetic construct

<400> SEQUENCE: 450

Val Arg Leu Arg Ile Arg Val Ala Val Ile Tyr Ala
1               5                   10

<210> SEQ ID NO 451
<211> LENGTH: 12
<212> TYPE: PRT
<213> ORGANISM: Artificial Sequence
<220> FEATURE:
<223> OTHER INFORMATION: Synthetic construct

<400> SEQUENCE: 451

Val Arg Leu Arg Ile Arg Val Ala Val Ile Arg Asp
1               5                   10

<210> SEQ ID NO 452
<211> LENGTH: 12
<212> TYPE: PRT
<213> ORGANISM: Artificial Sequence
<220> FEATURE:
<223> OTHER INFORMATION: Synthetic construct

<400> SEQUENCE: 452

Val Arg Leu Arg Ile Arg Val Ala Val Ile Arg Glu
1               5                   10

<210> SEQ ID NO 453
<211> LENGTH: 12
<212> TYPE: PRT
<213> ORGANISM: Artificial Sequence
<220> FEATURE:
<223> OTHER INFORMATION: Synthetic construct

<400> SEQUENCE: 453

Val Arg Leu Arg Ile Arg Val Ala Val Ile Arg Phe
1               5                   10

<210> SEQ ID NO 454
<211> LENGTH: 12
<212> TYPE: PRT
<213> ORGANISM: Artificial Sequence
<220> FEATURE:
<223> OTHER INFORMATION: Synthetic construct

<400> SEQUENCE: 454

Val Arg Leu Arg Ile Arg Val Ala Val Ile Arg Gly
1               5                   10

<210> SEQ ID NO 455
<211> LENGTH: 12
<212> TYPE: PRT
<213> ORGANISM: Artificial Sequence
<220> FEATURE:
<223> OTHER INFORMATION: Synthetic construct

<400> SEQUENCE: 455

Val Arg Leu Arg Ile Arg Val Ala Val Ile Arg His
1               5                   10

<210> SEQ ID NO 456
<211> LENGTH: 12
```

```
<212> TYPE: PRT
<213> ORGANISM: Artificial Sequence
<220> FEATURE:
<223> OTHER INFORMATION: Synthetic construct

<400> SEQUENCE: 456

Val Arg Leu Arg Ile Arg Val Ala Val Ile Arg Ile
1               5                   10

<210> SEQ ID NO 457

<400> SEQUENCE: 457

000

<210> SEQ ID NO 458
<211> LENGTH: 12
<212> TYPE: PRT
<213> ORGANISM: Artificial Sequence
<220> FEATURE:
<223> OTHER INFORMATION: Synthetic construct

<400> SEQUENCE: 458

Val Arg Leu Arg Ile Arg Val Ala Val Ile Arg Leu
1               5                   10

<210> SEQ ID NO 459
<211> LENGTH: 12
<212> TYPE: PRT
<213> ORGANISM: Artificial Sequence
<220> FEATURE:
<223> OTHER INFORMATION: Synthetic construct

<400> SEQUENCE: 459

Val Arg Leu Arg Ile Arg Val Ala Val Ile Arg Met
1               5                   10

<210> SEQ ID NO 460
<211> LENGTH: 12
<212> TYPE: PRT
<213> ORGANISM: Artificial Sequence
<220> FEATURE:
<223> OTHER INFORMATION: Synthetic construct

<400> SEQUENCE: 460

Val Arg Leu Arg Ile Arg Val Ala Val Ile Arg Asn
1               5                   10

<210> SEQ ID NO 461
<211> LENGTH: 12
<212> TYPE: PRT
<213> ORGANISM: Artificial Sequence
<220> FEATURE:
<223> OTHER INFORMATION: Synthetic construct

<400> SEQUENCE: 461

Val Arg Leu Arg Ile Arg Val Ala Val Ile Arg Pro
1               5                   10

<210> SEQ ID NO 462
<211> LENGTH: 12
<212> TYPE: PRT
<213> ORGANISM: Artificial Sequence
<220> FEATURE:
<223> OTHER INFORMATION: Synthetic construct

<400> SEQUENCE: 462
```

Val Arg Leu Arg Ile Arg Val Ala Val Ile Arg Gln
1               5                   10

<210> SEQ ID NO 463
<211> LENGTH: 12
<212> TYPE: PRT
<213> ORGANISM: Artificial Sequence
<220> FEATURE:
<223> OTHER INFORMATION: Synthetic construct

<400> SEQUENCE: 463

Val Arg Leu Arg Ile Arg Val Ala Val Ile Arg Arg
1               5                   10

<210> SEQ ID NO 464
<211> LENGTH: 12
<212> TYPE: PRT
<213> ORGANISM: Artificial Sequence
<220> FEATURE:
<223> OTHER INFORMATION: Synthetic construct

<400> SEQUENCE: 464

Val Arg Leu Arg Ile Arg Val Ala Val Ile Arg Ser
1               5                   10

<210> SEQ ID NO 465
<211> LENGTH: 12
<212> TYPE: PRT
<213> ORGANISM: Artificial Sequence
<220> FEATURE:
<223> OTHER INFORMATION: Synthetic construct

<400> SEQUENCE: 465

Val Arg Leu Arg Ile Arg Val Ala Val Ile Arg Thr
1               5                   10

<210> SEQ ID NO 466
<211> LENGTH: 12
<212> TYPE: PRT
<213> ORGANISM: Artificial Sequence
<220> FEATURE:
<223> OTHER INFORMATION: Synthetic construct

<400> SEQUENCE: 466

Val Arg Leu Arg Ile Arg Val Ala Val Ile Arg Val
1               5                   10

<210> SEQ ID NO 467
<211> LENGTH: 12
<212> TYPE: PRT
<213> ORGANISM: Artificial Sequence
<220> FEATURE:
<223> OTHER INFORMATION: Synthetic construct

<400> SEQUENCE: 467

Val Arg Leu Arg Ile Arg Val Ala Val Ile Arg Trp
1               5                   10

<210> SEQ ID NO 468
<211> LENGTH: 12
<212> TYPE: PRT
<213> ORGANISM: Artificial Sequence
<220> FEATURE:
<223> OTHER INFORMATION: Synthetic construct

<400> SEQUENCE: 468

Val Arg Leu Arg Ile Arg Val Ala Val Ile Arg Tyr

```
                 1               5                    10

<210> SEQ ID NO 469
<211> LENGTH: 9
<212> TYPE: PRT
<213> ORGANISM: Artificial Sequence
<220> FEATURE:
<223> OTHER INFORMATION: Synthetic construct

<400> SEQUENCE: 469

Arg Arg Arg Arg Val Lys Trp Trp Arg
1               5

<210> SEQ ID NO 470
<211> LENGTH: 9
<212> TYPE: PRT
<213> ORGANISM: Artificial Sequence
<220> FEATURE:
<223> OTHER INFORMATION: Synthetic construct

<400> SEQUENCE: 470

Trp Leu Arg Lys Lys Gln Gly Arg Leu
1               5

<210> SEQ ID NO 471
<211> LENGTH: 9
<212> TYPE: PRT
<213> ORGANISM: Artificial Sequence
<220> FEATURE:
<223> OTHER INFORMATION: Synthetic construct

<400> SEQUENCE: 471

Lys Trp Val Arg Val Tyr Leu Arg Trp
1               5

<210> SEQ ID NO 472
<211> LENGTH: 9
<212> TYPE: PRT
<213> ORGANISM: Artificial Sequence
<220> FEATURE:
<223> OTHER INFORMATION: Synthetic construct

<400> SEQUENCE: 472

Gly Lys Val Met Ile Ser Ile Val Arg
1               5

<210> SEQ ID NO 473
<211> LENGTH: 9
<212> TYPE: PRT
<213> ORGANISM: Artificial Sequence
<220> FEATURE:
<223> OTHER INFORMATION: Synthetic construct

<400> SEQUENCE: 473

Ile Lys Val Val Arg Trp Arg Trp Arg
1               5

<210> SEQ ID NO 474
<211> LENGTH: 9
<212> TYPE: PRT
<213> ORGANISM: Artificial Sequence
<220> FEATURE:
<223> OTHER INFORMATION: Synthetic construct

<400> SEQUENCE: 474

Arg Arg Arg Arg Arg Trp Val Arg Arg
1               5
```

<210> SEQ ID NO 475
<211> LENGTH: 9
<212> TYPE: PRT
<213> ORGANISM: Artificial Sequence
<220> FEATURE:
<223> OTHER INFORMATION: Synthetic construct

<400> SEQUENCE: 475

His Met Asn Arg Phe Arg Thr Val Tyr
1               5

<210> SEQ ID NO 476
<211> LENGTH: 9
<212> TYPE: PRT
<213> ORGANISM: Artificial Sequence
<220> FEATURE:
<223> OTHER INFORMATION: Synthetic construct

<400> SEQUENCE: 476

Val Arg Lys Arg Gly Ser Trp Arg Met
1               5

<210> SEQ ID NO 477
<211> LENGTH: 9
<212> TYPE: PRT
<213> ORGANISM: Artificial Sequence
<220> FEATURE:
<223> OTHER INFORMATION: Synthetic construct

<400> SEQUENCE: 477

Arg Ile Ile Arg Thr Tyr Lys Arg Gly
1               5

<210> SEQ ID NO 478
<211> LENGTH: 9
<212> TYPE: PRT
<213> ORGANISM: Artificial Sequence
<220> FEATURE:
<223> OTHER INFORMATION: Synthetic construct

<400> SEQUENCE: 478

Trp Trp Arg Trp Arg Leu Arg Leu Ile
1               5

<210> SEQ ID NO 479
<211> LENGTH: 9
<212> TYPE: PRT
<213> ORGANISM: Artificial Sequence
<220> FEATURE:
<223> OTHER INFORMATION: Synthetic construct

<400> SEQUENCE: 479

Trp Leu Asn Arg Leu Tyr Ile Arg Leu
1               5

<210> SEQ ID NO 480
<211> LENGTH: 9
<212> TYPE: PRT
<213> ORGANISM: Artificial Sequence
<220> FEATURE:
<223> OTHER INFORMATION: Synthetic construct

<400> SEQUENCE: 480

Ile Trp Arg Trp Thr Lys Trp Phe Trp
1               5

<210> SEQ ID NO 481
<211> LENGTH: 9
<212> TYPE: PRT
<213> ORGANISM: Artificial Sequence
<220> FEATURE:
<223> OTHER INFORMATION: Synthetic construct

<400> SEQUENCE: 481

Arg Phe Lys Gly Ser Trp Lys Tyr Arg
1               5

<210> SEQ ID NO 482
<211> LENGTH: 9
<212> TYPE: PRT
<213> ORGANISM: Artificial Sequence
<220> FEATURE:
<223> OTHER INFORMATION: Synthetic construct

<400> SEQUENCE: 482

Val Trp Val Ile Arg Lys Lys Lys Trp
1               5

<210> SEQ ID NO 483
<211> LENGTH: 9
<212> TYPE: PRT
<213> ORGANISM: Artificial Sequence
<220> FEATURE:
<223> OTHER INFORMATION: Synthetic construct

<400> SEQUENCE: 483

Arg Gly Arg Arg Val Trp Arg Leu Phe
1               5

<210> SEQ ID NO 484
<211> LENGTH: 9
<212> TYPE: PRT
<213> ORGANISM: Artificial Sequence
<220> FEATURE:
<223> OTHER INFORMATION: Synthetic construct

<400> SEQUENCE: 484

Trp Arg Trp Arg Lys Val Lys Gln Trp
1               5

<210> SEQ ID NO 485
<211> LENGTH: 9
<212> TYPE: PRT
<213> ORGANISM: Artificial Sequence
<220> FEATURE:
<223> OTHER INFORMATION: Synthetic construct

<400> SEQUENCE: 485

Trp Trp Lys Tyr Trp Arg Lys Val Ile
1               5

<210> SEQ ID NO 486
<211> LENGTH: 9
<212> TYPE: PRT
<213> ORGANISM: Artificial Sequence
<220> FEATURE:
<223> OTHER INFORMATION: Synthetic construct

<400> SEQUENCE: 486

Trp Leu Val Arg Ile Arg Lys Arg Ile
1               5

```
<210> SEQ ID NO 487
<211> LENGTH: 9
<212> TYPE: PRT
<213> ORGANISM: Artificial Sequence
<220> FEATURE:
<223> OTHER INFORMATION: Synthetic construct

<400> SEQUENCE: 487

Trp Trp Arg Trp Trp Gln Arg Arg Trp
1               5

<210> SEQ ID NO 488
<211> LENGTH: 9
<212> TYPE: PRT
<213> ORGANISM: Artificial Sequence
<220> FEATURE:
<223> OTHER INFORMATION: Synthetic construct

<400> SEQUENCE: 488

Arg Lys Lys Trp Trp Trp Lys Ile Arg
1               5

<210> SEQ ID NO 489
<211> LENGTH: 9
<212> TYPE: PRT
<213> ORGANISM: Artificial Sequence
<220> FEATURE:
<223> OTHER INFORMATION: Synthetic construct

<400> SEQUENCE: 489

Trp Val Arg Lys Lys Ile Arg Arg Arg
1               5

<210> SEQ ID NO 490
<211> LENGTH: 9
<212> TYPE: PRT
<213> ORGANISM: Artificial Sequence
<220> FEATURE:
<223> OTHER INFORMATION: Synthetic construct

<400> SEQUENCE: 490

Arg Tyr Arg Arg Arg Trp Tyr Ile Arg
1               5

<210> SEQ ID NO 491
<211> LENGTH: 9
<212> TYPE: PRT
<213> ORGANISM: Artificial Sequence
<220> FEATURE:
<223> OTHER INFORMATION: Synthetic construct

<400> SEQUENCE: 491

Leu Tyr Arg Trp Val Trp Lys Val Gly
1               5

<210> SEQ ID NO 492
<211> LENGTH: 9
<212> TYPE: PRT
<213> ORGANISM: Artificial Sequence
<220> FEATURE:
<223> OTHER INFORMATION: Synthetic construct

<400> SEQUENCE: 492

Val Arg Arg Arg Trp Phe Lys Trp Leu
1               5

<210> SEQ ID NO 493
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 493

Arg Arg Leu Trp Trp Trp Lys Trp Leu
1               5

<210> SEQ ID NO 494
<211> LENGTH: 9
<212> TYPE: PRT
<213> ORGANISM: Artificial Sequence
<220> FEATURE:
<223> OTHER INFORMATION: Synthetic construct

<400> SEQUENCE: 494

Trp Arg Phe Lys Trp Thr Arg Arg Gly
1               5

<210> SEQ ID NO 495
<211> LENGTH: 9
<212> TYPE: PRT
<213> ORGANISM: Artificial Sequence
<220> FEATURE:
<223> OTHER INFORMATION: Synthetic construct

<400> SEQUENCE: 495

Lys Trp Trp Arg His Arg Arg Met Trp
1               5

<210> SEQ ID NO 496
<211> LENGTH: 9
<212> TYPE: PRT
<213> ORGANISM: Artificial Sequence
<220> FEATURE:
<223> OTHER INFORMATION: Synthetic construct

<400> SEQUENCE: 496

Arg Arg Lys Arg Trp Trp Trp Arg Thr
1               5

<210> SEQ ID NO 497
<211> LENGTH: 9
<212> TYPE: PRT
<213> ORGANISM: Artificial Sequence
<220> FEATURE:
<223> OTHER INFORMATION: Synthetic construct

<400> SEQUENCE: 497

Trp Arg Arg Lys Ile Val Arg Val Trp
1               5

<210> SEQ ID NO 498
<211> LENGTH: 9
<212> TYPE: PRT
<213> ORGANISM: Artificial Sequence
<220> FEATURE:
<223> OTHER INFORMATION: Synthetic construct

<400> SEQUENCE: 498

Lys Leu Arg Arg Gly Ser Leu Trp Arg
1               5

<210> SEQ ID NO 499
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 499

Arg Val Ile Trp Trp Arg Arg Lys
1               5

<210> SEQ ID NO 500
<211> LENGTH: 9
<212> TYPE: PRT
<213> ORGANISM: Artificial Sequence
<220> FEATURE:
<223> OTHER INFORMATION: Synthetic construct

<400> SEQUENCE: 500

Thr Trp Arg Val Trp Lys Val Arg Trp
1               5

<210> SEQ ID NO 501
<211> LENGTH: 9
<212> TYPE: PRT
<213> ORGANISM: Artificial Sequence
<220> FEATURE:
<223> OTHER INFORMATION: Synthetic construct

<400> SEQUENCE: 501

Gln Arg Gly Ile Val Ile Trp Arg Lys
1               5

<210> SEQ ID NO 502
<211> LENGTH: 9
<212> TYPE: PRT
<213> ORGANISM: Artificial Sequence
<220> FEATURE:
<223> OTHER INFORMATION: Synthetic construct

<400> SEQUENCE: 502

Gly Lys Trp Trp Lys Trp Gly Ile Trp
1               5

<210> SEQ ID NO 503
<211> LENGTH: 9
<212> TYPE: PRT
<213> ORGANISM: Artificial Sequence
<220> FEATURE:
<223> OTHER INFORMATION: Synthetic construct

<400> SEQUENCE: 503

Arg Val Arg Arg Trp Trp Phe Val Arg
1               5

<210> SEQ ID NO 504
<211> LENGTH: 9
<212> TYPE: PRT
<213> ORGANISM: Artificial Sequence
<220> FEATURE:
<223> OTHER INFORMATION: Synthetic construct

<400> SEQUENCE: 504

Phe Trp Arg Arg Arg Val Lys Trp Arg
1               5

<210> SEQ ID NO 505
<211> LENGTH: 9
<212> TYPE: PRT
```

<213> ORGANISM: Artificial Sequence
<220> FEATURE:
<223> OTHER INFORMATION: Synthetic construct

<400> SEQUENCE: 505

Phe Arg Arg Tyr Gln Asn Ile Val Arg
1               5

<210> SEQ ID NO 506
<211> LENGTH: 9
<212> TYPE: PRT
<213> ORGANISM: Artificial Sequence
<220> FEATURE:
<223> OTHER INFORMATION: Synthetic construct

<400> SEQUENCE: 506

Arg Phe Trp Arg Trp Ile Phe Lys Trp
1               5

<210> SEQ ID NO 507
<211> LENGTH: 9
<212> TYPE: PRT
<213> ORGANISM: Artificial Sequence
<220> FEATURE:
<223> OTHER INFORMATION: Synthetic construct

<400> SEQUENCE: 507

Lys Arg Asn Val Lys Arg Asn Trp Lys
1               5

<210> SEQ ID NO 508
<211> LENGTH: 9
<212> TYPE: PRT
<213> ORGANISM: Artificial Sequence
<220> FEATURE:
<223> OTHER INFORMATION: Synthetic construct

<400> SEQUENCE: 508

Trp Tyr Ser Leu Ile Ile Phe Lys Arg
1               5

<210> SEQ ID NO 509
<211> LENGTH: 9
<212> TYPE: PRT
<213> ORGANISM: Artificial Sequence
<220> FEATURE:
<223> OTHER INFORMATION: Synthetic construct

<400> SEQUENCE: 509

Arg Lys Asn Arg Arg Ile Arg Val Val
1               5

<210> SEQ ID NO 510
<211> LENGTH: 9
<212> TYPE: PRT
<213> ORGANISM: Artificial Sequence
<220> FEATURE:
<223> OTHER INFORMATION: Synthetic construct

<400> SEQUENCE: 510

Phe Phe Arg Lys Arg Arg Trp Arg Ile
1               5

<210> SEQ ID NO 511
<211> LENGTH: 9
<212> TYPE: PRT
<213> ORGANISM: Artificial Sequence
<220> FEATURE:
<223> OTHER INFORMATION: Synthetic construct

<400> SEQUENCE: 511

Trp Lys Ile Arg Lys Val Ile Lys Trp
1               5

<210> SEQ ID NO 512
<211> LENGTH: 9
<212> TYPE: PRT
<213> ORGANISM: Artificial Sequence
<220> FEATURE:
<223> OTHER INFORMATION: Synthetic construct

<400> SEQUENCE: 512

Ile Lys Trp Tyr Trp Arg Lys Lys Lys
1               5

<210> SEQ ID NO 513
<211> LENGTH: 9
<212> TYPE: PRT
<213> ORGANISM: Artificial Sequence
<220> FEATURE:
<223> OTHER INFORMATION: Synthetic construct

<400> SEQUENCE: 513

Lys Arg Gly Trp Arg Lys Arg Trp Trp
1               5

<210> SEQ ID NO 514
<211> LENGTH: 9
<212> TYPE: PRT
<213> ORGANISM: Artificial Sequence
<220> FEATURE:
<223> OTHER INFORMATION: Synthetic construct

<400> SEQUENCE: 514

Arg Lys Trp Met Gly Arg Arg Ile Arg
1               5

<210> SEQ ID NO 515
<211> LENGTH: 9
<212> TYPE: PRT
<213> ORGANISM: Artificial Sequence
<220> FEATURE:
<223> OTHER INFORMATION: Synthetic construct

<400> SEQUENCE: 515

Trp Lys Gly Lys Lys Arg Arg Val Ile
1               5

<210> SEQ ID NO 516
<211> LENGTH: 9
<212> TYPE: PRT
<213> ORGANISM: Artificial Sequence
<220> FEATURE:
<223> OTHER INFORMATION: Synthetic construct

<400> SEQUENCE: 516

Lys Val Ile Arg Tyr Lys Val Tyr Ile
1               5

<210> SEQ ID NO 517
<211> LENGTH: 9
<212> TYPE: PRT
<213> ORGANISM: Artificial Sequence
<220> FEATURE:

<223> OTHER INFORMATION: Synthetic construct

<400> SEQUENCE: 517

Arg Arg Thr Arg Lys Trp Ile Leu Arg
1               5

<210> SEQ ID NO 518
<211> LENGTH: 9
<212> TYPE: PRT
<213> ORGANISM: Artificial Sequence
<220> FEATURE:
<223> OTHER INFORMATION: Synthetic construct

<400> SEQUENCE: 518

Tyr Asn Trp Asn Trp Leu Arg Arg Trp
1               5

<210> SEQ ID NO 519
<211> LENGTH: 9
<212> TYPE: PRT
<213> ORGANISM: Artificial Sequence
<220> FEATURE:
<223> OTHER INFORMATION: Synthetic construct

<400> SEQUENCE: 519

Lys Trp Lys His Trp Arg Trp Gln Trp
1               5

<210> SEQ ID NO 520
<211> LENGTH: 9
<212> TYPE: PRT
<213> ORGANISM: Artificial Sequence
<220> FEATURE:
<223> OTHER INFORMATION: Synthetic construct

<400> SEQUENCE: 520

Arg Lys Ile Val Val Lys Val Arg Val
1               5

<210> SEQ ID NO 521
<211> LENGTH: 9
<212> TYPE: PRT
<213> ORGANISM: Artificial Sequence
<220> FEATURE:
<223> OTHER INFORMATION: Synthetic construct

<400> SEQUENCE: 521

Gln Tyr Leu Gly Trp Arg Phe Lys Trp
1               5

<210> SEQ ID NO 522
<211> LENGTH: 9
<212> TYPE: PRT
<213> ORGANISM: Artificial Sequence
<220> FEATURE:
<223> OTHER INFORMATION: Synthetic construct

<400> SEQUENCE: 522

Lys Ile Lys Thr Arg Lys Val Lys Tyr
1               5

<210> SEQ ID NO 523
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 523

Val Trp Ile Arg Trp Arg Arg Arg Trp
1               5

<210> SEQ ID NO 524
<211> LENGTH: 9
<212> TYPE: PRT
<213> ORGANISM: Artificial Sequence
<220> FEATURE:
<223> OTHER INFORMATION: Synthetic construct

<400> SEQUENCE: 524

Trp Gly Val Arg Val Arg Arg Leu Ile
1               5

<210> SEQ ID NO 525
<211> LENGTH: 9
<212> TYPE: PRT
<213> ORGANISM: Artificial Sequence
<220> FEATURE:
<223> OTHER INFORMATION: Synthetic construct

<400> SEQUENCE: 525

Trp Trp Lys Arg Val Trp Lys Phe Ile
1               5

<210> SEQ ID NO 526
<211> LENGTH: 9
<212> TYPE: PRT
<213> ORGANISM: Artificial Sequence
<220> FEATURE:
<223> OTHER INFORMATION: Synthetic construct

<400> SEQUENCE: 526

Tyr Trp Ile Tyr Ser Arg Leu Arg Arg
1               5

<210> SEQ ID NO 527
<211> LENGTH: 9
<212> TYPE: PRT
<213> ORGANISM: Artificial Sequence
<220> FEATURE:
<223> OTHER INFORMATION: Synthetic construct

<400> SEQUENCE: 527

Arg Arg Tyr Trp Lys Phe Lys Arg Arg
1               5

<210> SEQ ID NO 528
<211> LENGTH: 9
<212> TYPE: PRT
<213> ORGANISM: Artificial Sequence
<220> FEATURE:
<223> OTHER INFORMATION: Synthetic construct

<400> SEQUENCE: 528

Ile Val Arg Arg Val Ile Ile Arg Val
1               5

<210> SEQ ID NO 529
<211> LENGTH: 9
<212> TYPE: PRT
<213> ORGANISM: Artificial Sequence
<220> FEATURE:
<223> OTHER INFORMATION: Synthetic construct
```

<400> SEQUENCE: 529

Ala Arg Arg Arg Gly Leu Lys Val Trp
1               5

<210> SEQ ID NO 530
<211> LENGTH: 9
<212> TYPE: PRT
<213> ORGANISM: Artificial Sequence
<220> FEATURE:
<223> OTHER INFORMATION: Synthetic construct

<400> SEQUENCE: 530

Arg Arg Trp Val Arg Arg Trp Trp Arg
1               5

<210> SEQ ID NO 531
<211> LENGTH: 9
<212> TYPE: PRT
<213> ORGANISM: Artificial Sequence
<220> FEATURE:
<223> OTHER INFORMATION: Synthetic construct

<400> SEQUENCE: 531

Trp Lys Trp Lys Trp Lys Trp Gln Ser
1               5

<210> SEQ ID NO 532
<211> LENGTH: 9
<212> TYPE: PRT
<213> ORGANISM: Artificial Sequence
<220> FEATURE:
<223> OTHER INFORMATION: Synthetic construct

<400> SEQUENCE: 532

Arg Trp Lys Val Lys Gln Arg Arg Arg
1               5

<210> SEQ ID NO 533
<211> LENGTH: 9
<212> TYPE: PRT
<213> ORGANISM: Artificial Sequence
<220> FEATURE:
<223> OTHER INFORMATION: Synthetic construct

<400> SEQUENCE: 533

Tyr Trp Thr Lys Phe Arg Leu Arg Ile
1               5

<210> SEQ ID NO 534
<211> LENGTH: 9
<212> TYPE: PRT
<213> ORGANISM: Artificial Sequence
<220> FEATURE:
<223> OTHER INFORMATION: Synthetic construct

<400> SEQUENCE: 534

Trp Val Ile Lys Val Arg Ile Arg Trp
1               5

<210> SEQ ID NO 535
<211> LENGTH: 9
<212> TYPE: PRT
<213> ORGANISM: Artificial Sequence
<220> FEATURE:
<223> OTHER INFORMATION: Synthetic construct

<400> SEQUENCE: 535

```
Ala Arg Val Gln Val Tyr Lys Tyr Arg
1               5

<210> SEQ ID NO 536
<211> LENGTH: 9
<212> TYPE: PRT
<213> ORGANISM: Artificial Sequence
<220> FEATURE:
<223> OTHER INFORMATION: Synthetic construct

<400> SEQUENCE: 536

Lys Trp Arg Trp His Trp Val Tyr Val
1               5

<210> SEQ ID NO 537
<211> LENGTH: 9
<212> TYPE: PRT
<213> ORGANISM: Artificial Sequence
<220> FEATURE:
<223> OTHER INFORMATION: Synthetic construct

<400> SEQUENCE: 537

Lys Val Lys Tyr Lys Phe Arg Arg Trp
1               5

<210> SEQ ID NO 538
<211> LENGTH: 9
<212> TYPE: PRT
<213> ORGANISM: Artificial Sequence
<220> FEATURE:
<223> OTHER INFORMATION: Synthetic construct

<400> SEQUENCE: 538

Arg Phe Arg Lys Arg Lys Asn Arg Ile
1               5

<210> SEQ ID NO 539
<211> LENGTH: 9
<212> TYPE: PRT
<213> ORGANISM: Artificial Sequence
<220> FEATURE:
<223> OTHER INFORMATION: Synthetic construct

<400> SEQUENCE: 539

Met Phe Arg Arg Arg Phe Ile Trp Lys
1               5

<210> SEQ ID NO 540
<211> LENGTH: 9
<212> TYPE: PRT
<213> ORGANISM: Artificial Sequence
<220> FEATURE:
<223> OTHER INFORMATION: Synthetic construct

<400> SEQUENCE: 540

Trp Arg Leu Arg Arg Phe Arg Leu Trp
1               5

<210> SEQ ID NO 541
<211> LENGTH: 9
<212> TYPE: PRT
<213> ORGANISM: Artificial Sequence
<220> FEATURE:
<223> OTHER INFORMATION: Synthetic construct

<400> SEQUENCE: 541
```

```
Trp Ile Gln Arg Ile Arg Ile Trp Val
1               5
```

<210> SEQ ID NO 542
<211> LENGTH: 9
<212> TYPE: PRT
<213> ORGANISM: Artificial Sequence
<220> FEATURE:
<223> OTHER INFORMATION: Synthetic construct

<400> SEQUENCE: 542

```
Arg Arg Tyr His Trp Arg Ile Tyr Ile
1               5
```

<210> SEQ ID NO 543
<211> LENGTH: 9
<212> TYPE: PRT
<213> ORGANISM: Artificial Sequence
<220> FEATURE:
<223> OTHER INFORMATION: Synthetic construct

<400> SEQUENCE: 543

```
Ser Arg Phe Trp Arg Arg Trp Arg Lys
1               5
```

<210> SEQ ID NO 544
<211> LENGTH: 9
<212> TYPE: PRT
<213> ORGANISM: Artificial Sequence
<220> FEATURE:
<223> OTHER INFORMATION: Synthetic construct

<400> SEQUENCE: 544

```
Tyr Arg Val Trp Ile Ile Arg Arg Lys
1               5
```

<210> SEQ ID NO 545
<211> LENGTH: 9
<212> TYPE: PRT
<213> ORGANISM: Artificial Sequence
<220> FEATURE:
<223> OTHER INFORMATION: Synthetic construct

<400> SEQUENCE: 545

```
Trp Arg Val Ser Trp Leu Ile Trp Arg
1               5
```

<210> SEQ ID NO 546
<211> LENGTH: 9
<212> TYPE: PRT
<213> ORGANISM: Artificial Sequence
<220> FEATURE:
<223> OTHER INFORMATION: Synthetic construct

<400> SEQUENCE: 546

```
Arg Phe Val Lys Arg Lys Ile Val Trp
1               5
```

<210> SEQ ID NO 547
<211> LENGTH: 9
<212> TYPE: PRT
<213> ORGANISM: Artificial Sequence
<220> FEATURE:
<223> OTHER INFORMATION: Synthetic construct

<400> SEQUENCE: 547

```
Arg Ile Tyr Lys Ile Arg Trp Ile Ile
```

-continued

```
1               5

<210> SEQ ID NO 548
<211> LENGTH: 9
<212> TYPE: PRT
<213> ORGANISM: Artificial Sequence
<220> FEATURE:
<223> OTHER INFORMATION: Synthetic construct

<400> SEQUENCE: 548

Arg Lys Phe Trp His Arg Gly Thr Ile
1               5

<210> SEQ ID NO 549
<211> LENGTH: 9
<212> TYPE: PRT
<213> ORGANISM: Artificial Sequence
<220> FEATURE:
<223> OTHER INFORMATION: Synthetic construct

<400> SEQUENCE: 549

Ala Trp Val Val Trp Arg Lys Arg Trp
1               5

<210> SEQ ID NO 550
<211> LENGTH: 9
<212> TYPE: PRT
<213> ORGANISM: Artificial Sequence
<220> FEATURE:
<223> OTHER INFORMATION: Synthetic construct

<400> SEQUENCE: 550

Trp Val Trp Gly Lys Val Arg Trp Gly
1               5

<210> SEQ ID NO 551
<211> LENGTH: 9
<212> TYPE: PRT
<213> ORGANISM: Artificial Sequence
<220> FEATURE:
<223> OTHER INFORMATION: Synthetic construct

<400> SEQUENCE: 551

Phe Gly Ile Arg Phe Arg Arg Met Val
1               5

<210> SEQ ID NO 552
<211> LENGTH: 9
<212> TYPE: PRT
<213> ORGANISM: Artificial Sequence
<220> FEATURE:
<223> OTHER INFORMATION: Synthetic construct

<400> SEQUENCE: 552

Phe Trp Ile Arg Lys Val Phe Arg Ile
1               5

<210> SEQ ID NO 553
<211> LENGTH: 9
<212> TYPE: PRT
<213> ORGANISM: Artificial Sequence
<220> FEATURE:
<223> OTHER INFORMATION: Synthetic construct

<400> SEQUENCE: 553

Lys Arg Trp Lys Val Arg Val Val Trp
1               5
```

```
<210> SEQ ID NO 554
<211> LENGTH: 9
<212> TYPE: PRT
<213> ORGANISM: Artificial Sequence
<220> FEATURE:
<223> OTHER INFORMATION: Synthetic construct

<400> SEQUENCE: 554

Lys Ile Arg Ile Trp Arg Ile Trp Val
1               5

<210> SEQ ID NO 555
<211> LENGTH: 9
<212> TYPE: PRT
<213> ORGANISM: Artificial Sequence
<220> FEATURE:
<223> OTHER INFORMATION: Synthetic construct

<400> SEQUENCE: 555

Arg Gly Arg Trp Lys Arg Ile Lys Lys
1               5

<210> SEQ ID NO 556
<211> LENGTH: 9
<212> TYPE: PRT
<213> ORGANISM: Artificial Sequence
<220> FEATURE:
<223> OTHER INFORMATION: Synthetic construct

<400> SEQUENCE: 556

Arg Leu Trp Phe Leu Val Leu Arg Arg
1               5

<210> SEQ ID NO 557
<211> LENGTH: 9
<212> TYPE: PRT
<213> ORGANISM: Artificial Sequence
<220> FEATURE:
<223> OTHER INFORMATION: Synthetic construct

<400> SEQUENCE: 557

Ile Ile Arg Val Thr Arg Trp Thr Lys
1               5

<210> SEQ ID NO 558
<211> LENGTH: 9
<212> TYPE: PRT
<213> ORGANISM: Artificial Sequence
<220> FEATURE:
<223> OTHER INFORMATION: Synthetic construct

<400> SEQUENCE: 558

Ala Met Trp Arg Trp Lys Trp Arg Lys
1               5

<210> SEQ ID NO 559
<211> LENGTH: 9
<212> TYPE: PRT
<213> ORGANISM: Artificial Sequence
<220> FEATURE:
<223> OTHER INFORMATION: Synthetic construct

<400> SEQUENCE: 559

Thr Arg Lys Tyr Phe Gly Arg Phe Val
1               5
```

<210> SEQ ID NO 560
<211> LENGTH: 9
<212> TYPE: PRT
<213> ORGANISM: Artificial Sequence
<220> FEATURE:
<223> OTHER INFORMATION: Synthetic construct

<400> SEQUENCE: 560

Ala Arg Arg Val Lys Lys Lys Arg Arg
1               5

<210> SEQ ID NO 561
<211> LENGTH: 9
<212> TYPE: PRT
<213> ORGANISM: Artificial Sequence
<220> FEATURE:
<223> OTHER INFORMATION: Synthetic construct

<400> SEQUENCE: 561

Arg Trp Trp Lys Ile Trp Lys Arg Arg
1               5

<210> SEQ ID NO 562
<211> LENGTH: 9
<212> TYPE: PRT
<213> ORGANISM: Artificial Sequence
<220> FEATURE:
<223> OTHER INFORMATION: Synthetic construct

<400> SEQUENCE: 562

Arg Trp Arg Tyr Lys Ile Gln Lys Trp
1               5

<210> SEQ ID NO 563
<211> LENGTH: 9
<212> TYPE: PRT
<213> ORGANISM: Artificial Sequence
<220> FEATURE:
<223> OTHER INFORMATION: Synthetic construct

<400> SEQUENCE: 563

Arg Val Gly Ile Lys Ile Lys Met Lys
1               5

<210> SEQ ID NO 564
<211> LENGTH: 9
<212> TYPE: PRT
<213> ORGANISM: Artificial Sequence
<220> FEATURE:
<223> OTHER INFORMATION: Synthetic construct

<400> SEQUENCE: 564

Trp Val Leu Lys Leu Arg Tyr Lys Trp
1               5

<210> SEQ ID NO 565
<211> LENGTH: 9
<212> TYPE: PRT
<213> ORGANISM: Artificial Sequence
<220> FEATURE:
<223> OTHER INFORMATION: Synthetic construct

<400> SEQUENCE: 565

Phe Arg Arg Lys Trp Ile Phe Lys Lys
1               5

```
<210> SEQ ID NO 566
<211> LENGTH: 9
<212> TYPE: PRT
<213> ORGANISM: Artificial Sequence
<220> FEATURE:
<223> OTHER INFORMATION: Synthetic construct

<400> SEQUENCE: 566

Trp Ile Gln Lys Leu Trp Arg Gln Arg
1               5

<210> SEQ ID NO 567
<211> LENGTH: 9
<212> TYPE: PRT
<213> ORGANISM: Artificial Sequence
<220> FEATURE:
<223> OTHER INFORMATION: Synthetic construct

<400> SEQUENCE: 567

Arg Ile Val Arg Leu His Val Arg Lys
1               5

<210> SEQ ID NO 568
<211> LENGTH: 9
<212> TYPE: PRT
<213> ORGANISM: Artificial Sequence
<220> FEATURE:
<223> OTHER INFORMATION: Synthetic construct

<400> SEQUENCE: 568

Val Arg Ile Gly Trp Arg Arg Val Lys
1               5

<210> SEQ ID NO 569
<211> LENGTH: 9
<212> TYPE: PRT
<213> ORGANISM: Artificial Sequence
<220> FEATURE:
<223> OTHER INFORMATION: Synthetic construct

<400> SEQUENCE: 569

Arg Arg Arg Ile Gly Ile Lys Arg Phe
1               5

<210> SEQ ID NO 570
<211> LENGTH: 9
<212> TYPE: PRT
<213> ORGANISM: Artificial Sequence
<220> FEATURE:
<223> OTHER INFORMATION: Synthetic construct

<400> SEQUENCE: 570

Arg Arg Arg Arg Lys Lys Val Arg Ile
1               5

<210> SEQ ID NO 571
<211> LENGTH: 9
<212> TYPE: PRT
<213> ORGANISM: Artificial Sequence
<220> FEATURE:
<223> OTHER INFORMATION: Synthetic construct

<400> SEQUENCE: 571

Lys Leu Trp Arg Tyr Lys Arg Trp Arg
1               5

<210> SEQ ID NO 572
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 572

Arg Ile Arg Arg Phe Ile Lys Lys Trp
1               5

<210> SEQ ID NO 573
<211> LENGTH: 9
<212> TYPE: PRT
<213> ORGANISM: Artificial Sequence
<220> FEATURE:
<223> OTHER INFORMATION: Synthetic construct

<400> SEQUENCE: 573

Leu Trp His Lys Lys Lys Lys Ile Trp
1               5

<210> SEQ ID NO 574
<211> LENGTH: 9
<212> TYPE: PRT
<213> ORGANISM: Artificial Sequence
<220> FEATURE:
<223> OTHER INFORMATION: Synthetic construct

<400> SEQUENCE: 574

Leu Thr Arg Arg Phe Trp Leu Arg Arg
1               5

<210> SEQ ID NO 575
<211> LENGTH: 9
<212> TYPE: PRT
<213> ORGANISM: Artificial Sequence
<220> FEATURE:
<223> OTHER INFORMATION: Synthetic construct

<400> SEQUENCE: 575

Arg Arg Arg Tyr Val Ile Arg Arg Arg
1               5

<210> SEQ ID NO 576
<211> LENGTH: 9
<212> TYPE: PRT
<213> ORGANISM: Artificial Sequence
<220> FEATURE:
<223> OTHER INFORMATION: Synthetic construct

<400> SEQUENCE: 576

Trp Gly Trp Arg Trp Ile Trp Ile Lys
1               5

<210> SEQ ID NO 577
<211> LENGTH: 9
<212> TYPE: PRT
<213> ORGANISM: Artificial Sequence
<220> FEATURE:
<223> OTHER INFORMATION: Synthetic construct

<400> SEQUENCE: 577

Arg Trp Arg Trp Gln Arg Gly Arg Phe
1               5

<210> SEQ ID NO 578
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 578

Arg Arg Lys Lys Trp Lys Val Arg Ile
1               5

<210> SEQ ID NO 579
<211> LENGTH: 9
<212> TYPE: PRT
<213> ORGANISM: Artificial Sequence
<220> FEATURE:
<223> OTHER INFORMATION: Synthetic construct

<400> SEQUENCE: 579

Lys Met Lys Leu Tyr Lys Gly Ser Met
1               5

<210> SEQ ID NO 580
<211> LENGTH: 9
<212> TYPE: PRT
<213> ORGANISM: Artificial Sequence
<220> FEATURE:
<223> OTHER INFORMATION: Synthetic construct

<400> SEQUENCE: 580

Gly Thr Ile Arg Trp Trp Arg Arg Arg
1               5

<210> SEQ ID NO 581
<211> LENGTH: 9
<212> TYPE: PRT
<213> ORGANISM: Artificial Sequence
<220> FEATURE:
<223> OTHER INFORMATION: Synthetic construct

<400> SEQUENCE: 581

Ser Leu Arg Arg Tyr Ile Trp Arg Phe
1               5

<210> SEQ ID NO 582
<211> LENGTH: 9
<212> TYPE: PRT
<213> ORGANISM: Artificial Sequence
<220> FEATURE:
<223> OTHER INFORMATION: Synthetic construct

<400> SEQUENCE: 582

Gly Arg Tyr Trp Lys Lys Trp Arg Arg
1               5

<210> SEQ ID NO 583
<211> LENGTH: 9
<212> TYPE: PRT
<213> ORGANISM: Artificial Sequence
<220> FEATURE:
<223> OTHER INFORMATION: Synthetic construct

<400> SEQUENCE: 583

Trp Ile Arg Gln Phe Arg Trp Lys Lys
1               5

<210> SEQ ID NO 584
<211> LENGTH: 9
<212> TYPE: PRT
```

<213> ORGANISM: Artificial Sequence
<220> FEATURE:
<223> OTHER INFORMATION: Synthetic construct

<400> SEQUENCE: 584

Ala Lys Val Arg Arg Ile Lys His Trp
1               5

<210> SEQ ID NO 585
<211> LENGTH: 9
<212> TYPE: PRT
<213> ORGANISM: Artificial Sequence
<220> FEATURE:
<223> OTHER INFORMATION: Synthetic construct

<400> SEQUENCE: 585

Tyr Ser Arg Arg Lys Thr Trp Trp Ile
1               5

<210> SEQ ID NO 586
<211> LENGTH: 9
<212> TYPE: PRT
<213> ORGANISM: Artificial Sequence
<220> FEATURE:
<223> OTHER INFORMATION: Synthetic construct

<400> SEQUENCE: 586

Arg Gly Arg Trp Trp Ile Arg Arg Gln
1               5

<210> SEQ ID NO 587
<211> LENGTH: 9
<212> TYPE: PRT
<213> ORGANISM: Artificial Sequence
<220> FEATURE:
<223> OTHER INFORMATION: Synthetic construct

<400> SEQUENCE: 587

Trp Val Phe Arg Trp Val Trp Trp Arg
1               5

<210> SEQ ID NO 588
<211> LENGTH: 9
<212> TYPE: PRT
<213> ORGANISM: Artificial Sequence
<220> FEATURE:
<223> OTHER INFORMATION: Synthetic construct

<400> SEQUENCE: 588

Val Tyr Arg Val Trp Trp Leu Lys Trp
1               5

<210> SEQ ID NO 589
<211> LENGTH: 9
<212> TYPE: PRT
<213> ORGANISM: Artificial Sequence
<220> FEATURE:
<223> OTHER INFORMATION: Synthetic construct

<400> SEQUENCE: 589

Trp Trp Val Arg Arg Arg Val Gly Trp
1               5

<210> SEQ ID NO 590
<211> LENGTH: 9
<212> TYPE: PRT
<213> ORGANISM: Artificial Sequence

```
<220> FEATURE:
<223> OTHER INFORMATION: Synthetic construct

<400> SEQUENCE: 590

Trp Phe Lys Ile Lys Arg Leu Tyr Leu
1               5

<210> SEQ ID NO 591
<211> LENGTH: 9
<212> TYPE: PRT
<213> ORGANISM: Artificial Sequence
<220> FEATURE:
<223> OTHER INFORMATION: Synthetic construct

<400> SEQUENCE: 591

Trp Lys Met Trp Lys Arg Gly Trp Thr
1               5

<210> SEQ ID NO 592
<211> LENGTH: 9
<212> TYPE: PRT
<213> ORGANISM: Artificial Sequence
<220> FEATURE:
<223> OTHER INFORMATION: Synthetic construct

<400> SEQUENCE: 592

Arg Trp Trp Arg Lys Ser Arg Arg Leu
1               5

<210> SEQ ID NO 593
<211> LENGTH: 9
<212> TYPE: PRT
<213> ORGANISM: Artificial Sequence
<220> FEATURE:
<223> OTHER INFORMATION: Synthetic construct

<400> SEQUENCE: 593

Phe Trp Arg Ile Arg Trp Trp Arg Trp
1               5

<210> SEQ ID NO 594
<211> LENGTH: 9
<212> TYPE: PRT
<213> ORGANISM: Artificial Sequence
<220> FEATURE:
<223> OTHER INFORMATION: Synthetic construct

<400> SEQUENCE: 594

Val Trp Trp Phe Gly Lys Arg Thr Thr
1               5

<210> SEQ ID NO 595
<211> LENGTH: 9
<212> TYPE: PRT
<213> ORGANISM: Artificial Sequence
<220> FEATURE:
<223> OTHER INFORMATION: Synthetic construct

<400> SEQUENCE: 595

Val Arg Ile Ile Trp Trp Ile Trp Arg
1               5

<210> SEQ ID NO 596
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 596

Trp Trp Val Arg Ile Trp Arg Trp Met
1               5

<210> SEQ ID NO 597
<211> LENGTH: 9
<212> TYPE: PRT
<213> ORGANISM: Artificial Sequence
<220> FEATURE:
<223> OTHER INFORMATION: Synthetic construct

<400> SEQUENCE: 597

Arg Lys Trp Lys Lys Trp Phe His Arg
1               5

<210> SEQ ID NO 598
<211> LENGTH: 9
<212> TYPE: PRT
<213> ORGANISM: Artificial Sequence
<220> FEATURE:
<223> OTHER INFORMATION: Synthetic construct

<400> SEQUENCE: 598

Arg Lys Trp Lys Phe Trp Gly Tyr Lys
1               5

<210> SEQ ID NO 599
<211> LENGTH: 9
<212> TYPE: PRT
<213> ORGANISM: Artificial Sequence
<220> FEATURE:
<223> OTHER INFORMATION: Synthetic construct

<400> SEQUENCE: 599

Phe Trp Tyr Ile Trp Ser Lys Arg Val
1               5

<210> SEQ ID NO 600
<211> LENGTH: 9
<212> TYPE: PRT
<213> ORGANISM: Artificial Sequence
<220> FEATURE:
<223> OTHER INFORMATION: Synthetic construct

<400> SEQUENCE: 600

Tyr Trp Arg Gln Phe Arg Arg Lys Gln
1               5

<210> SEQ ID NO 601
<211> LENGTH: 9
<212> TYPE: PRT
<213> ORGANISM: Artificial Sequence
<220> FEATURE:
<223> OTHER INFORMATION: Synthetic construct

<400> SEQUENCE: 601

Trp Trp Trp Lys Val Lys Ser Arg Arg
1               5

<210> SEQ ID NO 602
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 602

Trp Arg Leu Trp Ile Trp Trp Ile Arg
1               5

<210> SEQ ID NO 603
<211> LENGTH: 9
<212> TYPE: PRT
<213> ORGANISM: Artificial Sequence
<220> FEATURE:
<223> OTHER INFORMATION: Synthetic construct

<400> SEQUENCE: 603

Gln Phe Arg Val Asn Arg Arg Lys Tyr
1               5

<210> SEQ ID NO 604
<211> LENGTH: 9
<212> TYPE: PRT
<213> ORGANISM: Artificial Sequence
<220> FEATURE:
<223> OTHER INFORMATION: Synthetic construct

<400> SEQUENCE: 604

Arg Tyr Arg Phe Trp Trp Val Arg Arg
1               5

<210> SEQ ID NO 605
<211> LENGTH: 9
<212> TYPE: PRT
<213> ORGANISM: Artificial Sequence
<220> FEATURE:
<223> OTHER INFORMATION: Synthetic construct

<400> SEQUENCE: 605

Thr His Ile Trp Leu Arg Arg Arg Arg
1               5

<210> SEQ ID NO 606
<211> LENGTH: 9
<212> TYPE: PRT
<213> ORGANISM: Artificial Sequence
<220> FEATURE:
<223> OTHER INFORMATION: Synthetic construct

<400> SEQUENCE: 606

Arg Arg Arg Phe Arg Lys Arg Arg Met
1               5

<210> SEQ ID NO 607
<211> LENGTH: 9
<212> TYPE: PRT
<213> ORGANISM: Artificial Sequence
<220> FEATURE:
<223> OTHER INFORMATION: Synthetic construct

<400> SEQUENCE: 607

Leu Tyr Thr Arg Val Arg Arg Tyr Ser
1               5

<210> SEQ ID NO 608
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 608

Trp Ser Ile Arg Arg Leu Trp Trp Leu
1               5

<210> SEQ ID NO 609
<211> LENGTH: 9
<212> TYPE: PRT
<213> ORGANISM: Artificial Sequence
<220> FEATURE:
<223> OTHER INFORMATION: Synthetic construct

<400> SEQUENCE: 609

Tyr Lys Ile Lys Arg Arg Arg Tyr Gly
1               5

<210> SEQ ID NO 610
<211> LENGTH: 9
<212> TYPE: PRT
<213> ORGANISM: Artificial Sequence
<220> FEATURE:
<223> OTHER INFORMATION: Synthetic construct

<400> SEQUENCE: 610

Trp Lys Arg Ile Gln Phe Arg Arg Lys
1               5

<210> SEQ ID NO 611
<211> LENGTH: 9
<212> TYPE: PRT
<213> ORGANISM: Artificial Sequence
<220> FEATURE:
<223> OTHER INFORMATION: Synthetic construct

<400> SEQUENCE: 611

His Lys Lys Arg Arg Ile Trp Arg Lys
1               5

<210> SEQ ID NO 612
<211> LENGTH: 9
<212> TYPE: PRT
<213> ORGANISM: Artificial Sequence
<220> FEATURE:
<223> OTHER INFORMATION: Synthetic construct

<400> SEQUENCE: 612

Trp Arg Leu Ile Arg Trp Trp Ile Arg
1               5

<210> SEQ ID NO 613
<211> LENGTH: 9
<212> TYPE: PRT
<213> ORGANISM: Artificial Sequence
<220> FEATURE:
<223> OTHER INFORMATION: Synthetic construct

<400> SEQUENCE: 613

Leu Arg Lys Asn Trp Trp Trp Arg Arg
1               5

<210> SEQ ID NO 614
<211> LENGTH: 9
<212> TYPE: PRT
<213> ORGANISM: Artificial Sequence
<220> FEATURE:
<223> OTHER INFORMATION: Synthetic construct

<400> SEQUENCE: 614
```

Val Lys Arg Ile Arg Ile Trp Met Leu
1               5

<210> SEQ ID NO 615
<211> LENGTH: 9
<212> TYPE: PRT
<213> ORGANISM: Artificial Sequence
<220> FEATURE:
<223> OTHER INFORMATION: Synthetic construct

<400> SEQUENCE: 615

Ile Arg Tyr Arg Asn Trp Lys Trp Leu
1               5

<210> SEQ ID NO 616
<211> LENGTH: 9
<212> TYPE: PRT
<213> ORGANISM: Artificial Sequence
<220> FEATURE:
<223> OTHER INFORMATION: Synthetic construct

<400> SEQUENCE: 616

Gly Arg Ile Leu Ser Arg Arg Trp Lys
1               5

<210> SEQ ID NO 617
<211> LENGTH: 9
<212> TYPE: PRT
<213> ORGANISM: Artificial Sequence
<220> FEATURE:
<223> OTHER INFORMATION: Synthetic construct

<400> SEQUENCE: 617

Lys His Trp Lys Ile His Val Arg Trp
1               5

<210> SEQ ID NO 618
<211> LENGTH: 9
<212> TYPE: PRT
<213> ORGANISM: Artificial Sequence
<220> FEATURE:
<223> OTHER INFORMATION: Synthetic construct

<400> SEQUENCE: 618

Trp Ile Tyr Trp Lys Val Trp Arg Arg
1               5

<210> SEQ ID NO 619
<211> LENGTH: 9
<212> TYPE: PRT
<213> ORGANISM: Artificial Sequence
<220> FEATURE:
<223> OTHER INFORMATION: Synthetic construct

<400> SEQUENCE: 619

Lys Leu Trp Lys Val Arg Asn Arg Arg
1               5

<210> SEQ ID NO 620
<211> LENGTH: 9
<212> TYPE: PRT
<213> ORGANISM: Artificial Sequence
<220> FEATURE:
<223> OTHER INFORMATION: Synthetic construct

<400> SEQUENCE: 620

```
Arg Arg Val Tyr Tyr Lys Trp Val
1               5

<210> SEQ ID NO 621
<211> LENGTH: 9
<212> TYPE: PRT
<213> ORGANISM: Artificial Sequence
<220> FEATURE:
<223> OTHER INFORMATION: Synthetic construct

<400> SEQUENCE: 621

Trp Arg Trp Gly Val Phe Arg Leu Arg
1               5

<210> SEQ ID NO 622
<211> LENGTH: 9
<212> TYPE: PRT
<213> ORGANISM: Artificial Sequence
<220> FEATURE:
<223> OTHER INFORMATION: Synthetic construct

<400> SEQUENCE: 622

Ile Trp Arg Val Leu Lys Lys Arg Val
1               5

<210> SEQ ID NO 623
<211> LENGTH: 9
<212> TYPE: PRT
<213> ORGANISM: Artificial Sequence
<220> FEATURE:
<223> OTHER INFORMATION: Synthetic construct

<400> SEQUENCE: 623

Ala Lys Lys Phe Trp Arg Asn Trp Ile
1               5

<210> SEQ ID NO 624
<211> LENGTH: 9
<212> TYPE: PRT
<213> ORGANISM: Artificial Sequence
<220> FEATURE:
<223> OTHER INFORMATION: Synthetic construct

<400> SEQUENCE: 624

Arg Gln Trp Arg Lys Val Val Lys Lys
1               5

<210> SEQ ID NO 625
<211> LENGTH: 9
<212> TYPE: PRT
<213> ORGANISM: Artificial Sequence
<220> FEATURE:
<223> OTHER INFORMATION: Synthetic construct

<400> SEQUENCE: 625

Gly Trp Lys Arg Trp Trp Val Met Leu
1               5

<210> SEQ ID NO 626
<211> LENGTH: 9
<212> TYPE: PRT
<213> ORGANISM: Artificial Sequence
<220> FEATURE:
<223> OTHER INFORMATION: Synthetic construct

<400> SEQUENCE: 626

Lys Trp Arg Arg Thr Arg Arg Arg Lys
```

```
1               5

<210> SEQ ID NO 627
<211> LENGTH: 9
<212> TYPE: PRT
<213> ORGANISM: Artificial Sequence
<220> FEATURE:
<223> OTHER INFORMATION: Synthetic construct

<400> SEQUENCE: 627

Phe Arg Arg Met Lys Arg Phe Leu Arg
1               5

<210> SEQ ID NO 628
<211> LENGTH: 9
<212> TYPE: PRT
<213> ORGANISM: Artificial Sequence
<220> FEATURE:
<223> OTHER INFORMATION: Synthetic construct

<400> SEQUENCE: 628

Arg Ser Trp Asn Trp Trp Trp Ile Arg
1               5

<210> SEQ ID NO 629
<211> LENGTH: 9
<212> TYPE: PRT
<213> ORGANISM: Artificial Sequence
<220> FEATURE:
<223> OTHER INFORMATION: Synthetic construct

<400> SEQUENCE: 629

Trp Arg Arg Arg Ile Trp Ile Asn Arg
1               5

<210> SEQ ID NO 630
<211> LENGTH: 9
<212> TYPE: PRT
<213> ORGANISM: Artificial Sequence
<220> FEATURE:
<223> OTHER INFORMATION: Synthetic construct

<400> SEQUENCE: 630

Arg Trp Lys Trp Phe Tyr Leu Lys Arg
1               5

<210> SEQ ID NO 631
<211> LENGTH: 9
<212> TYPE: PRT
<213> ORGANISM: Artificial Sequence
<220> FEATURE:
<223> OTHER INFORMATION: Synthetic construct

<400> SEQUENCE: 631

Arg Lys Arg Thr Ile Trp Arg Ile Ile
1               5

<210> SEQ ID NO 632
<211> LENGTH: 9
<212> TYPE: PRT
<213> ORGANISM: Artificial Sequence
<220> FEATURE:
<223> OTHER INFORMATION: Synthetic construct

<400> SEQUENCE: 632

Arg Arg Arg Val Trp Trp Arg Arg Arg
1               5
```

```
<210> SEQ ID NO 633
<211> LENGTH: 9
<212> TYPE: PRT
<213> ORGANISM: Artificial Sequence
<220> FEATURE:
<223> OTHER INFORMATION: Synthetic construct

<400> SEQUENCE: 633

Lys Trp Arg Phe Lys Trp Trp Lys Arg
1               5

<210> SEQ ID NO 634
<211> LENGTH: 9
<212> TYPE: PRT
<213> ORGANISM: Artificial Sequence
<220> FEATURE:
<223> OTHER INFORMATION: Synthetic construct

<400> SEQUENCE: 634

Lys Trp Ile Trp Gly Trp Arg Arg Trp
1               5

<210> SEQ ID NO 635
<211> LENGTH: 9
<212> TYPE: PRT
<213> ORGANISM: Artificial Sequence
<220> FEATURE:
<223> OTHER INFORMATION: Synthetic construct

<400> SEQUENCE: 635

Trp Ile Lys Arg Lys Trp Lys Met Arg
1               5

<210> SEQ ID NO 636
<211> LENGTH: 9
<212> TYPE: PRT
<213> ORGANISM: Artificial Sequence
<220> FEATURE:
<223> OTHER INFORMATION: Synthetic construct

<400> SEQUENCE: 636

Met Trp Lys Lys Val Leu Arg Arg Val
1               5

<210> SEQ ID NO 637
<211> LENGTH: 9
<212> TYPE: PRT
<213> ORGANISM: Artificial Sequence
<220> FEATURE:
<223> OTHER INFORMATION: Synthetic construct

<400> SEQUENCE: 637

Trp Arg Trp Arg Ile Phe His Trp Leu
1               5

<210> SEQ ID NO 638
<211> LENGTH: 9
<212> TYPE: PRT
<213> ORGANISM: Artificial Sequence
<220> FEATURE:
<223> OTHER INFORMATION: Synthetic construct

<400> SEQUENCE: 638

Lys Ile Gln Arg Trp Lys Gly Lys Arg
1               5
```

<210> SEQ ID NO 639
<211> LENGTH: 9
<212> TYPE: PRT
<213> ORGANISM: Artificial Sequence
<220> FEATURE:
<223> OTHER INFORMATION: Synthetic construct

<400> SEQUENCE: 639

Leu Trp Tyr Lys Tyr Trp Arg Trp Arg
1               5

<210> SEQ ID NO 640
<211> LENGTH: 9
<212> TYPE: PRT
<213> ORGANISM: Artificial Sequence
<220> FEATURE:
<223> OTHER INFORMATION: Synthetic construct

<400> SEQUENCE: 640

Tyr Val Arg Arg Ile Trp Lys Ile Thr
1               5

<210> SEQ ID NO 641
<211> LENGTH: 9
<212> TYPE: PRT
<213> ORGANISM: Artificial Sequence
<220> FEATURE:
<223> OTHER INFORMATION: Synthetic construct

<400> SEQUENCE: 641

Arg Trp Arg Gln Tyr Arg Ser Arg Trp
1               5

<210> SEQ ID NO 642
<211> LENGTH: 9
<212> TYPE: PRT
<213> ORGANISM: Artificial Sequence
<220> FEATURE:
<223> OTHER INFORMATION: Synthetic construct

<400> SEQUENCE: 642

Val Gly Arg Trp Lys Arg Arg Arg Trp
1               5

<210> SEQ ID NO 643
<211> LENGTH: 9
<212> TYPE: PRT
<213> ORGANISM: Artificial Sequence
<220> FEATURE:
<223> OTHER INFORMATION: Synthetic construct

<400> SEQUENCE: 643

Lys Ser Ser Arg Ile Tyr Ile Leu Phe
1               5

<210> SEQ ID NO 644
<211> LENGTH: 9
<212> TYPE: PRT
<213> ORGANISM: Artificial Sequence
<220> FEATURE:
<223> OTHER INFORMATION: Synthetic construct

<400> SEQUENCE: 644

Ala Lys Trp Trp Trp Tyr Arg Lys Ile
1               5

```
<210> SEQ ID NO 645
<211> LENGTH: 9
<212> TYPE: PRT
<213> ORGANISM: Artificial Sequence
<220> FEATURE:
<223> OTHER INFORMATION: Synthetic construct

<400> SEQUENCE: 645

Phe Tyr Trp Trp Arg Trp Phe Arg Val
1               5

<210> SEQ ID NO 646
<211> LENGTH: 9
<212> TYPE: PRT
<213> ORGANISM: Artificial Sequence
<220> FEATURE:
<223> OTHER INFORMATION: Synthetic construct

<400> SEQUENCE: 646

Arg Thr Arg Trp Leu Arg Tyr Arg Arg
1               5

<210> SEQ ID NO 647
<211> LENGTH: 9
<212> TYPE: PRT
<213> ORGANISM: Artificial Sequence
<220> FEATURE:
<223> OTHER INFORMATION: Synthetic construct

<400> SEQUENCE: 647

Trp Asn Ile Ile Trp Trp Ile Arg Arg
1               5

<210> SEQ ID NO 648
<211> LENGTH: 9
<212> TYPE: PRT
<213> ORGANISM: Artificial Sequence
<220> FEATURE:
<223> OTHER INFORMATION: Synthetic construct

<400> SEQUENCE: 648

Lys Arg Gly Phe Trp Trp Trp Arg Ile
1               5

<210> SEQ ID NO 649
<211> LENGTH: 9
<212> TYPE: PRT
<213> ORGANISM: Artificial Sequence
<220> FEATURE:
<223> OTHER INFORMATION: Synthetic construct

<400> SEQUENCE: 649

Arg Arg Arg Lys Lys Tyr Ile Ile Arg
1               5

<210> SEQ ID NO 650
<211> LENGTH: 9
<212> TYPE: PRT
<213> ORGANISM: Artificial Sequence
<220> FEATURE:
<223> OTHER INFORMATION: Synthetic construct

<400> SEQUENCE: 650

Val Trp Lys Val Gly Trp Tyr Tyr Arg
1               5

<210> SEQ ID NO 651
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 651

Leu Lys Phe Ser Thr Gly Arg Val Arg
1               5

<210> SEQ ID NO 652
<211> LENGTH: 9
<212> TYPE: PRT
<213> ORGANISM: Artificial Sequence
<220> FEATURE:
<223> OTHER INFORMATION: Synthetic construct

<400> SEQUENCE: 652

Arg Arg Val Trp Val Arg Arg Lys Arg
1               5

<210> SEQ ID NO 653
<211> LENGTH: 9
<212> TYPE: PRT
<213> ORGANISM: Artificial Sequence
<220> FEATURE:
<223> OTHER INFORMATION: Synthetic construct

<400> SEQUENCE: 653

Arg Phe Trp Tyr Met Trp Lys Tyr Val
1               5

<210> SEQ ID NO 654
<211> LENGTH: 9
<212> TYPE: PRT
<213> ORGANISM: Artificial Sequence
<220> FEATURE:
<223> OTHER INFORMATION: Synthetic construct

<400> SEQUENCE: 654

Trp Tyr Val Arg Trp Met Gly Arg Arg
1               5

<210> SEQ ID NO 655
<211> LENGTH: 9
<212> TYPE: PRT
<213> ORGANISM: Artificial Sequence
<220> FEATURE:
<223> OTHER INFORMATION: Synthetic construct

<400> SEQUENCE: 655

Trp Lys Arg Arg Met Arg Arg Arg Lys
1               5

<210> SEQ ID NO 656
<211> LENGTH: 9
<212> TYPE: PRT
<213> ORGANISM: Artificial Sequence
<220> FEATURE:
<223> OTHER INFORMATION: Synthetic construct

<400> SEQUENCE: 656

Arg Val Leu Arg Arg Val Ser Trp Val
1               5

<210> SEQ ID NO 657
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 657

Arg Arg Leu Arg Lys Lys Trp Gly Trp
1               5

<210> SEQ ID NO 658
<211> LENGTH: 9
<212> TYPE: PRT
<213> ORGANISM: Artificial Sequence
<220> FEATURE:
<223> OTHER INFORMATION: Synthetic construct

<400> SEQUENCE: 658

Trp Tyr Lys Lys Ile Arg Leu Ile Ile
1               5

<210> SEQ ID NO 659
<211> LENGTH: 9
<212> TYPE: PRT
<213> ORGANISM: Artificial Sequence
<220> FEATURE:
<223> OTHER INFORMATION: Synthetic construct

<400> SEQUENCE: 659

Ile Tyr Ile Ile Ile Trp Arg Thr Lys
1               5

<210> SEQ ID NO 660
<211> LENGTH: 9
<212> TYPE: PRT
<213> ORGANISM: Artificial Sequence
<220> FEATURE:
<223> OTHER INFORMATION: Synthetic construct

<400> SEQUENCE: 660

Thr Trp Arg Met Arg Val Lys Val Ser
1               5

<210> SEQ ID NO 661
<211> LENGTH: 9
<212> TYPE: PRT
<213> ORGANISM: Artificial Sequence
<220> FEATURE:
<223> OTHER INFORMATION: Synthetic construct

<400> SEQUENCE: 661

Ala Trp Trp Lys Ile Arg Trp Arg Ile
1               5

<210> SEQ ID NO 662
<211> LENGTH: 9
<212> TYPE: PRT
<213> ORGANISM: Artificial Sequence
<220> FEATURE:
<223> OTHER INFORMATION: Synthetic construct

<400> SEQUENCE: 662

Arg Val Arg Arg Tyr Arg Trp Ser Trp
1               5

<210> SEQ ID NO 663
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 663

Ile Trp Arg Ile Arg Arg Phe Arg Ile
1               5

<210> SEQ ID NO 664
<211> LENGTH: 9
<212> TYPE: PRT
<213> ORGANISM: Artificial Sequence
<220> FEATURE:
<223> OTHER INFORMATION: Synthetic construct

<400> SEQUENCE: 664

Lys Ile Arg Arg Lys Trp Trp Trp Phe
1               5

<210> SEQ ID NO 665
<211> LENGTH: 9
<212> TYPE: PRT
<213> ORGANISM: Artificial Sequence
<220> FEATURE:
<223> OTHER INFORMATION: Synthetic construct

<400> SEQUENCE: 665

Arg Arg Phe Trp Trp Ile Lys Ile Arg
1               5

<210> SEQ ID NO 666
<211> LENGTH: 9
<212> TYPE: PRT
<213> ORGANISM: Artificial Sequence
<220> FEATURE:
<223> OTHER INFORMATION: Synthetic construct

<400> SEQUENCE: 666

Trp Tyr Trp Trp Arg Val Arg Arg Val
1               5

<210> SEQ ID NO 667
<211> LENGTH: 9
<212> TYPE: PRT
<213> ORGANISM: Artificial Sequence
<220> FEATURE:
<223> OTHER INFORMATION: Synthetic construct

<400> SEQUENCE: 667

Trp Tyr Lys Leu Trp Arg Arg Lys Val
1               5

<210> SEQ ID NO 668
<211> LENGTH: 9
<212> TYPE: PRT
<213> ORGANISM: Artificial Sequence
<220> FEATURE:
<223> OTHER INFORMATION: Synthetic construct

<400> SEQUENCE: 668

Trp Trp Phe Ser Trp Arg Trp Arg Val
1               5

<210> SEQ ID NO 669
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 669

Arg Phe Lys Thr Arg Arg Gly Trp Arg
1               5

<210> SEQ ID NO 670
<211> LENGTH: 9
<212> TYPE: PRT
<213> ORGANISM: Artificial Sequence
<220> FEATURE:
<223> OTHER INFORMATION: Synthetic construct

<400> SEQUENCE: 670

Trp Ile Trp Ile Val Arg Arg Arg Val
1               5

<210> SEQ ID NO 671
<211> LENGTH: 9
<212> TYPE: PRT
<213> ORGANISM: Artificial Sequence
<220> FEATURE:
<223> OTHER INFORMATION: Synthetic construct

<400> SEQUENCE: 671

Arg Arg Phe Lys Lys Trp Met Tyr Trp
1               5

<210> SEQ ID NO 672
<211> LENGTH: 9
<212> TYPE: PRT
<213> ORGANISM: Artificial Sequence
<220> FEATURE:
<223> OTHER INFORMATION: Synthetic construct

<400> SEQUENCE: 672

Arg Trp Tyr Arg Val Ile Arg Trp Lys
1               5

<210> SEQ ID NO 673
<211> LENGTH: 9
<212> TYPE: PRT
<213> ORGANISM: Artificial Sequence
<220> FEATURE:
<223> OTHER INFORMATION: Synthetic construct

<400> SEQUENCE: 673

Tyr Arg Trp Met Val Arg Trp Val Arg
1               5

<210> SEQ ID NO 674
<211> LENGTH: 9
<212> TYPE: PRT
<213> ORGANISM: Artificial Sequence
<220> FEATURE:
<223> OTHER INFORMATION: Synthetic construct

<400> SEQUENCE: 674

Lys Val Arg Arg Tyr Asn Arg Arg Arg
1               5

<210> SEQ ID NO 675
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 675

Trp Phe Val Trp Asn Arg Arg Val Val
1               5

<210> SEQ ID NO 676
<211> LENGTH: 9
<212> TYPE: PRT
<213> ORGANISM: Artificial Sequence
<220> FEATURE:
<223> OTHER INFORMATION: Synthetic construct

<400> SEQUENCE: 676

Arg Trp Lys Trp Arg Trp Arg Trp Tyr
1               5

<210> SEQ ID NO 677
<211> LENGTH: 9
<212> TYPE: PRT
<213> ORGANISM: Artificial Sequence
<220> FEATURE:
<223> OTHER INFORMATION: Synthetic construct

<400> SEQUENCE: 677

Ala Arg Trp Arg Val Arg Lys Trp Trp
1               5

<210> SEQ ID NO 678
<211> LENGTH: 9
<212> TYPE: PRT
<213> ORGANISM: Artificial Sequence
<220> FEATURE:
<223> OTHER INFORMATION: Synthetic construct

<400> SEQUENCE: 678

Lys Ile Lys Phe Trp Ile Ile Arg Arg
1               5

<210> SEQ ID NO 679
<211> LENGTH: 9
<212> TYPE: PRT
<213> ORGANISM: Artificial Sequence
<220> FEATURE:
<223> OTHER INFORMATION: Synthetic construct

<400> SEQUENCE: 679

Trp Tyr Trp Arg Val Arg Leu Gln Trp
1               5

<210> SEQ ID NO 680
<211> LENGTH: 9
<212> TYPE: PRT
<213> ORGANISM: Artificial Sequence
<220> FEATURE:
<223> OTHER INFORMATION: Synthetic construct

<400> SEQUENCE: 680

Tyr Trp Trp Trp Lys Arg Arg Arg Arg
1               5

<210> SEQ ID NO 681
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 681

Phe Ile Lys Arg Val Arg Arg Arg Trp
1               5

<210> SEQ ID NO 682
<211> LENGTH: 9
<212> TYPE: PRT
<213> ORGANISM: Artificial Sequence
<220> FEATURE:
<223> OTHER INFORMATION: Synthetic construct

<400> SEQUENCE: 682

Val Ser Val Val Phe Arg Arg Arg Tyr
1               5

<210> SEQ ID NO 683
<211> LENGTH: 9
<212> TYPE: PRT
<213> ORGANISM: Artificial Sequence
<220> FEATURE:
<223> OTHER INFORMATION: Synthetic construct

<400> SEQUENCE: 683

Lys Phe Arg Val Met Val Arg Val Leu
1               5

<210> SEQ ID NO 684
<211> LENGTH: 9
<212> TYPE: PRT
<213> ORGANISM: Artificial Sequence
<220> FEATURE:
<223> OTHER INFORMATION: Synthetic construct

<400> SEQUENCE: 684

Trp Met Tyr Tyr Lys Arg Arg Arg Arg
1               5

<210> SEQ ID NO 685
<211> LENGTH: 9
<212> TYPE: PRT
<213> ORGANISM: Artificial Sequence
<220> FEATURE:
<223> OTHER INFORMATION: Synthetic construct

<400> SEQUENCE: 685

Ile Trp Ile Trp Trp Arg Trp Arg Trp
1               5

<210> SEQ ID NO 686
<211> LENGTH: 9
<212> TYPE: PRT
<213> ORGANISM: Artificial Sequence
<220> FEATURE:
<223> OTHER INFORMATION: Synthetic construct

<400> SEQUENCE: 686

Trp Lys Lys Lys Lys Ile Ile Arg Val
1               5

<210> SEQ ID NO 687
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 687

Arg Arg Gly Trp Arg Arg Arg Arg
1               5

<210> SEQ ID NO 688
<211> LENGTH: 9
<212> TYPE: PRT
<213> ORGANISM: Artificial Sequence
<220> FEATURE:
<223> OTHER INFORMATION: Synthetic construct

<400> SEQUENCE: 688

Trp Arg Trp Arg Lys Ile Trp Lys Trp
1               5

<210> SEQ ID NO 689
<211> LENGTH: 9
<212> TYPE: PRT
<213> ORGANISM: Artificial Sequence
<220> FEATURE:
<223> OTHER INFORMATION: Synthetic construct

<400> SEQUENCE: 689

Trp Trp Arg Trp Lys Arg Arg Ile Ile
1               5

<210> SEQ ID NO 690
<211> LENGTH: 9
<212> TYPE: PRT
<213> ORGANISM: Artificial Sequence
<220> FEATURE:
<223> OTHER INFORMATION: Synthetic construct

<400> SEQUENCE: 690

Trp Lys Val Arg Trp Lys Ile Arg Arg
1               5

<210> SEQ ID NO 691
<211> LENGTH: 9
<212> TYPE: PRT
<213> ORGANISM: Artificial Sequence
<220> FEATURE:
<223> OTHER INFORMATION: Synthetic construct

<400> SEQUENCE: 691

Arg Phe Trp Val Arg Gly Arg Arg Ser
1               5

<210> SEQ ID NO 692
<211> LENGTH: 9
<212> TYPE: PRT
<213> ORGANISM: Artificial Sequence
<220> FEATURE:
<223> OTHER INFORMATION: Synthetic construct

<400> SEQUENCE: 692

Arg Arg Trp Val Leu Trp Arg Arg Arg
1               5

<210> SEQ ID NO 693
<211> LENGTH: 9
<212> TYPE: PRT
<213> ORGANISM: Artificial Sequence
<220> FEATURE:
<223> OTHER INFORMATION: Synthetic construct

<400> SEQUENCE: 693
```

```
Lys Tyr Ile Trp Lys Lys Arg Arg Tyr
1               5
```

<210> SEQ ID NO 694
<211> LENGTH: 9
<212> TYPE: PRT
<213> ORGANISM: Artificial Sequence
<220> FEATURE:
<223> OTHER INFORMATION: Synthetic construct

<400> SEQUENCE: 694

```
Lys Trp Gln Trp Ile Arg Lys Ile Arg
1               5
```

<210> SEQ ID NO 695
<211> LENGTH: 9
<212> TYPE: PRT
<213> ORGANISM: Artificial Sequence
<220> FEATURE:
<223> OTHER INFORMATION: Synthetic construct

<400> SEQUENCE: 695

```
Tyr Trp Ile Arg Arg Arg Trp Arg Leu
1               5
```

<210> SEQ ID NO 696
<211> LENGTH: 9
<212> TYPE: PRT
<213> ORGANISM: Artificial Sequence
<220> FEATURE:
<223> OTHER INFORMATION: Synthetic construct

<400> SEQUENCE: 696

```
Arg Val Lys Trp Ile Lys Trp Leu His
1               5
```

<210> SEQ ID NO 697
<211> LENGTH: 9
<212> TYPE: PRT
<213> ORGANISM: Artificial Sequence
<220> FEATURE:
<223> OTHER INFORMATION: Synthetic construct

<400> SEQUENCE: 697

```
Tyr Val Arg Gln Trp Lys Lys Arg Arg
1               5
```

<210> SEQ ID NO 698
<211> LENGTH: 9
<212> TYPE: PRT
<213> ORGANISM: Artificial Sequence
<220> FEATURE:
<223> OTHER INFORMATION: Synthetic construct

<400> SEQUENCE: 698

```
Trp Lys Ile Val Gly Val Phe Arg Val
1               5
```

<210> SEQ ID NO 699
<211> LENGTH: 9
<212> TYPE: PRT
<213> ORGANISM: Artificial Sequence
<220> FEATURE:
<223> OTHER INFORMATION: Synthetic construct

<400> SEQUENCE: 699

```
Val Ile Lys Tyr Val Arg Met Trp Trp
1               5

<210> SEQ ID NO 700
<211> LENGTH: 9
<212> TYPE: PRT
<213> ORGANISM: Artificial Sequence
<220> FEATURE:
<223> OTHER INFORMATION: Synthetic construct

<400> SEQUENCE: 700

Arg Arg Arg Arg Val Trp Arg Val Arg
1               5

<210> SEQ ID NO 701
<211> LENGTH: 9
<212> TYPE: PRT
<213> ORGANISM: Artificial Sequence
<220> FEATURE:
<223> OTHER INFORMATION: Synthetic construct

<400> SEQUENCE: 701

Arg Arg Arg Lys Ile Arg Val Tyr Arg
1               5

<210> SEQ ID NO 702
<211> LENGTH: 9
<212> TYPE: PRT
<213> ORGANISM: Artificial Sequence
<220> FEATURE:
<223> OTHER INFORMATION: Synthetic construct

<400> SEQUENCE: 702

Arg Arg Asn Arg Trp Arg Arg Ile Arg
1               5

<210> SEQ ID NO 703
<211> LENGTH: 9
<212> TYPE: PRT
<213> ORGANISM: Artificial Sequence
<220> FEATURE:
<223> OTHER INFORMATION: Synthetic construct

<400> SEQUENCE: 703

Ile Arg Lys Trp Ile Trp Arg Arg Val
1               5

<210> SEQ ID NO 704
<211> LENGTH: 9
<212> TYPE: PRT
<213> ORGANISM: Artificial Sequence
<220> FEATURE:
<223> OTHER INFORMATION: Synthetic construct

<400> SEQUENCE: 704

Gln Arg Trp Arg Val Arg Arg Arg Tyr
1               5

<210> SEQ ID NO 705
<211> LENGTH: 9
<212> TYPE: PRT
<213> ORGANISM: Artificial Sequence
<220> FEATURE:
<223> OTHER INFORMATION: Synthetic construct

<400> SEQUENCE: 705

Trp Trp Met Ile Ile Lys Ile Arg Asn
```

```
1               5

<210> SEQ ID NO 706
<211> LENGTH: 9
<212> TYPE: PRT
<213> ORGANISM: Artificial Sequence
<220> FEATURE:
<223> OTHER INFORMATION: Synthetic construct

<400> SEQUENCE: 706

Ala Arg Arg Arg Gly Arg Arg Val Met
1               5

<210> SEQ ID NO 707
<211> LENGTH: 9
<212> TYPE: PRT
<213> ORGANISM: Artificial Sequence
<220> FEATURE:
<223> OTHER INFORMATION: Synthetic construct

<400> SEQUENCE: 707

Arg Arg Trp His Trp Arg Lys Arg Lys
1               5

<210> SEQ ID NO 708
<211> LENGTH: 9
<212> TYPE: PRT
<213> ORGANISM: Artificial Sequence
<220> FEATURE:
<223> OTHER INFORMATION: Synthetic construct

<400> SEQUENCE: 708

Lys Arg Phe Leu Arg Lys Arg Arg Phe
1               5

<210> SEQ ID NO 709
<211> LENGTH: 9
<212> TYPE: PRT
<213> ORGANISM: Artificial Sequence
<220> FEATURE:
<223> OTHER INFORMATION: Synthetic construct

<400> SEQUENCE: 709

Arg Trp Lys Gly Trp Tyr Leu Arg Thr
1               5

<210> SEQ ID NO 710
<211> LENGTH: 9
<212> TYPE: PRT
<213> ORGANISM: Artificial Sequence
<220> FEATURE:
<223> OTHER INFORMATION: Synthetic construct

<400> SEQUENCE: 710

Trp Ser Trp Arg Gly Arg Arg Lys Phe
1               5

<210> SEQ ID NO 711
<211> LENGTH: 9
<212> TYPE: PRT
<213> ORGANISM: Artificial Sequence
<220> FEATURE:
<223> OTHER INFORMATION: Synthetic construct

<400> SEQUENCE: 711

Lys Ile Ile Met Lys Arg Arg Arg Trp
1               5
```

```
<210> SEQ ID NO 712
<211> LENGTH: 9
<212> TYPE: PRT
<213> ORGANISM: Artificial Sequence
<220> FEATURE:
<223> OTHER INFORMATION: Synthetic construct

<400> SEQUENCE: 712

Val Trp Lys Arg Phe Leu His Trp Arg
1               5

<210> SEQ ID NO 713
<211> LENGTH: 9
<212> TYPE: PRT
<213> ORGANISM: Artificial Sequence
<220> FEATURE:
<223> OTHER INFORMATION: Synthetic construct

<400> SEQUENCE: 713

Arg Leu Lys Arg Arg Lys Lys Trp Arg
1               5

<210> SEQ ID NO 714
<211> LENGTH: 9
<212> TYPE: PRT
<213> ORGANISM: Artificial Sequence
<220> FEATURE:
<223> OTHER INFORMATION: Synthetic construct

<400> SEQUENCE: 714

Ala Val Arg Lys Phe Arg Arg Val Thr
1               5

<210> SEQ ID NO 715
<211> LENGTH: 9
<212> TYPE: PRT
<213> ORGANISM: Artificial Sequence
<220> FEATURE:
<223> OTHER INFORMATION: Synthetic construct

<400> SEQUENCE: 715

Ile Lys Gln Arg Phe Trp Trp Arg Thr
1               5

<210> SEQ ID NO 716
<211> LENGTH: 9
<212> TYPE: PRT
<213> ORGANISM: Artificial Sequence
<220> FEATURE:
<223> OTHER INFORMATION: Synthetic construct

<400> SEQUENCE: 716

Trp Lys Ile Val Val Trp Ile Ile Lys
1               5

<210> SEQ ID NO 717
<211> LENGTH: 9
<212> TYPE: PRT
<213> ORGANISM: Artificial Sequence
<220> FEATURE:
<223> OTHER INFORMATION: Synthetic construct

<400> SEQUENCE: 717

Leu Tyr Arg Trp Ile Val Trp Lys Arg
1               5
```

<210> SEQ ID NO 718
<211> LENGTH: 9
<212> TYPE: PRT
<213> ORGANISM: Artificial Sequence
<220> FEATURE:
<223> OTHER INFORMATION: Synthetic construct

<400> SEQUENCE: 718

Trp Trp Trp Arg Trp Arg Ile Arg Lys
1               5

<210> SEQ ID NO 719
<211> LENGTH: 9
<212> TYPE: PRT
<213> ORGANISM: Artificial Sequence
<220> FEATURE:
<223> OTHER INFORMATION: Synthetic construct

<400> SEQUENCE: 719

Arg Leu Trp Arg Lys Trp Gln Trp Asn
1               5

<210> SEQ ID NO 720
<211> LENGTH: 9
<212> TYPE: PRT
<213> ORGANISM: Artificial Sequence
<220> FEATURE:
<223> OTHER INFORMATION: Synthetic construct

<400> SEQUENCE: 720

Arg Val Lys Leu Arg Trp Gly Trp Arg
1               5

<210> SEQ ID NO 721
<211> LENGTH: 9
<212> TYPE: PRT
<213> ORGANISM: Artificial Sequence
<220> FEATURE:
<223> OTHER INFORMATION: Synthetic construct

<400> SEQUENCE: 721

Ala Trp Arg Tyr Lys Arg Arg Ile Phe
1               5

<210> SEQ ID NO 722
<211> LENGTH: 9
<212> TYPE: PRT
<213> ORGANISM: Artificial Sequence
<220> FEATURE:
<223> OTHER INFORMATION: Synthetic construct

<400> SEQUENCE: 722

Lys Arg Trp Gln Ile Arg Gly Ile Thr
1               5

<210> SEQ ID NO 723
<211> LENGTH: 9
<212> TYPE: PRT
<213> ORGANISM: Artificial Sequence
<220> FEATURE:
<223> OTHER INFORMATION: Synthetic construct

<400> SEQUENCE: 723

Lys Arg Trp Arg Trp Arg Trp Arg Trp
1               5

```
<210> SEQ ID NO 724
<211> LENGTH: 9
<212> TYPE: PRT
<213> ORGANISM: Artificial Sequence
<220> FEATURE:
<223> OTHER INFORMATION: Synthetic construct

<400> SEQUENCE: 724

Lys Arg Trp Val Tyr Lys Tyr Arg Val
1               5

<210> SEQ ID NO 725
<211> LENGTH: 9
<212> TYPE: PRT
<213> ORGANISM: Artificial Sequence
<220> FEATURE:
<223> OTHER INFORMATION: Synthetic construct

<400> SEQUENCE: 725

Val His Trp Arg Trp Arg Phe Trp Lys
1               5

<210> SEQ ID NO 726
<211> LENGTH: 9
<212> TYPE: PRT
<213> ORGANISM: Artificial Sequence
<220> FEATURE:
<223> OTHER INFORMATION: Synthetic construct

<400> SEQUENCE: 726

Phe Val Gly Lys Thr Lys Arg Lys Arg
1               5

<210> SEQ ID NO 727
<211> LENGTH: 9
<212> TYPE: PRT
<213> ORGANISM: Artificial Sequence
<220> FEATURE:
<223> OTHER INFORMATION: Synthetic construct

<400> SEQUENCE: 727

Arg Leu Arg Phe Gly Trp Phe Leu Phe
1               5

<210> SEQ ID NO 728
<211> LENGTH: 9
<212> TYPE: PRT
<213> ORGANISM: Artificial Sequence
<220> FEATURE:
<223> OTHER INFORMATION: Synthetic construct

<400> SEQUENCE: 728

Ala Lys Arg Trp Ile Trp Ile Gln Val
1               5

<210> SEQ ID NO 729
<211> LENGTH: 9
<212> TYPE: PRT
<213> ORGANISM: Artificial Sequence
<220> FEATURE:
<223> OTHER INFORMATION: Synthetic construct

<400> SEQUENCE: 729

Arg Lys Tyr Val Arg Arg Trp Val Tyr
1               5

<210> SEQ ID NO 730
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 730

Tyr Arg Val Tyr Trp Trp Trp Trp Arg
1               5

<210> SEQ ID NO 731
<211> LENGTH: 9
<212> TYPE: PRT
<213> ORGANISM: Artificial Sequence
<220> FEATURE:
<223> OTHER INFORMATION: Synthetic construct

<400> SEQUENCE: 731

Lys Arg Arg Lys Lys Arg Arg Val Arg
1               5

<210> SEQ ID NO 732
<211> LENGTH: 9
<212> TYPE: PRT
<213> ORGANISM: Artificial Sequence
<220> FEATURE:
<223> OTHER INFORMATION: Synthetic construct

<400> SEQUENCE: 732

Lys Lys Val Arg Phe Thr Ile Thr Trp
1               5

<210> SEQ ID NO 733
<211> LENGTH: 9
<212> TYPE: PRT
<213> ORGANISM: Artificial Sequence
<220> FEATURE:
<223> OTHER INFORMATION: Synthetic construct

<400> SEQUENCE: 733

Lys Leu Trp Tyr Trp Lys Lys Val Val
1               5

<210> SEQ ID NO 734
<211> LENGTH: 9
<212> TYPE: PRT
<213> ORGANISM: Artificial Sequence
<220> FEATURE:
<223> OTHER INFORMATION: Synthetic construct

<400> SEQUENCE: 734

Trp Arg Trp Gly Leu Arg Trp Trp Gln
1               5

<210> SEQ ID NO 735
<211> LENGTH: 9
<212> TYPE: PRT
<213> ORGANISM: Artificial Sequence
<220> FEATURE:
<223> OTHER INFORMATION: Synthetic construct

<400> SEQUENCE: 735

Ala Phe Phe Tyr Arg Trp Trp Ile Arg
1               5

<210> SEQ ID NO 736
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 736

Trp Tyr Trp Arg Arg Arg Arg Leu Lys
1               5

<210> SEQ ID NO 737
<211> LENGTH: 9
<212> TYPE: PRT
<213> ORGANISM: Artificial Sequence
<220> FEATURE:
<223> OTHER INFORMATION: Synthetic construct

<400> SEQUENCE: 737

Tyr Lys Phe Arg Trp Arg Ile Tyr Ile
1               5

<210> SEQ ID NO 738
<211> LENGTH: 9
<212> TYPE: PRT
<213> ORGANISM: Artificial Sequence
<220> FEATURE:
<223> OTHER INFORMATION: Synthetic construct

<400> SEQUENCE: 738

Trp Leu Arg Lys Val Trp Asn Trp Arg
1               5

<210> SEQ ID NO 739
<211> LENGTH: 9
<212> TYPE: PRT
<213> ORGANISM: Artificial Sequence
<220> FEATURE:
<223> OTHER INFORMATION: Synthetic construct

<400> SEQUENCE: 739

Arg Val Arg Phe Lys Val Tyr Arg Val
1               5

<210> SEQ ID NO 740
<211> LENGTH: 9
<212> TYPE: PRT
<213> ORGANISM: Artificial Sequence
<220> FEATURE:
<223> OTHER INFORMATION: Synthetic construct

<400> SEQUENCE: 740

Arg Trp Leu Ser Lys Ile Trp Lys Val
1               5

<210> SEQ ID NO 741
<211> LENGTH: 9
<212> TYPE: PRT
<213> ORGANISM: Artificial Sequence
<220> FEATURE:
<223> OTHER INFORMATION: Synthetic construct

<400> SEQUENCE: 741

Arg Arg Arg Leu Gly Trp Arg Arg Gly
1               5

<210> SEQ ID NO 742
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 742

Lys Lys Trp Gly Gly Gly Leu Val Lys
1               5

<210> SEQ ID NO 743
<211> LENGTH: 9
<212> TYPE: PRT
<213> ORGANISM: Artificial Sequence
<220> FEATURE:
<223> OTHER INFORMATION: Synthetic construct

<400> SEQUENCE: 743

Tyr Trp Trp Leu Trp Arg Lys Lys Arg
1               5

<210> SEQ ID NO 744
<211> LENGTH: 9
<212> TYPE: PRT
<213> ORGANISM: Artificial Sequence
<220> FEATURE:
<223> OTHER INFORMATION: Synthetic construct

<400> SEQUENCE: 744

Trp Ile Arg Leu Trp Val Lys Trp Arg
1               5

<210> SEQ ID NO 745
<211> LENGTH: 9
<212> TYPE: PRT
<213> ORGANISM: Artificial Sequence
<220> FEATURE:
<223> OTHER INFORMATION: Synthetic construct

<400> SEQUENCE: 745

Gly Arg Arg Ser Thr His Trp Arg Ile
1               5

<210> SEQ ID NO 746
<211> LENGTH: 9
<212> TYPE: PRT
<213> ORGANISM: Artificial Sequence
<220> FEATURE:
<223> OTHER INFORMATION: Synthetic construct

<400> SEQUENCE: 746

Lys Lys Lys Leu Phe Ile Asn Thr Trp
1               5

<210> SEQ ID NO 747
<211> LENGTH: 9
<212> TYPE: PRT
<213> ORGANISM: Artificial Sequence
<220> FEATURE:
<223> OTHER INFORMATION: Synthetic construct

<400> SEQUENCE: 747

Val Tyr Arg Arg Arg Val Lys Gly
1               5

<210> SEQ ID NO 748
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 748

Lys Gly Trp Ile Ile Trp Lys Ile Val
1               5

<210> SEQ ID NO 749
<211> LENGTH: 9
<212> TYPE: PRT
<213> ORGANISM: Artificial Sequence
<220> FEATURE:
<223> OTHER INFORMATION: Synthetic construct

<400> SEQUENCE: 749

Val Phe His Arg Ile Arg Arg Ile Lys
1               5

<210> SEQ ID NO 750
<211> LENGTH: 9
<212> TYPE: PRT
<213> ORGANISM: Artificial Sequence
<220> FEATURE:
<223> OTHER INFORMATION: Synthetic construct

<400> SEQUENCE: 750

Arg Leu Arg Leu Trp Lys Ser Lys Arg
1               5

<210> SEQ ID NO 751
<211> LENGTH: 9
<212> TYPE: PRT
<213> ORGANISM: Artificial Sequence
<220> FEATURE:
<223> OTHER INFORMATION: Synthetic construct

<400> SEQUENCE: 751

Arg Arg Lys Val Phe Lys Leu Arg Arg
1               5

<210> SEQ ID NO 752
<211> LENGTH: 9
<212> TYPE: PRT
<213> ORGANISM: Artificial Sequence
<220> FEATURE:
<223> OTHER INFORMATION: Synthetic construct

<400> SEQUENCE: 752

Val Trp Leu Lys Val Tyr Trp Phe Lys
1               5

<210> SEQ ID NO 753
<211> LENGTH: 9
<212> TYPE: PRT
<213> ORGANISM: Artificial Sequence
<220> FEATURE:
<223> OTHER INFORMATION: Synthetic construct

<400> SEQUENCE: 753

Val Arg Trp Gly Arg Arg Arg Trp Val
1               5

<210> SEQ ID NO 754
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 754

Arg Tyr Asn Trp Val Arg Arg Lys Lys
1               5

<210> SEQ ID NO 755
<211> LENGTH: 9
<212> TYPE: PRT
<213> ORGANISM: Artificial Sequence
<220> FEATURE:
<223> OTHER INFORMATION: Synthetic construct

<400> SEQUENCE: 755

Lys Ile Arg Trp Arg Lys Tyr His Leu
1               5

<210> SEQ ID NO 756
<211> LENGTH: 9
<212> TYPE: PRT
<213> ORGANISM: Artificial Sequence
<220> FEATURE:
<223> OTHER INFORMATION: Synthetic construct

<400> SEQUENCE: 756

Val Ile Trp Arg Trp Arg Lys Phe Tyr
1               5

<210> SEQ ID NO 757
<211> LENGTH: 9
<212> TYPE: PRT
<213> ORGANISM: Artificial Sequence
<220> FEATURE:
<223> OTHER INFORMATION: Synthetic construct

<400> SEQUENCE: 757

Arg Arg Trp Trp Lys Trp Trp Trp Arg
1               5

<210> SEQ ID NO 758
<211> LENGTH: 9
<212> TYPE: PRT
<213> ORGANISM: Artificial Sequence
<220> FEATURE:
<223> OTHER INFORMATION: Synthetic construct

<400> SEQUENCE: 758

Trp Arg Val Lys Gly Lys Arg Ser Lys
1               5

<210> SEQ ID NO 759
<211> LENGTH: 9
<212> TYPE: PRT
<213> ORGANISM: Artificial Sequence
<220> FEATURE:
<223> OTHER INFORMATION: Synthetic construct

<400> SEQUENCE: 759

Arg Trp Arg Thr Arg Arg Asn Ile Val
1               5

<210> SEQ ID NO 760
<211> LENGTH: 9
<212> TYPE: PRT
<213> ORGANISM: Artificial Sequence
<220> FEATURE:
<223> OTHER INFORMATION: Synthetic construct

<400> SEQUENCE: 760

Trp Trp Phe Ser Ile Arg Leu Trp Arg
1               5

<210> SEQ ID NO 761
<211> LENGTH: 9
<212> TYPE: PRT
<213> ORGANISM: Artificial Sequence
<220> FEATURE:
<223> OTHER INFORMATION: Synthetic construct

<400> SEQUENCE: 761

Tyr Thr Trp Tyr Ile Lys Lys Lys Arg
1               5

<210> SEQ ID NO 762
<211> LENGTH: 9
<212> TYPE: PRT
<213> ORGANISM: Artificial Sequence
<220> FEATURE:
<223> OTHER INFORMATION: Synthetic construct

<400> SEQUENCE: 762

Val Trp Arg Arg Lys Lys Tyr Trp Arg
1               5

<210> SEQ ID NO 763
<211> LENGTH: 9
<212> TYPE: PRT
<213> ORGANISM: Artificial Sequence
<220> FEATURE:
<223> OTHER INFORMATION: Synthetic construct

<400> SEQUENCE: 763

Tyr Leu Thr Arg Phe Val Lys Tyr Phe
1               5

<210> SEQ ID NO 764
<211> LENGTH: 9
<212> TYPE: PRT
<213> ORGANISM: Artificial Sequence
<220> FEATURE:
<223> OTHER INFORMATION: Synthetic construct

<400> SEQUENCE: 764

Lys Arg Trp Lys His Ile Arg Arg Ile
1               5

<210> SEQ ID NO 765
<211> LENGTH: 9
<212> TYPE: PRT
<213> ORGANISM: Artificial Sequence
<220> FEATURE:
<223> OTHER INFORMATION: Synthetic construct

<400> SEQUENCE: 765

Trp Ile Val Trp Ile Arg Lys Arg Ile
1               5

<210> SEQ ID NO 766
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 766

Arg Arg Trp Val Ile Arg Ile Tyr Lys
1               5

<210> SEQ ID NO 767
<211> LENGTH: 9
<212> TYPE: PRT
<213> ORGANISM: Artificial Sequence
<220> FEATURE:
<223> OTHER INFORMATION: Synthetic construct

<400> SEQUENCE: 767

Trp Phe Trp Arg Arg Lys Met Ile Arg
1               5

<210> SEQ ID NO 768
<211> LENGTH: 9
<212> TYPE: PRT
<213> ORGANISM: Artificial Sequence
<220> FEATURE:
<223> OTHER INFORMATION: Synthetic construct

<400> SEQUENCE: 768

Arg Tyr Arg Arg Trp Val Arg Lys Arg
1               5

<210> SEQ ID NO 769
<211> LENGTH: 9
<212> TYPE: PRT
<213> ORGANISM: Artificial Sequence
<220> FEATURE:
<223> OTHER INFORMATION: Synthetic construct

<400> SEQUENCE: 769

Arg Lys Trp Trp Trp Lys Trp Arg Arg
1               5

<210> SEQ ID NO 770
<211> LENGTH: 9
<212> TYPE: PRT
<213> ORGANISM: Artificial Sequence
<220> FEATURE:
<223> OTHER INFORMATION: Synthetic construct

<400> SEQUENCE: 770

Arg Ile Trp Met Phe Lys Ile Phe Arg
1               5

<210> SEQ ID NO 771
<211> LENGTH: 9
<212> TYPE: PRT
<213> ORGANISM: Artificial Sequence
<220> FEATURE:
<223> OTHER INFORMATION: Synthetic construct

<400> SEQUENCE: 771

Ile Val Arg Val Gly Ile Phe Arg Leu
1               5

<210> SEQ ID NO 772
<211> LENGTH: 9
<212> TYPE: PRT
<213> ORGANISM: Artificial Sequence
<220> FEATURE:
<223> OTHER INFORMATION: Synthetic construct

<400> SEQUENCE: 772
```

```
Ile Ile Arg Leu Ile Lys Trp Trp Arg
1               5

<210> SEQ ID NO 773
<211> LENGTH: 9
<212> TYPE: PRT
<213> ORGANISM: Artificial Sequence
<220> FEATURE:
<223> OTHER INFORMATION: Synthetic construct

<400> SEQUENCE: 773

Trp Val Arg Arg Tyr Gln Met Arg Arg
1               5

<210> SEQ ID NO 774
<211> LENGTH: 9
<212> TYPE: PRT
<213> ORGANISM: Artificial Sequence
<220> FEATURE:
<223> OTHER INFORMATION: Synthetic construct

<400> SEQUENCE: 774

Trp Gln Val Val Met Arg Tyr Arg Arg
1               5

<210> SEQ ID NO 775
<211> LENGTH: 9
<212> TYPE: PRT
<213> ORGANISM: Artificial Sequence
<220> FEATURE:
<223> OTHER INFORMATION: Synthetic construct

<400> SEQUENCE: 775

Lys Lys Trp Lys Val Trp Arg Phe Gly
1               5

<210> SEQ ID NO 776
<211> LENGTH: 9
<212> TYPE: PRT
<213> ORGANISM: Artificial Sequence
<220> FEATURE:
<223> OTHER INFORMATION: Synthetic construct

<400> SEQUENCE: 776

Trp Arg Tyr Trp Trp Thr Arg Arg Ile
1               5

<210> SEQ ID NO 777
<211> LENGTH: 9
<212> TYPE: PRT
<213> ORGANISM: Artificial Sequence
<220> FEATURE:
<223> OTHER INFORMATION: Synthetic construct

<400> SEQUENCE: 777

Arg Ile Arg Lys Gly Trp Lys Trp Gly
1               5

<210> SEQ ID NO 778
<211> LENGTH: 9
<212> TYPE: PRT
<213> ORGANISM: Artificial Sequence
<220> FEATURE:
<223> OTHER INFORMATION: Synthetic construct

<400> SEQUENCE: 778
```

```
Lys Lys Arg Arg Gly Asn Arg Val Arg
1               5

<210> SEQ ID NO 779
<211> LENGTH: 9
<212> TYPE: PRT
<213> ORGANISM: Artificial Sequence
<220> FEATURE:
<223> OTHER INFORMATION: Synthetic construct

<400> SEQUENCE: 779

Val Met Arg Lys Leu Arg Arg Arg Trp
1               5

<210> SEQ ID NO 780
<211> LENGTH: 9
<212> TYPE: PRT
<213> ORGANISM: Artificial Sequence
<220> FEATURE:
<223> OTHER INFORMATION: Synthetic construct

<400> SEQUENCE: 780

Arg Asn Arg Thr His Trp Trp Arg Lys
1               5

<210> SEQ ID NO 781
<211> LENGTH: 9
<212> TYPE: PRT
<213> ORGANISM: Artificial Sequence
<220> FEATURE:
<223> OTHER INFORMATION: Synthetic construct

<400> SEQUENCE: 781

Arg Phe Thr Trp Trp Trp Arg Lys Phe
1               5

<210> SEQ ID NO 782
<211> LENGTH: 9
<212> TYPE: PRT
<213> ORGANISM: Artificial Sequence
<220> FEATURE:
<223> OTHER INFORMATION: Synthetic construct

<400> SEQUENCE: 782

Lys Arg Ile Arg Tyr Lys Arg Trp His
1               5

<210> SEQ ID NO 783
<211> LENGTH: 9
<212> TYPE: PRT
<213> ORGANISM: Artificial Sequence
<220> FEATURE:
<223> OTHER INFORMATION: Synthetic construct

<400> SEQUENCE: 783

Arg Trp Arg Arg Tyr Gly Arg Val Tyr
1               5

<210> SEQ ID NO 784
<211> LENGTH: 9
<212> TYPE: PRT
<213> ORGANISM: Artificial Sequence
<220> FEATURE:
<223> OTHER INFORMATION: Synthetic construct

<400> SEQUENCE: 784

Thr Val Val Lys Lys Arg Val Lys Lys
```

```
1               5

<210> SEQ ID NO 785
<211> LENGTH: 9
<212> TYPE: PRT
<213> ORGANISM: Artificial Sequence
<220> FEATURE:
<223> OTHER INFORMATION: Synthetic construct

<400> SEQUENCE: 785

Arg Lys Tyr Arg Arg Arg Tyr Arg Arg
1               5

<210> SEQ ID NO 786
<211> LENGTH: 9
<212> TYPE: PRT
<213> ORGANISM: Artificial Sequence
<220> FEATURE:
<223> OTHER INFORMATION: Synthetic construct

<400> SEQUENCE: 786

Tyr Phe Arg Trp Trp Lys Arg Trp Ile
1               5

<210> SEQ ID NO 787
<211> LENGTH: 9
<212> TYPE: PRT
<213> ORGANISM: Artificial Sequence
<220> FEATURE:
<223> OTHER INFORMATION: Synthetic construct

<400> SEQUENCE: 787

Trp Trp Gln Trp Ile Val Trp Arg Lys
1               5

<210> SEQ ID NO 788
<211> LENGTH: 9
<212> TYPE: PRT
<213> ORGANISM: Artificial Sequence
<220> FEATURE:
<223> OTHER INFORMATION: Synthetic construct

<400> SEQUENCE: 788

Arg Lys Arg Leu Tyr Arg Trp Ile Lys
1               5

<210> SEQ ID NO 789
<211> LENGTH: 9
<212> TYPE: PRT
<213> ORGANISM: Artificial Sequence
<220> FEATURE:
<223> OTHER INFORMATION: Synthetic construct

<400> SEQUENCE: 789

Gly Trp Trp Lys Asn Trp Arg Trp Trp
1               5

<210> SEQ ID NO 790
<211> LENGTH: 9
<212> TYPE: PRT
<213> ORGANISM: Artificial Sequence
<220> FEATURE:
<223> OTHER INFORMATION: Synthetic construct

<400> SEQUENCE: 790

Lys Trp Trp Trp Tyr Trp Tyr Arg Arg
1               5
```

<210> SEQ ID NO 791
<211> LENGTH: 9
<212> TYPE: PRT
<213> ORGANISM: Artificial Sequence
<220> FEATURE:
<223> OTHER INFORMATION: Synthetic construct

<400> SEQUENCE: 791

Arg Phe Lys Trp Phe Ile Arg Arg Phe
1               5

<210> SEQ ID NO 792
<211> LENGTH: 9
<212> TYPE: PRT
<213> ORGANISM: Artificial Sequence
<220> FEATURE:
<223> OTHER INFORMATION: Synthetic construct

<400> SEQUENCE: 792

Arg Ile Arg Arg Leu Trp Asn Ile Val
1               5

<210> SEQ ID NO 793
<211> LENGTH: 9
<212> TYPE: PRT
<213> ORGANISM: Artificial Sequence
<220> FEATURE:
<223> OTHER INFORMATION: Synthetic construct

<400> SEQUENCE: 793

Ala Arg Trp Met Trp Arg Arg Trp Arg
1               5

<210> SEQ ID NO 794
<211> LENGTH: 9
<212> TYPE: PRT
<213> ORGANISM: Artificial Sequence
<220> FEATURE:
<223> OTHER INFORMATION: Synthetic construct

<400> SEQUENCE: 794

Leu Val Arg Trp Val Trp Gly Lys Arg
1               5

<210> SEQ ID NO 795
<211> LENGTH: 9
<212> TYPE: PRT
<213> ORGANISM: Artificial Sequence
<220> FEATURE:
<223> OTHER INFORMATION: Synthetic construct

<400> SEQUENCE: 795

Lys Arg Trp Leu Lys Trp Trp Arg Val
1               5

<210> SEQ ID NO 796
<211> LENGTH: 9
<212> TYPE: PRT
<213> ORGANISM: Artificial Sequence
<220> FEATURE:
<223> OTHER INFORMATION: Synthetic construct

<400> SEQUENCE: 796

Phe Val Tyr Arg Gly Trp Arg Arg Lys
1               5

```
<210> SEQ ID NO 797
<211> LENGTH: 9
<212> TYPE: PRT
<213> ORGANISM: Artificial Sequence
<220> FEATURE:
<223> OTHER INFORMATION: Synthetic construct

<400> SEQUENCE: 797

Arg Arg Arg Trp Lys Ile Tyr Lys Trp
1               5

<210> SEQ ID NO 798
<211> LENGTH: 9
<212> TYPE: PRT
<213> ORGANISM: Artificial Sequence
<220> FEATURE:
<223> OTHER INFORMATION: Synthetic construct

<400> SEQUENCE: 798

Lys Arg Trp Trp Gln Trp Arg Trp Phe
1               5

<210> SEQ ID NO 799
<211> LENGTH: 9
<212> TYPE: PRT
<213> ORGANISM: Artificial Sequence
<220> FEATURE:
<223> OTHER INFORMATION: Synthetic construct

<400> SEQUENCE: 799

Lys Arg Val Lys Val Arg Trp Val Thr
1               5

<210> SEQ ID NO 800
<211> LENGTH: 9
<212> TYPE: PRT
<213> ORGANISM: Artificial Sequence
<220> FEATURE:
<223> OTHER INFORMATION: Synthetic construct

<400> SEQUENCE: 800

Arg Phe Lys Tyr Trp Arg Trp Trp Gln
1               5

<210> SEQ ID NO 801
<211> LENGTH: 9
<212> TYPE: PRT
<213> ORGANISM: Artificial Sequence
<220> FEATURE:
<223> OTHER INFORMATION: Synthetic construct

<400> SEQUENCE: 801

Lys Arg Gln Trp Trp Arg Val Phe Lys
1               5

<210> SEQ ID NO 802
<211> LENGTH: 9
<212> TYPE: PRT
<213> ORGANISM: Artificial Sequence
<220> FEATURE:
<223> OTHER INFORMATION: Synthetic construct

<400> SEQUENCE: 802

Phe Lys Ile Val Trp Trp Arg Arg Arg
1               5
```

```
<210> SEQ ID NO 803
<211> LENGTH: 9
<212> TYPE: PRT
<213> ORGANISM: Artificial Sequence
<220> FEATURE:
<223> OTHER INFORMATION: Synthetic construct

<400> SEQUENCE: 803

Gln Trp Trp Trp Lys Tyr Arg Trp Lys
1               5

<210> SEQ ID NO 804
<211> LENGTH: 9
<212> TYPE: PRT
<213> ORGANISM: Artificial Sequence
<220> FEATURE:
<223> OTHER INFORMATION: Synthetic construct

<400> SEQUENCE: 804

Arg Trp Leu Arg Ile Arg Lys Val Tyr
1               5

<210> SEQ ID NO 805
<211> LENGTH: 9
<212> TYPE: PRT
<213> ORGANISM: Artificial Sequence
<220> FEATURE:
<223> OTHER INFORMATION: Synthetic construct

<400> SEQUENCE: 805

Arg Tyr Lys Arg Val Val Tyr Arg His
1               5

<210> SEQ ID NO 806
<211> LENGTH: 9
<212> TYPE: PRT
<213> ORGANISM: Artificial Sequence
<220> FEATURE:
<223> OTHER INFORMATION: Synthetic construct

<400> SEQUENCE: 806

Lys Val Arg Trp Lys Trp Trp Gly Trp
1               5

<210> SEQ ID NO 807
<211> LENGTH: 9
<212> TYPE: PRT
<213> ORGANISM: Artificial Sequence
<220> FEATURE:
<223> OTHER INFORMATION: Synthetic construct

<400> SEQUENCE: 807

Ile Trp Lys Val Arg Ile Phe Lys Arg
1               5

<210> SEQ ID NO 808
<211> LENGTH: 9
<212> TYPE: PRT
<213> ORGANISM: Artificial Sequence
<220> FEATURE:
<223> OTHER INFORMATION: Synthetic construct

<400> SEQUENCE: 808

Ala Ile Trp His Lys Thr Arg Arg Leu
1               5

<210> SEQ ID NO 809
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 809

Ile Arg Gln Arg Val Arg Trp Arg Trp
1               5

<210> SEQ ID NO 810
<211> LENGTH: 9
<212> TYPE: PRT
<213> ORGANISM: Artificial Sequence
<220> FEATURE:
<223> OTHER INFORMATION: Synthetic construct

<400> SEQUENCE: 810

Met Lys Val Trp Ile Arg Trp Arg Ile
1               5

<210> SEQ ID NO 811
<211> LENGTH: 9
<212> TYPE: PRT
<213> ORGANISM: Artificial Sequence
<220> FEATURE:
<223> OTHER INFORMATION: Synthetic construct

<400> SEQUENCE: 811

Gln Arg Arg Trp Trp Gly Arg Phe Lys
1               5

<210> SEQ ID NO 812
<211> LENGTH: 9
<212> TYPE: PRT
<213> ORGANISM: Artificial Sequence
<220> FEATURE:
<223> OTHER INFORMATION: Synthetic construct

<400> SEQUENCE: 812

Asn Lys Arg Val Trp Phe Ile Tyr Arg
1               5

<210> SEQ ID NO 813
<211> LENGTH: 9
<212> TYPE: PRT
<213> ORGANISM: Artificial Sequence
<220> FEATURE:
<223> OTHER INFORMATION: Synthetic construct

<400> SEQUENCE: 813

Arg Val Val Asn Trp Lys Gly Gly Leu
1               5

<210> SEQ ID NO 814
<211> LENGTH: 9
<212> TYPE: PRT
<213> ORGANISM: Artificial Sequence
<220> FEATURE:
<223> OTHER INFORMATION: Synthetic construct

<400> SEQUENCE: 814

Arg Tyr Arg Arg Phe Arg Val Arg Trp
1               5

<210> SEQ ID NO 815
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 815

Lys Lys Val Arg Arg Val Ile Trp Trp
1               5

<210> SEQ ID NO 816
<211> LENGTH: 9
<212> TYPE: PRT
<213> ORGANISM: Artificial Sequence
<220> FEATURE:
<223> OTHER INFORMATION: Synthetic construct

<400> SEQUENCE: 816

Trp Phe Thr Arg Trp Lys Trp Arg Trp
1               5

<210> SEQ ID NO 817
<211> LENGTH: 9
<212> TYPE: PRT
<213> ORGANISM: Artificial Sequence
<220> FEATURE:
<223> OTHER INFORMATION: Synthetic construct

<400> SEQUENCE: 817

Lys Trp Val Trp Phe Arg Trp Arg Lys
1               5

<210> SEQ ID NO 818
<211> LENGTH: 9
<212> TYPE: PRT
<213> ORGANISM: Artificial Sequence
<220> FEATURE:
<223> OTHER INFORMATION: Synthetic construct

<400> SEQUENCE: 818

Lys Tyr Leu Arg Ser Val Ile Phe Tyr
1               5

<210> SEQ ID NO 819
<211> LENGTH: 9
<212> TYPE: PRT
<213> ORGANISM: Artificial Sequence
<220> FEATURE:
<223> OTHER INFORMATION: Synthetic construct

<400> SEQUENCE: 819

Phe Lys Arg Ser Trp Val Gln Ile Val
1               5

<210> SEQ ID NO 820
<211> LENGTH: 9
<212> TYPE: PRT
<213> ORGANISM: Artificial Sequence
<220> FEATURE:
<223> OTHER INFORMATION: Synthetic construct

<400> SEQUENCE: 820

Arg Trp Trp Phe Ile Arg Lys Trp Trp
1               5

<210> SEQ ID NO 821
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 821

Ile Arg Arg Trp Lys Arg Val Trp Trp
1               5

<210> SEQ ID NO 822
<211> LENGTH: 9
<212> TYPE: PRT
<213> ORGANISM: Artificial Sequence
<220> FEATURE:
<223> OTHER INFORMATION: Synthetic construct

<400> SEQUENCE: 822

Gln Lys Trp Tyr Arg Gln Arg Arg Asn
1               5

<210> SEQ ID NO 823
<211> LENGTH: 9
<212> TYPE: PRT
<213> ORGANISM: Artificial Sequence
<220> FEATURE:
<223> OTHER INFORMATION: Synthetic construct

<400> SEQUENCE: 823

Val Trp Arg Lys Trp Tyr Arg Val Lys
1               5

<210> SEQ ID NO 824
<211> LENGTH: 9
<212> TYPE: PRT
<213> ORGANISM: Artificial Sequence
<220> FEATURE:
<223> OTHER INFORMATION: Synthetic construct

<400> SEQUENCE: 824

Lys Lys Lys Leu Trp Arg Lys Phe Arg
1               5

<210> SEQ ID NO 825
<211> LENGTH: 9
<212> TYPE: PRT
<213> ORGANISM: Artificial Sequence
<220> FEATURE:
<223> OTHER INFORMATION: Synthetic construct

<400> SEQUENCE: 825

Arg Arg Trp Trp Trp Trp Arg Phe Asn
1               5

<210> SEQ ID NO 826
<211> LENGTH: 9
<212> TYPE: PRT
<213> ORGANISM: Artificial Sequence
<220> FEATURE:
<223> OTHER INFORMATION: Synthetic construct

<400> SEQUENCE: 826

Trp Phe Phe Lys Ser Lys Val Tyr Trp
1               5

<210> SEQ ID NO 827
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 827

Arg Val Val Asn Leu Asn Trp Arg Trp
1               5

<210> SEQ ID NO 828
<211> LENGTH: 9
<212> TYPE: PRT
<213> ORGANISM: Artificial Sequence
<220> FEATURE:
<223> OTHER INFORMATION: Synthetic construct

<400> SEQUENCE: 828

Arg Trp Arg Arg Asn Trp Met Thr Lys
1               5

<210> SEQ ID NO 829
<211> LENGTH: 9
<212> TYPE: PRT
<213> ORGANISM: Artificial Sequence
<220> FEATURE:
<223> OTHER INFORMATION: Synthetic construct

<400> SEQUENCE: 829

Trp Lys Ile Trp Lys Ile Arg Trp Phe
1               5

<210> SEQ ID NO 830
<211> LENGTH: 9
<212> TYPE: PRT
<213> ORGANISM: Artificial Sequence
<220> FEATURE:
<223> OTHER INFORMATION: Synthetic construct

<400> SEQUENCE: 830

Trp Trp Phe Trp Val Ile Arg Lys Tyr
1               5

<210> SEQ ID NO 831
<211> LENGTH: 9
<212> TYPE: PRT
<213> ORGANISM: Artificial Sequence
<220> FEATURE:
<223> OTHER INFORMATION: Synthetic construct

<400> SEQUENCE: 831

Arg Tyr Val Lys Ile Arg Trp Val Arg
1               5

<210> SEQ ID NO 832
<211> LENGTH: 9
<212> TYPE: PRT
<213> ORGANISM: Artificial Sequence
<220> FEATURE:
<223> OTHER INFORMATION: Synthetic construct

<400> SEQUENCE: 832

Arg Ile Trp Ile Leu Ser Trp Arg Trp
1               5

<210> SEQ ID NO 833
<211> LENGTH: 9
<212> TYPE: PRT
<213> ORGANISM: Artificial Sequence
<220> FEATURE:
```

```
<223> OTHER INFORMATION: Synthetic construct

<400> SEQUENCE: 833

Lys Ser Trp Arg Lys Leu Phe Ile Trp
1               5

<210> SEQ ID NO 834
<211> LENGTH: 9
<212> TYPE: PRT
<213> ORGANISM: Artificial Sequence
<220> FEATURE:
<223> OTHER INFORMATION: Synthetic construct

<400> SEQUENCE: 834

Val Trp Val Arg Trp Lys Ile Trp Tyr
1               5

<210> SEQ ID NO 835
<211> LENGTH: 9
<212> TYPE: PRT
<213> ORGANISM: Artificial Sequence
<220> FEATURE:
<223> OTHER INFORMATION: Synthetic construct

<400> SEQUENCE: 835

Lys Lys Arg Arg Phe Lys Arg Arg Tyr
1               5

<210> SEQ ID NO 836
<211> LENGTH: 9
<212> TYPE: PRT
<213> ORGANISM: Artificial Sequence
<220> FEATURE:
<223> OTHER INFORMATION: Synthetic construct

<400> SEQUENCE: 836

Arg Phe Trp Lys Lys Ile Arg Arg His
1               5

<210> SEQ ID NO 837
<211> LENGTH: 9
<212> TYPE: PRT
<213> ORGANISM: Artificial Sequence
<220> FEATURE:
<223> OTHER INFORMATION: Synthetic construct

<400> SEQUENCE: 837

Arg Lys Val Trp Trp Arg Val Phe Tyr
1               5

<210> SEQ ID NO 838
<211> LENGTH: 9
<212> TYPE: PRT
<213> ORGANISM: Artificial Sequence
<220> FEATURE:
<223> OTHER INFORMATION: Synthetic construct

<400> SEQUENCE: 838

Tyr Trp Arg Arg Lys Trp Arg Arg Lys
1               5

<210> SEQ ID NO 839
<211> LENGTH: 9
<212> TYPE: PRT
<213> ORGANISM: Artificial Sequence
<220> FEATURE:
<223> OTHER INFORMATION: Synthetic construct
```

<400> SEQUENCE: 839

Lys Arg Ile Arg Arg Trp Lys Trp Trp
1               5

<210> SEQ ID NO 840
<211> LENGTH: 9
<212> TYPE: PRT
<213> ORGANISM: Artificial Sequence
<220> FEATURE:
<223> OTHER INFORMATION: Synthetic construct

<400> SEQUENCE: 840

Tyr Trp Arg Tyr Leu Trp Ile Arg Phe
1               5

<210> SEQ ID NO 841
<211> LENGTH: 9
<212> TYPE: PRT
<213> ORGANISM: Artificial Sequence
<220> FEATURE:
<223> OTHER INFORMATION: Synthetic construct

<400> SEQUENCE: 841

Ile Ile Tyr Lys Trp Arg Trp Tyr Trp
1               5

<210> SEQ ID NO 842
<211> LENGTH: 9
<212> TYPE: PRT
<213> ORGANISM: Artificial Sequence
<220> FEATURE:
<223> OTHER INFORMATION: Synthetic construct

<400> SEQUENCE: 842

Gln Thr Val Tyr Leu Ile Phe Arg Arg
1               5

<210> SEQ ID NO 843
<211> LENGTH: 9
<212> TYPE: PRT
<213> ORGANISM: Artificial Sequence
<220> FEATURE:
<223> OTHER INFORMATION: Synthetic construct

<400> SEQUENCE: 843

Ala Lys Lys Ile Lys Trp Leu Val Trp
1               5

<210> SEQ ID NO 844
<211> LENGTH: 9
<212> TYPE: PRT
<213> ORGANISM: Artificial Sequence
<220> FEATURE:
<223> OTHER INFORMATION: Synthetic construct

<400> SEQUENCE: 844

Tyr Arg Phe Val Arg Arg Trp Ile Val
1               5

<210> SEQ ID NO 845
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 845

Val Trp Arg Arg Tyr Trp Trp Tyr Arg
1               5

<210> SEQ ID NO 846
<211> LENGTH: 9
<212> TYPE: PRT
<213> ORGANISM: Artificial Sequence
<220> FEATURE:
<223> OTHER INFORMATION: Synthetic construct

<400> SEQUENCE: 846

Ala Arg Lys Trp Lys Tyr Trp Arg Phe
1               5

<210> SEQ ID NO 847
<211> LENGTH: 9
<212> TYPE: PRT
<213> ORGANISM: Artificial Sequence
<220> FEATURE:
<223> OTHER INFORMATION: Synthetic construct

<400> SEQUENCE: 847

Arg Lys Arg Val Ile Lys Arg Trp Arg
1               5

<210> SEQ ID NO 848
<211> LENGTH: 9
<212> TYPE: PRT
<213> ORGANISM: Artificial Sequence
<220> FEATURE:
<223> OTHER INFORMATION: Synthetic construct

<400> SEQUENCE: 848

Arg Ser Phe Trp Trp Met Trp Phe Lys
1               5

<210> SEQ ID NO 849
<211> LENGTH: 9
<212> TYPE: PRT
<213> ORGANISM: Artificial Sequence
<220> FEATURE:
<223> OTHER INFORMATION: Synthetic construct

<400> SEQUENCE: 849

Trp Arg Ile Asn Ile Phe Lys Arg Ile
1               5

<210> SEQ ID NO 850
<211> LENGTH: 9
<212> TYPE: PRT
<213> ORGANISM: Artificial Sequence
<220> FEATURE:
<223> OTHER INFORMATION: Synthetic construct

<400> SEQUENCE: 850

Arg Trp Arg Val Leu Lys Arg Arg Lys
1               5

<210> SEQ ID NO 851
<211> LENGTH: 9
<212> TYPE: PRT
<213> ORGANISM: Artificial Sequence
<220> FEATURE:
<223> OTHER INFORMATION: Synthetic construct

<400> SEQUENCE: 851
```

```
Arg Trp Trp Val Ile Trp Trp Trp Lys
1               5

<210> SEQ ID NO 852
<211> LENGTH: 9
<212> TYPE: PRT
<213> ORGANISM: Artificial Sequence
<220> FEATURE:
<223> OTHER INFORMATION: Synthetic construct

<400> SEQUENCE: 852

Lys Leu Ile Arg Ile Trp Trp Trp Trp
1               5

<210> SEQ ID NO 853
<211> LENGTH: 9
<212> TYPE: PRT
<213> ORGANISM: Artificial Sequence
<220> FEATURE:
<223> OTHER INFORMATION: Synthetic construct

<400> SEQUENCE: 853

Phe Lys Arg Lys Arg Trp Trp Gly Ile
1               5

<210> SEQ ID NO 854
<211> LENGTH: 9
<212> TYPE: PRT
<213> ORGANISM: Artificial Sequence
<220> FEATURE:
<223> OTHER INFORMATION: Synthetic construct

<400> SEQUENCE: 854

Val Trp His Trp Trp Arg Trp Arg Trp
1               5

<210> SEQ ID NO 855
<211> LENGTH: 9
<212> TYPE: PRT
<213> ORGANISM: Artificial Sequence
<220> FEATURE:
<223> OTHER INFORMATION: Synthetic construct

<400> SEQUENCE: 855

Trp Lys Arg Trp Leu Ile Ile Gly Arg
1               5

<210> SEQ ID NO 856
<211> LENGTH: 9
<212> TYPE: PRT
<213> ORGANISM: Artificial Sequence
<220> FEATURE:
<223> OTHER INFORMATION: Synthetic construct

<400> SEQUENCE: 856

Ala Tyr Arg Trp Trp Thr Arg Phe Lys
1               5

<210> SEQ ID NO 857
<211> LENGTH: 9
<212> TYPE: PRT
<213> ORGANISM: Artificial Sequence
<220> FEATURE:
<223> OTHER INFORMATION: Synthetic construct

<400> SEQUENCE: 857
```

```
Ser Trp Trp Trp Ile Trp Leu Lys Lys
1               5
```

<210> SEQ ID NO 858
<211> LENGTH: 9
<212> TYPE: PRT
<213> ORGANISM: Artificial Sequence
<220> FEATURE:
<223> OTHER INFORMATION: Synthetic construct

<400> SEQUENCE: 858

```
Phe Val Ile Trp Lys Tyr Ile Arg Val
1               5
```

<210> SEQ ID NO 859
<211> LENGTH: 9
<212> TYPE: PRT
<213> ORGANISM: Artificial Sequence
<220> FEATURE:
<223> OTHER INFORMATION: Synthetic construct

<400> SEQUENCE: 859

```
Arg Trp Val Arg Thr Arg Arg Arg Arg
1               5
```

<210> SEQ ID NO 860
<211> LENGTH: 9
<212> TYPE: PRT
<213> ORGANISM: Artificial Sequence
<220> FEATURE:
<223> OTHER INFORMATION: Synthetic construct

<400> SEQUENCE: 860

```
Arg Arg Ser Trp Trp Tyr Lys Arg Arg
1               5
```

<210> SEQ ID NO 861
<211> LENGTH: 9
<212> TYPE: PRT
<213> ORGANISM: Artificial Sequence
<220> FEATURE:
<223> OTHER INFORMATION: Synthetic construct

<400> SEQUENCE: 861

```
Arg Lys Tyr Val Trp Trp Lys Ser Ile
1               5
```

<210> SEQ ID NO 862
<211> LENGTH: 9
<212> TYPE: PRT
<213> ORGANISM: Artificial Sequence
<220> FEATURE:
<223> OTHER INFORMATION: Synthetic construct

<400> SEQUENCE: 862

```
Trp Trp Lys Arg Tyr Ile Val Lys Lys
1               5
```

<210> SEQ ID NO 863
<211> LENGTH: 9
<212> TYPE: PRT
<213> ORGANISM: Artificial Sequence
<220> FEATURE:
<223> OTHER INFORMATION: Synthetic construct

<400> SEQUENCE: 863

Trp Phe Ile Arg Val Trp Arg Tyr Arg

```
1               5

<210> SEQ ID NO 864
<211> LENGTH: 9
<212> TYPE: PRT
<213> ORGANISM: Artificial Sequence
<220> FEATURE:
<223> OTHER INFORMATION: Synthetic construct

<400> SEQUENCE: 864

Trp Lys Met Trp Leu Arg Lys His Trp
1               5

<210> SEQ ID NO 865
<211> LENGTH: 9
<212> TYPE: PRT
<213> ORGANISM: Artificial Sequence
<220> FEATURE:
<223> OTHER INFORMATION: Synthetic construct

<400> SEQUENCE: 865

Arg Arg Phe Phe Trp Lys Lys Gly Ile
1               5

<210> SEQ ID NO 866
<211> LENGTH: 9
<212> TYPE: PRT
<213> ORGANISM: Artificial Sequence
<220> FEATURE:
<223> OTHER INFORMATION: Synthetic construct

<400> SEQUENCE: 866

Lys Arg Trp Thr Phe Trp Ser Arg Arg
1               5

<210> SEQ ID NO 867
<211> LENGTH: 9
<212> TYPE: PRT
<213> ORGANISM: Artificial Sequence
<220> FEATURE:
<223> OTHER INFORMATION: Synthetic construct

<400> SEQUENCE: 867

Ala Val Gln Arg Trp Arg Trp Val Val
1               5

<210> SEQ ID NO 868
<211> LENGTH: 9
<212> TYPE: PRT
<213> ORGANISM: Artificial Sequence
<220> FEATURE:
<223> OTHER INFORMATION: Synthetic construct

<400> SEQUENCE: 868

Ile Trp Lys Tyr Gly Trp Arg Tyr Lys
1               5

<210> SEQ ID NO 869
<211> LENGTH: 9
<212> TYPE: PRT
<213> ORGANISM: Artificial Sequence
<220> FEATURE:
<223> OTHER INFORMATION: Synthetic construct

<400> SEQUENCE: 869

Ile Ile Lys Trp Trp Arg Arg Trp Arg
1               5
```

<210> SEQ ID NO 870
<211> LENGTH: 9
<212> TYPE: PRT
<213> ORGANISM: Artificial Sequence
<220> FEATURE:
<223> OTHER INFORMATION: Synthetic construct

<400> SEQUENCE: 870

Ala Phe Arg Lys Val Lys Arg Trp Gly
1               5

<210> SEQ ID NO 871
<211> LENGTH: 9
<212> TYPE: PRT
<213> ORGANISM: Artificial Sequence
<220> FEATURE:
<223> OTHER INFORMATION: Synthetic construct

<400> SEQUENCE: 871

Met Gly Phe Thr Arg Lys Trp Gln Phe
1               5

<210> SEQ ID NO 872
<211> LENGTH: 9
<212> TYPE: PRT
<213> ORGANISM: Artificial Sequence
<220> FEATURE:
<223> OTHER INFORMATION: Synthetic construct

<400> SEQUENCE: 872

Asn Trp Ile Arg Trp Arg Lys Trp Arg
1               5

<210> SEQ ID NO 873
<211> LENGTH: 9
<212> TYPE: PRT
<213> ORGANISM: Artificial Sequence
<220> FEATURE:
<223> OTHER INFORMATION: Synthetic construct

<400> SEQUENCE: 873

Arg Ile Gly Arg Lys Leu Arg Ile Arg
1               5

<210> SEQ ID NO 874
<211> LENGTH: 9
<212> TYPE: PRT
<213> ORGANISM: Artificial Sequence
<220> FEATURE:
<223> OTHER INFORMATION: Synthetic construct

<400> SEQUENCE: 874

Arg Trp Trp Arg Trp Arg His Val Ile
1               5

<210> SEQ ID NO 875
<211> LENGTH: 9
<212> TYPE: PRT
<213> ORGANISM: Artificial Sequence
<220> FEATURE:
<223> OTHER INFORMATION: Synthetic construct

<400> SEQUENCE: 875

Arg Leu Val Ser Lys Arg Arg Arg Lys
1               5

<210> SEQ ID NO 876
<211> LENGTH: 9
<212> TYPE: PRT
<213> ORGANISM: Artificial Sequence
<220> FEATURE:
<223> OTHER INFORMATION: Synthetic construct

<400> SEQUENCE: 876

Arg Arg Lys Tyr Trp Lys Lys Tyr Arg
1               5

<210> SEQ ID NO 877
<211> LENGTH: 9
<212> TYPE: PRT
<213> ORGANISM: Artificial Sequence
<220> FEATURE:
<223> OTHER INFORMATION: Synthetic construct

<400> SEQUENCE: 877

Ile Ile Leu Trp Trp Tyr Arg Arg Lys
1               5

<210> SEQ ID NO 878
<211> LENGTH: 9
<212> TYPE: PRT
<213> ORGANISM: Artificial Sequence
<220> FEATURE:
<223> OTHER INFORMATION: Synthetic construct

<400> SEQUENCE: 878

Ile Tyr Phe Trp Trp Trp Arg Ile Arg
1               5

<210> SEQ ID NO 879
<211> LENGTH: 9
<212> TYPE: PRT
<213> ORGANISM: Artificial Sequence
<220> FEATURE:
<223> OTHER INFORMATION: Synthetic construct

<400> SEQUENCE: 879

His Lys Arg Lys Trp Trp Arg Phe Arg
1               5

<210> SEQ ID NO 880
<211> LENGTH: 9
<212> TYPE: PRT
<213> ORGANISM: Artificial Sequence
<220> FEATURE:
<223> OTHER INFORMATION: Synthetic construct

<400> SEQUENCE: 880

Ile Gly Arg Phe Trp Arg Arg Trp Leu
1               5

<210> SEQ ID NO 881
<211> LENGTH: 9
<212> TYPE: PRT
<213> ORGANISM: Artificial Sequence
<220> FEATURE:
<223> OTHER INFORMATION: Synthetic construct

<400> SEQUENCE: 881

Arg Ile Arg Arg Val Leu Val Tyr Val
1               5

```
<210> SEQ ID NO 882
<211> LENGTH: 9
<212> TYPE: PRT
<213> ORGANISM: Artificial Sequence
<220> FEATURE:
<223> OTHER INFORMATION: Synthetic construct

<400> SEQUENCE: 882

Trp Trp Leu Arg Gly Arg Arg Trp Leu
1               5

<210> SEQ ID NO 883
<211> LENGTH: 9
<212> TYPE: PRT
<213> ORGANISM: Artificial Sequence
<220> FEATURE:
<223> OTHER INFORMATION: Synthetic construct

<400> SEQUENCE: 883

Val Arg Ile Arg Lys Arg Arg Trp Arg
1               5

<210> SEQ ID NO 884
<211> LENGTH: 9
<212> TYPE: PRT
<213> ORGANISM: Artificial Sequence
<220> FEATURE:
<223> OTHER INFORMATION: Synthetic construct

<400> SEQUENCE: 884

Trp Trp Arg Arg Lys Trp Trp Arg Arg
1               5

<210> SEQ ID NO 885
<211> LENGTH: 9
<212> TYPE: PRT
<213> ORGANISM: Artificial Sequence
<220> FEATURE:
<223> OTHER INFORMATION: Synthetic construct

<400> SEQUENCE: 885

Trp Trp Trp Arg Ser Phe Arg Lys Arg
1               5

<210> SEQ ID NO 886
<211> LENGTH: 9
<212> TYPE: PRT
<213> ORGANISM: Artificial Sequence
<220> FEATURE:
<223> OTHER INFORMATION: Synthetic construct

<400> SEQUENCE: 886

Val Gly Gln Lys Trp Arg Lys Arg Thr
1               5

<210> SEQ ID NO 887
<211> LENGTH: 9
<212> TYPE: PRT
<213> ORGANISM: Artificial Sequence
<220> FEATURE:
<223> OTHER INFORMATION: Synthetic construct

<400> SEQUENCE: 887

Phe Arg Arg Arg Tyr Arg Val Tyr Arg
1               5

<210> SEQ ID NO 888
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 888

Arg Ile Arg Arg Lys Arg Lys Gly Arg
1               5

<210> SEQ ID NO 889
<211> LENGTH: 9
<212> TYPE: PRT
<213> ORGANISM: Artificial Sequence
<220> FEATURE:
<223> OTHER INFORMATION: Synthetic construct

<400> SEQUENCE: 889

Trp Lys Trp Val Thr Arg Met Tyr Ile
1               5

<210> SEQ ID NO 890
<211> LENGTH: 9
<212> TYPE: PRT
<213> ORGANISM: Artificial Sequence
<220> FEATURE:
<223> OTHER INFORMATION: Synthetic construct

<400> SEQUENCE: 890

Lys Val Val Arg Lys Lys Arg Leu Arg
1               5

<210> SEQ ID NO 891
<211> LENGTH: 9
<212> TYPE: PRT
<213> ORGANISM: Artificial Sequence
<220> FEATURE:
<223> OTHER INFORMATION: Synthetic construct

<400> SEQUENCE: 891

Arg Lys Arg Arg Lys His Trp Arg Tyr
1               5

<210> SEQ ID NO 892
<211> LENGTH: 9
<212> TYPE: PRT
<213> ORGANISM: Artificial Sequence
<220> FEATURE:
<223> OTHER INFORMATION: Synthetic construct

<400> SEQUENCE: 892

Arg Val Thr Arg Thr Trp Gln Arg Trp
1               5

<210> SEQ ID NO 893
<211> LENGTH: 9
<212> TYPE: PRT
<213> ORGANISM: Artificial Sequence
<220> FEATURE:
<223> OTHER INFORMATION: Synthetic construct

<400> SEQUENCE: 893

Arg Arg Arg Ile Thr Arg Lys Arg Ile
1               5

<210> SEQ ID NO 894
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 894

Arg Leu Ile Leu Ile Lys Lys Lys Trp
1               5

<210> SEQ ID NO 895
<211> LENGTH: 9
<212> TYPE: PRT
<213> ORGANISM: Artificial Sequence
<220> FEATURE:
<223> OTHER INFORMATION: Synthetic construct

<400> SEQUENCE: 895

Trp Lys Arg Arg Trp Ser Arg Ser Arg
1               5

<210> SEQ ID NO 896
<211> LENGTH: 9
<212> TYPE: PRT
<213> ORGANISM: Artificial Sequence
<220> FEATURE:
<223> OTHER INFORMATION: Synthetic construct

<400> SEQUENCE: 896

Met Trp Trp Trp Phe Leu Trp Arg Arg
1               5

<210> SEQ ID NO 897
<211> LENGTH: 9
<212> TYPE: PRT
<213> ORGANISM: Artificial Sequence
<220> FEATURE:
<223> OTHER INFORMATION: Synthetic construct

<400> SEQUENCE: 897

Arg Trp Val Arg Ile Trp Lys Lys Lys
1               5

<210> SEQ ID NO 898
<211> LENGTH: 9
<212> TYPE: PRT
<213> ORGANISM: Artificial Sequence
<220> FEATURE:
<223> OTHER INFORMATION: Synthetic construct

<400> SEQUENCE: 898

Lys Arg Arg Val Trp Arg Met Trp Arg
1               5

<210> SEQ ID NO 899
<211> LENGTH: 9
<212> TYPE: PRT
<213> ORGANISM: Artificial Sequence
<220> FEATURE:
<223> OTHER INFORMATION: Synthetic construct

<400> SEQUENCE: 899

Trp His Trp Trp Ile Arg Trp Trp Arg
1               5

<210> SEQ ID NO 900
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 900

Trp Trp Arg Arg Leu Arg Trp Leu Val
1               5

<210> SEQ ID NO 901
<211> LENGTH: 9
<212> TYPE: PRT
<213> ORGANISM: Artificial Sequence
<220> FEATURE:
<223> OTHER INFORMATION: Synthetic construct

<400> SEQUENCE: 901

Lys Trp Trp Ile Trp Lys Arg Arg Arg
1               5

<210> SEQ ID NO 902
<211> LENGTH: 9
<212> TYPE: PRT
<213> ORGANISM: Artificial Sequence
<220> FEATURE:
<223> OTHER INFORMATION: Synthetic construct

<400> SEQUENCE: 902

Arg Tyr Gly Arg Lys Trp Met Ile Trp
1               5

<210> SEQ ID NO 903
<211> LENGTH: 9
<212> TYPE: PRT
<213> ORGANISM: Artificial Sequence
<220> FEATURE:
<223> OTHER INFORMATION: Synthetic construct

<400> SEQUENCE: 903

Arg Val Lys Lys Ile Lys Leu Phe Ile
1               5

<210> SEQ ID NO 904
<211> LENGTH: 9
<212> TYPE: PRT
<213> ORGANISM: Artificial Sequence
<220> FEATURE:
<223> OTHER INFORMATION: Synthetic construct

<400> SEQUENCE: 904

Arg Ile Arg Tyr Ile Gln Arg Val Trp
1               5

<210> SEQ ID NO 905
<211> LENGTH: 9
<212> TYPE: PRT
<213> ORGANISM: Artificial Sequence
<220> FEATURE:
<223> OTHER INFORMATION: Synthetic construct

<400> SEQUENCE: 905

Arg Leu Ile Arg Trp Trp Arg Lys Arg
1               5

<210> SEQ ID NO 906
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 906

Gln Arg Gly Arg Trp Leu Arg Arg Gly
1               5

<210> SEQ ID NO 907
<211> LENGTH: 9
<212> TYPE: PRT
<213> ORGANISM: Artificial Sequence
<220> FEATURE:
<223> OTHER INFORMATION: Synthetic construct

<400> SEQUENCE: 907

Arg Arg Arg Arg Trp Ile Arg Lys Lys
1               5

<210> SEQ ID NO 908
<211> LENGTH: 9
<212> TYPE: PRT
<213> ORGANISM: Artificial Sequence
<220> FEATURE:
<223> OTHER INFORMATION: Synthetic construct

<400> SEQUENCE: 908

Leu Gly Arg Arg Trp Arg Tyr Arg Arg
1               5

<210> SEQ ID NO 909
<211> LENGTH: 9
<212> TYPE: PRT
<213> ORGANISM: Artificial Sequence
<220> FEATURE:
<223> OTHER INFORMATION: Synthetic construct

<400> SEQUENCE: 909

Phe Lys Ile Val His Val Lys Val Arg
1               5

<210> SEQ ID NO 910
<211> LENGTH: 9
<212> TYPE: PRT
<213> ORGANISM: Artificial Sequence
<220> FEATURE:
<223> OTHER INFORMATION: Synthetic construct

<400> SEQUENCE: 910

Phe Arg Lys Lys Tyr Arg Val Arg Arg
1               5

<210> SEQ ID NO 911
<211> LENGTH: 9
<212> TYPE: PRT
<213> ORGANISM: Artificial Sequence
<220> FEATURE:
<223> OTHER INFORMATION: Synthetic construct

<400> SEQUENCE: 911

Trp Lys Tyr Lys Tyr Arg Ile Arg Leu
1               5

<210> SEQ ID NO 912
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 912

His Val Arg Arg Trp Trp Arg Ile Ile
1               5

<210> SEQ ID NO 913
<211> LENGTH: 9
<212> TYPE: PRT
<213> ORGANISM: Artificial Sequence
<220> FEATURE:
<223> OTHER INFORMATION: Synthetic construct

<400> SEQUENCE: 913

Arg Phe Lys Trp Trp Arg Arg Tyr Trp
1               5

<210> SEQ ID NO 914
<211> LENGTH: 9
<212> TYPE: PRT
<213> ORGANISM: Artificial Sequence
<220> FEATURE:
<223> OTHER INFORMATION: Synthetic construct

<400> SEQUENCE: 914

Arg Arg Arg Arg Met Arg Lys Lys Ile
1               5

<210> SEQ ID NO 915
<211> LENGTH: 9
<212> TYPE: PRT
<213> ORGANISM: Artificial Sequence
<220> FEATURE:
<223> OTHER INFORMATION: Synthetic construct

<400> SEQUENCE: 915

Arg Arg Ile Arg Gly Arg Val Gly Arg
1               5

<210> SEQ ID NO 916
<211> LENGTH: 9
<212> TYPE: PRT
<213> ORGANISM: Artificial Sequence
<220> FEATURE:
<223> OTHER INFORMATION: Synthetic construct

<400> SEQUENCE: 916

Ala Phe Trp Arg Trp Ile Arg Phe Lys
1               5

<210> SEQ ID NO 917
<211> LENGTH: 9
<212> TYPE: PRT
<213> ORGANISM: Artificial Sequence
<220> FEATURE:
<223> OTHER INFORMATION: Synthetic construct

<400> SEQUENCE: 917

Val Lys Lys Arg Lys Ile Val Ile Tyr
1               5

<210> SEQ ID NO 918
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 918

Lys Arg Val Lys Trp Thr Trp Arg Lys
1               5

<210> SEQ ID NO 919
<211> LENGTH: 9
<212> TYPE: PRT
<213> ORGANISM: Artificial Sequence
<220> FEATURE:
<223> OTHER INFORMATION: Synthetic construct

<400> SEQUENCE: 919

Thr Gly Val Gly Arg Gly Tyr Arg Ile
1               5

<210> SEQ ID NO 920
<211> LENGTH: 9
<212> TYPE: PRT
<213> ORGANISM: Artificial Sequence
<220> FEATURE:
<223> OTHER INFORMATION: Synthetic construct

<400> SEQUENCE: 920

Leu Ser Trp Lys Trp Trp Arg Arg Val
1               5

<210> SEQ ID NO 921
<211> LENGTH: 9
<212> TYPE: PRT
<213> ORGANISM: Artificial Sequence
<220> FEATURE:
<223> OTHER INFORMATION: Synthetic construct

<400> SEQUENCE: 921

Ile Lys Thr Phe Ile Lys Arg Trp Arg
1               5

<210> SEQ ID NO 922
<211> LENGTH: 9
<212> TYPE: PRT
<213> ORGANISM: Artificial Sequence
<220> FEATURE:
<223> OTHER INFORMATION: Synthetic construct

<400> SEQUENCE: 922

Lys Met Arg Leu Lys Trp Lys Arg Arg
1               5

<210> SEQ ID NO 923
<211> LENGTH: 9
<212> TYPE: PRT
<213> ORGANISM: Artificial Sequence
<220> FEATURE:
<223> OTHER INFORMATION: Synthetic construct

<400> SEQUENCE: 923

Trp Arg Trp Tyr Val Thr Arg Arg Lys
1               5

<210> SEQ ID NO 924
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 924

Ile Tyr Arg Arg Arg Arg Lys Leu Arg
1               5

<210> SEQ ID NO 925
<211> LENGTH: 9
<212> TYPE: PRT
<213> ORGANISM: Artificial Sequence
<220> FEATURE:
<223> OTHER INFORMATION: Synthetic construct

<400> SEQUENCE: 925

Val Trp Trp Lys Trp Trp Arg Trp Trp
1               5

<210> SEQ ID NO 926
<211> LENGTH: 9
<212> TYPE: PRT
<213> ORGANISM: Artificial Sequence
<220> FEATURE:
<223> OTHER INFORMATION: Synthetic construct

<400> SEQUENCE: 926

Lys Tyr Lys Lys Gly Trp Arg Val Val
1               5

<210> SEQ ID NO 927
<211> LENGTH: 9
<212> TYPE: PRT
<213> ORGANISM: Artificial Sequence
<220> FEATURE:
<223> OTHER INFORMATION: Synthetic construct

<400> SEQUENCE: 927

Lys Trp Arg Arg Trp Tyr Tyr Trp Arg
1               5

<210> SEQ ID NO 928
<211> LENGTH: 9
<212> TYPE: PRT
<213> ORGANISM: Artificial Sequence
<220> FEATURE:
<223> OTHER INFORMATION: Synthetic construct

<400> SEQUENCE: 928

Arg Arg Trp Val Phe Gly Arg Arg Tyr
1               5

<210> SEQ ID NO 929
<211> LENGTH: 9
<212> TYPE: PRT
<213> ORGANISM: Artificial Sequence
<220> FEATURE:
<223> OTHER INFORMATION: Synthetic construct

<400> SEQUENCE: 929

Gly Phe Thr Trp Lys Lys Lys Arg Arg
1               5

<210> SEQ ID NO 930
<211> LENGTH: 9
<212> TYPE: PRT
<213> ORGANISM: Artificial Sequence
<220> FEATURE:
<223> OTHER INFORMATION: Synthetic construct

<400> SEQUENCE: 930
```

```
Tyr Lys Lys Ile Arg Ile Lys Arg Arg
1               5

<210> SEQ ID NO 931
<211> LENGTH: 9
<212> TYPE: PRT
<213> ORGANISM: Artificial Sequence
<220> FEATURE:
<223> OTHER INFORMATION: Synthetic construct

<400> SEQUENCE: 931

Val Trp Ile Arg Arg Ile Lys Arg Arg
1               5

<210> SEQ ID NO 932
<211> LENGTH: 9
<212> TYPE: PRT
<213> ORGANISM: Artificial Sequence
<220> FEATURE:
<223> OTHER INFORMATION: Synthetic construct

<400> SEQUENCE: 932

Trp Trp Lys Trp Ile Arg Lys Ile Val
1               5

<210> SEQ ID NO 933
<211> LENGTH: 9
<212> TYPE: PRT
<213> ORGANISM: Artificial Sequence
<220> FEATURE:
<223> OTHER INFORMATION: Synthetic construct

<400> SEQUENCE: 933

Trp Arg Arg Lys Trp Trp Ser Arg Trp
1               5

<210> SEQ ID NO 934
<211> LENGTH: 9
<212> TYPE: PRT
<213> ORGANISM: Artificial Sequence
<220> FEATURE:
<223> OTHER INFORMATION: Synthetic construct

<400> SEQUENCE: 934

Val Thr Arg Arg Arg Thr Arg Ile Lys
1               5

<210> SEQ ID NO 935
<211> LENGTH: 9
<212> TYPE: PRT
<213> ORGANISM: Artificial Sequence
<220> FEATURE:
<223> OTHER INFORMATION: Synthetic construct

<400> SEQUENCE: 935

Arg Lys Arg Trp Phe Val Tyr Ile Trp
1               5

<210> SEQ ID NO 936
<211> LENGTH: 9
<212> TYPE: PRT
<213> ORGANISM: Artificial Sequence
<220> FEATURE:
<223> OTHER INFORMATION: Synthetic construct

<400> SEQUENCE: 936
```

```
Ile Ile Lys Trp Lys Arg Ile Met Ile
1               5
```

<210> SEQ ID NO 937
<211> LENGTH: 9
<212> TYPE: PRT
<213> ORGANISM: Artificial Sequence
<220> FEATURE:
<223> OTHER INFORMATION: Synthetic construct

<400> SEQUENCE: 937

```
Phe Asn Arg Trp Trp Trp Lys Lys Ile
1               5
```

<210> SEQ ID NO 938
<211> LENGTH: 9
<212> TYPE: PRT
<213> ORGANISM: Artificial Sequence
<220> FEATURE:
<223> OTHER INFORMATION: Synthetic construct

<400> SEQUENCE: 938

```
Arg Tyr Lys Ser Arg Arg Val Arg Arg
1               5
```

<210> SEQ ID NO 939
<211> LENGTH: 9
<212> TYPE: PRT
<213> ORGANISM: Artificial Sequence
<220> FEATURE:
<223> OTHER INFORMATION: Synthetic construct

<400> SEQUENCE: 939

```
Val Lys Val Ile Lys Lys Phe Val Arg
1               5
```

<210> SEQ ID NO 940
<211> LENGTH: 9
<212> TYPE: PRT
<213> ORGANISM: Artificial Sequence
<220> FEATURE:
<223> OTHER INFORMATION: Synthetic construct

<400> SEQUENCE: 940

```
Lys Trp Lys Trp Leu Gln Gly Arg Arg
1               5
```

<210> SEQ ID NO 941
<211> LENGTH: 9
<212> TYPE: PRT
<213> ORGANISM: Artificial Sequence
<220> FEATURE:
<223> OTHER INFORMATION: Synthetic construct

<400> SEQUENCE: 941

```
Lys Val Arg Trp Trp Tyr Asn Ile Lys
1               5
```

<210> SEQ ID NO 942
<211> LENGTH: 9
<212> TYPE: PRT
<213> ORGANISM: Artificial Sequence
<220> FEATURE:
<223> OTHER INFORMATION: Synthetic construct

<400> SEQUENCE: 942

```
Phe Trp Phe Arg Ile Arg Lys Leu Lys
```

```
<210> SEQ ID NO 943
<211> LENGTH: 9
<212> TYPE: PRT
<213> ORGANISM: Artificial Sequence
<220> FEATURE:
<223> OTHER INFORMATION: Synthetic construct

<400> SEQUENCE: 943

Lys Arg Arg Lys Gln Arg Lys Tyr Arg
1               5

<210> SEQ ID NO 944
<211> LENGTH: 9
<212> TYPE: PRT
<213> ORGANISM: Artificial Sequence
<220> FEATURE:
<223> OTHER INFORMATION: Synthetic construct

<400> SEQUENCE: 944

Ala Lys Asn Ser Lys Arg Arg Leu Trp
1               5

<210> SEQ ID NO 945
<211> LENGTH: 9
<212> TYPE: PRT
<213> ORGANISM: Artificial Sequence
<220> FEATURE:
<223> OTHER INFORMATION: Synthetic construct

<400> SEQUENCE: 945

Arg Asn Arg Arg Ile Phe Arg Tyr Ser
1               5

<210> SEQ ID NO 946
<211> LENGTH: 9
<212> TYPE: PRT
<213> ORGANISM: Artificial Sequence
<220> FEATURE:
<223> OTHER INFORMATION: Synthetic construct

<400> SEQUENCE: 946

Arg Trp Thr Lys Trp Phe Leu Val Arg
1               5

<210> SEQ ID NO 947
<211> LENGTH: 9
<212> TYPE: PRT
<213> ORGANISM: Artificial Sequence
<220> FEATURE:
<223> OTHER INFORMATION: Synthetic construct

<400> SEQUENCE: 947

Arg Ile Arg Arg Thr Arg Arg Thr Arg
1               5

<210> SEQ ID NO 948
<211> LENGTH: 9
<212> TYPE: PRT
<213> ORGANISM: Artificial Sequence
<220> FEATURE:
<223> OTHER INFORMATION: Synthetic construct

<400> SEQUENCE: 948

Lys Ile Arg Trp Trp Arg Ile Ser Ile
1               5
```

<210> SEQ ID NO 949
<211> LENGTH: 9
<212> TYPE: PRT
<213> ORGANISM: Artificial Sequence
<220> FEATURE:
<223> OTHER INFORMATION: Synthetic construct

<400> SEQUENCE: 949

Tyr Lys Gly Arg Trp Gly Arg Arg Trp
1               5

<210> SEQ ID NO 950
<211> LENGTH: 9
<212> TYPE: PRT
<213> ORGANISM: Artificial Sequence
<220> FEATURE:
<223> OTHER INFORMATION: Synthetic construct

<400> SEQUENCE: 950

Met Tyr Tyr Arg Ile Lys Gln Lys Trp
1               5

<210> SEQ ID NO 951
<211> LENGTH: 9
<212> TYPE: PRT
<213> ORGANISM: Artificial Sequence
<220> FEATURE:
<223> OTHER INFORMATION: Synthetic construct

<400> SEQUENCE: 951

Trp Arg Ile Gln Arg Trp Arg Trp Gln
1               5

<210> SEQ ID NO 952
<211> LENGTH: 9
<212> TYPE: PRT
<213> ORGANISM: Artificial Sequence
<220> FEATURE:
<223> OTHER INFORMATION: Synthetic construct

<400> SEQUENCE: 952

Ile Arg Arg Trp Ser Tyr Arg Arg Trp
1               5

<210> SEQ ID NO 953
<211> LENGTH: 9
<212> TYPE: PRT
<213> ORGANISM: Artificial Sequence
<220> FEATURE:
<223> OTHER INFORMATION: Synthetic construct

<400> SEQUENCE: 953

Val Arg Ile Trp Lys Ile Ile Trp Trp
1               5

<210> SEQ ID NO 954
<211> LENGTH: 9
<212> TYPE: PRT
<213> ORGANISM: Artificial Sequence
<220> FEATURE:
<223> OTHER INFORMATION: Synthetic construct

<400> SEQUENCE: 954

Arg Trp Arg Trp Trp Trp Leu Trp Lys
1               5

<210> SEQ ID NO 955
<211> LENGTH: 9
<212> TYPE: PRT
<213> ORGANISM: Artificial Sequence
<220> FEATURE:
<223> OTHER INFORMATION: Synthetic construct

<400> SEQUENCE: 955

Thr Lys Arg Arg Trp Ile Trp Ile Thr
1               5

<210> SEQ ID NO 956
<211> LENGTH: 9
<212> TYPE: PRT
<213> ORGANISM: Artificial Sequence
<220> FEATURE:
<223> OTHER INFORMATION: Synthetic construct

<400> SEQUENCE: 956

Arg Arg Trp His Tyr Trp Lys Gly Trp
1               5

<210> SEQ ID NO 957
<211> LENGTH: 9
<212> TYPE: PRT
<213> ORGANISM: Artificial Sequence
<220> FEATURE:
<223> OTHER INFORMATION: Synthetic construct

<400> SEQUENCE: 957

Trp Arg Ile Arg Lys Trp Trp Met Arg
1               5

<210> SEQ ID NO 958
<211> LENGTH: 9
<212> TYPE: PRT
<213> ORGANISM: Artificial Sequence
<220> FEATURE:
<223> OTHER INFORMATION: Synthetic construct

<400> SEQUENCE: 958

Lys Arg Arg Thr Arg Trp Trp Val Arg
1               5

<210> SEQ ID NO 959
<211> LENGTH: 9
<212> TYPE: PRT
<213> ORGANISM: Artificial Sequence
<220> FEATURE:
<223> OTHER INFORMATION: Synthetic construct

<400> SEQUENCE: 959

Arg Lys Trp Arg Val Trp Lys Arg Arg
1               5

<210> SEQ ID NO 960
<211> LENGTH: 9
<212> TYPE: PRT
<213> ORGANISM: Artificial Sequence
<220> FEATURE:
<223> OTHER INFORMATION: Synthetic construct

<400> SEQUENCE: 960

Trp Arg Val Trp Lys Ile Arg Val Arg
1               5

-continued

```
<210> SEQ ID NO 961
<211> LENGTH: 9
<212> TYPE: PRT
<213> ORGANISM: Artificial Sequence
<220> FEATURE:
<223> OTHER INFORMATION: Synthetic construct

<400> SEQUENCE: 961

Lys Tyr Trp Gly Ile Gly Gly Trp Arg
1               5

<210> SEQ ID NO 962
<211> LENGTH: 9
<212> TYPE: PRT
<213> ORGANISM: Artificial Sequence
<220> FEATURE:
<223> OTHER INFORMATION: Synthetic construct

<400> SEQUENCE: 962

Arg Leu Ile Ser Arg Arg Arg Lys Lys
1               5

<210> SEQ ID NO 963
<211> LENGTH: 9
<212> TYPE: PRT
<213> ORGANISM: Artificial Sequence
<220> FEATURE:
<223> OTHER INFORMATION: Synthetic construct

<400> SEQUENCE: 963

Val Ser Arg Arg Ile Val Arg Arg Met
1               5

<210> SEQ ID NO 964
<211> LENGTH: 9
<212> TYPE: PRT
<213> ORGANISM: Artificial Sequence
<220> FEATURE:
<223> OTHER INFORMATION: Synthetic construct

<400> SEQUENCE: 964

Ile Thr Lys Trp Trp Arg Lys Arg Arg
1               5

<210> SEQ ID NO 965
<211> LENGTH: 9
<212> TYPE: PRT
<213> ORGANISM: Artificial Sequence
<220> FEATURE:
<223> OTHER INFORMATION: Synthetic construct

<400> SEQUENCE: 965

Lys Trp Lys Ile Gln Leu Trp Lys Ile
1               5

<210> SEQ ID NO 966
<211> LENGTH: 9
<212> TYPE: PRT
<213> ORGANISM: Artificial Sequence
<220> FEATURE:
<223> OTHER INFORMATION: Synthetic construct

<400> SEQUENCE: 966

Lys Lys Trp Thr Trp Trp Tyr Val Ile
1               5

<210> SEQ ID NO 967
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 967

Ser Trp Lys Lys Asn Arg Lys Ile Trp
1               5

<210> SEQ ID NO 968
<211> LENGTH: 9
<212> TYPE: PRT
<213> ORGANISM: Artificial Sequence
<220> FEATURE:
<223> OTHER INFORMATION: Synthetic construct

<400> SEQUENCE: 968

His Lys Arg Gln Tyr Arg Lys Trp Phe
1               5

<210> SEQ ID NO 969
<211> LENGTH: 9
<212> TYPE: PRT
<213> ORGANISM: Artificial Sequence
<220> FEATURE:
<223> OTHER INFORMATION: Synthetic construct

<400> SEQUENCE: 969

Ile Phe Lys Trp Phe Tyr Arg Arg Lys
1               5

<210> SEQ ID NO 970
<211> LENGTH: 12
<212> TYPE: PRT
<213> ORGANISM: Artificial Sequence
<220> FEATURE:
<223> OTHER INFORMATION: Synthetic construct

<400> SEQUENCE: 970

Arg Leu Ala Arg Ile Val Val Ile Arg Val Ala Arg
1               5                   10

<210> SEQ ID NO 971
<211> LENGTH: 13
<212> TYPE: PRT
<213> ORGANISM: Artificial Sequence
<220> FEATURE:
<223> OTHER INFORMATION: Synthetic construct

<400> SEQUENCE: 971

Ile Leu Pro Trp Lys Trp Pro Trp Trp Pro Trp Arg Arg
1               5                   10

<210> SEQ ID NO 972
<211> LENGTH: 12
<212> TYPE: PRT
<213> ORGANISM: Artificial Sequence
<220> FEATURE:
<223> OTHER INFORMATION: Synthetic construct

<400> SEQUENCE: 972

Val Arg Leu Arg Ile Arg Val Ala Val Ile Arg Ala
1               5                   10

<210> SEQ ID NO 973
<211> LENGTH: 13
```

```
<212> TYPE: PRT
<213> ORGANISM: Artificial Sequence
<220> FEATURE:
<223> OTHER INFORMATION: Synthetic construct

<400> SEQUENCE: 973

Ile Leu Lys Trp Lys Trp Pro Trp Trp Lys Trp Arg Arg
1               5                   10

<210> SEQ ID NO 974
<211> LENGTH: 13
<212> TYPE: PRT
<213> ORGANISM: Artificial Sequence
<220> FEATURE:
<223> OTHER INFORMATION: Synthetic construct

<400> SEQUENCE: 974

Ile Leu Pro Trp Lys Trp Arg Trp Trp Lys Trp Arg Arg
1               5                   10

<210> SEQ ID NO 975
<211> LENGTH: 13
<212> TYPE: PRT
<213> ORGANISM: Artificial Sequence
<220> FEATURE:
<223> OTHER INFORMATION: Synthetic construct

<400> SEQUENCE: 975

Phe Leu Pro Lys Lys Phe Arg Trp Trp Lys Tyr Arg Lys
1               5                   10

<210> SEQ ID NO 976
<211> LENGTH: 13
<212> TYPE: PRT
<213> ORGANISM: Artificial Sequence
<220> FEATURE:
<223> OTHER INFORMATION: Synthetic construct

<400> SEQUENCE: 976

Phe Ile Lys Trp Lys Phe Arg Trp Trp Lys Trp Arg Lys
1               5                   10

<210> SEQ ID NO 977
<211> LENGTH: 9
<212> TYPE: PRT
<213> ORGANISM: Artificial Sequence
<220> FEATURE:
<223> OTHER INFORMATION: Synthetic construct

<400> SEQUENCE: 977

Lys Trp Pro Trp Trp Pro Trp Arg Arg
1               5

<210> SEQ ID NO 978
<211> LENGTH: 9
<212> TYPE: PRT
<213> ORGANISM: Artificial Sequence
<220> FEATURE:
<223> OTHER INFORMATION: Synthetic construct

<400> SEQUENCE: 978

Lys Trp Pro Trp Trp Pro Trp Arg Lys
1               5

<210> SEQ ID NO 979
<211> LENGTH: 9
<212> TYPE: PRT
```

<213> ORGANISM: Artificial Sequence
<220> FEATURE:
<223> OTHER INFORMATION: Synthetic construct

<400> SEQUENCE: 979

Lys Phe Pro Trp Trp Pro Trp Arg Arg
1               5

<210> SEQ ID NO 980
<211> LENGTH: 9
<212> TYPE: PRT
<213> ORGANISM: Artificial Sequence
<220> FEATURE:
<223> OTHER INFORMATION: Synthetic construct

<400> SEQUENCE: 980

Lys Lys Pro Trp Trp Pro Trp Arg Arg
1               5

<210> SEQ ID NO 981
<211> LENGTH: 9
<212> TYPE: PRT
<213> ORGANISM: Artificial Sequence
<220> FEATURE:
<223> OTHER INFORMATION: Synthetic construct

<400> SEQUENCE: 981

Lys Trp Arg Trp Trp Pro Trp Arg Arg
1               5

<210> SEQ ID NO 982
<211> LENGTH: 9
<212> TYPE: PRT
<213> ORGANISM: Artificial Sequence
<220> FEATURE:
<223> OTHER INFORMATION: Synthetic construct

<400> SEQUENCE: 982

Lys Trp Pro Lys Trp Pro Trp Arg Arg
1               5

<210> SEQ ID NO 983
<211> LENGTH: 9
<212> TYPE: PRT
<213> ORGANISM: Artificial Sequence
<220> FEATURE:
<223> OTHER INFORMATION: Synthetic construct

<400> SEQUENCE: 983

Lys Trp Pro Trp Lys Pro Trp Arg Arg
1               5

<210> SEQ ID NO 984
<211> LENGTH: 9
<212> TYPE: PRT
<213> ORGANISM: Artificial Sequence
<220> FEATURE:
<223> OTHER INFORMATION: Synthetic construct

<400> SEQUENCE: 984

Lys Trp Pro Trp Trp Lys Trp Arg Arg
1               5

<210> SEQ ID NO 985
<211> LENGTH: 9
<212> TYPE: PRT
<213> ORGANISM: Artificial Sequence

```
<220> FEATURE:
<223> OTHER INFORMATION: Synthetic construct

<400> SEQUENCE: 985

Lys Trp Pro Trp Trp Pro Lys Arg Arg
1               5

<210> SEQ ID NO 986

<400> SEQUENCE: 986

000

<210> SEQ ID NO 987
<211> LENGTH: 9
<212> TYPE: PRT
<213> ORGANISM: Artificial Sequence
<220> FEATURE:
<223> OTHER INFORMATION: Synthetic construct

<400> SEQUENCE: 987

Lys Phe Arg Trp Trp Pro Trp Arg Arg
1               5

<210> SEQ ID NO 988
<211> LENGTH: 9
<212> TYPE: PRT
<213> ORGANISM: Artificial Sequence
<220> FEATURE:
<223> OTHER INFORMATION: Synthetic construct

<400> SEQUENCE: 988

Lys Phe Arg Trp Trp Lys Trp Arg Arg
1               5

<210> SEQ ID NO 989
<211> LENGTH: 9
<212> TYPE: PRT
<213> ORGANISM: Artificial Sequence
<220> FEATURE:
<223> OTHER INFORMATION: Synthetic construct

<400> SEQUENCE: 989

Lys Trp Arg Trp Trp Lys Lys Arg Arg
1               5

<210> SEQ ID NO 990
<211> LENGTH: 9
<212> TYPE: PRT
<213> ORGANISM: Artificial Sequence
<220> FEATURE:
<223> OTHER INFORMATION: Synthetic construct

<400> SEQUENCE: 990

Lys Lys Lys Trp Trp Lys Trp Arg Arg
1               5

<210> SEQ ID NO 991
<211> LENGTH: 9
<212> TYPE: PRT
<213> ORGANISM: Artificial Sequence
<220> FEATURE:
<223> OTHER INFORMATION: Synthetic construct

<400> SEQUENCE: 991

Lys Phe His Trp Trp Ile Trp Arg Lys
1               5
```

<210> SEQ ID NO 992
<211> LENGTH: 9
<212> TYPE: PRT
<213> ORGANISM: Artificial Sequence
<220> FEATURE:
<223> OTHER INFORMATION: Synthetic construct

<400> SEQUENCE: 992

Lys Phe His Trp Trp Lys Trp Arg Lys
1               5

<210> SEQ ID NO 993
<211> LENGTH: 9
<212> TYPE: PRT
<213> ORGANISM: Artificial Sequence
<220> FEATURE:
<223> OTHER INFORMATION: Synthetic construct

<400> SEQUENCE: 993

Lys Phe Lys Trp Trp Lys Tyr Arg Lys
1               5

<210> SEQ ID NO 994
<211> LENGTH: 9
<212> TYPE: PRT
<213> ORGANISM: Artificial Sequence
<220> FEATURE:
<223> OTHER INFORMATION: Synthetic construct

<400> SEQUENCE: 994

Lys Phe Lys Phe Phe Lys Tyr Arg Lys
1               5

<210> SEQ ID NO 995
<211> LENGTH: 9
<212> TYPE: PRT
<213> ORGANISM: Artificial Sequence
<220> FEATURE:
<223> OTHER INFORMATION: Synthetic construct

<400> SEQUENCE: 995

Lys Phe Lys Phe Phe Lys Phe Arg Lys
1               5

<210> SEQ ID NO 996
<211> LENGTH: 7
<212> TYPE: PRT
<213> ORGANISM: Artificial Sequence
<220> FEATURE:
<223> OTHER INFORMATION: Synthetic construct

<400> SEQUENCE: 996

Pro Trp Trp Pro Trp Arg Arg
1               5

<210> SEQ ID NO 997
<211> LENGTH: 7
<212> TYPE: PRT
<213> ORGANISM: Artificial Sequence
<220> FEATURE:
<223> OTHER INFORMATION: Synthetic construct

<400> SEQUENCE: 997

Lys Trp Trp Pro Trp Arg Arg
1               5

<210> SEQ ID NO 998
<211> LENGTH: 7
<212> TYPE: PRT
<213> ORGANISM: Artificial Sequence
<220> FEATURE:
<223> OTHER INFORMATION: Synthetic construct

<400> SEQUENCE: 998

Lys Trp Trp Pro Trp Arg Arg
1               5

<210> SEQ ID NO 999
<211> LENGTH: 7
<212> TYPE: PRT
<213> ORGANISM: Artificial Sequence
<220> FEATURE:
<223> OTHER INFORMATION: Synthetic construct

<400> SEQUENCE: 999

Arg Trp Trp Pro Trp Arg Arg
1               5

<210> SEQ ID NO 1000
<211> LENGTH: 7
<212> TYPE: PRT
<213> ORGANISM: Artificial Sequence
<220> FEATURE:
<223> OTHER INFORMATION: Synthetic construct

<400> SEQUENCE: 1000

Pro Lys Trp Pro Trp Arg Arg
1               5

<210> SEQ ID NO 1001
<211> LENGTH: 7
<212> TYPE: PRT
<213> ORGANISM: Artificial Sequence
<220> FEATURE:
<223> OTHER INFORMATION: Synthetic construct

<400> SEQUENCE: 1001

Pro Trp Lys Pro Trp Arg Arg
1               5

<210> SEQ ID NO 1002

<400> SEQUENCE: 1002

000

<210> SEQ ID NO 1003
<211> LENGTH: 7
<212> TYPE: PRT
<213> ORGANISM: Artificial Sequence
<220> FEATURE:
<223> OTHER INFORMATION: Synthetic construct

<400> SEQUENCE: 1003

Pro Trp Trp Pro Lys Arg Arg
1               5

<210> SEQ ID NO 1004
<211> LENGTH: 7
<212> TYPE: PRT
<213> ORGANISM: Artificial Sequence
<220> FEATURE:
<223> OTHER INFORMATION: Synthetic construct

<400> SEQUENCE: 1004

Pro Trp Trp Pro Trp Arg Lys
1               5

<210> SEQ ID NO 1005
<211> LENGTH: 7
<212> TYPE: PRT
<213> ORGANISM: Artificial Sequence
<220> FEATURE:
<223> OTHER INFORMATION: Synthetic construct

<400> SEQUENCE: 1005

Arg Trp Trp Lys Trp Arg Arg
1               5

<210> SEQ ID NO 1006
<211> LENGTH: 7
<212> TYPE: PRT
<213> ORGANISM: Artificial Sequence
<220> FEATURE:
<223> OTHER INFORMATION: Synthetic construct

<400> SEQUENCE: 1006

Arg Trp Trp Lys Trp Arg Lys
1               5

<210> SEQ ID NO 1007
<211> LENGTH: 7
<212> TYPE: PRT
<213> ORGANISM: Artificial Sequence
<220> FEATURE:
<223> OTHER INFORMATION: Synthetic construct

<400> SEQUENCE: 1007

Arg Phe Trp Lys Trp Arg Arg
1               5

<210> SEQ ID NO 1008
<211> LENGTH: 7
<212> TYPE: PRT
<213> ORGANISM: Artificial Sequence
<220> FEATURE:
<223> OTHER INFORMATION: Synthetic construct

<400> SEQUENCE: 1008

Arg Trp Trp Ile Lys Arg Arg
1               5

<210> SEQ ID NO 1009
<211> LENGTH: 7
<212> TYPE: PRT
<213> ORGANISM: Artificial Sequence
<220> FEATURE:
<223> OTHER INFORMATION: Synthetic construct

<400> SEQUENCE: 1009

Arg Trp Trp Ile Tyr Arg Arg
1               5

<210> SEQ ID NO 1010
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 1010

Arg Phe Phe Lys Phe Arg Arg
1               5

<210> SEQ ID NO 1011
<211> LENGTH: 7
<212> TYPE: PRT
<213> ORGANISM: Artificial Sequence
<220> FEATURE:
<223> OTHER INFORMATION: Synthetic construct

<400> SEQUENCE: 1011

Lys Trp Trp Lys Trp Lys Lys
1               5

<210> SEQ ID NO 1012
<211> LENGTH: 7
<212> TYPE: PRT
<213> ORGANISM: Artificial Sequence
<220> FEATURE:
<223> OTHER INFORMATION: Synthetic construct

<400> SEQUENCE: 1012

Lys Phe Phe Lys Phe Lys Lys
1               5

<210> SEQ ID NO 1013
<211> LENGTH: 9
<212> TYPE: PRT
<213> ORGANISM: Artificial Sequence
<220> FEATURE:
<223> OTHER INFORMATION: Synthetic construct

<400> SEQUENCE: 1013

Arg Trp Arg Trp Lys Arg Trp Trp Trp
1               5

<210> SEQ ID NO 1014
<211> LENGTH: 9
<212> TYPE: PRT
<213> ORGANISM: Artificial Sequence
<220> FEATURE:
<223> OTHER INFORMATION: Synthetic construct

<400> SEQUENCE: 1014

Arg Trp Arg Arg Trp Lys Trp Trp Trp
1               5

<210> SEQ ID NO 1015
<211> LENGTH: 9
<212> TYPE: PRT
<213> ORGANISM: Artificial Sequence
<220> FEATURE:
<223> OTHER INFORMATION: Synthetic construct

<400> SEQUENCE: 1015

Arg Trp Trp Arg Trp Arg Lys Trp Trp
1               5

<210> SEQ ID NO 1016
<211> LENGTH: 9
<212> TYPE: PRT
<213> ORGANISM: Artificial Sequence
<220> FEATURE:
<223> OTHER INFORMATION: Synthetic construct

<400> SEQUENCE: 1016
```

```
Arg Trp Arg Arg Lys Trp Trp Trp Trp
1               5
```

<210> SEQ ID NO 1017
<211> LENGTH: 9
<212> TYPE: PRT
<213> ORGANISM: Artificial Sequence
<220> FEATURE:
<223> OTHER INFORMATION: Synthetic construct

<400> SEQUENCE: 1017

```
Arg Trp Arg Trp Trp Lys Arg Trp Tyr
1               5
```

<210> SEQ ID NO 1018
<211> LENGTH: 9
<212> TYPE: PRT
<213> ORGANISM: Artificial Sequence
<220> FEATURE:
<223> OTHER INFORMATION: Synthetic construct

<400> SEQUENCE: 1018

```
Arg Arg Lys Arg Trp Trp Trp Trp Trp
1               5
```

<210> SEQ ID NO 1019
<211> LENGTH: 9
<212> TYPE: PRT
<213> ORGANISM: Artificial Sequence
<220> FEATURE:
<223> OTHER INFORMATION: Synthetic construct

<400> SEQUENCE: 1019

```
Arg Trp Arg Ile Lys Arg Trp Trp Trp
1               5
```

<210> SEQ ID NO 1020
<211> LENGTH: 9
<212> TYPE: PRT
<213> ORGANISM: Artificial Sequence
<220> FEATURE:
<223> OTHER INFORMATION: Synthetic construct

<400> SEQUENCE: 1020

```
Lys Ile Trp Trp Trp Trp Arg Lys Arg
1               5
```

<210> SEQ ID NO 1021
<211> LENGTH: 9
<212> TYPE: PRT
<213> ORGANISM: Artificial Sequence
<220> FEATURE:
<223> OTHER INFORMATION: Synthetic construct

<400> SEQUENCE: 1021

```
Arg Trp Arg Arg Trp Lys Trp Trp Leu
1               5
```

<210> SEQ ID NO 1022
<211> LENGTH: 9
<212> TYPE: PRT
<213> ORGANISM: Artificial Sequence
<220> FEATURE:
<223> OTHER INFORMATION: Synthetic construct

<400> SEQUENCE: 1022

```
Lys Arg Trp Trp Lys Trp Ile Arg Trp
1               5
```

<210> SEQ ID NO 1023
<211> LENGTH: 9
<212> TYPE: PRT
<213> ORGANISM: Artificial Sequence
<220> FEATURE:
<223> OTHER INFORMATION: Synthetic construct

<400> SEQUENCE: 1023

```
Lys Arg Trp Trp Trp Trp Trp Lys Arg
1               5
```

<210> SEQ ID NO 1024
<211> LENGTH: 9
<212> TYPE: PRT
<213> ORGANISM: Artificial Sequence
<220> FEATURE:
<223> OTHER INFORMATION: Synthetic construct

<400> SEQUENCE: 1024

```
Ile Arg Trp Trp Lys Arg Trp Trp Arg
1               5
```

<210> SEQ ID NO 1025
<211> LENGTH: 9
<212> TYPE: PRT
<213> ORGANISM: Artificial Sequence
<220> FEATURE:
<223> OTHER INFORMATION: Synthetic construct

<400> SEQUENCE: 1025

```
Ile Lys Arg Trp Trp Arg Trp Trp Arg
1               5
```

<210> SEQ ID NO 1026
<211> LENGTH: 9
<212> TYPE: PRT
<213> ORGANISM: Artificial Sequence
<220> FEATURE:
<223> OTHER INFORMATION: Synthetic construct

<400> SEQUENCE: 1026

```
Arg Arg Lys Trp Trp Trp Arg Trp Trp
1               5
```

<210> SEQ ID NO 1027
<211> LENGTH: 9
<212> TYPE: PRT
<213> ORGANISM: Artificial Sequence
<220> FEATURE:
<223> OTHER INFORMATION: Synthetic construct

<400> SEQUENCE: 1027

```
Arg Lys Trp Trp Arg Trp Trp Arg Trp
1               5
```

<210> SEQ ID NO 1028
<211> LENGTH: 9
<212> TYPE: PRT
<213> ORGANISM: Artificial Sequence
<220> FEATURE:
<223> OTHER INFORMATION: Synthetic construct

<400> SEQUENCE: 1028

```
Lys Arg Trp Trp Trp Trp Arg Phe Arg
```

```
1               5
```

<210> SEQ ID NO 1029
<211> LENGTH: 9
<212> TYPE: PRT
<213> ORGANISM: Artificial Sequence
<220> FEATURE:
<223> OTHER INFORMATION: Synthetic construct

<400> SEQUENCE: 1029

```
Ile Lys Arg Trp Trp Trp Arg Arg Trp
1               5
```

<210> SEQ ID NO 1030
<211> LENGTH: 9
<212> TYPE: PRT
<213> ORGANISM: Artificial Sequence
<220> FEATURE:
<223> OTHER INFORMATION: Synthetic construct

<400> SEQUENCE: 1030

```
Lys Arg Trp Trp Trp Val Trp Lys Arg
1               5
```

<210> SEQ ID NO 1031
<211> LENGTH: 9
<212> TYPE: PRT
<213> ORGANISM: Artificial Sequence
<220> FEATURE:
<223> OTHER INFORMATION: Synthetic construct

<400> SEQUENCE: 1031

```
Lys Trp Arg Arg Trp Lys Arg Trp Trp
1               5
```

<210> SEQ ID NO 1032
<211> LENGTH: 9
<212> TYPE: PRT
<213> ORGANISM: Artificial Sequence
<220> FEATURE:
<223> OTHER INFORMATION: Synthetic construct

<400> SEQUENCE: 1032

```
Trp Arg Trp Trp Lys Ile Trp Lys Arg
1               5
```

<210> SEQ ID NO 1033
<211> LENGTH: 9
<212> TYPE: PRT
<213> ORGANISM: Artificial Sequence
<220> FEATURE:
<223> OTHER INFORMATION: Synthetic construct

<400> SEQUENCE: 1033

```
Trp Arg Trp Arg Trp Trp Lys Arg Trp
1               5
```

<210> SEQ ID NO 1034
<211> LENGTH: 9
<212> TYPE: PRT
<213> ORGANISM: Artificial Sequence
<220> FEATURE:
<223> OTHER INFORMATION: Synthetic construct

<400> SEQUENCE: 1034

```
Trp Lys Arg Trp Lys Trp Trp Lys Arg
1               5
```

```
<210> SEQ ID NO 1035
<211> LENGTH: 9
<212> TYPE: PRT
<213> ORGANISM: Artificial Sequence
<220> FEATURE:
<223> OTHER INFORMATION: Synthetic construct

<400> SEQUENCE: 1035

Arg Ile Lys Arg Trp Trp Trp Trp Arg
1               5

<210> SEQ ID NO 1036
<211> LENGTH: 9
<212> TYPE: PRT
<213> ORGANISM: Artificial Sequence
<220> FEATURE:
<223> OTHER INFORMATION: Synthetic construct

<400> SEQUENCE: 1036

Ile Trp Lys Arg Trp Trp Arg Arg Trp
1               5

<210> SEQ ID NO 1037
<211> LENGTH: 9
<212> TYPE: PRT
<213> ORGANISM: Artificial Sequence
<220> FEATURE:
<223> OTHER INFORMATION: Synthetic construct

<400> SEQUENCE: 1037

Lys Trp Trp Lys Ile Trp Trp Lys Arg
1               5

<210> SEQ ID NO 1038
<211> LENGTH: 9
<212> TYPE: PRT
<213> ORGANISM: Artificial Sequence
<220> FEATURE:
<223> OTHER INFORMATION: Synthetic construct

<400> SEQUENCE: 1038

Arg Lys Arg Trp Leu Trp Arg Trp Trp
1               5

<210> SEQ ID NO 1039
<211> LENGTH: 9
<212> TYPE: PRT
<213> ORGANISM: Artificial Sequence
<220> FEATURE:
<223> OTHER INFORMATION: Synthetic construct

<400> SEQUENCE: 1039

Lys Arg Trp Arg Trp Trp Arg Trp Trp
1               5

<210> SEQ ID NO 1040
<211> LENGTH: 9
<212> TYPE: PRT
<213> ORGANISM: Artificial Sequence
<220> FEATURE:
<223> OTHER INFORMATION: Synthetic construct

<400> SEQUENCE: 1040

Lys Lys Arg Trp Leu Trp Trp Trp Arg
1               5
```

<210> SEQ ID NO 1041
<211> LENGTH: 9
<212> TYPE: PRT
<213> ORGANISM: Artificial Sequence
<220> FEATURE:
<223> OTHER INFORMATION: Synthetic construct

<400> SEQUENCE: 1041

Arg Trp Trp Arg Lys Trp Trp Ile Arg
1               5

<210> SEQ ID NO 1042
<211> LENGTH: 9
<212> TYPE: PRT
<213> ORGANISM: Artificial Sequence
<220> FEATURE:
<223> OTHER INFORMATION: Synthetic construct

<400> SEQUENCE: 1042

Lys Trp Trp Arg Trp Trp Arg Lys Trp
1               5

<210> SEQ ID NO 1043
<211> LENGTH: 9
<212> TYPE: PRT
<213> ORGANISM: Artificial Sequence
<220> FEATURE:
<223> OTHER INFORMATION: Synthetic construct

<400> SEQUENCE: 1043

Lys Arg Trp Trp Ile Arg Trp Trp Arg
1               5

<210> SEQ ID NO 1044
<211> LENGTH: 9
<212> TYPE: PRT
<213> ORGANISM: Artificial Sequence
<220> FEATURE:
<223> OTHER INFORMATION: Synthetic construct

<400> SEQUENCE: 1044

Lys Ile Trp Trp Trp Trp Arg Arg Arg
1               5

<210> SEQ ID NO 1045
<211> LENGTH: 9
<212> TYPE: PRT
<213> ORGANISM: Artificial Sequence
<220> FEATURE:
<223> OTHER INFORMATION: Synthetic construct

<400> SEQUENCE: 1045

Arg Arg Arg Lys Trp Trp Ile Trp Trp
1               5

<210> SEQ ID NO 1046
<211> LENGTH: 9
<212> TYPE: PRT
<213> ORGANISM: Artificial Sequence
<220> FEATURE:
<223> OTHER INFORMATION: Synthetic construct

<400> SEQUENCE: 1046

Arg Arg Arg Trp Trp Trp Trp Trp Trp
1               5

```
<210> SEQ ID NO 1047
<211> LENGTH: 9
<212> TYPE: PRT
<213> ORGANISM: Artificial Sequence
<220> FEATURE:
<223> OTHER INFORMATION: Synthetic construct

<400> SEQUENCE: 1047

Arg Trp Trp Ile Arg Lys Trp Trp Arg
1               5

<210> SEQ ID NO 1048
<211> LENGTH: 9
<212> TYPE: PRT
<213> ORGANISM: Artificial Sequence
<220> FEATURE:
<223> OTHER INFORMATION: Synthetic construct

<400> SEQUENCE: 1048

Lys Arg Trp Trp Lys Trp Trp Arg Arg
1               5

<210> SEQ ID NO 1049
<211> LENGTH: 9
<212> TYPE: PRT
<213> ORGANISM: Artificial Sequence
<220> FEATURE:
<223> OTHER INFORMATION: Synthetic construct

<400> SEQUENCE: 1049

Lys Arg Trp Trp Arg Lys Trp Trp Arg
1               5

<210> SEQ ID NO 1050
<211> LENGTH: 9
<212> TYPE: PRT
<213> ORGANISM: Artificial Sequence
<220> FEATURE:
<223> OTHER INFORMATION: Synthetic construct

<400> SEQUENCE: 1050

Arg Arg Ile Trp Arg Trp Trp Trp Trp
1               5

<210> SEQ ID NO 1051
<211> LENGTH: 9
<212> TYPE: PRT
<213> ORGANISM: Artificial Sequence
<220> FEATURE:
<223> OTHER INFORMATION: Synthetic construct

<400> SEQUENCE: 1051

Ile Arg Arg Arg Lys Trp Trp Trp Trp
1               5

<210> SEQ ID NO 1052
<211> LENGTH: 9
<212> TYPE: PRT
<213> ORGANISM: Artificial Sequence
<220> FEATURE:
<223> OTHER INFORMATION: Synthetic construct

<400> SEQUENCE: 1052

Lys Arg Lys Ile Trp Trp Trp Ile Arg
1               5

<210> SEQ ID NO 1053
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 1053

Arg Lys Ile Trp Trp Trp Arg Ile Arg
1               5

<210> SEQ ID NO 1054
<211> LENGTH: 9
<212> TYPE: PRT
<213> ORGANISM: Artificial Sequence
<220> FEATURE:
<223> OTHER INFORMATION: Synthetic construct

<400> SEQUENCE: 1054

Lys Arg Trp Trp Ile Trp Arg Ile Arg
1               5

<210> SEQ ID NO 1055
<211> LENGTH: 9
<212> TYPE: PRT
<213> ORGANISM: Artificial Sequence
<220> FEATURE:
<223> OTHER INFORMATION: Synthetic construct

<400> SEQUENCE: 1055

Arg Trp Phe Arg Trp Trp Lys Arg Trp
1               5

<210> SEQ ID NO 1056
<211> LENGTH: 9
<212> TYPE: PRT
<213> ORGANISM: Artificial Sequence
<220> FEATURE:
<223> OTHER INFORMATION: Synthetic construct

<400> SEQUENCE: 1056

Trp Arg Trp Trp Trp Lys Lys Trp Arg
1               5

<210> SEQ ID NO 1057
<211> LENGTH: 9
<212> TYPE: PRT
<213> ORGANISM: Artificial Sequence
<220> FEATURE:
<223> OTHER INFORMATION: Synthetic construct

<400> SEQUENCE: 1057

Trp Lys Arg Trp Trp Lys Lys Trp Arg
1               5

<210> SEQ ID NO 1058
<211> LENGTH: 9
<212> TYPE: PRT
<213> ORGANISM: Artificial Sequence
<220> FEATURE:
<223> OTHER INFORMATION: Synthetic construct

<400> SEQUENCE: 1058

Trp Lys Arg Trp Arg Trp Ile Arg Trp
1               5

<210> SEQ ID NO 1059
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 1059

Trp Arg Trp Trp Lys Trp Trp Arg Arg
1               5

<210> SEQ ID NO 1060
<211> LENGTH: 9
<212> TYPE: PRT
<213> ORGANISM: Artificial Sequence
<220> FEATURE:
<223> OTHER INFORMATION: Synthetic construct

<400> SEQUENCE: 1060

Trp Lys Lys Trp Trp Lys Arg Arg Trp
1               5

<210> SEQ ID NO 1061
<211> LENGTH: 9
<212> TYPE: PRT
<213> ORGANISM: Artificial Sequence
<220> FEATURE:
<223> OTHER INFORMATION: Synthetic construct

<400> SEQUENCE: 1061

Trp Arg Trp Tyr Trp Trp Lys Lys Arg
1               5

<210> SEQ ID NO 1062
<211> LENGTH: 9
<212> TYPE: PRT
<213> ORGANISM: Artificial Sequence
<220> FEATURE:
<223> OTHER INFORMATION: Synthetic construct

<400> SEQUENCE: 1062

Trp Arg Arg Trp Trp Lys Trp Trp Arg
1               5

<210> SEQ ID NO 1063
<211> LENGTH: 9
<212> TYPE: PRT
<213> ORGANISM: Artificial Sequence
<220> FEATURE:
<223> OTHER INFORMATION: Synthetic construct

<400> SEQUENCE: 1063

Ile Arg Met Trp Val Lys Arg Trp Arg
1               5

<210> SEQ ID NO 1064
<211> LENGTH: 9
<212> TYPE: PRT
<213> ORGANISM: Artificial Sequence
<220> FEATURE:
<223> OTHER INFORMATION: Synthetic construct

<400> SEQUENCE: 1064

Arg Ile Trp Tyr Trp Tyr Lys Arg Trp
1               5

<210> SEQ ID NO 1065
<211> LENGTH: 9
<212> TYPE: PRT
```

<213> ORGANISM: Artificial Sequence
<220> FEATURE:
<223> OTHER INFORMATION: Synthetic construct

<400> SEQUENCE: 1065

Phe Arg Arg Trp Trp Lys Trp Phe Lys
1               5

<210> SEQ ID NO 1066
<211> LENGTH: 9
<212> TYPE: PRT
<213> ORGANISM: Artificial Sequence
<220> FEATURE:
<223> OTHER INFORMATION: Synthetic construct

<400> SEQUENCE: 1066

Arg Val Arg Trp Trp Lys Lys Arg Trp
1               5

<210> SEQ ID NO 1067
<211> LENGTH: 9
<212> TYPE: PRT
<213> ORGANISM: Artificial Sequence
<220> FEATURE:
<223> OTHER INFORMATION: Synthetic construct

<400> SEQUENCE: 1067

Arg Leu Lys Lys Val Arg Trp Trp Trp
1               5

<210> SEQ ID NO 1068
<211> LENGTH: 9
<212> TYPE: PRT
<213> ORGANISM: Artificial Sequence
<220> FEATURE:
<223> OTHER INFORMATION: Synthetic construct

<400> SEQUENCE: 1068

Arg Trp Trp Leu Lys Ile Arg Lys Trp
1               5

<210> SEQ ID NO 1069
<211> LENGTH: 9
<212> TYPE: PRT
<213> ORGANISM: Artificial Sequence
<220> FEATURE:
<223> OTHER INFORMATION: Synthetic construct

<400> SEQUENCE: 1069

Leu Arg Trp Trp Trp Ile Lys Arg Ile
1               5

<210> SEQ ID NO 1070
<211> LENGTH: 9
<212> TYPE: PRT
<213> ORGANISM: Artificial Sequence
<220> FEATURE:
<223> OTHER INFORMATION: Synthetic construct

<400> SEQUENCE: 1070

Thr Arg Lys Val Trp Trp Trp Arg Trp
1               5

<210> SEQ ID NO 1071
<211> LENGTH: 9
<212> TYPE: PRT
<213> ORGANISM: Artificial Sequence

```
<220> FEATURE:
<223> OTHER INFORMATION: Synthetic construct

<400> SEQUENCE: 1071

Lys Arg Phe Trp Ile Trp Phe Trp Arg
1               5

<210> SEQ ID NO 1072
<211> LENGTH: 9
<212> TYPE: PRT
<213> ORGANISM: Artificial Sequence
<220> FEATURE:
<223> OTHER INFORMATION: Synthetic construct

<400> SEQUENCE: 1072

Lys Lys Arg Trp Val Trp Val Ile Arg
1               5

<210> SEQ ID NO 1073
<211> LENGTH: 9
<212> TYPE: PRT
<213> ORGANISM: Artificial Sequence
<220> FEATURE:
<223> OTHER INFORMATION: Synthetic construct

<400> SEQUENCE: 1073

Lys Arg Trp Val Trp Tyr Arg Tyr Trp
1               5

<210> SEQ ID NO 1074
<211> LENGTH: 9
<212> TYPE: PRT
<213> ORGANISM: Artificial Sequence
<220> FEATURE:
<223> OTHER INFORMATION: Synthetic construct

<400> SEQUENCE: 1074

Ile Arg Lys Trp Arg Arg Trp Trp Lys
1               5

<210> SEQ ID NO 1075
<211> LENGTH: 9
<212> TYPE: PRT
<213> ORGANISM: Artificial Sequence
<220> FEATURE:
<223> OTHER INFORMATION: Synthetic construct

<400> SEQUENCE: 1075

Arg His Trp Lys Thr Trp Trp Lys Arg
1               5

<210> SEQ ID NO 1076
<211> LENGTH: 9
<212> TYPE: PRT
<213> ORGANISM: Artificial Sequence
<220> FEATURE:
<223> OTHER INFORMATION: Synthetic construct

<400> SEQUENCE: 1076

Arg Arg Phe Lys Lys Trp Tyr Trp Tyr
1               5

<210> SEQ ID NO 1077
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 1077

Arg Ile Lys Val Ile Trp Trp Trp Arg
1               5

<210> SEQ ID NO 1078
<211> LENGTH: 9
<212> TYPE: PRT
<213> ORGANISM: Artificial Sequence
<220> FEATURE:
<223> OTHER INFORMATION: Synthetic construct

<400> SEQUENCE: 1078

Arg Lys Arg Leu Lys Trp Trp Ile Tyr
1               5

<210> SEQ ID NO 1079
<211> LENGTH: 9
<212> TYPE: PRT
<213> ORGANISM: Artificial Sequence
<220> FEATURE:
<223> OTHER INFORMATION: Synthetic construct

<400> SEQUENCE: 1079

Leu Val Phe Arg Lys Tyr Trp Lys Arg
1               5

<210> SEQ ID NO 1080
<211> LENGTH: 9
<212> TYPE: PRT
<213> ORGANISM: Artificial Sequence
<220> FEATURE:
<223> OTHER INFORMATION: Synthetic construct

<400> SEQUENCE: 1080

Arg Arg Arg Trp Trp Trp Ile Ile Val
1               5

<210> SEQ ID NO 1081
<211> LENGTH: 9
<212> TYPE: PRT
<213> ORGANISM: Artificial Sequence
<220> FEATURE:
<223> OTHER INFORMATION: Synthetic construct

<400> SEQUENCE: 1081

Lys Lys Arg Trp Val Trp Ile Arg Tyr
1               5

<210> SEQ ID NO 1082
<211> LENGTH: 9
<212> TYPE: PRT
<213> ORGANISM: Artificial Sequence
<220> FEATURE:
<223> OTHER INFORMATION: Synthetic construct

<400> SEQUENCE: 1082

Arg Trp Arg Ile Lys Phe Lys Arg Trp
1               5

<210> SEQ ID NO 1083
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 1083

Lys Trp Lys Ile Phe Arg Arg Trp Trp
1               5

<210> SEQ ID NO 1084
<211> LENGTH: 9
<212> TYPE: PRT
<213> ORGANISM: Artificial Sequence
<220> FEATURE:
<223> OTHER INFORMATION: Synthetic construct

<400> SEQUENCE: 1084

Ile Trp Lys Arg Trp Arg Lys Arg Leu
1               5

<210> SEQ ID NO 1085
<211> LENGTH: 9
<212> TYPE: PRT
<213> ORGANISM: Artificial Sequence
<220> FEATURE:
<223> OTHER INFORMATION: Synthetic construct

<400> SEQUENCE: 1085

Arg Arg Arg Lys Trp Trp Ile Trp Gly
1               5

<210> SEQ ID NO 1086
<211> LENGTH: 9
<212> TYPE: PRT
<213> ORGANISM: Artificial Sequence
<220> FEATURE:
<223> OTHER INFORMATION: Synthetic construct

<400> SEQUENCE: 1086

Arg Trp Leu Val Leu Arg Lys Arg Trp
1               5

<210> SEQ ID NO 1087
<211> LENGTH: 9
<212> TYPE: PRT
<213> ORGANISM: Artificial Sequence
<220> FEATURE:
<223> OTHER INFORMATION: Synthetic construct

<400> SEQUENCE: 1087

Arg Lys Trp Ile Trp Arg Trp Phe Leu
1               5

<210> SEQ ID NO 1088
<211> LENGTH: 9
<212> TYPE: PRT
<213> ORGANISM: Artificial Sequence
<220> FEATURE:
<223> OTHER INFORMATION: Synthetic construct

<400> SEQUENCE: 1088

Lys Arg Arg Arg Ile Trp Trp Trp Lys
1               5

<210> SEQ ID NO 1089
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 1089

Ile Trp Trp Lys Trp Arg Arg Trp Val
1               5

<210> SEQ ID NO 1090
<211> LENGTH: 9
<212> TYPE: PRT
<213> ORGANISM: Artificial Sequence
<220> FEATURE:
<223> OTHER INFORMATION: Synthetic construct

<400> SEQUENCE: 1090

Leu Arg Trp Arg Trp Trp Lys Ile Lys
1               5

<210> SEQ ID NO 1091
<211> LENGTH: 9
<212> TYPE: PRT
<213> ORGANISM: Artificial Sequence
<220> FEATURE:
<223> OTHER INFORMATION: Synthetic construct

<400> SEQUENCE: 1091

Arg Trp Lys Met Trp Trp Arg Trp Val
1               5

<210> SEQ ID NO 1092
<211> LENGTH: 9
<212> TYPE: PRT
<213> ORGANISM: Artificial Sequence
<220> FEATURE:
<223> OTHER INFORMATION: Synthetic construct

<400> SEQUENCE: 1092

Val Lys Arg Tyr Tyr Trp Arg Trp Arg
1               5

<210> SEQ ID NO 1093
<211> LENGTH: 9
<212> TYPE: PRT
<213> ORGANISM: Artificial Sequence
<220> FEATURE:
<223> OTHER INFORMATION: Synthetic construct

<400> SEQUENCE: 1093

Arg Trp Tyr Arg Lys Arg Trp Ser Trp
1               5

<210> SEQ ID NO 1094
<211> LENGTH: 9
<212> TYPE: PRT
<213> ORGANISM: Artificial Sequence
<220> FEATURE:
<223> OTHER INFORMATION: Synthetic construct

<400> SEQUENCE: 1094

Lys Arg Lys Leu Ile Arg Trp Trp Trp
1               5

<210> SEQ ID NO 1095
<211> LENGTH: 9
<212> TYPE: PRT
<213> ORGANISM: Artificial Sequence
<220> FEATURE:
<223> OTHER INFORMATION: Synthetic construct

<400> SEQUENCE: 1095
```

```
Arg Trp Arg Trp Trp Ile Lys Ile Ile
1               5

<210> SEQ ID NO 1096
<211> LENGTH: 9
<212> TYPE: PRT
<213> ORGANISM: Artificial Sequence
<220> FEATURE:
<223> OTHER INFORMATION: Synthetic construct

<400> SEQUENCE: 1096

Lys Phe Arg Lys Arg Val Trp Trp Trp
1               5

<210> SEQ ID NO 1097
<211> LENGTH: 9
<212> TYPE: PRT
<213> ORGANISM: Artificial Sequence
<220> FEATURE:
<223> OTHER INFORMATION: Synthetic construct

<400> SEQUENCE: 1097

Ile Trp Ile Trp Arg Lys Leu Arg Trp
1               5

<210> SEQ ID NO 1098
<211> LENGTH: 9
<212> TYPE: PRT
<213> ORGANISM: Artificial Sequence
<220> FEATURE:
<223> OTHER INFORMATION: Synthetic construct

<400> SEQUENCE: 1098

Leu Arg Phe Ile Leu Trp Trp Lys Arg
1               5

<210> SEQ ID NO 1099
<211> LENGTH: 9
<212> TYPE: PRT
<213> ORGANISM: Artificial Sequence
<220> FEATURE:
<223> OTHER INFORMATION: Synthetic construct

<400> SEQUENCE: 1099

Arg Val Trp Phe Lys Arg Arg Trp Trp
1               5

<210> SEQ ID NO 1100
<211> LENGTH: 9
<212> TYPE: PRT
<213> ORGANISM: Artificial Sequence
<220> FEATURE:
<223> OTHER INFORMATION: Synthetic construct

<400> SEQUENCE: 1100

Arg Arg Trp Phe Val Lys Trp Trp Tyr
1               5

<210> SEQ ID NO 1101
<211> LENGTH: 9
<212> TYPE: PRT
<213> ORGANISM: Artificial Sequence
<220> FEATURE:
<223> OTHER INFORMATION: Synthetic construct

<400> SEQUENCE: 1101
```

```
Lys Trp Trp Leu Val Trp Lys Arg Lys
1               5

<210> SEQ ID NO 1102
<211> LENGTH: 9
<212> TYPE: PRT
<213> ORGANISM: Artificial Sequence
<220> FEATURE:
<223> OTHER INFORMATION: Synthetic construct

<400> SEQUENCE: 1102

Arg Trp Ile Leu Trp Trp Trp Arg Ile
1               5

<210> SEQ ID NO 1103
<211> LENGTH: 9
<212> TYPE: PRT
<213> ORGANISM: Artificial Sequence
<220> FEATURE:
<223> OTHER INFORMATION: Synthetic construct

<400> SEQUENCE: 1103

Lys Arg Trp Leu Thr Trp Arg Phe Arg
1               5

<210> SEQ ID NO 1104
<211> LENGTH: 9
<212> TYPE: PRT
<213> ORGANISM: Artificial Sequence
<220> FEATURE:
<223> OTHER INFORMATION: Synthetic construct

<400> SEQUENCE: 1104

Arg Lys Trp Arg Trp Arg Trp Leu Lys
1               5

<210> SEQ ID NO 1105
<211> LENGTH: 9
<212> TYPE: PRT
<213> ORGANISM: Artificial Sequence
<220> FEATURE:
<223> OTHER INFORMATION: Synthetic construct

<400> SEQUENCE: 1105

Ile Arg Arg Arg Trp Trp Trp Ile Val
1               5

<210> SEQ ID NO 1106
<211> LENGTH: 9
<212> TYPE: PRT
<213> ORGANISM: Artificial Sequence
<220> FEATURE:
<223> OTHER INFORMATION: Synthetic construct

<400> SEQUENCE: 1106

Ile Lys Trp Trp Trp Arg Met Arg Ile
1               5

<210> SEQ ID NO 1107
<211> LENGTH: 9
<212> TYPE: PRT
<213> ORGANISM: Artificial Sequence
<220> FEATURE:
<223> OTHER INFORMATION: Synthetic construct

<400> SEQUENCE: 1107

Arg Trp Lys Ile Phe Ile Arg Trp Trp
```

```
1               5
```

<210> SEQ ID NO 1108
<211> LENGTH: 9
<212> TYPE: PRT
<213> ORGANISM: Artificial Sequence
<220> FEATURE:
<223> OTHER INFORMATION: Synthetic construct

<400> SEQUENCE: 1108

```
Ile Arg Gln Trp Trp Arg Arg Trp Trp
1               5
```

<210> SEQ ID NO 1109
<211> LENGTH: 9
<212> TYPE: PRT
<213> ORGANISM: Artificial Sequence
<220> FEATURE:
<223> OTHER INFORMATION: Synthetic construct

<400> SEQUENCE: 1109

```
Arg Arg Arg Lys Thr Trp Tyr Trp Trp
1               5
```

<210> SEQ ID NO 1110
<211> LENGTH: 9
<212> TYPE: PRT
<213> ORGANISM: Artificial Sequence
<220> FEATURE:
<223> OTHER INFORMATION: Synthetic construct

<400> SEQUENCE: 1110

```
Arg Arg Trp Trp Met Arg Trp Trp Val
1               5
```

<210> SEQ ID NO 1111
<211> LENGTH: 9
<212> TYPE: PRT
<213> ORGANISM: Artificial Sequence
<220> FEATURE:
<223> OTHER INFORMATION: Synthetic construct

<400> SEQUENCE: 1111

```
Arg Arg Trp Trp Met Arg Trp Trp Val
1               5
```

<210> SEQ ID NO 1112
<211> LENGTH: 9
<212> TYPE: PRT
<213> ORGANISM: Artificial Sequence
<220> FEATURE:
<223> OTHER INFORMATION: Synthetic construct

<400> SEQUENCE: 1112

```
Arg Arg Phe Lys Phe Ile Arg Trp Trp
1               5
```

<210> SEQ ID NO 1113
<211> LENGTH: 9
<212> TYPE: PRT
<213> ORGANISM: Artificial Sequence
<220> FEATURE:
<223> OTHER INFORMATION: Synthetic construct

<400> SEQUENCE: 1113

```
Ile Asn Arg Lys Arg Arg Leu Arg Trp
1               5
```

<210> SEQ ID NO 1114
<211> LENGTH: 9
<212> TYPE: PRT
<213> ORGANISM: Artificial Sequence
<220> FEATURE:
<223> OTHER INFORMATION: Synthetic construct

<400> SEQUENCE: 1114

Arg Arg Met Lys Lys Leu Arg Arg Lys
1               5

<210> SEQ ID NO 1115
<211> LENGTH: 9
<212> TYPE: PRT
<213> ORGANISM: Artificial Sequence
<220> FEATURE:
<223> OTHER INFORMATION: Synthetic construct

<400> SEQUENCE: 1115

Arg Lys Val Arg Trp Lys Ile Arg Val
1               5

<210> SEQ ID NO 1116
<211> LENGTH: 9
<212> TYPE: PRT
<213> ORGANISM: Artificial Sequence
<220> FEATURE:
<223> OTHER INFORMATION: Synthetic construct

<400> SEQUENCE: 1116

Val Arg Ile Val Arg Val Arg Ile Arg
1               5

<210> SEQ ID NO 1117
<211> LENGTH: 9
<212> TYPE: PRT
<213> ORGANISM: Artificial Sequence
<220> FEATURE:
<223> OTHER INFORMATION: Synthetic construct

<400> SEQUENCE: 1117

Ile Lys Arg Val Lys Arg Arg Lys Arg
1               5

<210> SEQ ID NO 1118
<211> LENGTH: 9
<212> TYPE: PRT
<213> ORGANISM: Artificial Sequence
<220> FEATURE:
<223> OTHER INFORMATION: Synthetic construct

<400> SEQUENCE: 1118

Arg Val Lys Thr Trp Arg Val Arg Thr
1               5

<210> SEQ ID NO 1119
<211> LENGTH: 9
<212> TYPE: PRT
<213> ORGANISM: Artificial Sequence
<220> FEATURE:
<223> OTHER INFORMATION: Synthetic construct

<400> SEQUENCE: 1119

Arg Val Phe Val Lys Ile Arg Met Lys
1               5

<210> SEQ ID NO 1120
<211> LENGTH: 9
<212> TYPE: PRT
<213> ORGANISM: Artificial Sequence
<220> FEATURE:
<223> OTHER INFORMATION: Synthetic construct

<400> SEQUENCE: 1120

Ile Arg Gly Arg Ile Ile Phe Trp Val
1               5

<210> SEQ ID NO 1121
<211> LENGTH: 9
<212> TYPE: PRT
<213> ORGANISM: Artificial Sequence
<220> FEATURE:
<223> OTHER INFORMATION: Synthetic construct

<400> SEQUENCE: 1121

Ala Thr Trp Ile Trp Val Phe Arg Arg
1               5

<210> SEQ ID NO 1122
<211> LENGTH: 9
<212> TYPE: PRT
<213> ORGANISM: Artificial Sequence
<220> FEATURE:
<223> OTHER INFORMATION: Synthetic construct

<400> SEQUENCE: 1122

Lys Lys Ser Lys Gln Leu Trp Lys Arg
1               5

<210> SEQ ID NO 1123
<211> LENGTH: 9
<212> TYPE: PRT
<213> ORGANISM: Artificial Sequence
<220> FEATURE:
<223> OTHER INFORMATION: Synthetic construct

<400> SEQUENCE: 1123

Met Ile Asn Arg Val Arg Leu Arg Trp
1               5

<210> SEQ ID NO 1124
<211> LENGTH: 9
<212> TYPE: PRT
<213> ORGANISM: Artificial Sequence
<220> FEATURE:
<223> OTHER INFORMATION: Synthetic construct

<400> SEQUENCE: 1124

Gly Gly Ile Arg Arg Leu Arg Trp Tyr
1               5

<210> SEQ ID NO 1125
<211> LENGTH: 9
<212> TYPE: PRT
<213> ORGANISM: Artificial Sequence
<220> FEATURE:
<223> OTHER INFORMATION: Synthetic construct

<400> SEQUENCE: 1125

Arg Leu Val His Trp Ile Arg Arg Val
1               5

```
<210> SEQ ID NO 1126
<211> LENGTH: 9
<212> TYPE: PRT
<213> ORGANISM: Artificial Sequence
<220> FEATURE:
<223> OTHER INFORMATION: Synthetic construct

<400> SEQUENCE: 1126

Ala Trp Lys Ile Lys Lys Gly Arg Ile
1               5

<210> SEQ ID NO 1127
<211> LENGTH: 9
<212> TYPE: PRT
<213> ORGANISM: Artificial Sequence
<220> FEATURE:
<223> OTHER INFORMATION: Synthetic construct

<400> SEQUENCE: 1127

Phe Val Val Met Lys Arg Ile Val Trp
1               5

<210> SEQ ID NO 1128
<211> LENGTH: 9
<212> TYPE: PRT
<213> ORGANISM: Artificial Sequence
<220> FEATURE:
<223> OTHER INFORMATION: Synthetic construct

<400> SEQUENCE: 1128

Gly Ile Lys Trp Arg Ser Arg Arg Trp
1               5

<210> SEQ ID NO 1129
<211> LENGTH: 9
<212> TYPE: PRT
<213> ORGANISM: Artificial Sequence
<220> FEATURE:
<223> OTHER INFORMATION: Synthetic construct

<400> SEQUENCE: 1129

Arg Trp Met Val Ser Lys Ile Trp Tyr
1               5

<210> SEQ ID NO 1130
<211> LENGTH: 9
<212> TYPE: PRT
<213> ORGANISM: Artificial Sequence
<220> FEATURE:
<223> OTHER INFORMATION: Synthetic construct

<400> SEQUENCE: 1130

Ile Val Val Arg Val Trp Val Val Arg
1               5

<210> SEQ ID NO 1131
<211> LENGTH: 9
<212> TYPE: PRT
<213> ORGANISM: Artificial Sequence
<220> FEATURE:
<223> OTHER INFORMATION: Synthetic construct

<400> SEQUENCE: 1131

Arg Trp Ile Gly Val Ile Ile Lys Tyr
1               5

<210> SEQ ID NO 1132
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 1132

Trp Ile Arg Lys Arg Ser Arg Ile Phe
1               5

<210> SEQ ID NO 1133
<211> LENGTH: 9
<212> TYPE: PRT
<213> ORGANISM: Artificial Sequence
<220> FEATURE:
<223> OTHER INFORMATION: Synthetic construct

<400> SEQUENCE: 1133

Gly Trp Lys Ile Leu Arg Lys Arg Lys
1               5

<210> SEQ ID NO 1134
<211> LENGTH: 9
<212> TYPE: PRT
<213> ORGANISM: Artificial Sequence
<220> FEATURE:
<223> OTHER INFORMATION: Synthetic construct

<400> SEQUENCE: 1134

Tyr Gln Arg Leu Phe Val Arg Ile Arg
1               5

<210> SEQ ID NO 1135
<211> LENGTH: 9
<212> TYPE: PRT
<213> ORGANISM: Artificial Sequence
<220> FEATURE:
<223> OTHER INFORMATION: Synthetic construct

<400> SEQUENCE: 1135

Ala Val Trp Lys Phe Val Lys Arg Val
1               5

<210> SEQ ID NO 1136
<211> LENGTH: 9
<212> TYPE: PRT
<213> ORGANISM: Artificial Sequence
<220> FEATURE:
<223> OTHER INFORMATION: Synthetic construct

<400> SEQUENCE: 1136

Ile Arg Lys Lys Arg Arg Arg Trp Thr
1               5

<210> SEQ ID NO 1137
<211> LENGTH: 9
<212> TYPE: PRT
<213> ORGANISM: Artificial Sequence
<220> FEATURE:
<223> OTHER INFORMATION: Synthetic construct

<400> SEQUENCE: 1137

Ile Leu Arg Val Ile Ser Lys Arg Arg
1               5

<210> SEQ ID NO 1138
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 1138

Ala Trp Arg Phe Lys Asn Ile Arg Lys
1               5

<210> SEQ ID NO 1139
<211> LENGTH: 9
<212> TYPE: PRT
<213> ORGANISM: Artificial Sequence
<220> FEATURE:
<223> OTHER INFORMATION: Synthetic construct

<400> SEQUENCE: 1139

His Tyr Lys Phe Gln Arg Trp Ile Lys
1               5

<210> SEQ ID NO 1140
<211> LENGTH: 9
<212> TYPE: PRT
<213> ORGANISM: Artificial Sequence
<220> FEATURE:
<223> OTHER INFORMATION: Synthetic construct

<400> SEQUENCE: 1140

Arg Arg Ile Arg Arg Val Arg Trp Gly
1               5

<210> SEQ ID NO 1141
<211> LENGTH: 9
<212> TYPE: PRT
<213> ORGANISM: Artificial Sequence
<220> FEATURE:
<223> OTHER INFORMATION: Synthetic construct

<400> SEQUENCE: 1141

Val Leu Val Lys Lys Arg Arg Arg Arg
1               5

<210> SEQ ID NO 1142
<211> LENGTH: 9
<212> TYPE: PRT
<213> ORGANISM: Artificial Sequence
<220> FEATURE:
<223> OTHER INFORMATION: Synthetic construct

<400> SEQUENCE: 1142

Arg Trp Arg Gly Ile Val His Ile Arg
1               5

<210> SEQ ID NO 1143
<211> LENGTH: 9
<212> TYPE: PRT
<213> ORGANISM: Artificial Sequence
<220> FEATURE:
<223> OTHER INFORMATION: Synthetic construct

<400> SEQUENCE: 1143

Trp Arg Asn Arg Lys Val Val Trp Arg
1               5

<210> SEQ ID NO 1144
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 1144

Lys Phe Trp Trp Trp Asn Tyr Leu Lys
1               5

<210> SEQ ID NO 1145
<211> LENGTH: 9
<212> TYPE: PRT
<213> ORGANISM: Artificial Sequence
<220> FEATURE:
<223> OTHER INFORMATION: Synthetic construct

<400> SEQUENCE: 1145

Lys Arg Ile Met Lys Leu Lys Met Arg
1               5

<210> SEQ ID NO 1146
<211> LENGTH: 9
<212> TYPE: PRT
<213> ORGANISM: Artificial Sequence
<220> FEATURE:
<223> OTHER INFORMATION: Synthetic construct

<400> SEQUENCE: 1146

Ile Arg Arg Arg Lys Lys Arg Ile Lys
1               5

<210> SEQ ID NO 1147
<211> LENGTH: 9
<212> TYPE: PRT
<213> ORGANISM: Artificial Sequence
<220> FEATURE:
<223> OTHER INFORMATION: Synthetic construct

<400> SEQUENCE: 1147

Arg Lys Trp Met Gly Arg Phe Leu Met
1               5

<210> SEQ ID NO 1148
<211> LENGTH: 9
<212> TYPE: PRT
<213> ORGANISM: Artificial Sequence
<220> FEATURE:
<223> OTHER INFORMATION: Synthetic construct

<400> SEQUENCE: 1148

Arg Arg Val Gln Arg Gly Lys Trp Trp
1               5

<210> SEQ ID NO 1149
<211> LENGTH: 9
<212> TYPE: PRT
<213> ORGANISM: Artificial Sequence
<220> FEATURE:
<223> OTHER INFORMATION: Synthetic construct

<400> SEQUENCE: 1149

Trp His Gly Val Arg Trp Trp Lys Trp
1               5

<210> SEQ ID NO 1150
<211> LENGTH: 9
<212> TYPE: PRT
<213> ORGANISM: Artificial Sequence
```

<220> FEATURE:
<223> OTHER INFORMATION: Synthetic construct

<400> SEQUENCE: 1150

Trp Val Arg Phe Val Tyr Arg Tyr Trp
1               5

<210> SEQ ID NO 1151
<211> LENGTH: 9
<212> TYPE: PRT
<213> ORGANISM: Artificial Sequence
<220> FEATURE:
<223> OTHER INFORMATION: Synthetic construct

<400> SEQUENCE: 1151

Arg Lys Arg Thr Lys Val Thr Trp Ile
1               5

<210> SEQ ID NO 1152
<211> LENGTH: 9
<212> TYPE: PRT
<213> ORGANISM: Artificial Sequence
<220> FEATURE:
<223> OTHER INFORMATION: Synthetic construct

<400> SEQUENCE: 1152

Ile Arg Arg Ile Val Arg Arg Lys Ile
1               5

<210> SEQ ID NO 1153
<211> LENGTH: 9
<212> TYPE: PRT
<213> ORGANISM: Artificial Sequence
<220> FEATURE:
<223> OTHER INFORMATION: Synthetic construct

<400> SEQUENCE: 1153

Lys Ile Arg Arg Lys Val Arg Trp Gly
1               5

<210> SEQ ID NO 1154
<211> LENGTH: 9
<212> TYPE: PRT
<213> ORGANISM: Artificial Sequence
<220> FEATURE:
<223> OTHER INFORMATION: Synthetic construct

<400> SEQUENCE: 1154

Ala Ile Arg Arg Trp Arg Ile Arg Lys
1               5

<210> SEQ ID NO 1155
<211> LENGTH: 9
<212> TYPE: PRT
<213> ORGANISM: Artificial Sequence
<220> FEATURE:
<223> OTHER INFORMATION: Synthetic construct

<400> SEQUENCE: 1155

Trp Arg Phe Lys Val Leu Arg Gln Arg
1               5

<210> SEQ ID NO 1156
<211> LENGTH: 9
<212> TYPE: PRT
<213> ORGANISM: Artificial Sequence
<220> FEATURE:

```
<223> OTHER INFORMATION: Synthetic construct

<400> SEQUENCE: 1156

Arg Ser Gly Lys Lys Arg Trp Arg Arg
1               5

<210> SEQ ID NO 1157
<211> LENGTH: 9
<212> TYPE: PRT
<213> ORGANISM: Artificial Sequence
<220> FEATURE:
<223> OTHER INFORMATION: Synthetic construct

<400> SEQUENCE: 1157

Phe Met Trp Val Tyr Arg Tyr Lys Lys
1               5

<210> SEQ ID NO 1158
<211> LENGTH: 9
<212> TYPE: PRT
<213> ORGANISM: Artificial Sequence
<220> FEATURE:
<223> OTHER INFORMATION: Synthetic construct

<400> SEQUENCE: 1158

Arg Gly Lys Tyr Ile Arg Trp Arg Lys
1               5

<210> SEQ ID NO 1159
<211> LENGTH: 9
<212> TYPE: PRT
<213> ORGANISM: Artificial Sequence
<220> FEATURE:
<223> OTHER INFORMATION: Synthetic construct

<400> SEQUENCE: 1159

Trp Val Lys Val Trp Lys Tyr Thr Trp
1               5

<210> SEQ ID NO 1160
<211> LENGTH: 9
<212> TYPE: PRT
<213> ORGANISM: Artificial Sequence
<220> FEATURE:
<223> OTHER INFORMATION: Synthetic construct

<400> SEQUENCE: 1160

Val Val Leu Lys Ile Val Arg Arg Phe
1               5

<210> SEQ ID NO 1161
<211> LENGTH: 9
<212> TYPE: PRT
<213> ORGANISM: Artificial Sequence
<220> FEATURE:
<223> OTHER INFORMATION: Synthetic construct

<400> SEQUENCE: 1161

Gly Lys Phe Tyr Lys Val Trp Val Arg
1               5

<210> SEQ ID NO 1162
<211> LENGTH: 9
<212> TYPE: PRT
<213> ORGANISM: Artificial Sequence
<220> FEATURE:
<223> OTHER INFORMATION: Synthetic construct
```

<400> SEQUENCE: 1162

Ser Trp Tyr Arg Thr Arg Lys Arg Val
1               5

<210> SEQ ID NO 1163
<211> LENGTH: 9
<212> TYPE: PRT
<213> ORGANISM: Artificial Sequence
<220> FEATURE:
<223> OTHER INFORMATION: Synthetic construct

<400> SEQUENCE: 1163

Lys Asn Arg Gly Arg Trp Phe Ser His
1               5

<210> SEQ ID NO 1164
<211> LENGTH: 9
<212> TYPE: PRT
<213> ORGANISM: Artificial Sequence
<220> FEATURE:
<223> OTHER INFORMATION: Synthetic construct

<400> SEQUENCE: 1164

Ala Phe Arg Gly Ser Arg His Arg Met
1               5

<210> SEQ ID NO 1165
<211> LENGTH: 9
<212> TYPE: PRT
<213> ORGANISM: Artificial Sequence
<220> FEATURE:
<223> OTHER INFORMATION: Synthetic construct

<400> SEQUENCE: 1165

Gly Arg Asn Gly Trp Tyr Arg Ile Asn
1               5

<210> SEQ ID NO 1166
<211> LENGTH: 9
<212> TYPE: PRT
<213> ORGANISM: Artificial Sequence
<220> FEATURE:
<223> OTHER INFORMATION: Synthetic construct

<400> SEQUENCE: 1166

Ala Gly Gly Met Arg Lys Arg Thr Arg
1               5

<210> SEQ ID NO 1167
<211> LENGTH: 9
<212> TYPE: PRT
<213> ORGANISM: Artificial Sequence
<220> FEATURE:
<223> OTHER INFORMATION: Synthetic construct

<400> SEQUENCE: 1167

Ala Thr Arg Lys Gly Tyr Ser Lys Phe
1               5

<210> SEQ ID NO 1168
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 1168

Ser Ser Gly Val Arg Trp Ser Trp Arg
1               5

<210> SEQ ID NO 1169
<211> LENGTH: 9
<212> TYPE: PRT
<213> ORGANISM: Artificial Sequence
<220> FEATURE:
<223> OTHER INFORMATION: Synthetic construct

<400> SEQUENCE: 1169

Arg Val Trp Arg Asn Gly Tyr Ser Arg
1               5

<210> SEQ ID NO 1170
<211> LENGTH: 9
<212> TYPE: PRT
<213> ORGANISM: Artificial Sequence
<220> FEATURE:
<223> OTHER INFORMATION: Synthetic construct

<400> SEQUENCE: 1170

Trp Gly Arg Thr Arg Trp Ser Ser Arg
1               5

<210> SEQ ID NO 1171
<211> LENGTH: 9
<212> TYPE: PRT
<213> ORGANISM: Artificial Sequence
<220> FEATURE:
<223> OTHER INFORMATION: Synthetic construct

<400> SEQUENCE: 1171

Gly Lys Arg Val Trp Gly Arg Gly Arg
1               5

<210> SEQ ID NO 1172
<211> LENGTH: 9
<212> TYPE: PRT
<213> ORGANISM: Artificial Sequence
<220> FEATURE:
<223> OTHER INFORMATION: Synthetic construct

<400> SEQUENCE: 1172

Ser Phe Asn Trp Lys Arg Ser Gly Lys
1               5

<210> SEQ ID NO 1173
<211> LENGTH: 9
<212> TYPE: PRT
<213> ORGANISM: Artificial Sequence
<220> FEATURE:
<223> OTHER INFORMATION: Synthetic construct

<400> SEQUENCE: 1173

Trp Gly Arg Gly Gly Trp Thr Asn Arg
1               5

<210> SEQ ID NO 1174
<211> LENGTH: 9
<212> TYPE: PRT
<213> ORGANISM: Artificial Sequence
<220> FEATURE:
<223> OTHER INFORMATION: Synthetic construct

<400> SEQUENCE: 1174
```

Ala Asn Arg Trp Gly Arg Gly Ile Arg
1               5

<210> SEQ ID NO 1175
<211> LENGTH: 9
<212> TYPE: PRT
<213> ORGANISM: Artificial Sequence
<220> FEATURE:
<223> OTHER INFORMATION: Synthetic construct

<400> SEQUENCE: 1175

Trp Gly Gly His Lys Arg Arg Gly Trp
1               5

<210> SEQ ID NO 1176
<211> LENGTH: 9
<212> TYPE: PRT
<213> ORGANISM: Artificial Sequence
<220> FEATURE:
<223> OTHER INFORMATION: Synthetic construct

<400> SEQUENCE: 1176

Trp His Gly Gly Gln Lys Trp Arg Lys
1               5

<210> SEQ ID NO 1177
<211> LENGTH: 9
<212> TYPE: PRT
<213> ORGANISM: Artificial Sequence
<220> FEATURE:
<223> OTHER INFORMATION: Synthetic construct

<400> SEQUENCE: 1177

Phe Val Trp Gln Lys Gly Thr Asn Arg
1               5

<210> SEQ ID NO 1178
<211> LENGTH: 9
<212> TYPE: PRT
<213> ORGANISM: Artificial Sequence
<220> FEATURE:
<223> OTHER INFORMATION: Synthetic construct

<400> SEQUENCE: 1178

His Gly Val Trp Gly Asn Arg Lys Arg
1               5

<210> SEQ ID NO 1179
<211> LENGTH: 9
<212> TYPE: PRT
<213> ORGANISM: Artificial Sequence
<220> FEATURE:
<223> OTHER INFORMATION: Synthetic construct

<400> SEQUENCE: 1179

Thr Arg Gly Trp Ser Leu Gly Thr Arg
1               5

<210> SEQ ID NO 1180
<211> LENGTH: 9
<212> TYPE: PRT
<213> ORGANISM: Artificial Sequence
<220> FEATURE:
<223> OTHER INFORMATION: Synthetic construct

<400> SEQUENCE: 1180

Gly Arg Arg Val Met Asn Gln Lys Arg
1               5

<210> SEQ ID NO 1181
<211> LENGTH: 9
<212> TYPE: PRT
<213> ORGANISM: Artificial Sequence
<220> FEATURE:
<223> OTHER INFORMATION: Synthetic construct

<400> SEQUENCE: 1181

Arg Asn Lys Phe Gly Gly Asn Trp Arg
1               5

<210> SEQ ID NO 1182
<211> LENGTH: 9
<212> TYPE: PRT
<213> ORGANISM: Artificial Sequence
<220> FEATURE:
<223> OTHER INFORMATION: Synthetic construct

<400> SEQUENCE: 1182

Gly Val Arg Val Gln Arg Asn Ser Lys
1               5

<210> SEQ ID NO 1183
<211> LENGTH: 9
<212> TYPE: PRT
<213> ORGANISM: Artificial Sequence
<220> FEATURE:
<223> OTHER INFORMATION: Synthetic construct

<400> SEQUENCE: 1183

Asn Gln Lys Trp Ser Gly Arg Arg Arg
1               5

<210> SEQ ID NO 1184
<211> LENGTH: 9
<212> TYPE: PRT
<213> ORGANISM: Artificial Sequence
<220> FEATURE:
<223> OTHER INFORMATION: Synthetic construct

<400> SEQUENCE: 1184

Arg Gln Asn Gly Val Trp Arg Val Phe
1               5

<210> SEQ ID NO 1185
<211> LENGTH: 9
<212> TYPE: PRT
<213> ORGANISM: Artificial Sequence
<220> FEATURE:
<223> OTHER INFORMATION: Synthetic construct

<400> SEQUENCE: 1185

Gly Arg Met Arg Leu Trp Asn Gly Arg
1               5

<210> SEQ ID NO 1186
<211> LENGTH: 9
<212> TYPE: PRT
<213> ORGANISM: Artificial Sequence
<220> FEATURE:
<223> OTHER INFORMATION: Synthetic construct

<400> SEQUENCE: 1186

Trp His Tyr Arg Ser Gln Val Gly Arg

```
1               5

<210> SEQ ID NO 1187
<211> LENGTH: 9
<212> TYPE: PRT
<213> ORGANISM: Artificial Sequence
<220> FEATURE:
<223> OTHER INFORMATION: Synthetic construct

<400> SEQUENCE: 1187

Gly Trp Asn Thr Met Gly Arg Arg Trp
1               5

<210> SEQ ID NO 1188
<211> LENGTH: 9
<212> TYPE: PRT
<213> ORGANISM: Artificial Sequence
<220> FEATURE:
<223> OTHER INFORMATION: Synthetic construct

<400> SEQUENCE: 1188

Arg Arg Met Gly Asn Gly Gly Phe Arg
1               5

<210> SEQ ID NO 1189
<211> LENGTH: 9
<212> TYPE: PRT
<213> ORGANISM: Artificial Sequence
<220> FEATURE:
<223> OTHER INFORMATION: Synthetic construct

<400> SEQUENCE: 1189

Ser Lys Asn Val Arg Thr Trp Arg Gln
1               5

<210> SEQ ID NO 1190
<211> LENGTH: 9
<212> TYPE: PRT
<213> ORGANISM: Artificial Sequence
<220> FEATURE:
<223> OTHER INFORMATION: Synthetic construct

<400> SEQUENCE: 1190

Ala Arg Gly Arg Trp Ile Asn Gly Arg
1               5

<210> SEQ ID NO 1191
<211> LENGTH: 9
<212> TYPE: PRT
<213> ORGANISM: Artificial Sequence
<220> FEATURE:
<223> OTHER INFORMATION: Synthetic construct

<400> SEQUENCE: 1191

Gly Ser Arg Arg Ser Val Trp Val Phe
1               5

<210> SEQ ID NO 1192
<211> LENGTH: 9
<212> TYPE: PRT
<213> ORGANISM: Artificial Sequence
<220> FEATURE:
<223> OTHER INFORMATION: Synthetic construct

<400> SEQUENCE: 1192

Trp Ser Gln Asn Val Arg Thr Arg Ile
1               5
```

<210> SEQ ID NO 1193
<211> LENGTH: 9
<212> TYPE: PRT
<213> ORGANISM: Artificial Sequence
<220> FEATURE:
<223> OTHER INFORMATION: Synthetic construct

<400> SEQUENCE: 1193

Gly Met Arg Arg Trp Arg Gly Lys Asn
1               5

<210> SEQ ID NO 1194
<211> LENGTH: 9
<212> TYPE: PRT
<213> ORGANISM: Artificial Sequence
<220> FEATURE:
<223> OTHER INFORMATION: Synthetic construct

<400> SEQUENCE: 1194

Arg Gly Arg Thr Ser Asn Trp Lys Met
1               5

<210> SEQ ID NO 1195
<211> LENGTH: 9
<212> TYPE: PRT
<213> ORGANISM: Artificial Sequence
<220> FEATURE:
<223> OTHER INFORMATION: Synthetic construct

<400> SEQUENCE: 1195

Trp Gly Lys Arg Arg Gly Trp Asn Thr
1               5

<210> SEQ ID NO 1196
<211> LENGTH: 9
<212> TYPE: PRT
<213> ORGANISM: Artificial Sequence
<220> FEATURE:
<223> OTHER INFORMATION: Synthetic construct

<400> SEQUENCE: 1196

Trp Gly Lys Arg Arg Gly Trp Asn Thr
1               5

<210> SEQ ID NO 1197
<211> LENGTH: 9
<212> TYPE: PRT
<213> ORGANISM: Artificial Sequence
<220> FEATURE:
<223> OTHER INFORMATION: Synthetic construct

<400> SEQUENCE: 1197

Ala Met Leu Gly Gly Arg Gln Trp Arg
1               5

<210> SEQ ID NO 1198
<211> LENGTH: 9
<212> TYPE: PRT
<213> ORGANISM: Artificial Sequence
<220> FEATURE:
<223> OTHER INFORMATION: Synthetic construct

<400> SEQUENCE: 1198

Gln Arg Asn Lys Gly Leu Arg His His
1               5

<210> SEQ ID NO 1199
<211> LENGTH: 9
<212> TYPE: PRT
<213> ORGANISM: Artificial Sequence
<220> FEATURE:
<223> OTHER INFORMATION: Synthetic construct

<400> SEQUENCE: 1199

Ala Arg Gly Lys Ser Ile Lys Asn Arg
1               5

<210> SEQ ID NO 1200
<211> LENGTH: 9
<212> TYPE: PRT
<213> ORGANISM: Artificial Sequence
<220> FEATURE:
<223> OTHER INFORMATION: Synthetic construct

<400> SEQUENCE: 1200

Asn Arg Arg Asn Gly Gln Met Arg Arg
1               5

<210> SEQ ID NO 1201
<211> LENGTH: 9
<212> TYPE: PRT
<213> ORGANISM: Artificial Sequence
<220> FEATURE:
<223> OTHER INFORMATION: Synthetic construct

<400> SEQUENCE: 1201

Arg Gly Arg Arg Gln Ile Gly Lys Phe
1               5

<210> SEQ ID NO 1202
<211> LENGTH: 9
<212> TYPE: PRT
<213> ORGANISM: Artificial Sequence
<220> FEATURE:
<223> OTHER INFORMATION: Synthetic construct

<400> SEQUENCE: 1202

Ala Ser Lys Arg Val Gly Val Arg Asn
1               5

<210> SEQ ID NO 1203
<211> LENGTH: 9
<212> TYPE: PRT
<213> ORGANISM: Artificial Sequence
<220> FEATURE:
<223> OTHER INFORMATION: Synthetic construct

<400> SEQUENCE: 1203

Gly Arg Ile Gly Gly Lys Asn Val Arg
1               5

<210> SEQ ID NO 1204
<211> LENGTH: 9
<212> TYPE: PRT
<213> ORGANISM: Artificial Sequence
<220> FEATURE:
<223> OTHER INFORMATION: Synthetic construct

<400> SEQUENCE: 1204

Asn Lys Thr Gly Tyr Arg Trp Arg Asn
1               5

```
<210> SEQ ID NO 1205
<211> LENGTH: 9
<212> TYPE: PRT
<213> ORGANISM: Artificial Sequence
<220> FEATURE:
<223> OTHER INFORMATION: Synthetic construct

<400> SEQUENCE: 1205

Val Ser Gly Asn Trp Arg Gly Ser Arg
1               5

<210> SEQ ID NO 1206
<211> LENGTH: 9
<212> TYPE: PRT
<213> ORGANISM: Artificial Sequence
<220> FEATURE:
<223> OTHER INFORMATION: Synthetic construct

<400> SEQUENCE: 1206

Gly Trp Gly Gly Lys Arg Arg Asn Phe
1               5

<210> SEQ ID NO 1207
<211> LENGTH: 9
<212> TYPE: PRT
<213> ORGANISM: Artificial Sequence
<220> FEATURE:
<223> OTHER INFORMATION: Synthetic construct

<400> SEQUENCE: 1207

Lys Asn Asn Arg Arg Trp Gln Gly Arg
1               5

<210> SEQ ID NO 1208
<211> LENGTH: 9
<212> TYPE: PRT
<213> ORGANISM: Artificial Sequence
<220> FEATURE:
<223> OTHER INFORMATION: Synthetic construct

<400> SEQUENCE: 1208

Gly Arg Thr Met Gly Asn Gly Arg Trp
1               5

<210> SEQ ID NO 1209
<211> LENGTH: 9
<212> TYPE: PRT
<213> ORGANISM: Artificial Sequence
<220> FEATURE:
<223> OTHER INFORMATION: Synthetic construct

<400> SEQUENCE: 1209

Gly Arg Gln Ile Ser Trp Gly Arg Thr
1               5

<210> SEQ ID NO 1210
<211> LENGTH: 9
<212> TYPE: PRT
<213> ORGANISM: Artificial Sequence
<220> FEATURE:
<223> OTHER INFORMATION: Synthetic construct

<400> SEQUENCE: 1210

Gly Gly Arg Gly Thr Arg Trp His Gly
1               5

<210> SEQ ID NO 1211
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 1211

Gly Val Arg Ser Trp Ser Gln Arg Thr
1               5

<210> SEQ ID NO 1212
<211> LENGTH: 9
<212> TYPE: PRT
<213> ORGANISM: Artificial Sequence
<220> FEATURE:
<223> OTHER INFORMATION: Synthetic construct

<400> SEQUENCE: 1212

Gly Ser Arg Arg Phe Gly Trp Asn Arg
1               5

<210> SEQ ID NO 1213
<211> LENGTH: 12
<212> TYPE: PRT
<213> ORGANISM: Artificial Sequence
<220> FEATURE:
<223> OTHER INFORMATION: Synthetic construct

<400> SEQUENCE: 1213

Leu Val Arg Ala Ile Gln Val Arg Ala Val Ile Arg
1               5                   10

<210> SEQ ID NO 1214
<211> LENGTH: 12
<212> TYPE: PRT
<213> ORGANISM: Artificial Sequence
<220> FEATURE:
<223> OTHER INFORMATION: Synthetic construct

<400> SEQUENCE: 1214

Val Gln Arg Trp Leu Ile Val Trp Arg Ile Arg Lys
1               5                   10

<210> SEQ ID NO 1215
<211> LENGTH: 12
<212> TYPE: PRT
<213> ORGANISM: Artificial Sequence
<220> FEATURE:
<223> OTHER INFORMATION: Synthetic construct

<400> SEQUENCE: 1215

Ile Val Trp Lys Ile Lys Arg Trp Trp Val Gly Arg
1               5                   10

<210> SEQ ID NO 1216
<211> LENGTH: 12
<212> TYPE: PRT
<213> ORGANISM: Artificial Sequence
<220> FEATURE:
<223> OTHER INFORMATION: Synthetic construct

<400> SEQUENCE: 1216

Arg Phe Trp Lys Val Arg Val Lys Tyr Ile Arg Phe
1               5                   10

<210> SEQ ID NO 1217
<211> LENGTH: 9
```

```
<212> TYPE: PRT
<213> ORGANISM: Artificial Sequence
<220> FEATURE:
<223> OTHER INFORMATION: Synthetic construct

<400> SEQUENCE: 1217

Val Gln Leu Arg Ile Arg Val Ala Val
1               5

<210> SEQ ID NO 1218
<211> LENGTH: 9
<212> TYPE: PRT
<213> ORGANISM: Artificial Sequence
<220> FEATURE:
<223> OTHER INFORMATION: Synthetic construct

<400> SEQUENCE: 1218

Val Gln Leu Arg Ile Trp Val Arg Arg
1               5

<210> SEQ ID NO 1219
<211> LENGTH: 9
<212> TYPE: PRT
<213> ORGANISM: Artificial Sequence
<220> FEATURE:
<223> OTHER INFORMATION: Synthetic construct

<400> SEQUENCE: 1219

Trp Asn Arg Val Lys Trp Ile Arg Arg
1               5

<210> SEQ ID NO 1220
<211> LENGTH: 9
<212> TYPE: PRT
<213> ORGANISM: Artificial Sequence
<220> FEATURE:
<223> OTHER INFORMATION: Synthetic construct

<400> SEQUENCE: 1220

Arg Ile Lys Trp Ile Val Arg Phe Arg
1               5

<210> SEQ ID NO 1221
<211> LENGTH: 12
<212> TYPE: PRT
<213> ORGANISM: Artificial Sequence
<220> FEATURE:
<223> OTHER INFORMATION: Synthetic construct

<400> SEQUENCE: 1221

Ala Ile Arg Val Val Arg Ala Arg Leu Val Arg Arg
1               5                   10

<210> SEQ ID NO 1222
<211> LENGTH: 12
<212> TYPE: PRT
<213> ORGANISM: Artificial Sequence
<220> FEATURE:
<223> OTHER INFORMATION: Synthetic construct

<400> SEQUENCE: 1222

Ile Arg Trp Arg Ile Arg Val Trp Val Arg Arg Ile
1               5                   10

<210> SEQ ID NO 1223
<211> LENGTH: 12
<212> TYPE: PRT
```

<213> ORGANISM: Artificial Sequence
<220> FEATURE:
<223> OTHER INFORMATION: Synthetic construct

<400> SEQUENCE: 1223

Arg Arg Trp Val Val Trp Arg Ile Val Gln Arg Arg
1               5                   10

<210> SEQ ID NO 1224
<211> LENGTH: 12
<212> TYPE: PRT
<213> ORGANISM: Artificial Sequence
<220> FEATURE:
<223> OTHER INFORMATION: Synthetic construct

<400> SEQUENCE: 1224

Ile Phe Trp Arg Arg Ile Val Ile Val Lys Lys Phe
1               5                   10

<210> SEQ ID NO 1225
<211> LENGTH: 9
<212> TYPE: PRT
<213> ORGANISM: Artificial Sequence
<220> FEATURE:
<223> OTHER INFORMATION: Synthetic construct

<400> SEQUENCE: 1225

Val Arg Leu Arg Ile Arg Val Ala Val
1               5

<210> SEQ ID NO 1226
<211> LENGTH: 8
<212> TYPE: PRT
<213> ORGANISM: Artificial Sequence
<220> FEATURE:
<223> OTHER INFORMATION: Synthetic construct

<400> SEQUENCE: 1226

Arg Gln Val Ile Val Arg Arg Trp
1               5

<210> SEQ ID NO 1227
<211> LENGTH: 9
<212> TYPE: PRT
<213> ORGANISM: Artificial Sequence
<220> FEATURE:
<223> OTHER INFORMATION: Synthetic construct

<400> SEQUENCE: 1227

Val Leu Ile Arg Trp Asn Gly Lys Lys
1               5

<210> SEQ ID NO 1228
<211> LENGTH: 9
<212> TYPE: PRT
<213> ORGANISM: Artificial Sequence
<220> FEATURE:
<223> OTHER INFORMATION: Synthetic construct

<400> SEQUENCE: 1228

Leu Arg Ile Arg Trp Ile Phe Lys Arg
1               5

<210> SEQ ID NO 1229
<211> LENGTH: 12
<212> TYPE: PRT
<213> ORGANISM: Artificial Sequence

```
<220> FEATURE:
<223> OTHER INFORMATION: Synthetic construct

<400> SEQUENCE: 1229

Lys Arg Ile Val Arg Arg Leu Val Ala Arg Ile Val
1               5                   10

<210> SEQ ID NO 1230
<211> LENGTH: 12
<212> TYPE: PRT
<213> ORGANISM: Artificial Sequence
<220> FEATURE:
<223> OTHER INFORMATION: Synthetic construct

<400> SEQUENCE: 1230

Val Arg Leu Ile Val Ala Val Arg Ile Trp Arg Arg
1               5                   10

<210> SEQ ID NO 1231
<211> LENGTH: 12
<212> TYPE: PRT
<213> ORGANISM: Artificial Sequence
<220> FEATURE:
<223> OTHER INFORMATION: Synthetic construct

<400> SEQUENCE: 1231

Ile Val Val Trp Arg Arg Gln Leu Val Lys Asn Lys
1               5                   10

<210> SEQ ID NO 1232
<211> LENGTH: 12
<212> TYPE: PRT
<213> ORGANISM: Artificial Sequence
<220> FEATURE:
<223> OTHER INFORMATION: Synthetic construct

<400> SEQUENCE: 1232

Val Arg Leu Arg Ile Arg Trp Trp Val Leu Arg Lys
1               5                   10

<210> SEQ ID NO 1233

<400> SEQUENCE: 1233

000

<210> SEQ ID NO 1234
<211> LENGTH: 9
<212> TYPE: PRT
<213> ORGANISM: Artificial Sequence
<220> FEATURE:
<223> OTHER INFORMATION: Synthetic construct

<400> SEQUENCE: 1234

Leu Arg Ile Arg Val Ile Val Trp Arg
1               5

<210> SEQ ID NO 1235
<211> LENGTH: 9
<212> TYPE: PRT
<213> ORGANISM: Artificial Sequence
<220> FEATURE:
<223> OTHER INFORMATION: Synthetic construct

<400> SEQUENCE: 1235

Ile Arg Val Trp Val Leu Arg Gln Arg
1               5
```

```
<210> SEQ ID NO 1236
<211> LENGTH: 9
<212> TYPE: PRT
<213> ORGANISM: Artificial Sequence
<220> FEATURE:
<223> OTHER INFORMATION: Synthetic construct

<400> SEQUENCE: 1236

Arg Ile Arg Val Ile Val Leu Lys Lys
1               5

<210> SEQ ID NO 1237
<211> LENGTH: 12
<212> TYPE: PRT
<213> ORGANISM: Artificial Sequence
<220> FEATURE:
<223> OTHER INFORMATION: Synthetic construct

<400> SEQUENCE: 1237

Arg Arg Ile Val Lys Lys Phe Gln Ile Val Arg Arg
1               5                   10

<210> SEQ ID NO 1238
<211> LENGTH: 12
<212> TYPE: PRT
<213> ORGANISM: Artificial Sequence
<220> FEATURE:
<223> OTHER INFORMATION: Synthetic construct

<400> SEQUENCE: 1238

Val Gln Trp Arg Ile Arg Val Arg Val Ile Lys Lys
1               5                   10

<210> SEQ ID NO 1239
<211> LENGTH: 12
<212> TYPE: PRT
<213> ORGANISM: Artificial Sequence
<220> FEATURE:
<223> OTHER INFORMATION: Synthetic construct

<400> SEQUENCE: 1239

Lys Lys Gln Val Ser Arg Val Lys Val Trp Arg Lys
1               5                   10

<210> SEQ ID NO 1240
<211> LENGTH: 12
<212> TYPE: PRT
<213> ORGANISM: Artificial Sequence
<220> FEATURE:
<223> OTHER INFORMATION: Synthetic construct

<400> SEQUENCE: 1240

Leu Ile Gln Arg Ile Arg Val Arg Asn Ile Val Lys
1               5                   10

<210> SEQ ID NO 1241
<211> LENGTH: 9
<212> TYPE: PRT
<213> ORGANISM: Artificial Sequence
<220> FEATURE:
<223> OTHER INFORMATION: Synthetic construct

<400> SEQUENCE: 1241

Lys Gln Phe Arg Ile Arg Val Arg Val
1               5
```

<210> SEQ ID NO 1242
<211> LENGTH: 9
<212> TYPE: PRT
<213> ORGANISM: Artificial Sequence
<220> FEATURE:
<223> OTHER INFORMATION: Synthetic construct

<400> SEQUENCE: 1242

Phe Arg Ile Arg Val Arg Val Ile Arg
1               5

<210> SEQ ID NO 1243
<211> LENGTH: 9
<212> TYPE: PRT
<213> ORGANISM: Artificial Sequence
<220> FEATURE:
<223> OTHER INFORMATION: Synthetic construct

<400> SEQUENCE: 1243

Trp Arg Trp Arg Val Arg Val Trp Arg
1               5

<210> SEQ ID NO 1244
<211> LENGTH: 9
<212> TYPE: PRT
<213> ORGANISM: Artificial Sequence
<220> FEATURE:
<223> OTHER INFORMATION: Synthetic construct

<400> SEQUENCE: 1244

Ile Arg Val Arg Val Ile Trp Arg Lys
1               5

<210> SEQ ID NO 1245
<211> LENGTH: 12
<212> TYPE: PRT
<213> ORGANISM: Artificial Sequence
<220> FEATURE:
<223> OTHER INFORMATION: Synthetic construct

<400> SEQUENCE: 1245

Arg Arg Val Ile Val Lys Lys Phe Arg Ile Arg Arg
1               5                   10

<210> SEQ ID NO 1246
<211> LENGTH: 12
<212> TYPE: PRT
<213> ORGANISM: Artificial Sequence
<220> FEATURE:
<223> OTHER INFORMATION: Synthetic construct

<400> SEQUENCE: 1246

Lys Gln Phe Arg Asn Arg Leu Arg Ile Val Lys Lys
1               5                   10

<210> SEQ ID NO 1247
<211> LENGTH: 12
<212> TYPE: PRT
<213> ORGANISM: Artificial Sequence
<220> FEATURE:
<223> OTHER INFORMATION: Synthetic construct

<400> SEQUENCE: 1247

Lys Arg Trp Arg Trp Ile Val Arg Asn Ile Arg Arg
1               5                   10

```
<210> SEQ ID NO 1248
<211> LENGTH: 12
<212> TYPE: PRT
<213> ORGANISM: Artificial Sequence
<220> FEATURE:
<223> OTHER INFORMATION: Synthetic construct

<400> SEQUENCE: 1248

Val Gln Phe Arg Ile Arg Val Ile Val Ile Arg Lys
1               5                   10

<210> SEQ ID NO 1249
<211> LENGTH: 9
<212> TYPE: PRT
<213> ORGANISM: Artificial Sequence
<220> FEATURE:
<223> OTHER INFORMATION: Synthetic construct

<400> SEQUENCE: 1249

Lys Arg Phe Arg Ile Arg Val Arg Val
1               5

<210> SEQ ID NO 1250
<211> LENGTH: 9
<212> TYPE: PRT
<213> ORGANISM: Artificial Sequence
<220> FEATURE:
<223> OTHER INFORMATION: Synthetic construct

<400> SEQUENCE: 1250

Ile Val Val Arg Arg Val Ile Arg Lys
1               5

<210> SEQ ID NO 1251
<211> LENGTH: 9
<212> TYPE: PRT
<213> ORGANISM: Artificial Sequence
<220> FEATURE:
<223> OTHER INFORMATION: Synthetic construct

<400> SEQUENCE: 1251

Ile Trp Val Ile Arg Arg Val Trp Arg
1               5

<210> SEQ ID NO 1252
<211> LENGTH: 9
<212> TYPE: PRT
<213> ORGANISM: Artificial Sequence
<220> FEATURE:
<223> OTHER INFORMATION: Synthetic construct

<400> SEQUENCE: 1252

Phe Gln Val Val Lys Ile Lys Val Arg
1               5

<210> SEQ ID NO 1253
<211> LENGTH: 7
<212> TYPE: PRT
<213> ORGANISM: Artificial Sequence
<220> FEATURE:
<223> OTHER INFORMATION: Synthetic construct

<400> SEQUENCE: 1253

Val Ile Trp Ile Arg Trp Arg
1               5

<210> SEQ ID NO 1254
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 1254

Ile Val Trp Ile Trp Arg Arg
1               5

<210> SEQ ID NO 1255
<211> LENGTH: 7
<212> TYPE: PRT
<213> ORGANISM: Artificial Sequence
<220> FEATURE:
<223> OTHER INFORMATION: Synthetic construct

<400> SEQUENCE: 1255

Trp Ile Val Ile Trp Arg Arg
1               5

<210> SEQ ID NO 1256
<211> LENGTH: 7
<212> TYPE: PRT
<213> ORGANISM: Artificial Sequence
<220> FEATURE:
<223> OTHER INFORMATION: Synthetic construct

<400> SEQUENCE: 1256

Arg Arg Trp Ile Val Trp Ile
1               5

<210> SEQ ID NO 1257
<211> LENGTH: 7
<212> TYPE: PRT
<213> ORGANISM: Artificial Sequence
<220> FEATURE:
<223> OTHER INFORMATION: Synthetic construct

<400> SEQUENCE: 1257

Arg Trp Trp Arg Ile Val Ile
1               5

<210> SEQ ID NO 1258
<211> LENGTH: 7
<212> TYPE: PRT
<213> ORGANISM: Artificial Sequence
<220> FEATURE:
<223> OTHER INFORMATION: Synthetic construct

<400> SEQUENCE: 1258

Trp Ile Arg Val Ile Arg Trp
1               5

<210> SEQ ID NO 1259
<211> LENGTH: 7
<212> TYPE: PRT
<213> ORGANISM: Artificial Sequence
<220> FEATURE:
<223> OTHER INFORMATION: Synthetic construct

<400> SEQUENCE: 1259

Ile Ile Arg Arg Trp Trp Val
1               5

<210> SEQ ID NO 1260
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 1260

Ile Arg Trp Val Ile Arg Trp
1               5

<210> SEQ ID NO 1261
<211> LENGTH: 13
<212> TYPE: PRT
<213> ORGANISM: Artificial Sequence
<220> FEATURE:
<223> OTHER INFORMATION: Synthetic construct

<400> SEQUENCE: 1261

Ile Leu Arg Trp Lys Trp Arg Trp Trp Arg Trp Arg Arg
1               5                   10

<210> SEQ ID NO 1262
<211> LENGTH: 9
<212> TYPE: PRT
<213> ORGANISM: Artificial Sequence
<220> FEATURE:
<223> OTHER INFORMATION: Synthetic construct

<400> SEQUENCE: 1262

Arg Trp Arg Trp Trp Arg Trp Arg Arg
1               5

<210> SEQ ID NO 1263
<211> LENGTH: 9
<212> TYPE: PRT
<213> ORGANISM: Artificial Sequence
<220> FEATURE:
<223> OTHER INFORMATION: Synthetic construct

<400> SEQUENCE: 1263

Lys Trp Lys Trp Trp Lys Trp Lys Lys
1               5

<210> SEQ ID NO 1264
<211> LENGTH: 7
<212> TYPE: PRT
<213> ORGANISM: Artificial Sequence
<220> FEATURE:
<223> OTHER INFORMATION: Synthetic construct

<400> SEQUENCE: 1264

Arg Trp Trp Arg Trp Arg Arg
1               5

<210> SEQ ID NO 1265
<211> LENGTH: 6
<212> TYPE: PRT
<213> ORGANISM: Artificial Sequence
<220> FEATURE:
<223> OTHER INFORMATION: Synthetic construct

<400> SEQUENCE: 1265

Arg Ile Arg Val Ala Val
1               5

<210> SEQ ID NO 1266
<211> LENGTH: 8
<212> TYPE: PRT
```

```
<213> ORGANISM: Artificial Sequence
<220> FEATURE:
<223> OTHER INFORMATION: Synthetic construct

<400> SEQUENCE: 1266

Trp Lys Trp Pro Trp Trp Pro Trp
1               5

<210> SEQ ID NO 1267
<211> LENGTH: 9
<212> TYPE: PRT
<213> ORGANISM: Artificial Sequence
<220> FEATURE:
<223> OTHER INFORMATION: Synthetic construct

<400> SEQUENCE: 1267

Lys Ile Trp Val Ile Arg Trp Trp Arg
1               5

<210> SEQ ID NO 1268
<211> LENGTH: 12
<212> TYPE: PRT
<213> ORGANISM: Artificial Sequence
<220> FEATURE:
<223> OTHER INFORMATION: Synthetic construct

<400> SEQUENCE: 1268

Arg Leu Cys Arg Ile Val Val Ile Arg Val Cys Arg
1               5                   10
```